US011166954B2

(12) United States Patent
Song et al.

(10) Patent No.: US 11,166,954 B2
(45) Date of Patent: Nov. 9, 2021

(54) DIHYDROPYRIMIDINE COMPOUND AND PREPARATION METHOD AND USE THEREOF

(71) Applicant: SICHUAN KELUN-BIOTECH BIOPHARMACEUTICAL CO., LTD., Chengdu (CN)

(72) Inventors: Shuai Song, Chengdu (CN); Jiaqiang Cai, Chengdu (CN); Qiang Tian, Chengdu (CN); Hong Zeng, Chengdu (CN); Hongmei Song, Chengdu (CN); Hanwen Deng, Chengdu (CN); Zujian Tang, Chengdu (CN); Xiaofan Duan, Chengdu (CN); Rongrong Long, Chengdu (CN); Yao Liu, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 0 days.

(21) Appl. No.: 16/859,910

(22) Filed: Apr. 27, 2020

(65) Prior Publication Data

US 2020/0253971 A1     Aug. 13, 2020

Related U.S. Application Data

(63) Continuation-in-part of application No. 16/334,237, filed as application No. PCT/CN2017/110123 on Nov. 9, 2017, now Pat. No. 10,696,669.

(30) Foreign Application Priority Data

Nov. 18, 2016  (CN) .......................... 201611015150.5
May 11, 2017   (CN) .......................... 201710328659.3

(51) Int. Cl.
    *A61K 31/506*   (2006.01)
    *A61K 31/5377*  (2006.01)
    *A61P 31/16*    (2006.01)

(52) U.S. Cl.
    CPC ........ *A61K 31/506* (2013.01); *A61K 31/5377* (2013.01); *A61P 31/16* (2018.01)

(58) Field of Classification Search
    CPC .... A61K 31/506; A61K 31/5377; A61P 31/16
    See application file for complete search history.

(56) References Cited

U.S. PATENT DOCUMENTS

| 9,498,479 B2 | 11/2016 | Zhang et al. |
| 9,771,358 B2 | 9/2017 | Zhang et al. |
| 9,895,349 B2 | 2/2018 | Vandyck et al. |
| 2010/0010013 A1 | 1/2010 | Li et al. |
| 2014/0343032 A1 | 11/2014 | Guo et al. |
| 2015/0031687 A1 | 1/2015 | Guo et al. |
| 2015/0152096 A1 | 6/2015 | Zhang et al. |
| 2015/0174115 A1 | 6/2015 | Hartman |
| 2015/0252057 A1 | 9/2015 | Guo et al. |
| 2016/0206616 A1 | 7/2016 | Zhang et al. |
| 2016/0264562 A1 | 9/2016 | Liu et al. |

FOREIGN PATENT DOCUMENTS

| CN | 103626752 A | 3/2014 | |
| CN | 103664899 A | 3/2014 | |
| CN | 104144924 A | 11/2014 | |
| CN | 104650068 A | 5/2015 | |
| CN | 105209470 A | 12/2015 | |
| WO | 2008/086729 A1 | 7/2008 | |
| WO | 2013/144129 A1 | 10/2013 | |
| WO | 2014/037480 A1 | 3/2014 | |
| WO | WO 2015/074546 A1 | 5/2015 | |
| WO | 2015/078391 A1 | 6/2015 | |
| WO | 2015/132276 A1 | 9/2015 | |
| WO | 2015/144093 A1 | 10/2015 | |
| WO | 2019/218883 A1 | 11/2019 | |
| WO | WO 2019/218883 | * 11/2019 | ........... C07D 417/14 |

OTHER PUBLICATIONS

IP Australia; Examination Report No. 1 for standard patent application; App. No. AU 2017359773; dated Nov. 24, 2020; 6 pgs.
State Intellectual Property Office of People's Republic of China; First Office Action; Appl. No. 201780057446.X; dated May 26, 2020.
Machine Translation of First Office Action; State Intellectual Property Office of PRC; Appl. No. 201780057446.X; dated May 28, 2020.
State Intellectual Property Office of the P.R. China; International Search Report; International Application No. PCT/CN2017/110123; dated Feb. 6, 2018.
Zongxing Qui, et al.; Design and Synthesis of Orally Bioavailable 4-Methyl Heteroaryldihydropyrimidine based Hepatitis B Virus (HBV) Capsid Inhibitors; Jour. of Medicinal Chemistry; Aug. 25, 2016; vol. 59, No. 16; 7651-7666.
European Patent Office; Supplementary Partial European Search Report; EP Appl. No. 17870982; dated Jan. 3, 2020.
ISA/CN; Written Opinion of the International Searching Authority; dated Jan. 31, 2018; 4 pgs.
Xiaofan Tang—International Bureau of WIPO; International Preliminary Report on Patentability; dated May 21, 2019; 1 pg.
Eurasian Patent Office; Official Action; Appl. No. 201990528; dated Feb. 7, 2020.
Eurasian Patent Office; English translation of Official Action; Appl. No. 201990528; dated Feb. 7, 2020.

(Continued)

*Primary Examiner* — Erich A Leeser

(74) *Attorney, Agent, or Firm* — Kilpatrick Townsend & Stockton LLP

(57) ABSTRACT

The present invention relates to a method for prophylactically treating or treating a viral disease, comprising administering to a subject in need thereof a dihydropyrimidine compound, and the viral diseases include, but are not limited to, Hepatitis A, Hepatitis B, Hepatitis C, influenza, herpes and acquired immunodeficiency syndrome (AIDS).

9 Claims, 1 Drawing Sheet

(56) References Cited

OTHER PUBLICATIONS

European Patent Office; Communication—Extended European Search Report; EP Appl. No. 17870982.0; dated Mar. 16, 2020; 11 pgs.
Australian Government—IP Australia; Examination Report No. 2 for standard patent application; Application No. 2017359773; dated Feb. 15, 2021; 6 pgs.
Intellectual Property Offic of Singapore; Written Opinion for Application No. 11201902373P; dated Jun. 27, 2020; 6 pgs.
Intellectual Property Office of Indonesia; First Office Action; Application No. PID201902773; dated Mar. 31, 2021; 6 pgs.
Eurasian Patent Office; Second Office Action; Application No. 201990528; dated Mar. 9, 2021; 4 pgs.

* cited by examiner

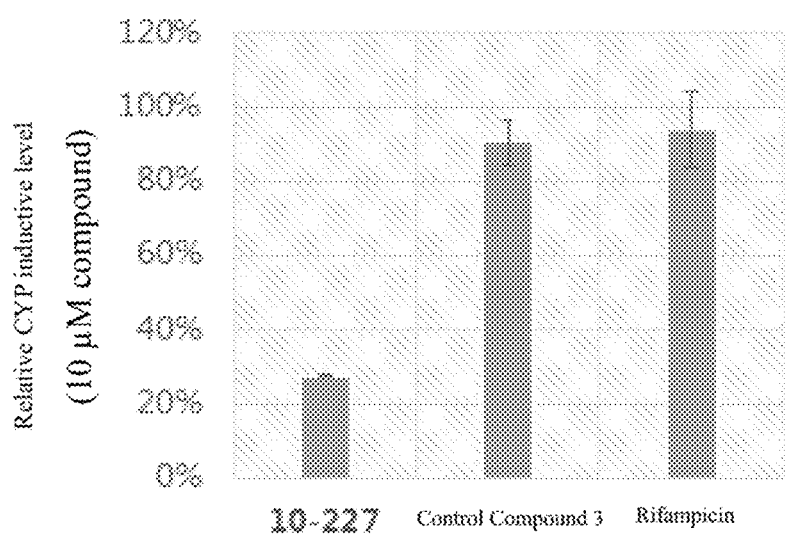

DIHYDROPYRIMIDINE COMPOUND AND PREPARATION METHOD AND USE THEREOF

CROSS-REFERENCE TO RELATED APPLICATIONS

This application is a continuation-in-part of U.S. application Ser. No. 16/334,237, filed Mar. 18, 2019, allowed, which application is a National Phase Entry of PCT/CN2017/110123, filed Nov. 9, 2017, which claims the benefit of priority to CN Patent Application No. 201710328659.3, filed May 11, 2017, and CN Patent Application No. 201611015150.5, filed Nov. 18, 2016, the teaching of which are hereby incorporated by reference in their entireties for all purposes.

FIELD OF THE INVENTION

The present invention relates to a dihydropyrimidine compound having antiviral activity, a pharmaceutical composition comprising the same, a preparation method therefor and use thereof in the prevention or treatment of viral diseases including, but not limited to, viral hepatitis type A, viral hepatitis type B, viral hepatitis type C, influenza, herpes and acquired immunodeficiency syndrome (AIDS).

BACKGROUND OF THE INVENTION

A virus is composed of a nucleic acid molecule (DNA or RNA) and proteins or only composed of proteins (such as prion). Viruses can cause various infectious diseases. Common diseases caused by a virus include but are not limited to viral hepatitis type A, viral hepatitis type B, viral hepatitis C, influenza, herpes and acquired immunodeficiency syndrome (AIDS).

At present, antiviral drugs in clinical use take effects by inhibiting attachment and uncoating of the virus, virus gene replication and maturation or release, or by affecting the immune system of a host. Such antiviral drugs mainly include reverse transcriptase inhibitors, capsid protein assembly inhibitors and the like.

Hepatitis type B virus (HBV) is a common hepatophilic DNA viral pathogen. The virus may result in acute hepatitis, chronic hepatitis, hepatic fibrosis, liver cirrhosis, liver cancer and the like.

Drugs for treating hepatitis type B include interferon and nucleoside analogues (such as lamivudine and adefovir dipivoxil). Among them, interferon interacts with a cell surface receptor to enable cells to produce antiviral proteins, thereby inhibiting the replication of hepatitis B virus. Disadvantages thereof are a relatively low effective response rate and need for long-term injection administration. The nucleoside analogues take effects mainly by inhibiting replication of viral polymerase (reverse transcriptase). The Disadvantage thereof is that the drugs need long lasting application which often results in viral mutation and leads to drug resistance.

Further, viral hepatitis type B can be treated with non-nucleoside analogues. A heteroaryl dihydropyrimidine compound (Bay41-4109) discovered by Deres et al. may prevent HBV virus replication by inhibiting viral capsid protein assembly (*Science*, 2003, 299, 893-896). The specific mechanism of action is as follows: the dihydropyrimidine compound induces defective assembly of core proteins, resulting in formation of unstable capsid proteins and acceleration of the degradation of the core proteins (*Biochem. Pharmacol.*, 2003, 66, 2273-2279). Heteroaryl dihydropyrimidine compound HAP1 discovered by Zlotnick et al. (*Proc. Natl. Acad. Sci.*, 2005, 102, 8138-8143) and a heteroaryl dihydropyrimidine compound (GLS4) reported by SUNSHINE LAKE PHARMA CO., LTD. (*Antimicrob. Agents Chemother.*, 2013, 57, 5344-5354; WO2015078391, US2016206616 and WO2015144093) also have anti-HBV activity.

Although the above compounds exhibit some degree of viral suppression, the antiviral activity thereof is still not satisfied. Moreover, some compounds also exhibit significant toxic effects (e.g., GLS4 exhibits significant hERG cardiotoxicity).

SUMMARY OF THE INVENTION

Through intensive study, the dihydropyrimidine compound was discovered. The dihydropyrimidine of the present invention is surprisingly more effective in inhibiting DNA replication of HBV than the disclosed dihydropyrimidine HBV capsid protein assembly modulators (e.g., at a cellular level, the antiviral activity of preferred compounds of the present invention are about 10 times of that of the preferred compound in WO2015144093 (the compound of Example 9)). The compound of the present invention does not have the cardiotoxicity exhibited by the disclosed dihydropyrinidine compounds (e.g. the hERG inhibitory activity of GLS4 and the preferred compound in WO2015144093 (the compound of Example 9)). Moreover, compared with disclosed dihydropyrimidine compounds (such as the compound of Example 5 in WO201403748), the compound of the present invention has a significantly reduced effect on induction of CYP450 isoform 3A4. In addition, the compound of the present invention exhibited better pharmacokinetic properties (such as better amount of exposure, blood-drug concentration and bioavailability) in pharmacokinetic tests on rats, Beagle dogs and cynomolgus macaques. Meanwhile, the preferred compounds of the present invention had excellent liver targeting properties, and the amount of drug exposure in liver can reach about 10 times of that in plasma, which indicates that the compounds have the ability to enrich in liver, thereby facilitating the improvement of the efficacy on liver diseases.

An aspect of the present invention provides a compound or a pharmaceutically acceptable salt, ester, stereoisomer, tautomer, polymorph, solvate, metabolite, isotopically labeled compound, or prodrug thereof, wherein the compound has the structure of Formula I or Formula Ia:

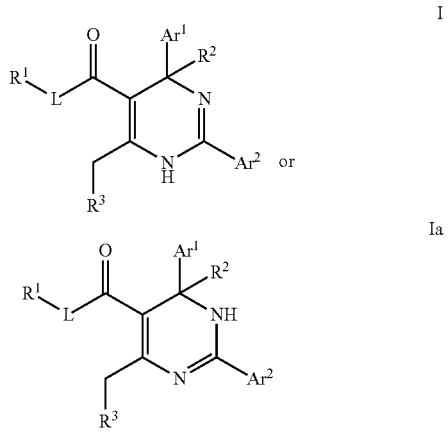

wherein:

Ar$^1$ and Ar$^2$ are each independently selected from the group consisting of C$_{6-14}$ aryl and 5- to 14-membered heteroaryl, which are optionally substituted with one or more substituents selected from the group consisting of halogen, —OH, —CN, —NO$_2$, —N(R)$_2$, C$_{1-6}$ alkyl, C$_{1-6}$ haloalkyl, C$_{1-6}$ alkylthio and C$_{3-6}$ cycloalkyl;

L is absent or is selected from the group consisting of —O—, —S— and —NR—;

R$^1$ and R$^2$ are each independently selected from the group consisting of H (including $^1$H, $^2$H, $^3$H), C$_{1-6}$ alkyl (e.g., C$_{1-6}$ deuteroalkyl) and C$_{3-6}$ cycloalkyl;

R$^3$ is a 4-, 5-, 6-, or 7-membered nitrogen containing heterocyclic system having the following structure:

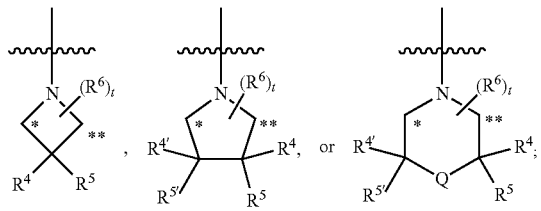

Q is selected from the group consisting of —(CR$^a$R$^{a'}$)$_g$—, —NR$^a$—, —O—, —S—, —S(=O)— and —S(=O)$_2$—;

R$^a$, R$^{a'}$, R$^4$, R$^{4'}$, R$^5$, R$^{5'}$ and R$^6$, at each occurrence, are each independently selected from the group consisting of H, halogen, —OH, —COOH, —CN, —NO$_2$, —N(R)$_2$, C$_{1-6}$ alkyl, C$_{1-6}$ haloalkyl, —W—C$_{1-6}$ alkyl, —C$_{1-6}$ alkylene-W—R, —W—C$_{1-6}$ alkylene-W'—R, —W—C$_{2-6}$ alkenyl, —C$_{2-6}$ alkenylene-W—R, —W—C$_{2-6}$ alkenylene-W'—R and C$_3$— cycloalkyl, wherein the alkylene and alkenylene are optionally further interrupted by one or more W; alternatively, each of R$^a$ together with R$^{a'}$, R$^4$ together with R$^5$ and/or R$^{4'}$ together with R$^5$, at each occurrence, independently forms a group =CH—W—R; provided that when R$^3$ is not a 4-membered nitrogen containing heterocyclic system, R$^a$, R$^{a'}$, R$^4$, R$^{4'}$, R$^5$, R$^{5'}$ and R$^6$ are not H at the same time, and is not a group selected from the group consisting of —COOH, —C$_{1-6}$ alkylene-OH and —C$_{1-6}$ alkylene-C(=O)OH; and when R$^3$ is a 4-membered nitrogen containing heterocycle, R$^4$, R$^5$ and R$^6$ are not H at the same time;

R$^6$ is attached to the ring carbon atom(s) marked with * and/or ** in the above structure of the nitrogen containing heterocyclic system;

W and W', at each occurrence, are each independently selected from the group consisting of O, C(=O), C(=O)O, NR, NC(=O), N(S=O), NS(=O)$_2$, S, S=O and S(=O)$_2$;

R, at each occurrence, is each independently selected from the group consisting of H, C$_{1-6}$ alkyl and C$_{3-6}$ cycloalkyl;

g is 1 or 2; and t is 0, 1, 2 or 3, provided that t is not greater than the number of substitutable positions in a corresponding group, and when t is greater than 1, each R$^6$ can be the same or different.

Another aspect of the present invention provides a pharmaceutical composition comprising a prophylactically or therapeutically effective amount of the compound of the present invention or a pharmaceutically acceptable salt, ester, stereoisomer, tautomer, polymorph, solvate, metabolite, isotopically labeled compound, or prodrug thereof and one or more pharmaceutically acceptable carriers, and the pharmaceutical composition is preferably in the form of a solid, liquid, or transdermal formulation.

Another aspect of the present invention provides a method for preparing a pharmaceutical composition comprising combining the compound of the present invention or a pharmaceutically acceptable salt, ester, stereoisomer, tautomer, polymorph, solvate, metabolite, isotopically labeled compound, or prodrug thereof and one or more pharmaceutically acceptable carriers.

Another aspect of the present invention provides the compound of the present invention or a pharmaceutically acceptable salt, ester, stereoisomer, tautomer, polymorph, solvate, metabolite, isotopically labeled compound, or prodrug thereof or the pharmaceutical composition of the present invention in the manufacture of a medicament for preventing or treating a viral disease.

Another aspect of the present invention provides the compound of the present invention or a pharmaceutically acceptable salt, ester, stereoisomer, tautomer, polymorph, solvate, metabolite, isotopically labeled compound, or prodrug thereof or the pharmaceutical composition of the present invention for use in the prevention or treatment of a viral disease.

Another aspect of the present invention provides a method for the prevention or treatment of a viral disease, comprising administering to a subject in need thereof an effective amount of the compound of the present invention or a pharmaceutically acceptable salt, ester, stereoisomer, tautomer, polymorph, solvate, metabolite, isotopically labeled compound, or prodrug thereof or the pharmaceutical composition of the present invention.

The viral disease includes, but is not limited to, viral hepatitis type A, viral hepatitis type B, viral hepatitis type C, influenza, herpes and acquired immunodeficiency syndrome (AIDS).

Another aspect of the present invention provides a method for the preparation of the compound of the present invention, the method comprises the following steps:

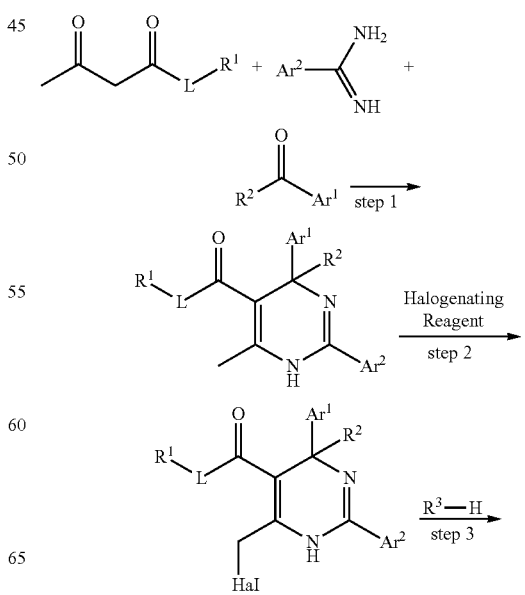

-continued

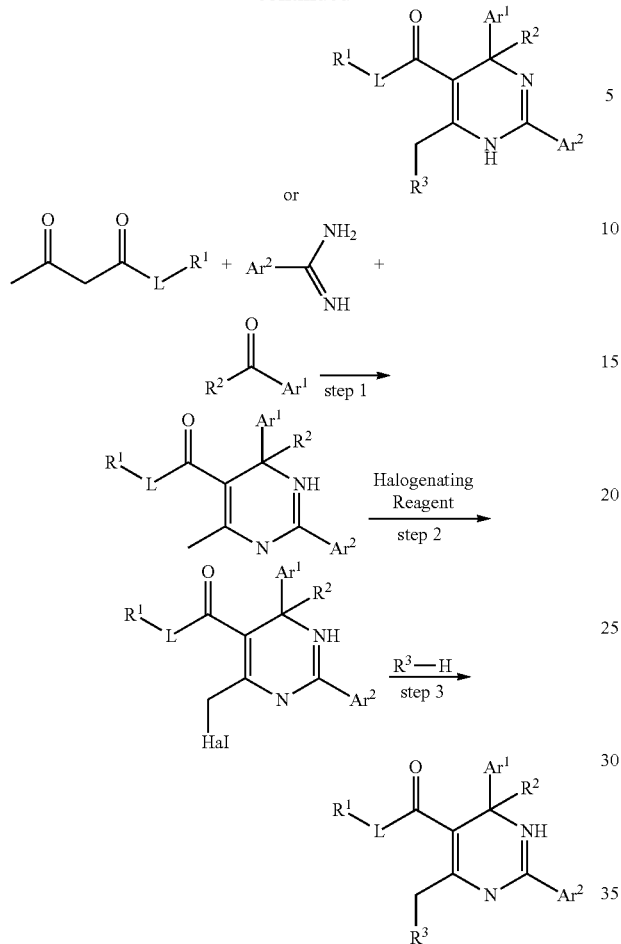

or wherein:
Hal is selected from the group consisting of F, Cl, Br and I;
the halogenating reagent is selected from the group consisting of Cl$_2$, Br$_2$, I$_2$, N-chlorosuccinimide, N-bromosuccinimide and N-iodosuccinimide;
the remaining groups are as defined above;
step 1 is performed in a protic solvent in the presence of an alkali metal salt;
step 2 is performed in an aprotic solvent; and
step 3 is performed in an aprotic solvent in the presence of an organic or inorganic base;
when R$^2$ in the compound of the present invention is C$_{1-6}$ alkyl, the compound can also be synthesized by a method comprising the following steps:

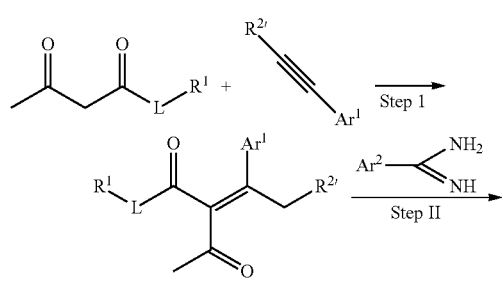

-continued

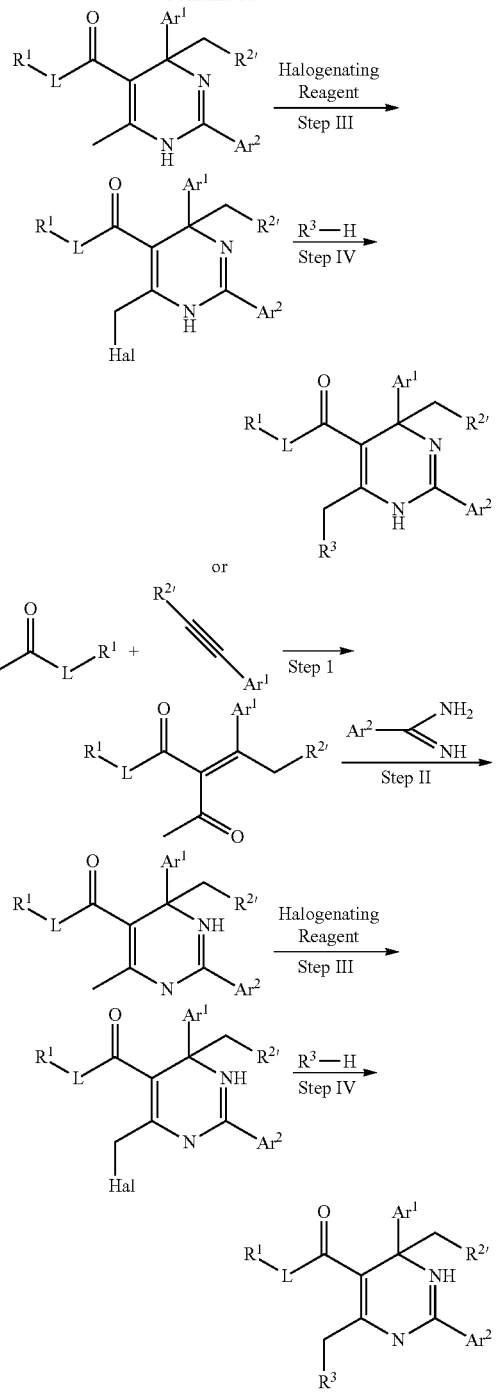

wherein:
R$^{2'}$ is H or C$_{1-5}$ alkyl;
Hal is selected from the group consisting of F, Cl, Br and I;
the halogenating reagent is selected from the group consisting of Cl$_2$, Br$_2$, I$_2$, N-chlorosuccinimide, N-bromosuccinimide and N-iodosuccinimide;
the remaining groups are as defined above;
step I is performed in a nonpolar solvent in the presence of a Lewis acid;
step II is performed in an aprotic solvent in the presence of an organic or inorganic base;

step III is performed in an aprotic solvent; and step IV is performed in an aprotic solvent in the presence of an organic or inorganic base.

BRIEF DESCRIPTION OF THE DRAWING

The FIGURE depicts the effect of compound 10-227, Control compound 3 and rifampicin on the induction of CYP450 isoform 3A4.

DEFINITIONS

Unless otherwise defined in the context, all technical and scientific terms used herein have the same meaning as commonly understood by a person skilled in the art. Techniques employed herein refer to the techniques as commonly understood in the art, including variations on those techniques or substitutions of equivalent techniques which would be appreciated by a person skilled in the art. While it is believed that the following terms can be understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkenylene" refers to a divalent hydrocarbyl having one or more double bonds, preferably having 2, 3, 4, 5 or 6 carbon atoms, such as vinylene, propenylene or allylidene. When the compound of the present invention contains an alkenylene group, the compound may exist as the pure E (entgegen) form, the pure Z (zusammen) form, or any mixture thereof.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, or n-hexyl), which is optionally substituted with one or more (e.g., 1 to 3) suitable substituents such as halogen (in which case the group may be referred to as "haloalkyl") (e.g., $CF_3$, $C_2F_5$, $CHF_2$, $CH_2F$, $CH_2CF_3$, $CH_2Cl$ or $-CH_2CH_2CF_3$ etc.). The term "$C_{1-4}$alkyl" refers to a linear or branched aliphatic hydrocarbon chain having 1-4 carbon atoms (i.e., methyl, ethyl, n-propyl; isopropyl, n-butyl, isobutyl, sec-butyl or tert-butyl).

As used herein, the term "cycloalkyl" refers to a saturated or unsaturated, nonaromatic monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated or unsaturated, nonaromatic monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the term "aryl" refers to an all-carbon monocyclic or fused-ring polycyclic aromatic group having a conjugated π electron system. For example, as used herein, the term "$C_{6-14}$ aryl" refers to an aromatic group containing 6 to 14 carbon atoms, such as phenyl or naphthyl. Aryl is optionally substituted with one or more (such as 1 to 3) suitable substituents (e.g., halogen, $-OH$, $-CN$, $-NO_2$, $C_{1-6}$ alkyl, etc.).

The term "aralkyl" preferably means aryl substituted alkyl, wherein aryl and alkyl are as defined herein. Normally, the aryl group may have 6-14 carbon atoms, and the alkyl group may have 1-6 carbon atoms. Exemplary aralkyl group includes, but is not limited to, benzyl, phenylethyl, phenylpropyl, phenylbutyl.

As used herein, the term "heteroaryl" refers to a monovalent monocyclic, bicyclic or tricyclic aromatic ring system having 5, 6, 7, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in certain instances, it can be benzo-fused. In particular, heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl etc., and benzo derivatives thereof; or pyridinyl, pyridazinyl, pyrimidinyl, pyrazinyl, triazinyl, etc., and benzo derivatives thereof.

As used herein, the term "halo" or "halogen" are defined to include F, Cl, Br, or I.

As used herein, the term "alkylthio" means an alkyl group as defined above linked to the core molecular moiety via a sulfur atom. Typical examples of $C_1$ alkylthio include, but are not limited to, methylthio, ethylthio, tert-butylthio, and hexylthio.

As used herein, the term "nitrogen containing heterocyclic system" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C=O, S, S=O and $S(=O)_2$. The nitrogen containing heterocyclic system is attached to the rest of the molecule through the nitrogen atom. Particularly, 3- to 14-membered nitrogen containing heterocyclic system is a group having 3-14 carbon atoms and heteroatoms (wherein at least one is nitrogen) in the ring, including, but not limited to, 3-membered nitrogen containing heterocyclic system (such as aziridinyl), 4-membered nitrogen containing heterocyclic system (such as azetidinyl), 5-membered nitrogen containing heterocyclic system (such as pyrrolyl, pyrrolidinyl, pyrrolinyl, pyrrolidone, imidazolyl, imidazolidinyl, imidazolinyl, pyrazolyl, pyrazolinyl), 6-membered nitrogen containing heterocyclic system (such as piperidinyl, morpholinyl, thiomorpholinyl, piperazinyl), 7-membered nitrogen containing heterocyclic system and the like.

The term "substituted" means that one or more (e.g., one, two, three, or four) hydrogens on the designated atom is replaced with a selected group, provided that the designated atom's normal valency under the existing circumstances is not exceeded, and that the substitution results in a stable compound. The number of the selected substituents is permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon may separately and/or together be replaced with an independently selected optional substituent. If a nitrogen of a substituent is described as being optionally substituted with one or more of a list of substituents, one or more of the hydrogens on the nitrogen may each be replaced with an independently selected optional substituent.

If substituents are described as being "independently selected", each substituent may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a ring and the position of the attachment is not specified, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as deuterium (D, $^{2}$H), tritium (T, $^{3}$H); carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention are useful in drug and/or substrate tissue distribution studies (e.g., assays). Pharmaceutically acceptable solvates in accordance with the invention include those wherein the solvent of crystallization may be isotopically substituted, e.g., D$_2$O, acetone-d$_6$, or DMSO-d$_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. For example, a dihydropyrimidine group may exist as the following tautomers in equilibrium in a solution:

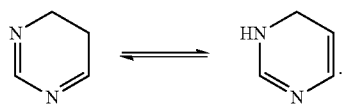

It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention. The carbon-carbon bonds of the compound of the present invention may be depicted herein using a solid line (—), a solid wedge ( ▬ ), a dotted wedge ( ⋯⋯ ) or a wavy line ( ∿ ).). The use of a solid line to depict bonds to asymmetric carbon atoms is meant to indicate that all possible stereoisomers (e.g., specific enantiomers, racemic mixtures, etc.) at that carbon atom are included. The use of a wavy line to depict bonds to an alkenyl group is meant to indicate that all possible stereoisomers (e.g., specific cis-trans isomer, a mixture of cis and trans isomers in any ration, or racemic mixtures, etc.) at that chemical bond are included. The use of either a solid or dotted wedge to depict bonds to asymmetric carbon atoms indicates that the stereoisomer shown is present. When present in racemic compounds, solid and dotted wedges are used to define relative stereochemistry, rather than absolute stereochemistry. Unless stated otherwise, the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, the compound of the present invention can be used for the treatment in a free from, or where appropriate, in a form of a pharmaceutically acceptable derivative. In the present invention, the pharmaceutically acceptable derivative includes, but is not limited to a pharmaceutically acceptable salt, ester, solvate, metabolite, isotopically labeled compound or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid (including suitable inorganic acids and organic acids) which forms a pharmaceutically acceptable salt. Specific examples include aspartate, benzoate, bicarbonate/carbonate, bisulfate/sulfate, fumarate, gluceptate, gluconate, glucuronate, hexafluorophosphate, hydrobromide/bromide, hydroiodide/iodide, maleate, malonate, methylsulfate, naphthylate, nicotinate, nitrate, orotate, oxalate, palmitate and the like.

A suitable base addition salt is formed from a base (including suitable inorganic bases and organic bases) which forms a pharmaceutically acceptable salt. Specific examples include aluminum, arginine, choline, diethylamine, lysine, magnesium, meglumine, potassium and the like.

For a review on suitable salts, see "Hand book of Pharmaceutical Salts: Properties, Selection, and Use" by Stahl and Wennuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (e.g., a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have or not have pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems, Vol. 14, ACS Symposium Series (T. Higuchi and V. Stella) and "Bioreversible Carriers in Drug Design," Pergamon Press, 1987 (E. B. Roche ed., American Pharmaceutical Association). The prodrug in accordance with the invention can, for example, be produced by replacing appropriate functionalities present in the compound of the present invention with certain moieties known to those skilled in the art as "promoieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in Protective Groups in Organic Chemistry, ed. J. F. W. McOmie, Plenum Press, 1973 and T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

As used herein, the term "about" refers to a range within ±10%, preferably within ±5%, and more preferably within ±2% of the specified value.

DETAILED DESCRIPTION OF THE INVENTION

Compound and Preparation Method Therefor

In embodiments, the present invention provides a compound or a pharmaceutically acceptable salt, ester, stereoisomer, tautomer, polymorph, solvate, metabolite, isotopically labeled compound, or prodrug thereof, wherein the compound has the structure of Formula I or Formula Ia:

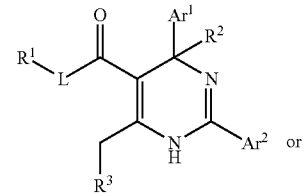

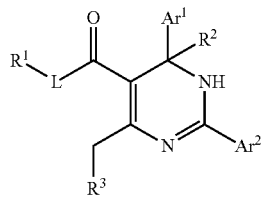

wherein:

$Ar^1$ and $Ar^2$ are each independently selected from the group consisting of $C_{6-14}$ aryl and 5- to 14-membered heteroaryl, which are optionally substituted with one or more substituents selected from the group consisting of halogen, —OH, —CN, —NO$_2$, —N(R)$_2$, $C_{1-6}$ alkyl, $C_{1-6}$ haloalkyl, $C_{1-6}$ alkylthio and $C_{3-6}$ cycloalkyl;

L is absent or is selected from the group consisting of —O—, —S— and —NR—;

$R^1$ and $R^2$ are each independently selected from the group consisting of H (including $^1$H, $^2$H, $^3$H), $C_{1-6}$ alkyl (e.g., $C_{1-6}$ deuteroalkyl) and $C_{3-6}$ cycloalkyl;

$R^3$ is a 4-, 5-, 6-, or 7-membered nitrogen containing heterocyclic system having the following structure:

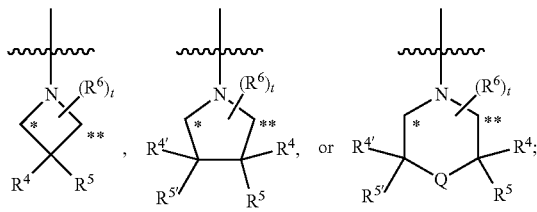

Q is selected from the group consisting of —(CR$^a$R$^{a'}$)$_g$—, —NR$^a$—, —O—, —S—, —S(=O)— and —S(=O)$_2$—;

R$^a$, R$^{a'}$, R$^4$, R$^{4'}$, R$^5$, R$^{5'}$ and R$^6$, at each occurrence, are each independently selected from the group consisting of H, halogen, —OH, —COOH, —CN, —NO$_2$, —N(R)$_2$, $C_{1-6}$ alkyl, $C_{1-6}$ haloalkyl, —W—$C_{1-6}$ alkyl, —$C_{1-6}$ alkylene-W—R, —W—$C_{1-6}$ alkylene-W'—R, —W—$C_{2-6}$ alkenyl, —$C_{2-6}$ alkenylene-W—R, —W—$C_{2-6}$ alkenylene-W'—R and $C_{3-6}$ cycloalkyl, wherein the alkylene and alkenylene are optionally further interrupted by one or more W; alternatively, each of R$^a$ together with R$^{a'}$, R$^4$ together with R$^5$ and/or R$^{4'}$ together with R$^{5'}$, at each occurrence, independently forms a group =CH—W—R; provided that when R$^3$ is not a 4-membered nitrogen containing heterocyclic system, R$^a$, R$^{a'}$, R$^4$, R$^{4'}$, R$^5$, R$^{5'}$ and R$^6$ are not H at the same time, and is not a group selected from the group consisting of —COOH, —$C_{1-6}$ alkylene-OH and —$C_{1-6}$ alkylene-C(=O)OH; and when R$^3$ is a 4-membered nitrogen containing heterocycle, R$^4$, R$^5$ and R$^6$ are not H at the same time;

R$^6$ is attached to the ring carbon atom(s) marked with * and/or ** in the above structure of the nitrogen containing heterocyclic system;

W and W', at each occurrence, are each independently selected from the group consisting of O, C(=O), C(=O)O, NR, NC(=O), N(S=O), NS(=O)$_2$, S, S=O and S(=O)$_2$;

R, at each occurrence, is each independently selected from the group consisting of H, $C_{1-6}$ alkyl and $C_{3-6}$ cycloalkyl;

g is 1 or 2; and t is 0, 1, 2 or 3, provided that t is not greater than the number of substitutable positions in a corresponding group, and when t is greater than 1, each $R^6$ can be the same or different.

In preferred embodiments, the present invention provides a compound or a pharmaceutically acceptable salt, ester, stereoisomer, tautomer, polymorph, solvate, metabolite, isotopically labeled compound, or prodrug thereof, wherein the compound has the structure of Formula II or Formula IIa:

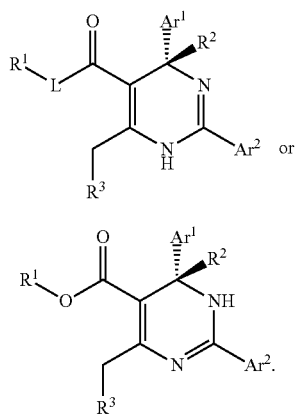

In preferred embodiments, the present invention provides a compound or a pharmaceutically acceptable salt, ester, stereoisomer, tautomer, polymorph, solvate, metabolite, isotopically labeled compound, or prodrug thereof, wherein $Ar^1$ is selected from the group consisting of:

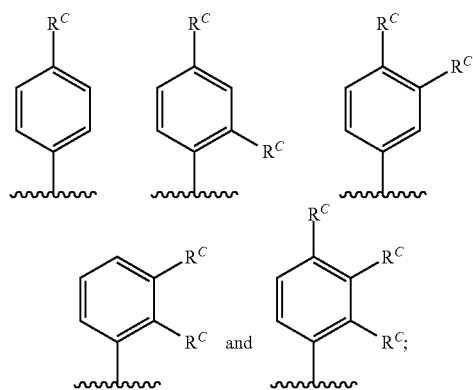

wherein $R^c$, at each occurrence, is each independently selected from the group consisting of F, Cl, Br, I, $C_{1-6}$ haloalkyl, $C_{1-6}$ alkyl and $C_{3-6}$ cycloalkyl;

Preferably, $R^c$, at each occurrence, is each independently selected from the group consisting of F, Cl, Br, I, $C_{1-6}$ alkyl and $C_{3-6}$ cycloalkyl;

$Ar^1$ is more preferably selected from the group consisting of

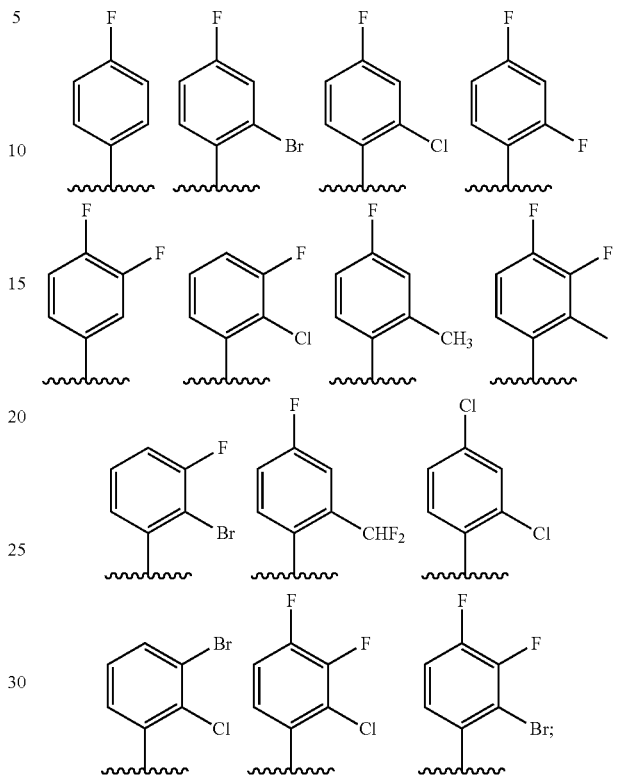

$Ar^1$ is particularly preferably selected from the group consisting of

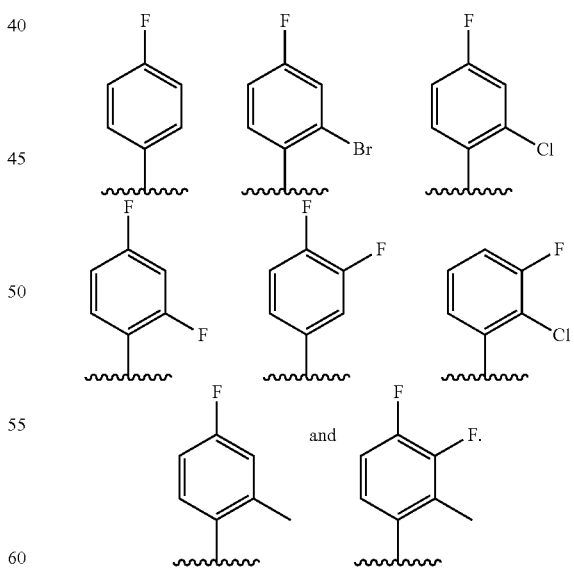

In preferred embodiments, the present invention provides a compound or a pharmaceutically acceptable salt, ester, stereoisomer, tautomer, polymorph, solvate, metabolite, isotopically labeled compound, or prodrug thereof, wherein $Ar^2$ is selected from the group consisting of:

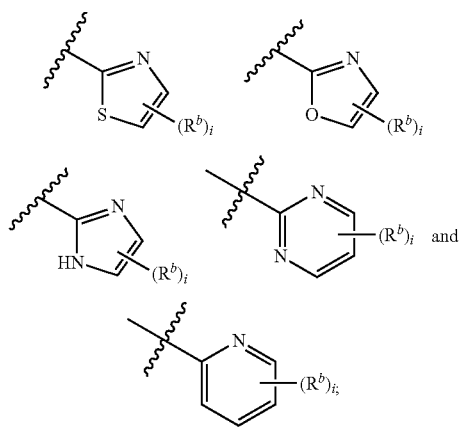

$R^b$, at each occurrence, is each independently selected from the group consisting of H, halogen, $C_{1-6}$ haloalkyl, $C_{1-6}$ alkyl and $C_{3-6}$ cycloalkyl; preferably, $R^b$, at each occurrence, is each independently selected from the group consisting of H, halogen, $C_{1-6}$ alkyl and $C_{3-6}$ cycloalkyl; and i is 0, 1 or 2;

$Ar^2$ is preferably selected from the group consisting of

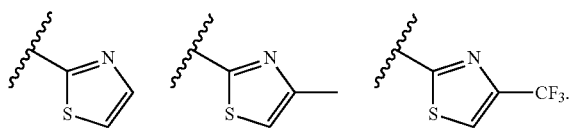

In preferred embodiments, L is —O—.

In preferred embodiments, $R^1$ and $R^2$ are each independently selected from the group consisting of H (including $^1H$, $^2H$, $^3H$), methyl, ethyl, n-propyl and isopropyl.

In preferred embodiments, $R^3$ is a 4-, 5-, 6-, or 7-membered nitrogen containing heterocyclic system having the following structure:

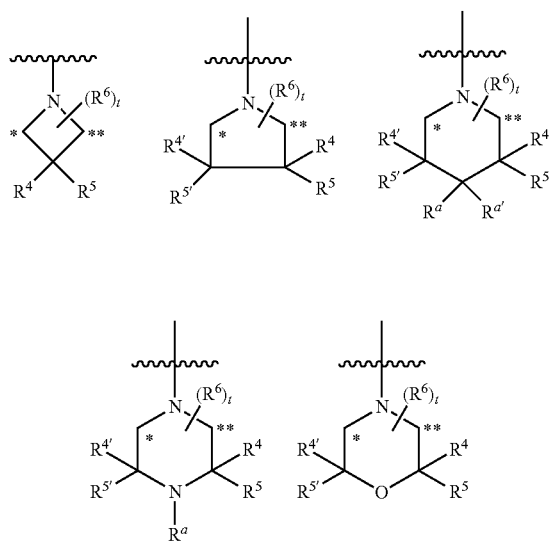

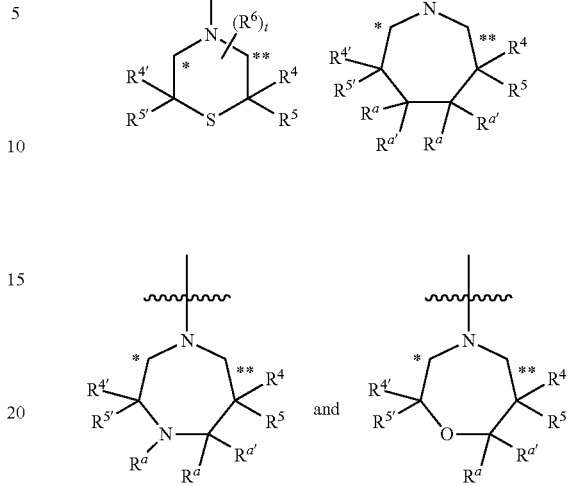

$R^6$ is attached to the ring carbon atom(s) marked with * and/or ** in the above structure of the nitrogen containing heterocyclic system.

In preferred embodiments, $R^a$, $R^{a'}$, $R^4$, $R^{4'}$, $R^5$, $R^{5'}$ and $R^6$, at each occurrence, are each independently selected from the group consisting of H, F, Cl, Br, —$(CR^7R^a)_m$OH, —O—$C_{1-6}$ alkyl, —$(CR^7R^{7a})_m$COOH, —$C(R^7)$=$C(R^{7a'})$ $(CR^7R^{7a})_m$COOH and —$(CR^7R^{7a})_m$—W—$(CR^7R^{7a'})_m$ COOH, the —$(CR^7R^{7a})_m$—W—$(CR^7R^{7a'})_m$COOH is preferably —$(CR^7R^{7a})_m$O$(CR^7R^{7a'})$COOH, —$(CR^7R^{7a})_m$NR $(CR^7R^{7a'})_n$COOH or —$(CR^7R^{7a})_m$S(=O)$_j(CR^7R^{7a'})_n$ COOH; alternatively, each of $R^a$ together with $R^{a'}$, $R^4$ together with $R^5$ and/or $R^{4'}$ together with $R^{5'}$, at each occurrence, independently forms a group =CH—W—R;

$R^7$, $R^{7'}$, $R^{7a}$, $R^{7a'}$, at each occurrence, are each independently selected from the group consisting of H, $C_{1-4}$ alkyl and $C_{3-6}$ cycloalkyl;

R is selected from the group consisting of H, methyl, ethyl, propyl and cyclopropyl;

m is 0, 1, 2, 3 or 4;

n is 1, 2, 3 or 4; and j is 0, 1 or 2.

In more preferred embodiments, $R^a$, $R^{a'}$, $R^4$, $R^{4'}$, $R^5$, $R^{5'}$ and $R^6$, at each occurrence, are each independently selected from the group consisting of H, F, —OH, —$CH_2$OH, —$OCH_3$, —COOH, —$CH_2$COOH, —$(CH_2)_2$COOH, —$(CH_2)_3$COOH, —CH=CHCOOH, —$OCH_2$COOH, —$SCH_2$COOH, —$N(CH_3)CH_2$COOH, —$CH_2OCH_2$COOH, —$CH_2SCH_2$COOH, —$CH_2N(CH_3)$ $CH_2$COOH, —$C(CH_3)$=CHCOOH and —CH=$C(CH_3)$ COOH.

In particularly preferred embodiments, $R^a$, $R^{a'}$, $R^4$, $R^{4'}$, $R^5$, $R^{5'}$ and $R^6$, at each occurrence, are each independently selected from the group consisting of H, F, —OH, —$CH_2$OH, —$OCH_3$, —COOH, —$CH_2$COOH, —$(CH_2)_2$ COOH, —$(CH_2)_3$COOH, —CH=CHCOOH, —$OCH_2$COOH, —$SCH_2$COOH, —$N(CH_3)CH_2$COOH, —$CH_2OCH_2$COOH, —$CH_2SCH_2$COOH and —$CH_2N$ $(CH_3)CH_2$COOH.

In preferred embodiments, $R^3$ is selected from the group consisting of:
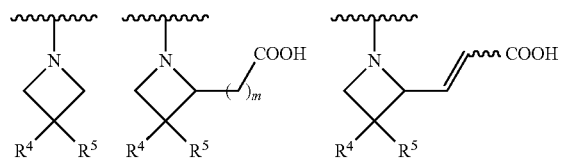
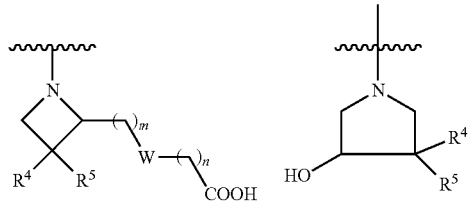
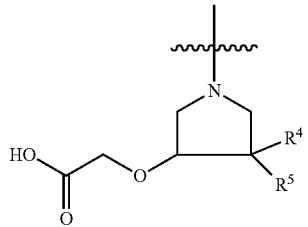
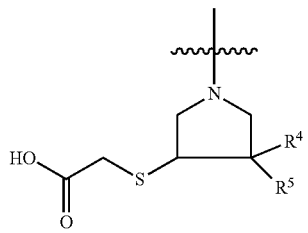
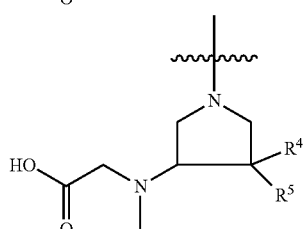
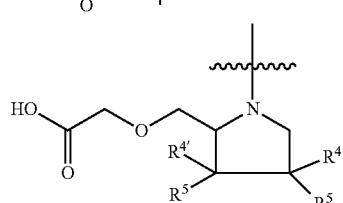
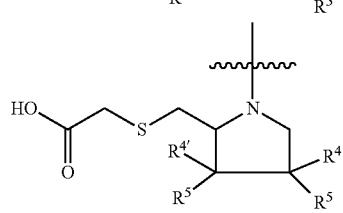
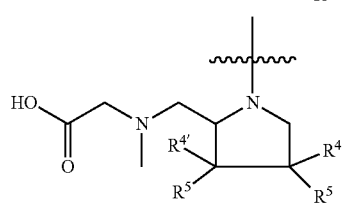
-continued
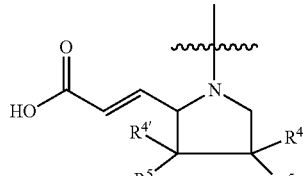
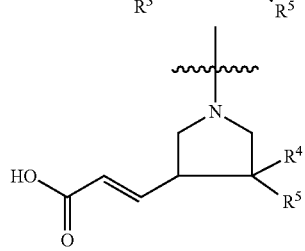
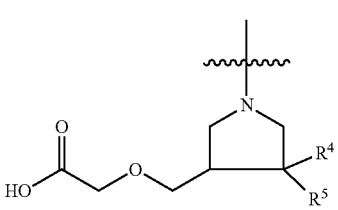
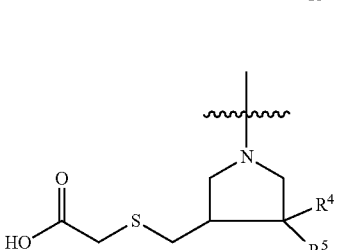
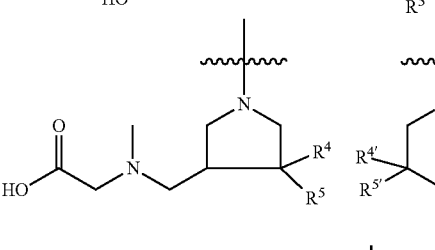
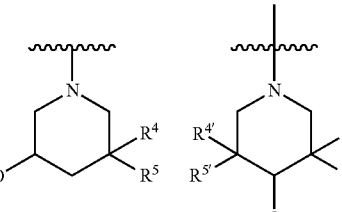
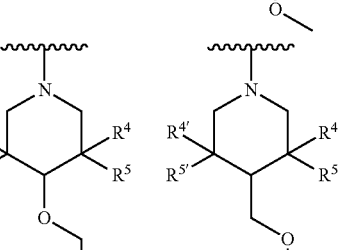

-continued
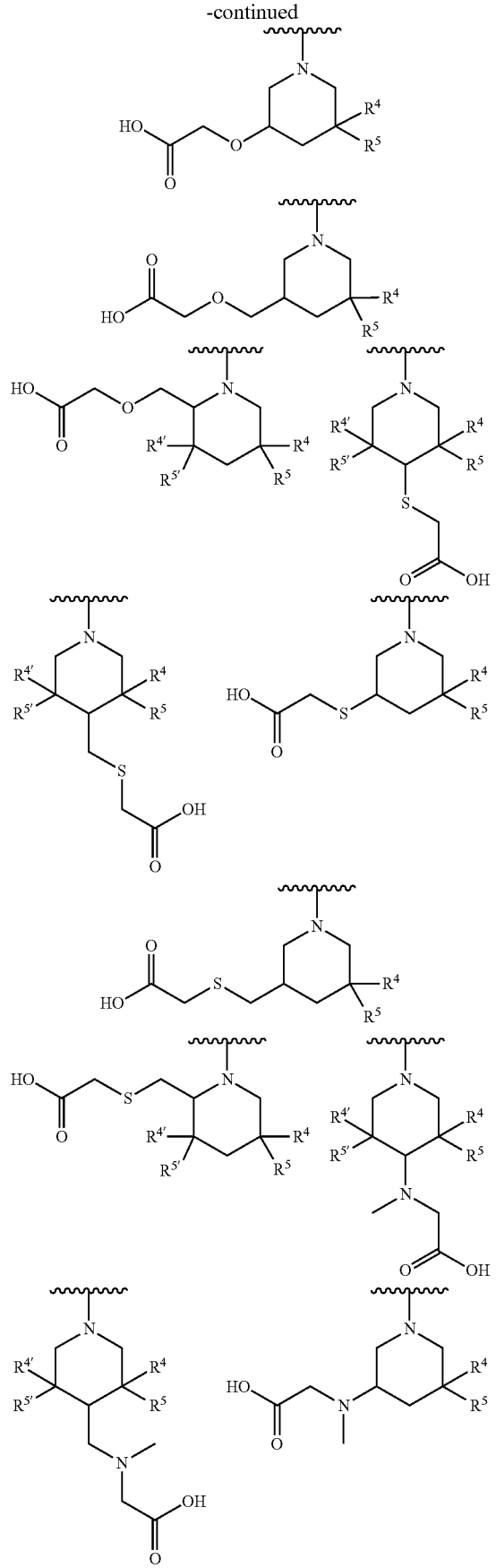
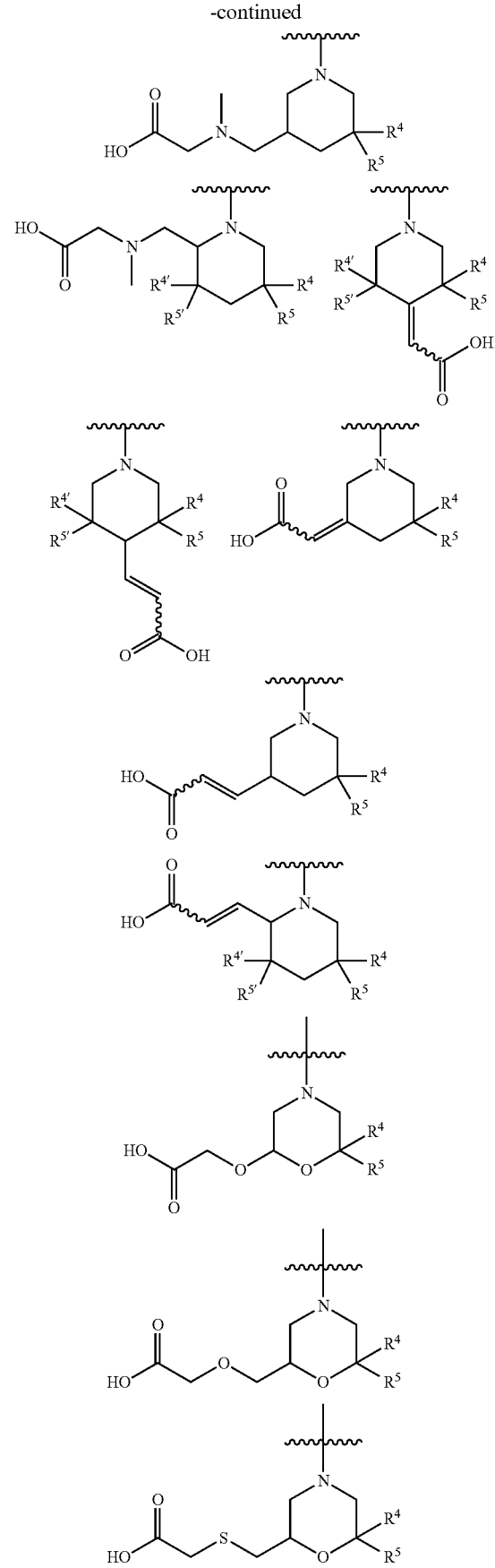

-continued
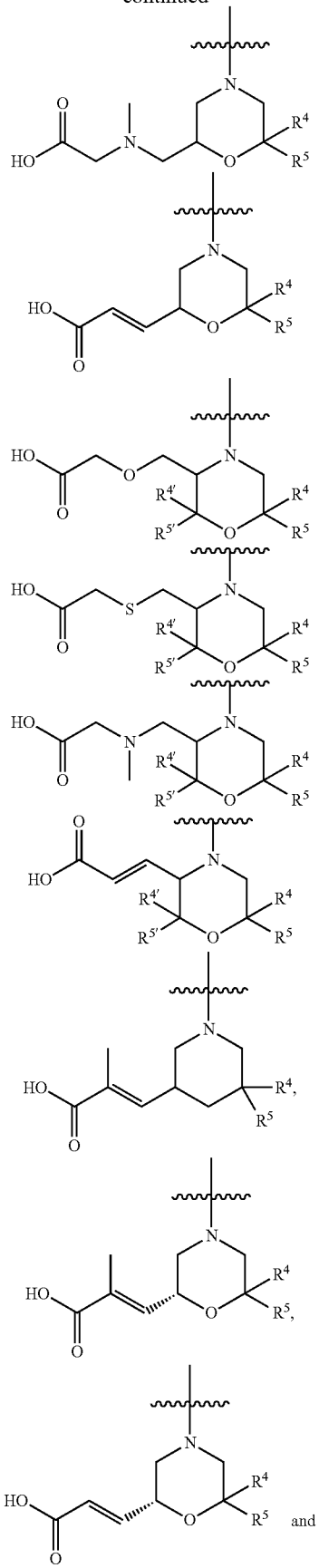
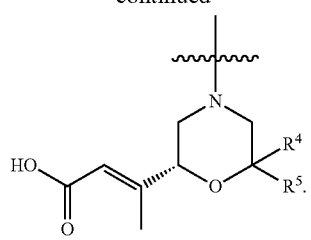
In more preferred embodiments, $R^3$ is selected from the group consisting of.
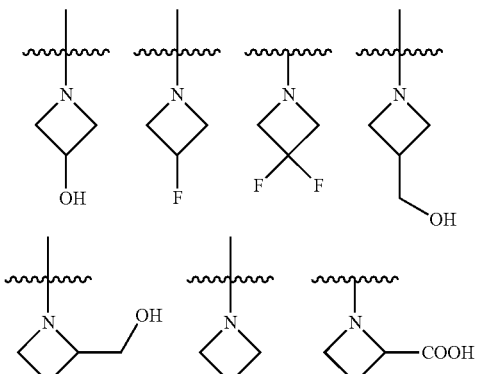
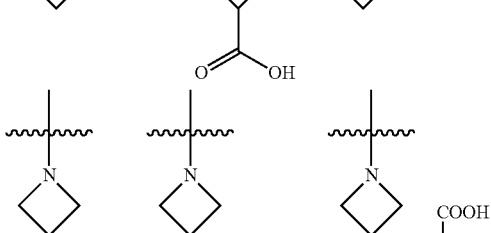
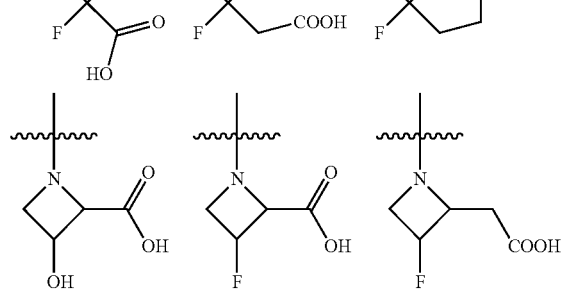
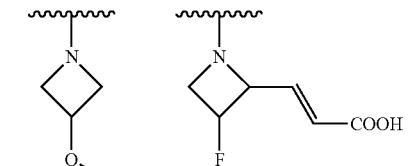
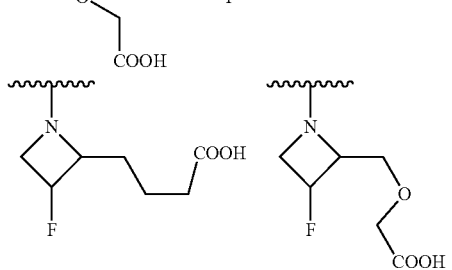

-continued
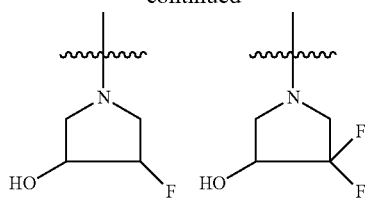
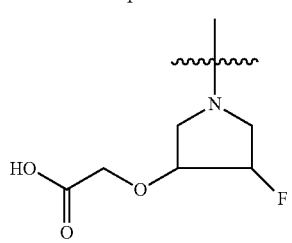
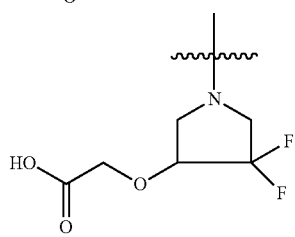
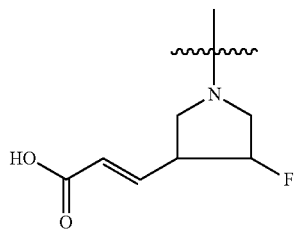
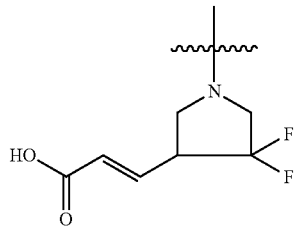
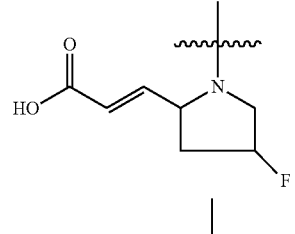
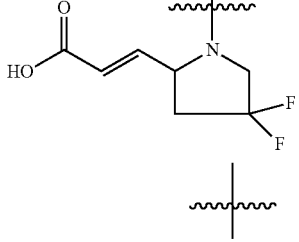
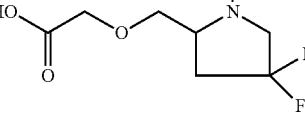
-continued
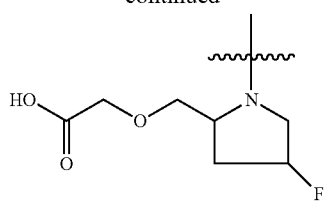
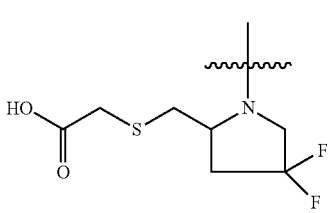
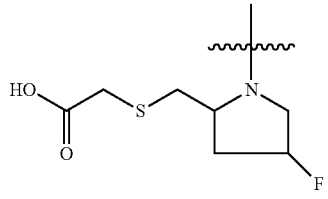
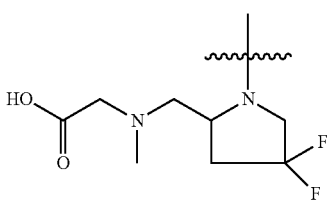
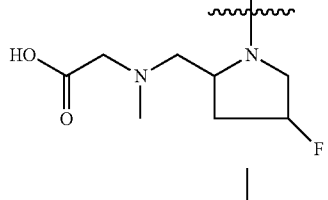
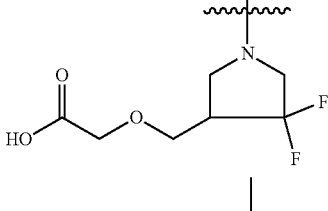
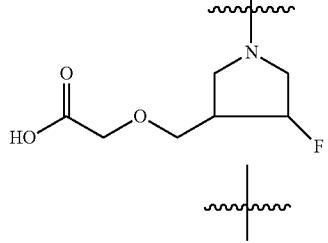
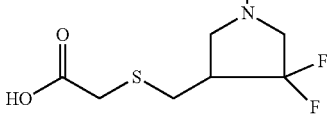

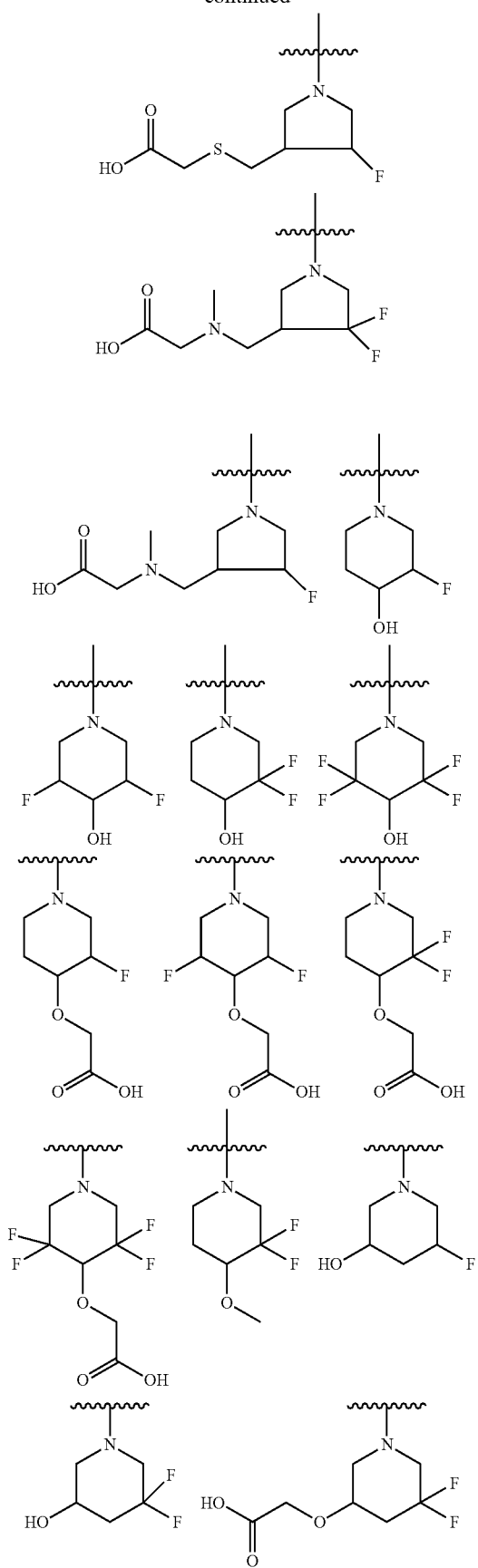
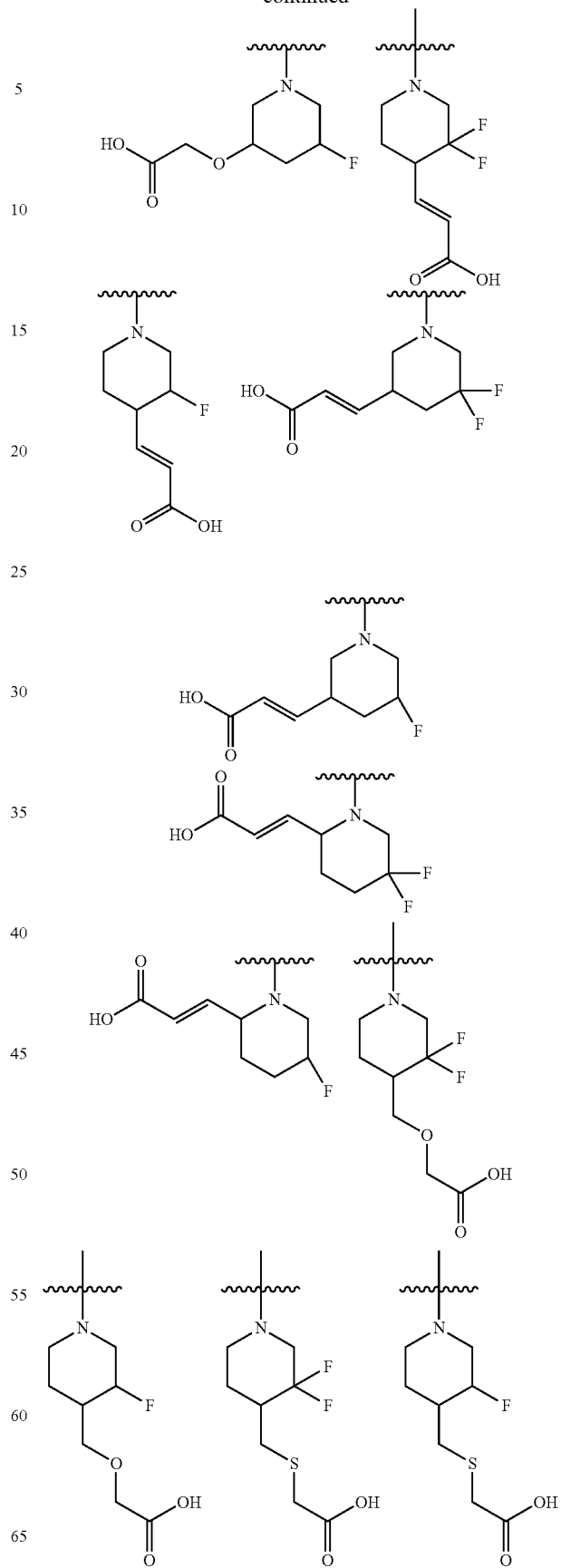

27
-continued
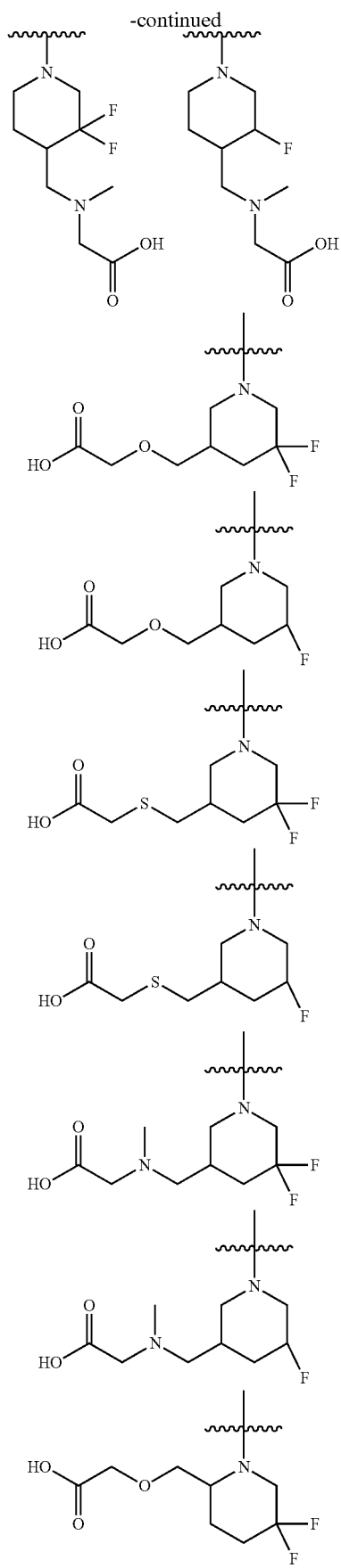
28
-continued
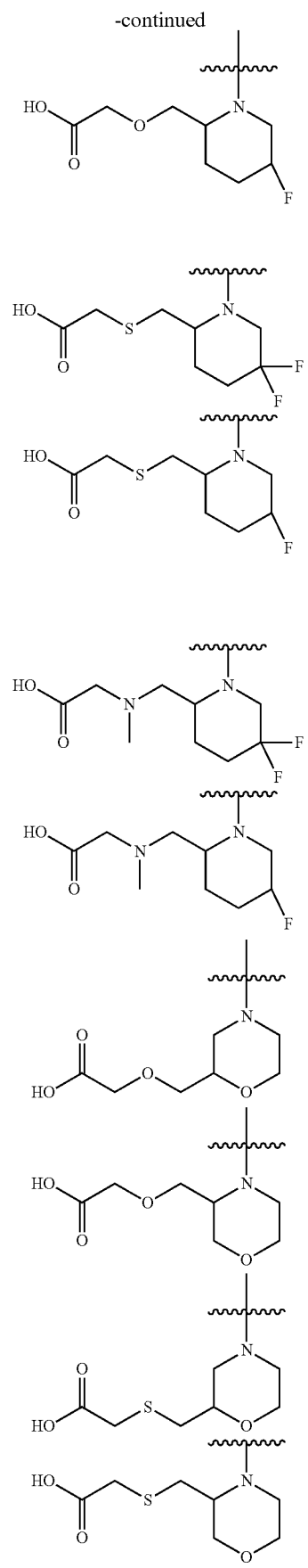

-continued
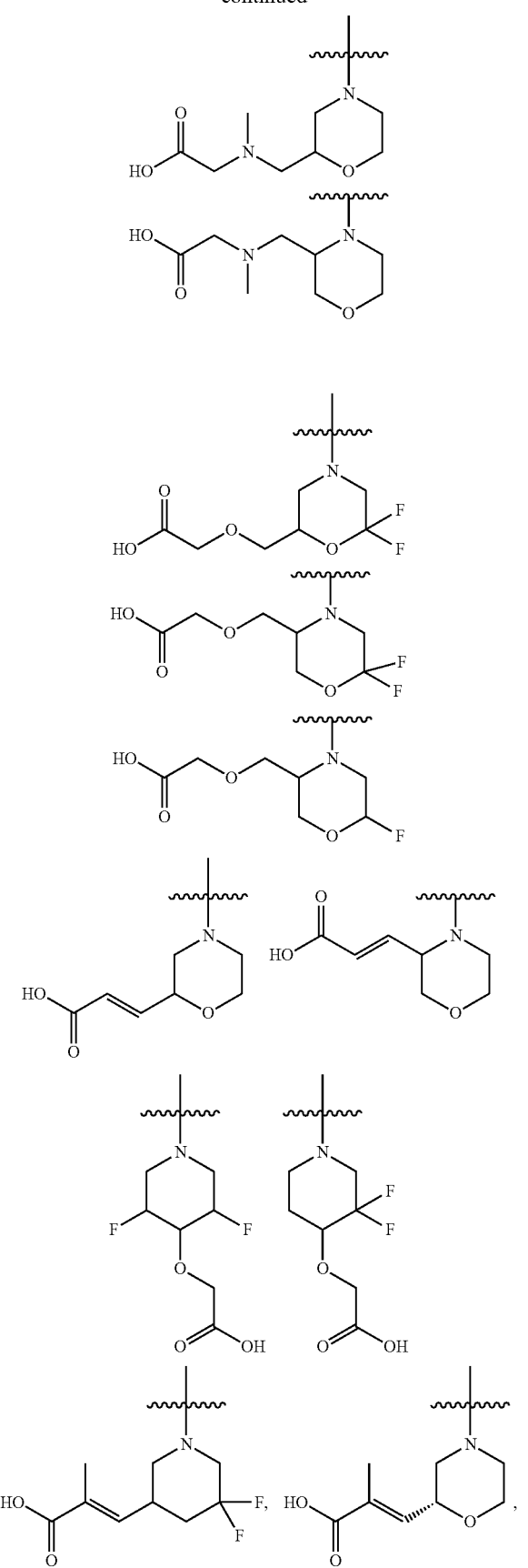
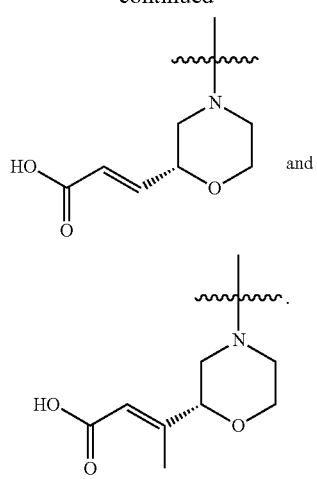 and
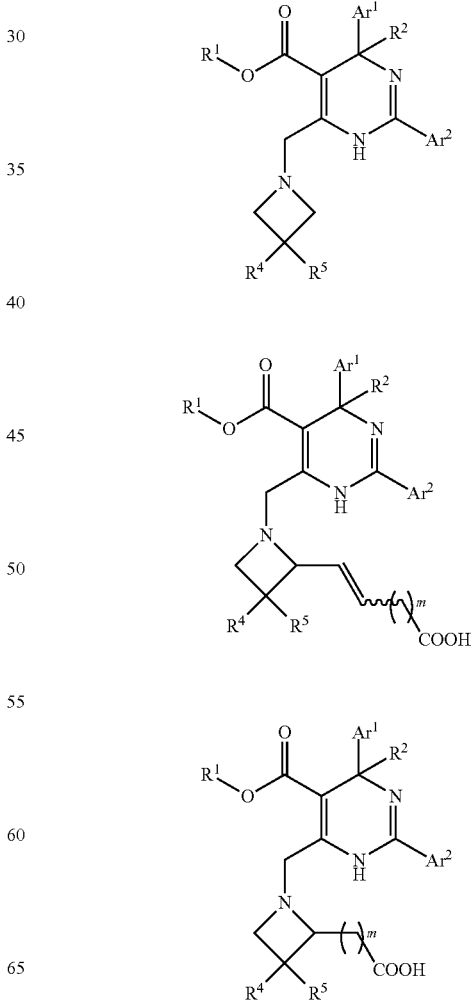
In certain embodiments, the present invention provides a compound or a pharmaceutically acceptable salt, ester, stereoisomer, tautomer, polymorph, solvate, metabolite, isotopically labeled compound, or prodrug thereof, wherein the compound has the following structure:

-continued
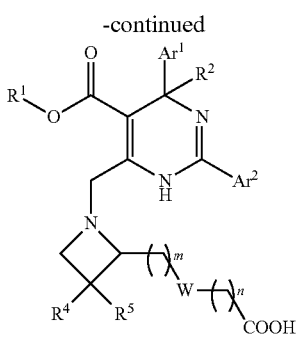
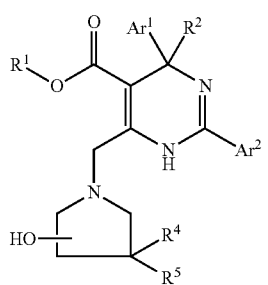
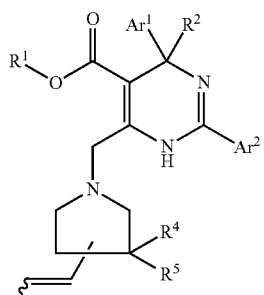
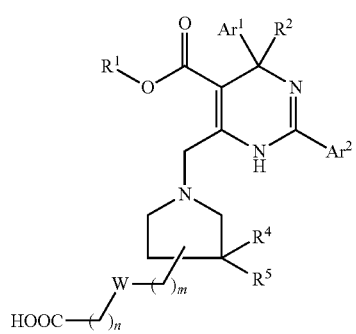
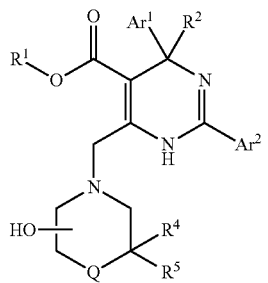
-continued
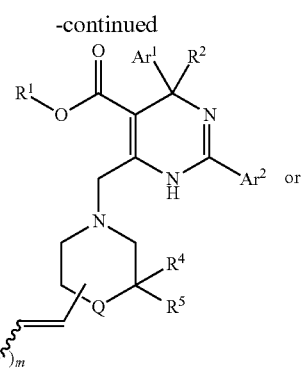
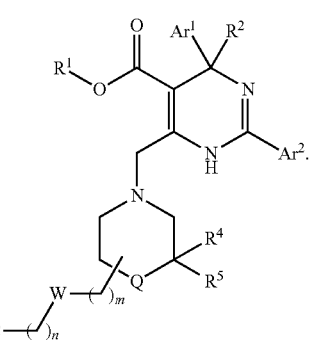
In certain embodiments, the present invention provides a compound or a pharmaceutically acceptable salt, ester, stereoisomer, tautomer, polymorph, solvate, metabolite, isotopically labeled compound, or prodrug thereof, wherein the compound has the following structure:
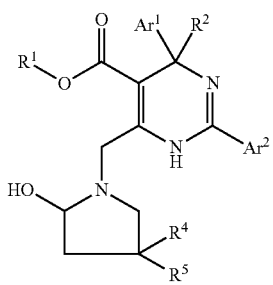
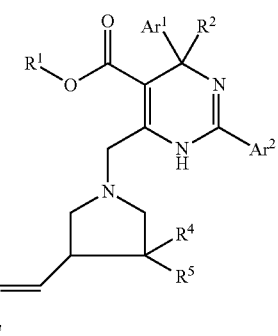

-continued
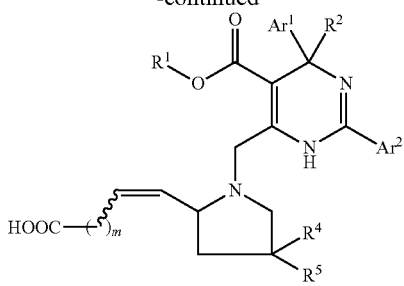
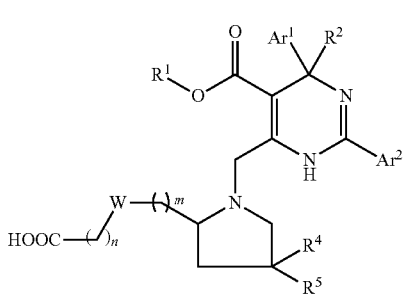
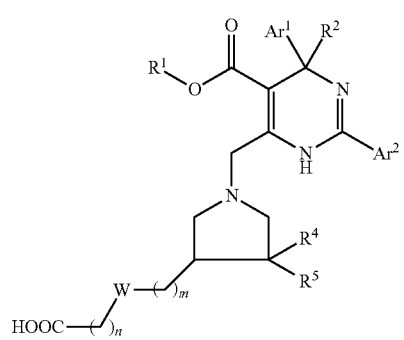
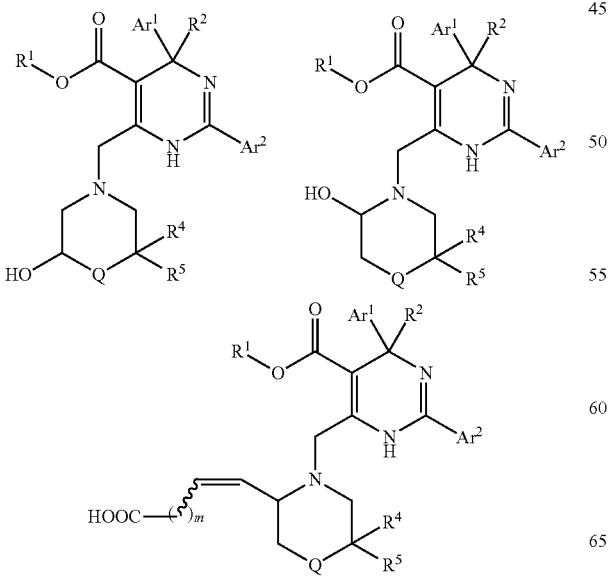
-continued
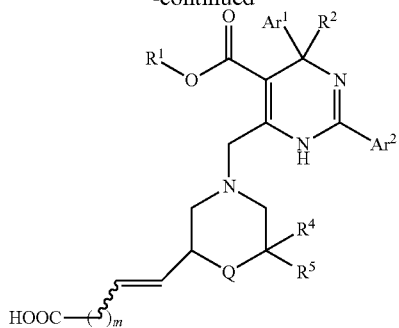
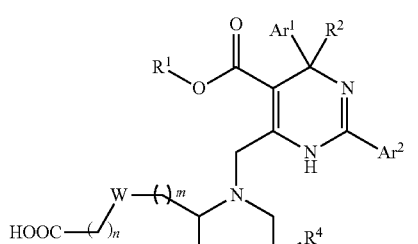
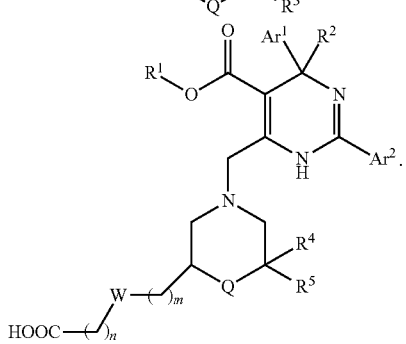
or
In certain embodiments, the present invention provides a compound or a pharmaceutically acceptable salt, ester, stereoisomer, tautomer, polymorph, solvate, metabolite, isotopically labeled compound, or prodrug thereof, wherein the compound has the following structure:
III
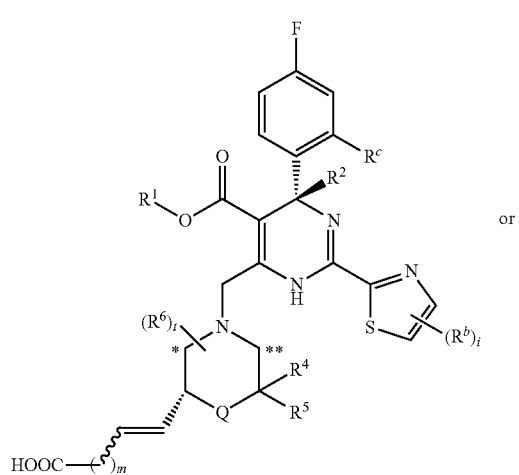
or

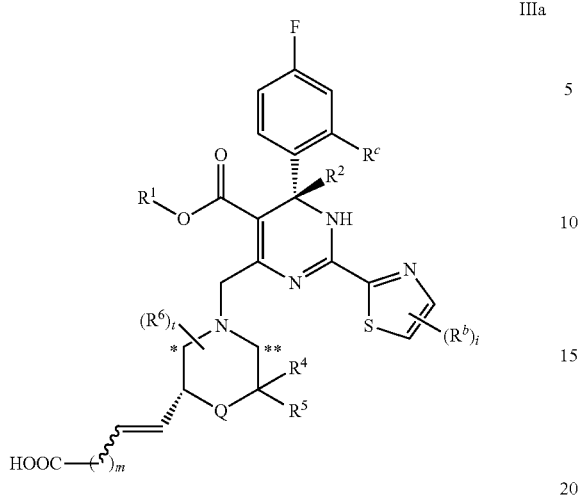

IIIa

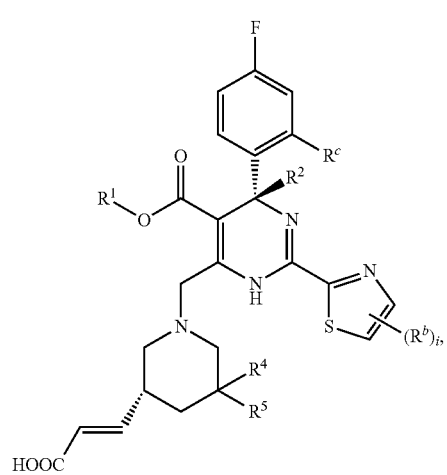

IV wherein:

R¹ and R² are each independently selected from the group consisting of H (including $^1$H, $^2$H, $^3$H), $C_{1-6}$ alkyl (e.g., $C_{1-6}$ deuteroalkyl) and $C_{3-6}$ cycloalkyl, and R¹ is preferably methyl, ethyl, n-propyl, isopropyl or cyclopropyl;

Q is —(CR$^a$R$^{a'}$)$_g$— or —O—;

R$^a$, R$^{a'}$, R⁴, R⁵ and R⁶, at each occurrence, are each independently selected from the group consisting of H, halogen (e.g., F), —OH, —COOH, —CN, —NO$_2$, —N(R)$_2$, $C_{1-6}$ alkyl, $C_{1-6}$ haloalkyl, —W—$C_{1-6}$ alkyl, —$C_{1-6}$ alkylene-W—R, —W—$C_{1-6}$ alkylene-W'—R, —W—$C_{2-6}$ alkenyl, —W—$C_{2-6}$ alkenylene-W—R, —W—$C_{2-6}$ alkenylene-W'—R and $C_{3-6}$ cycloalkyl, wherein the alkylene and alkenylene are optionally further interrupted by one or more W;

R$^b$, at each occurrence, is each independently selected from the group consisting of H, halogen, $C_{1-6}$ haloalkyl, $C_{1-6}$ alkyl and $C_{3-6}$ cycloalkyl;

R$^c$, at each occurrence, is each independently selected from the group consisting of F, Cl, Br, I, $C_{1-6}$ haloalkyl, $C_{1-6}$ alkyl and $C_{3-6}$ cycloalkyl, and R$^c$ is preferably Cl or Br;

R⁶ is attached to the ring carbon atom(s) marked with * and/or ** in the general formula;

W and W', at each occurrence, are each independently selected from the group consisting of O, C(=O), C(=O)O, NR, NC(=O), N(S=O), NS(=O)$_2$, S, S=O and S(=O)$_2$;

R, at each occurrence, is each independently selected from the group consisting of H, $C_{1-6}$ alkyl and $C_{3-6}$ cycloalkyl;

g is 1 or 2;
i is 0, 1 or 2;
m is 0, 1, 2, 3 or 4; and
t is 0, 1 or 2, provided that when t is greater than 1, each R⁶ can be the same or different.

In certain embodiments, R$^b$, at each occurrence, is each independently selected from the group consisting of H, halogen, $C_{1-6}$ alkyl and $C_{3-6}$ cycloalkyl;

In certain embodiments, R$^c$, at each occurrence, is each independently selected from the group consisting of F, Cl, Br, I, $C_{1-6}$ alkyl and $C_{3-6}$ cycloalkyl, and R$^c$ is preferably Cl or Br;

In certain embodiments, the present invention provides a compound or a pharmaceutically acceptable salt, ester, stereoisomer, tautomer, polymorph, solvate, metabolite, isotopically labeled compound, or prodrug thereof, wherein the compound has the following structure:

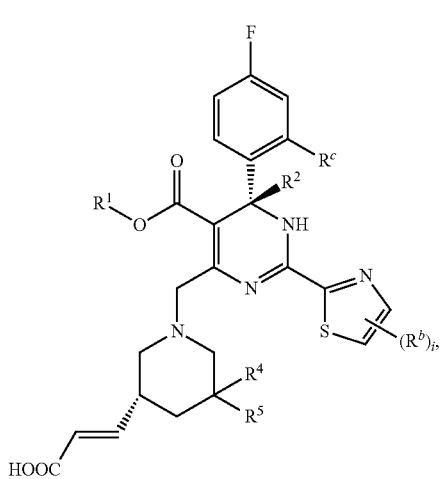

IVa

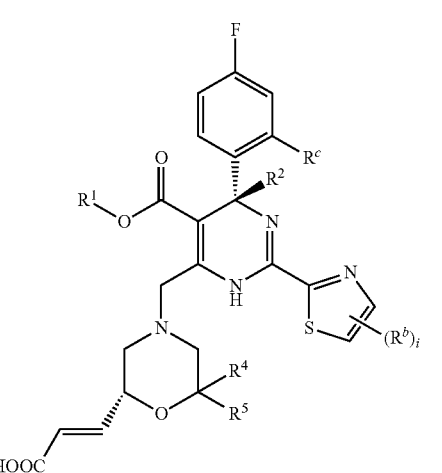

V or

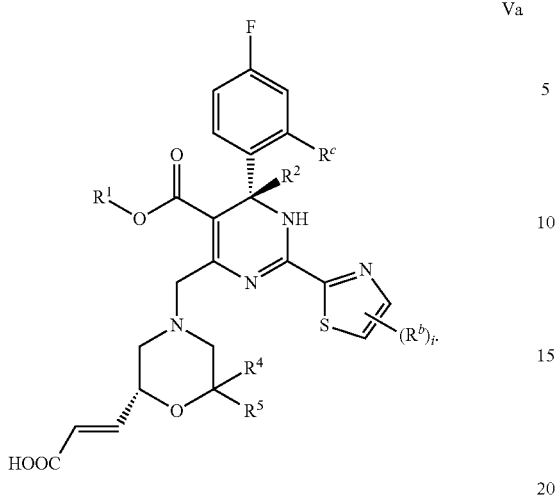

Va

The compound obtained by any combination of the various embodiments is encompassed by the invention.

In preferred embodiments, the present invention provides a compound or a pharmaceutically acceptable salt, ester, stereoisomer, tautomer, polymorph, solvate, metabolite, isotopically labeled compound, or prodrug thereof, wherein the compound is selected from the group consisting of:

10-1

10-2

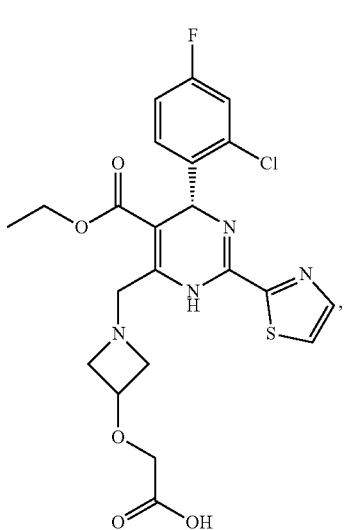

10-3

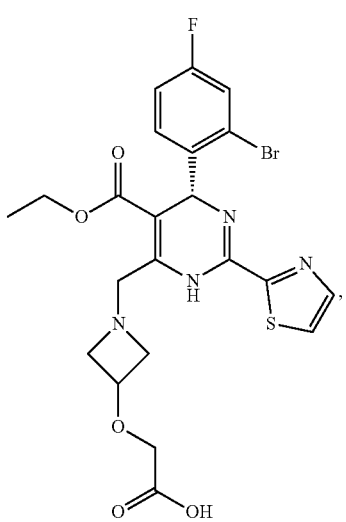

10-4

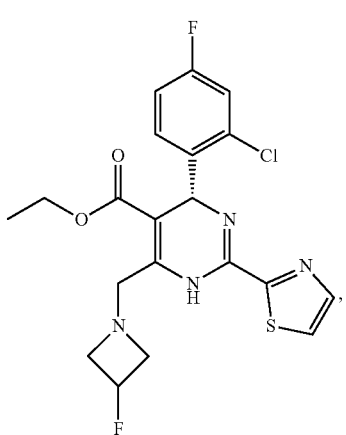

10-5

10-6
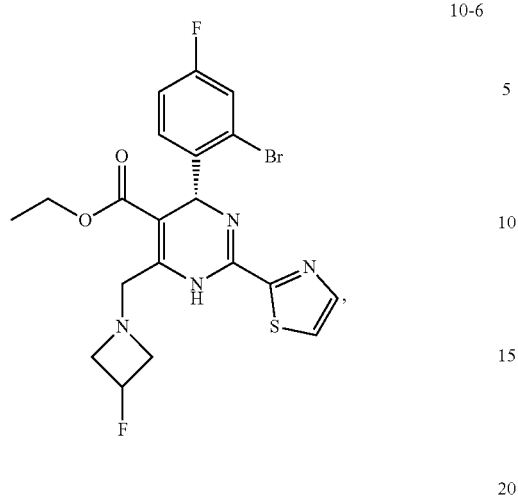
10-7
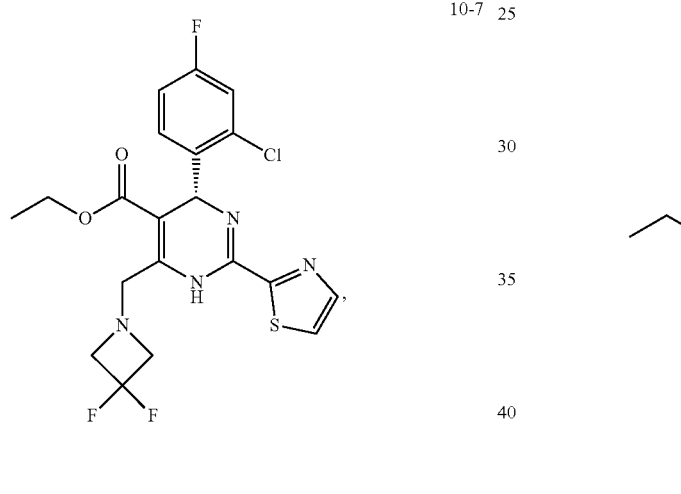
10-8
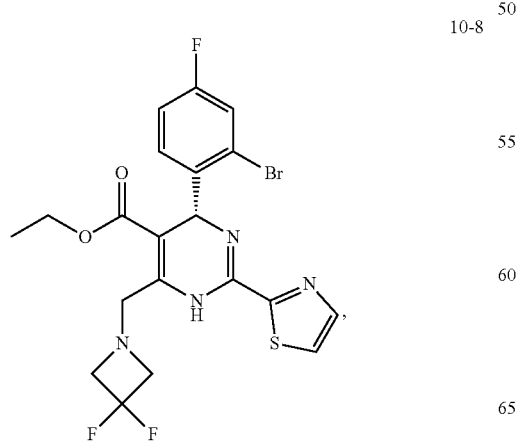
10-9
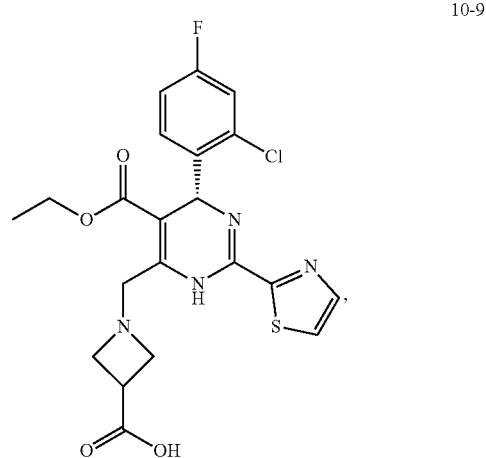
10-10
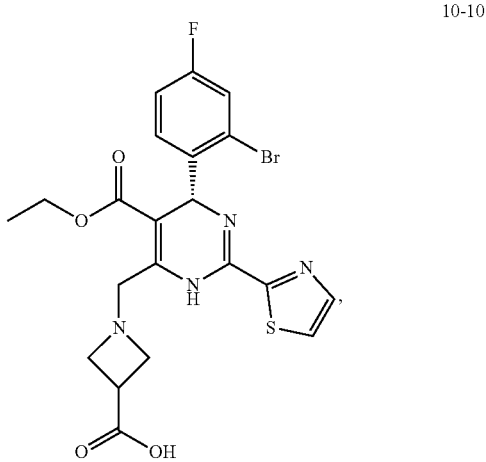
10-11
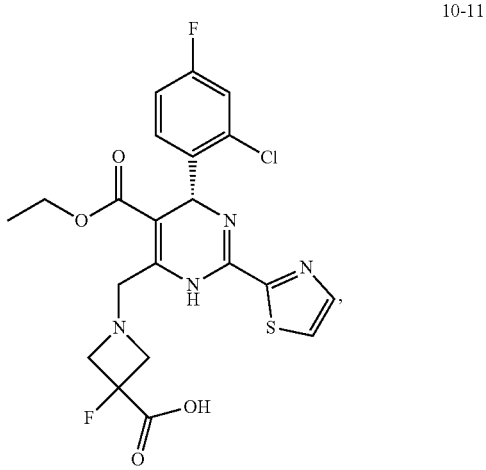

10-12
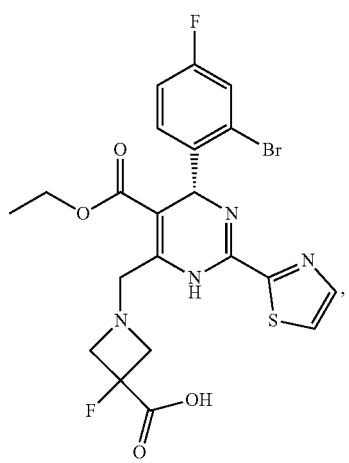
10-13
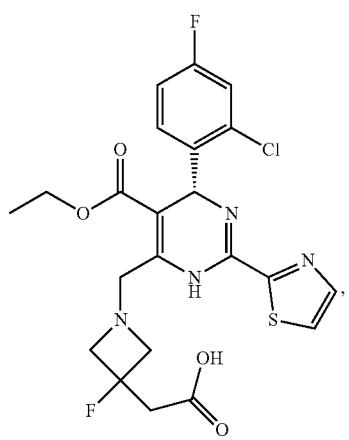
10-14
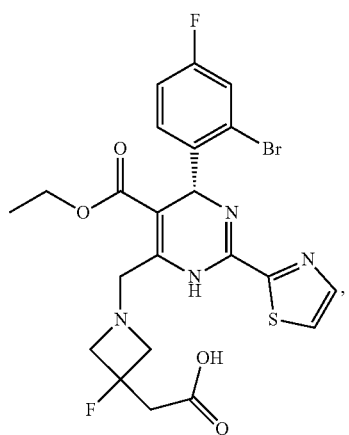
10-15
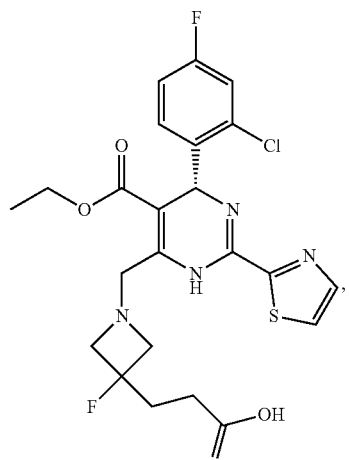
10-16
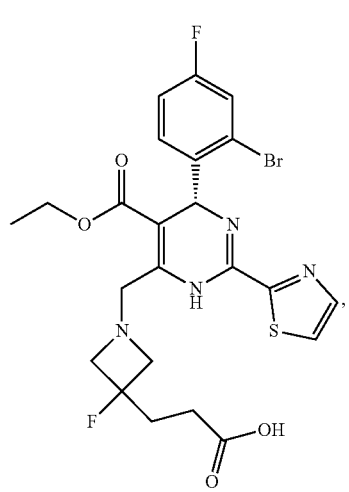
10-17
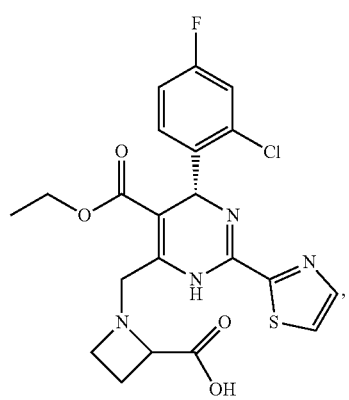

10-18
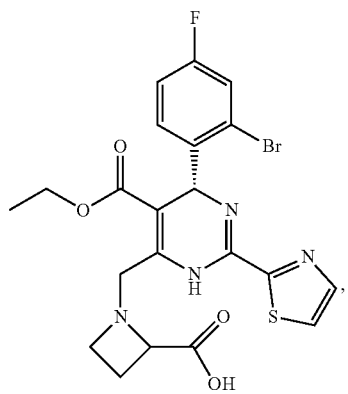
10-19
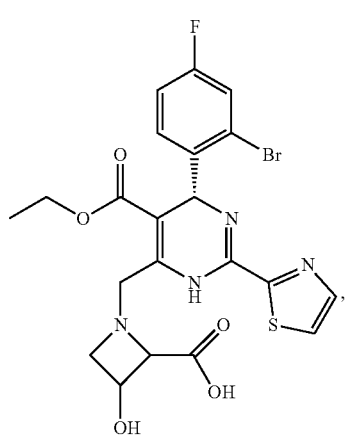
10-20
10-21
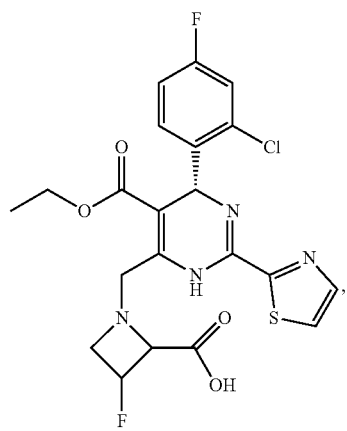
10-22
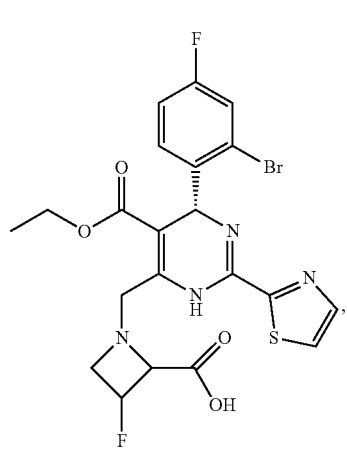
10-23
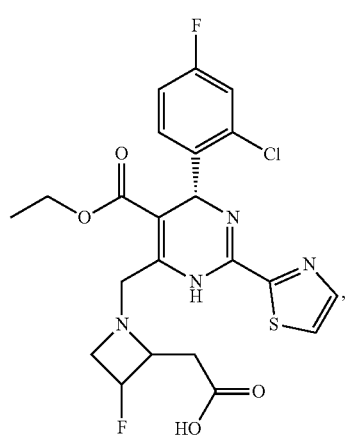

10-24
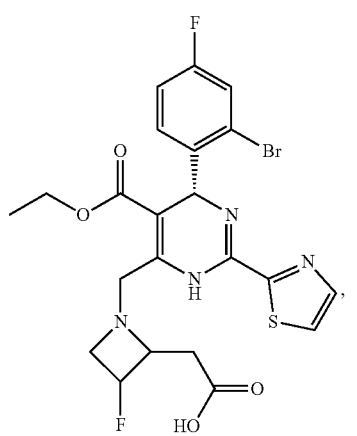
10-25
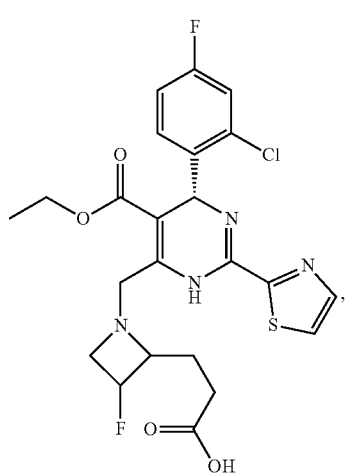
10-26
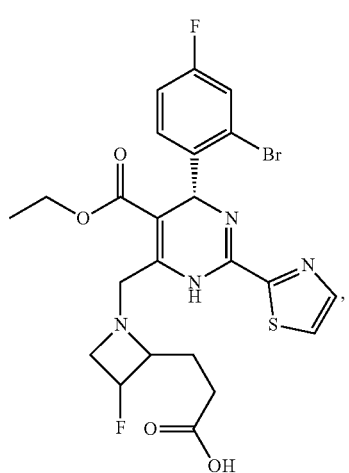
10-27
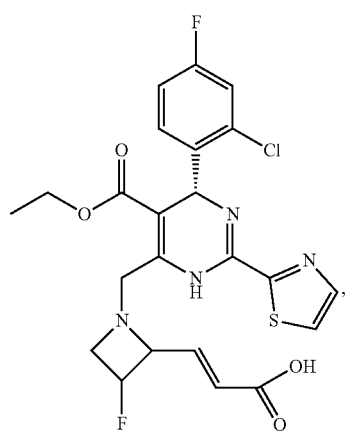
10-28
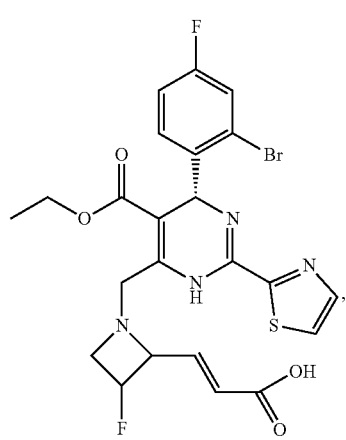
10-29
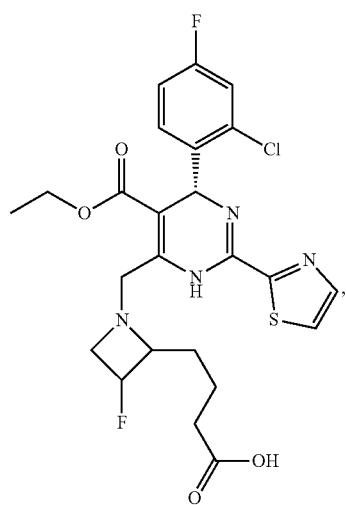

10-30
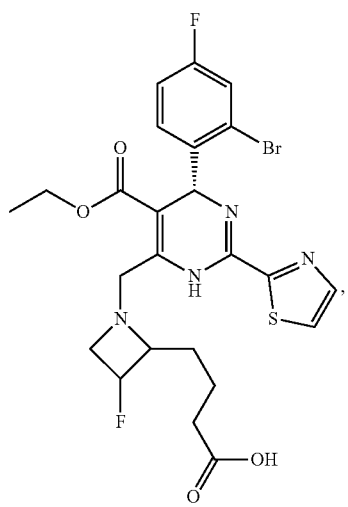
10-31
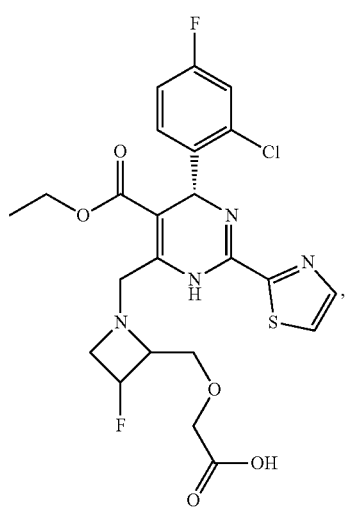
10-32
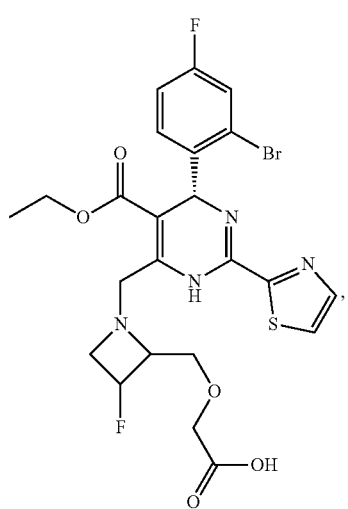
10-33
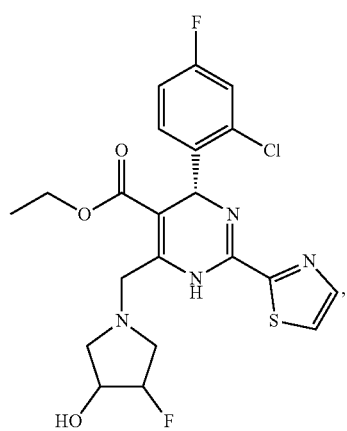
10-34
10-35
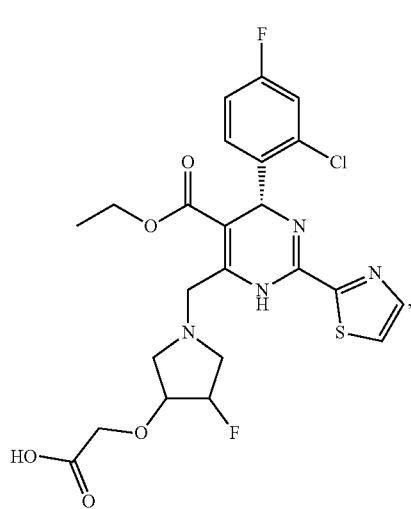

10-36
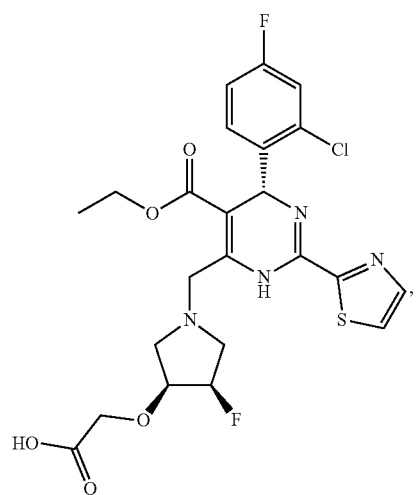
10-37
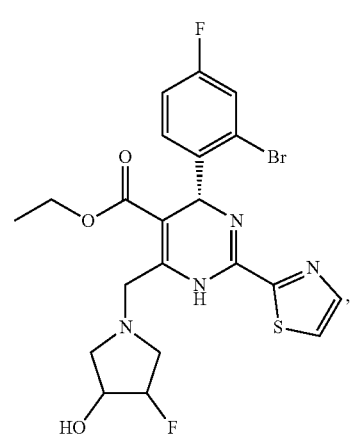
10-38
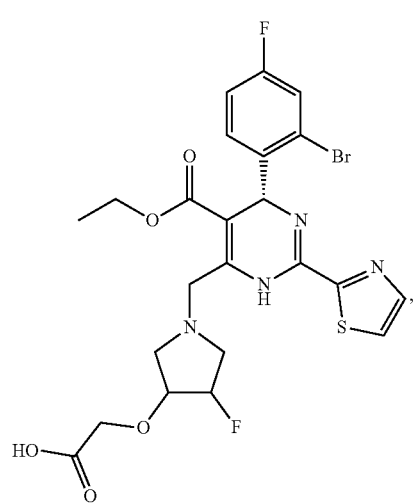
10-40
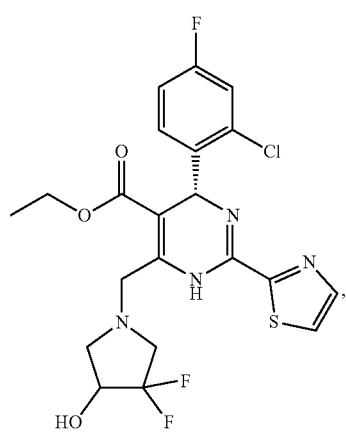
10-41
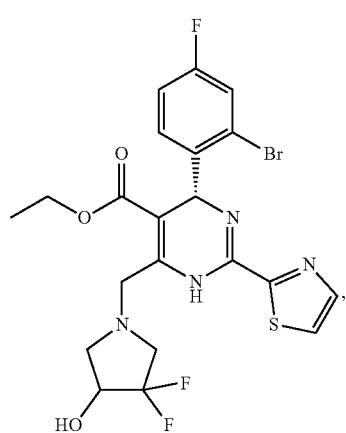
10-42
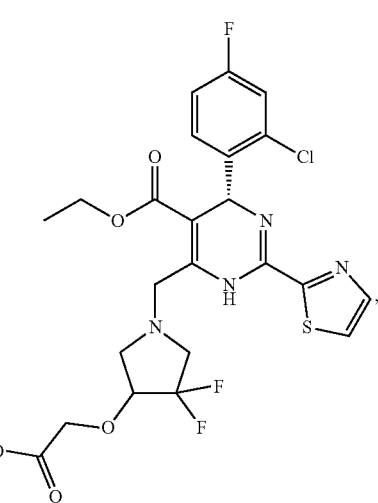

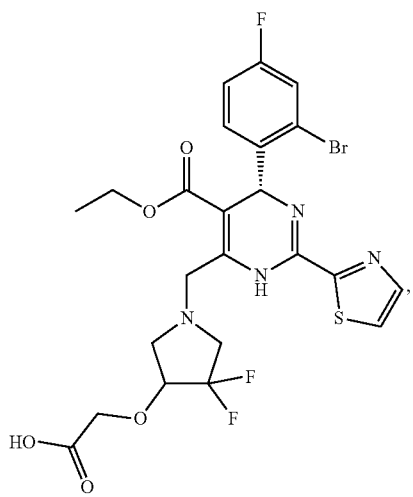
10-43
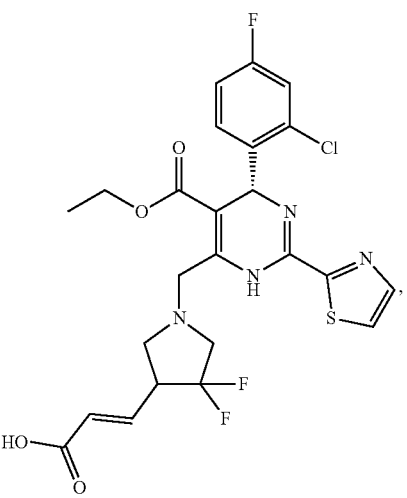
10-50
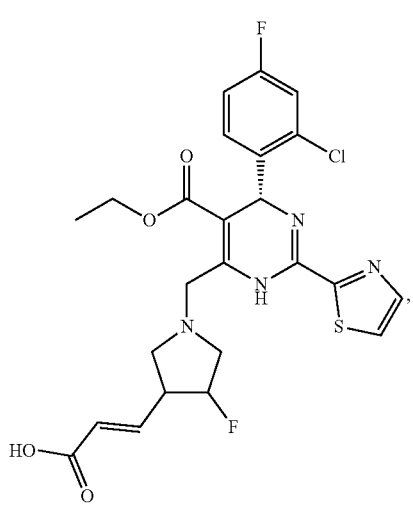
10-48
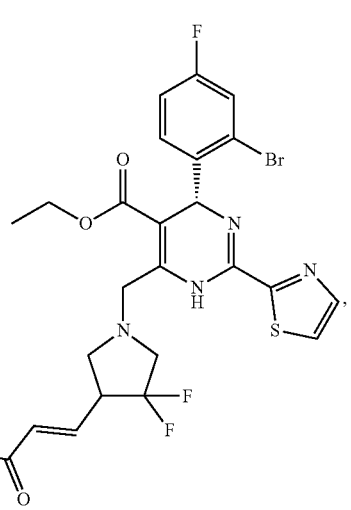
10-51
10-49
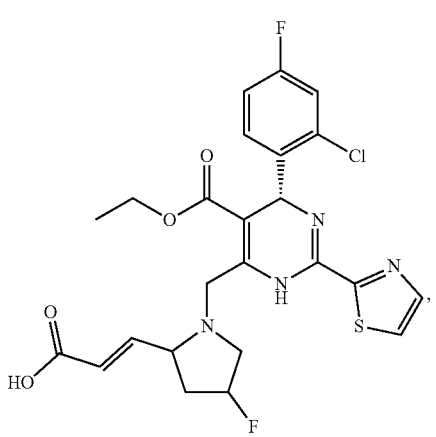
10-52

-continued
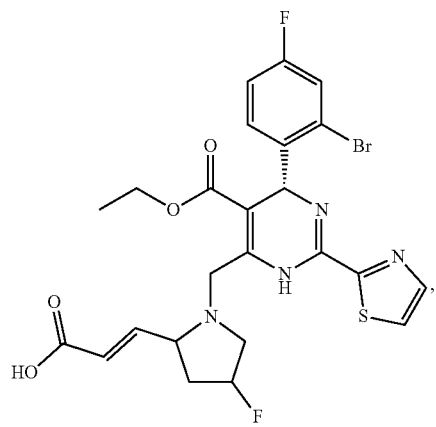
10-53
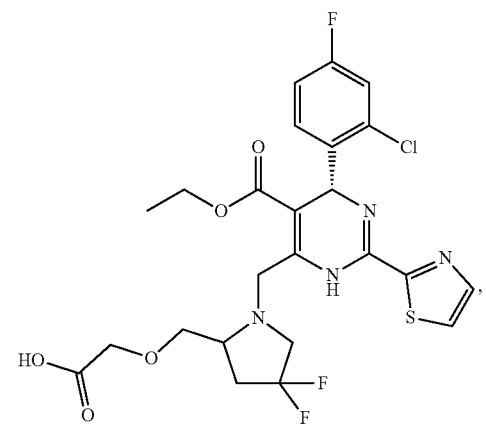
10-56
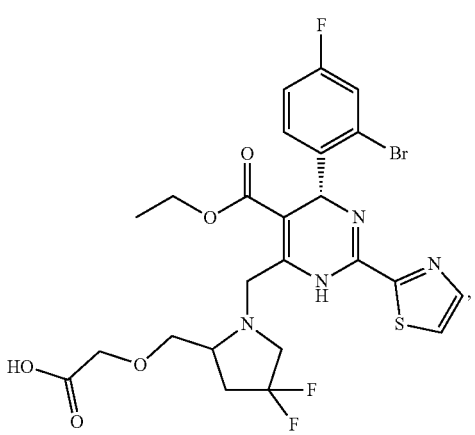
10-54
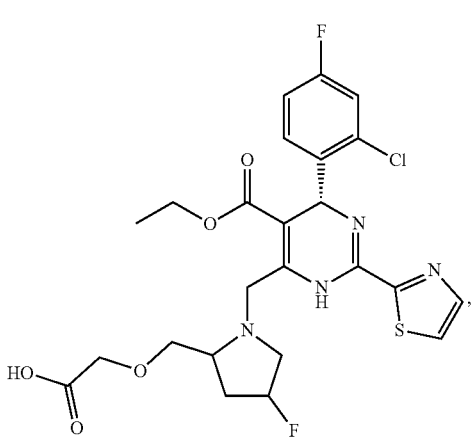
10-57
10-55
10-58

-continued
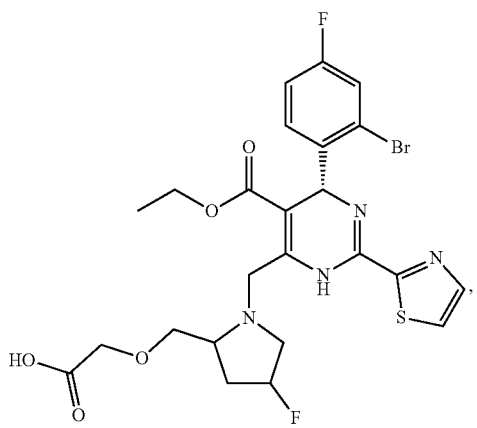
10-59
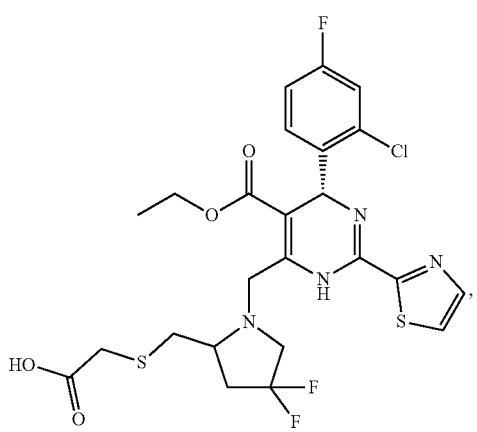
10-60
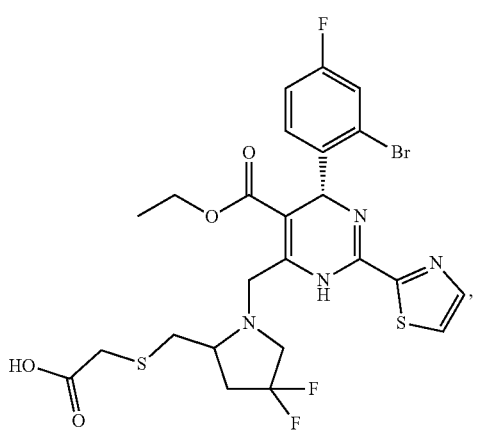
10-61
-continued
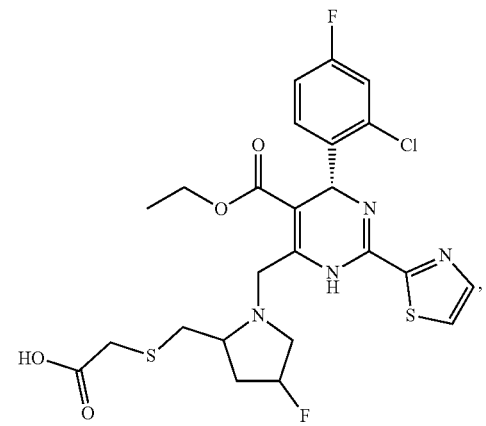
10-62
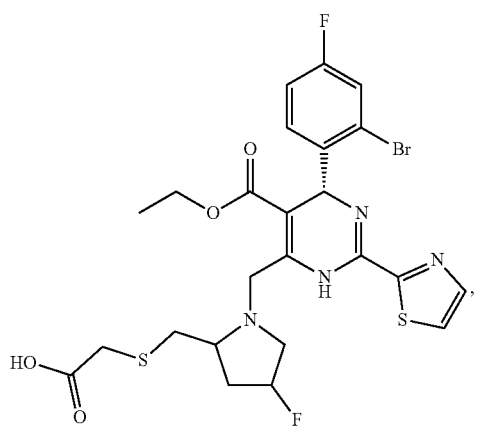
10-63
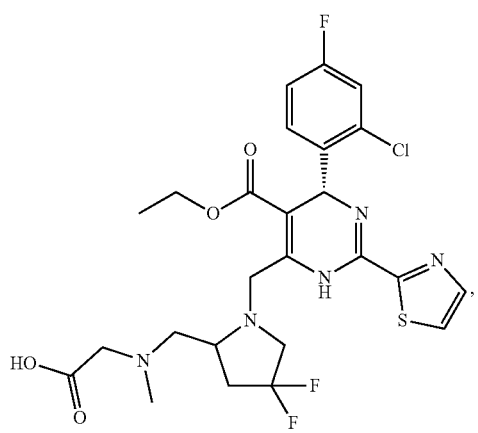
10-64

10-65
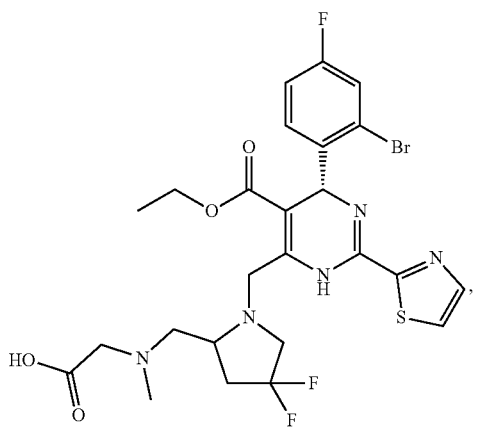
10-66
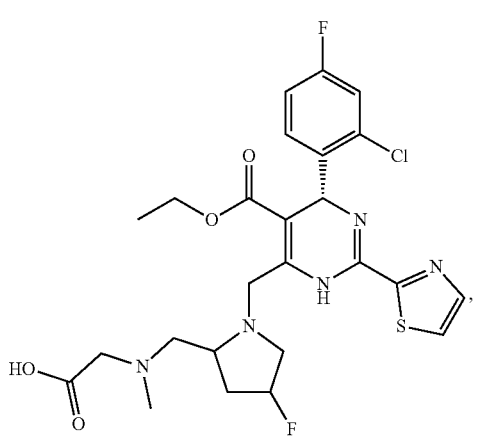
10-67
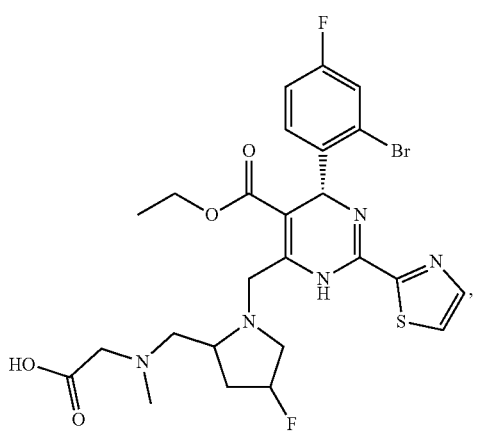
10-68
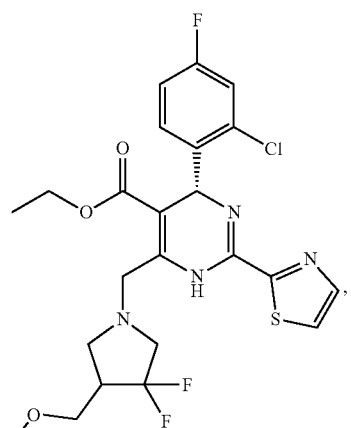
10-69
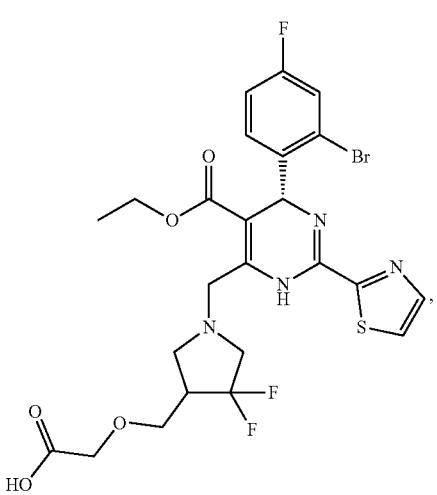
10-70
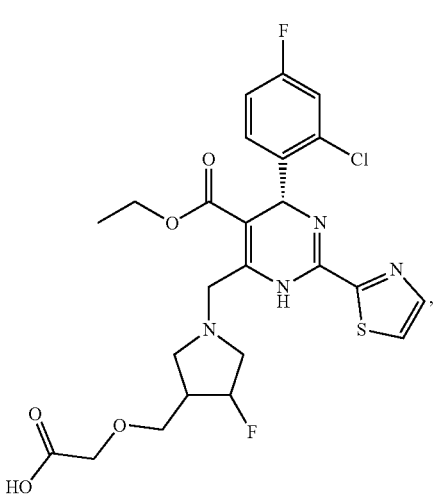

10-71
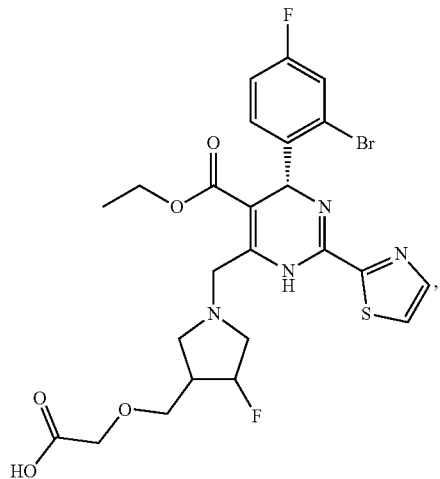
10-72
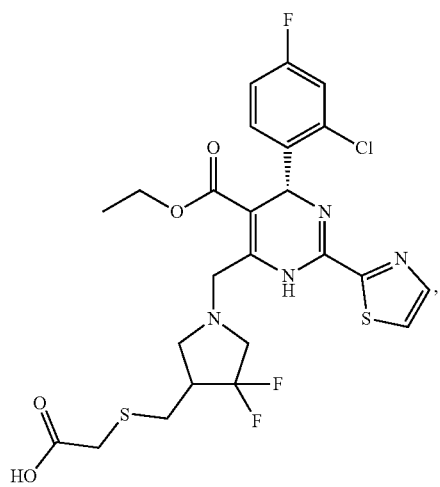
10-73
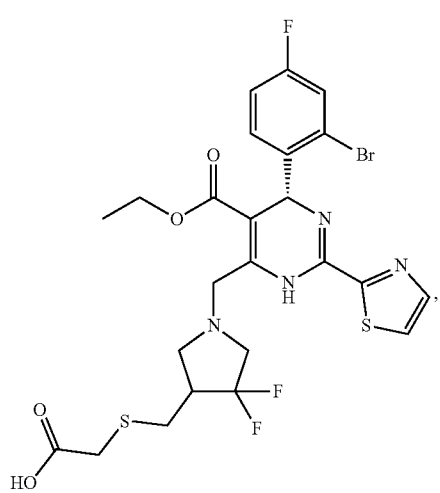
10-74
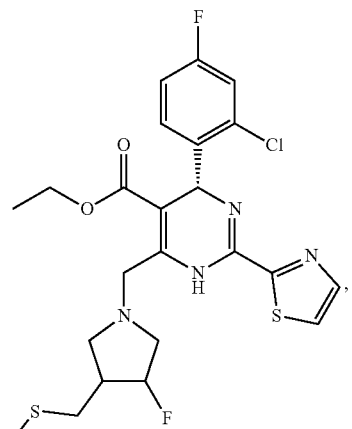
10-75
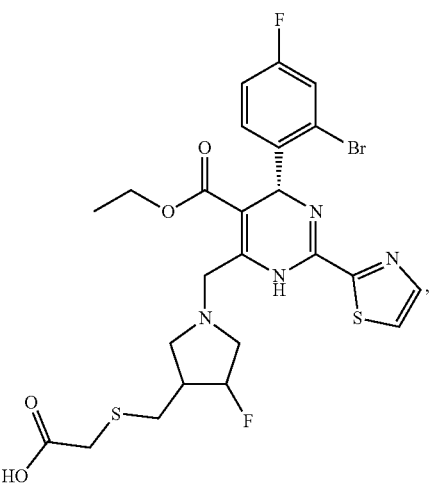
10-76
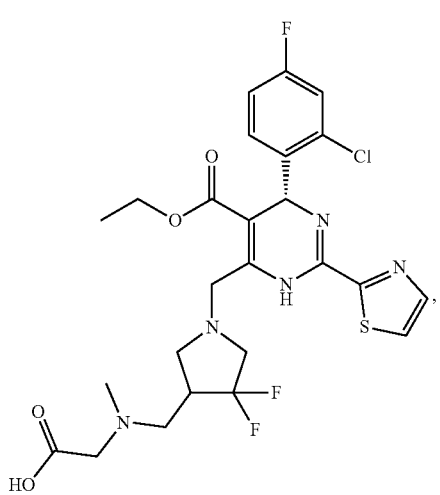

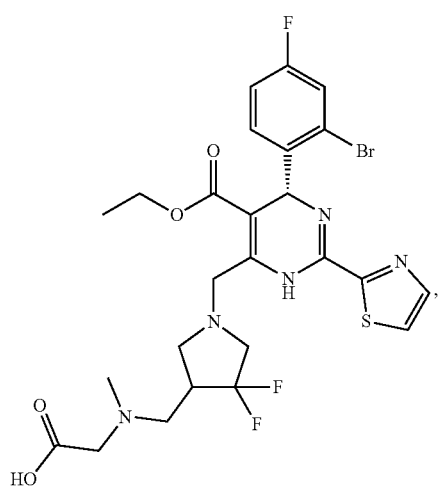
10-77
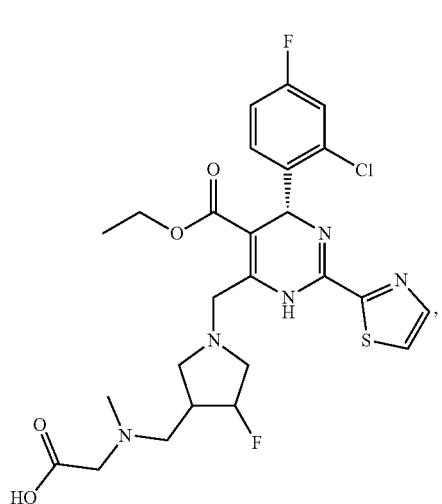
10-78
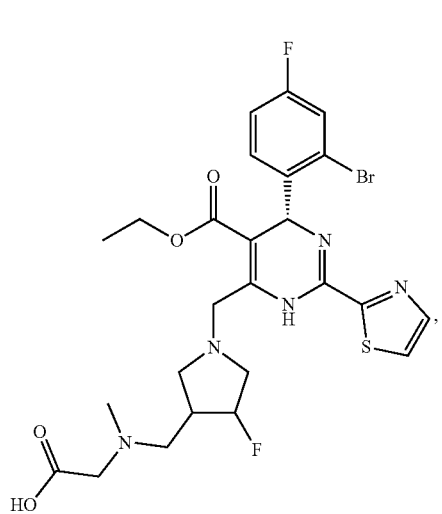
10-79
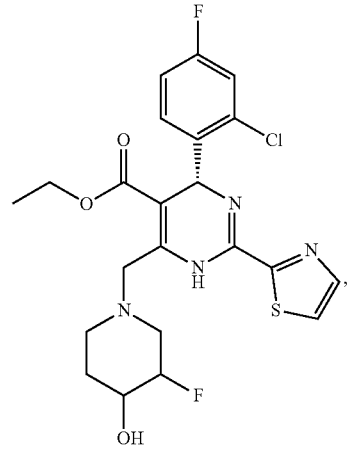
10-80
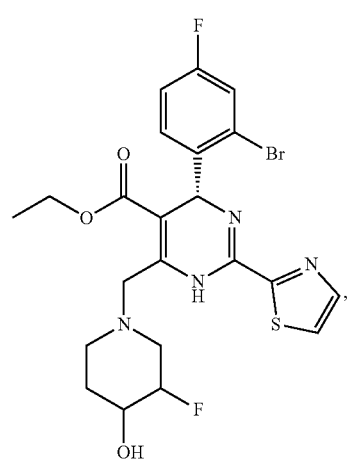
10-81
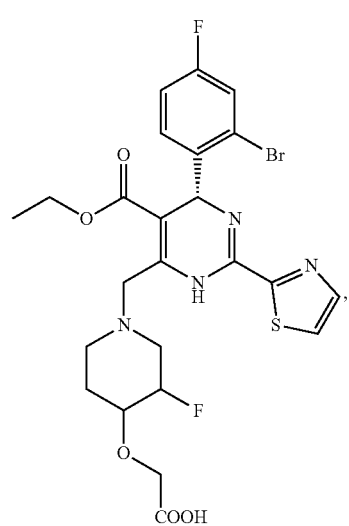
10-83

10-84
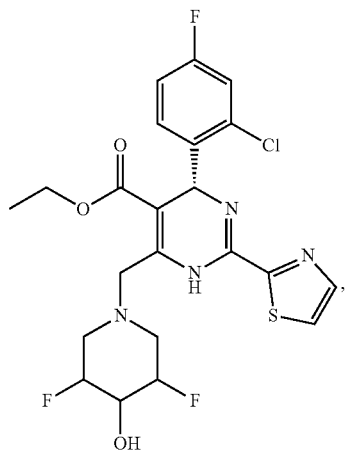
10-85
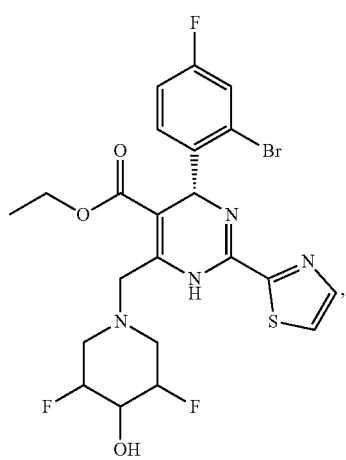
10-86
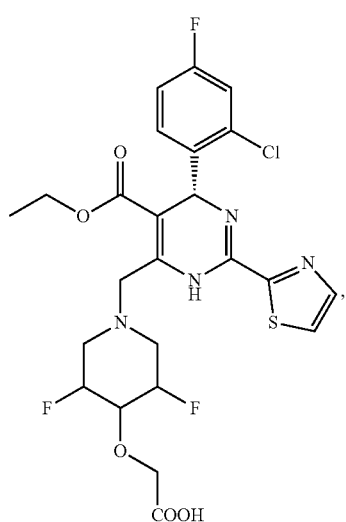
10-87
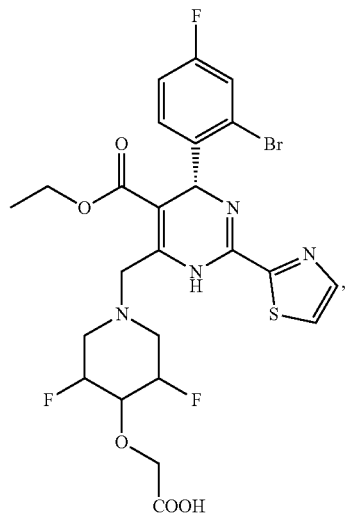
10-88
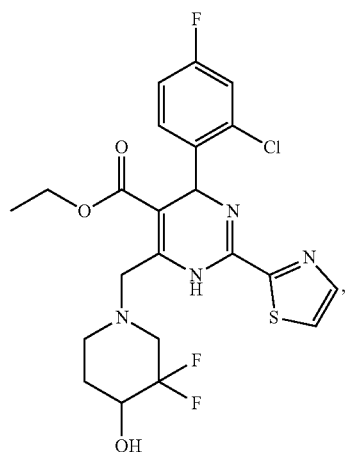
10-89
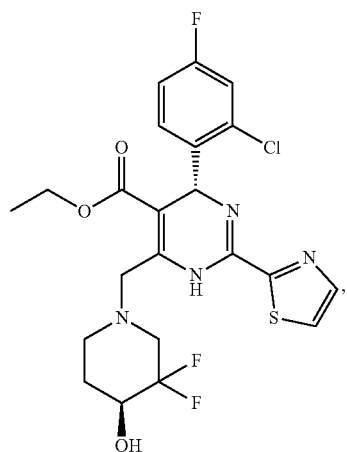

10-90
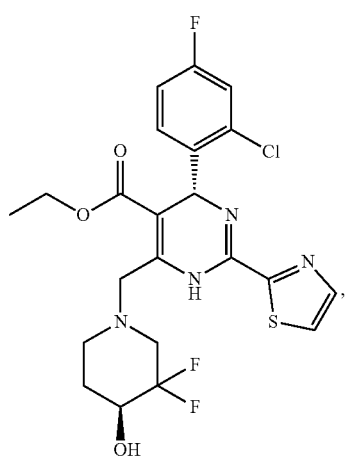
10-91
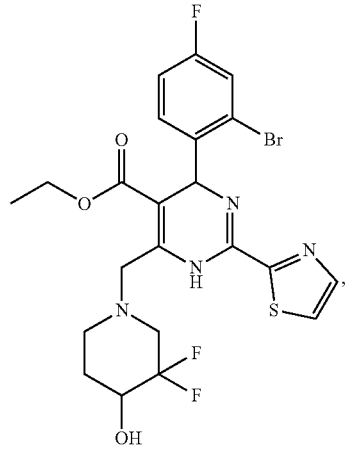
10-92
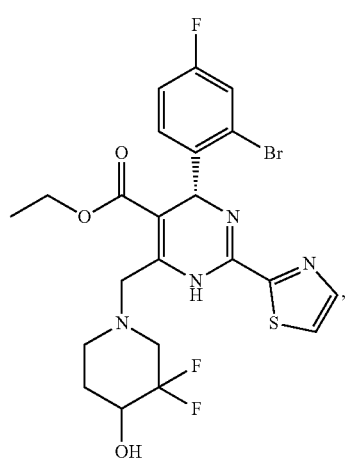
10-93
10-94
10-95
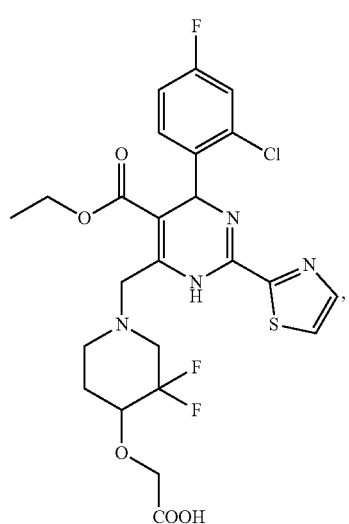

10-96
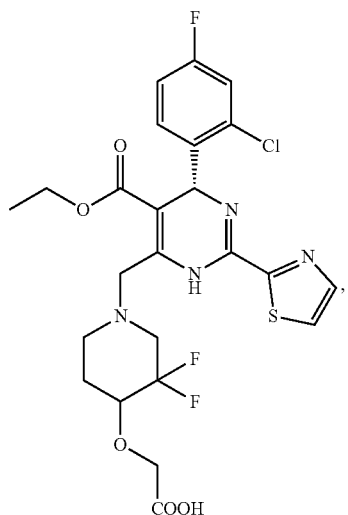
10-97
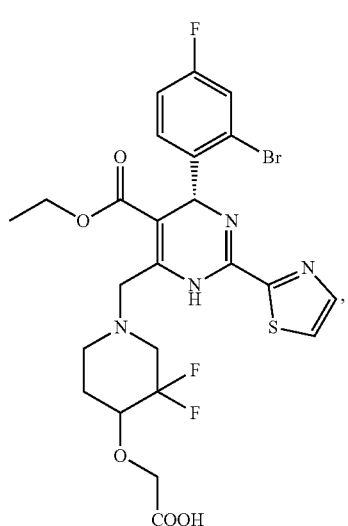
10-98
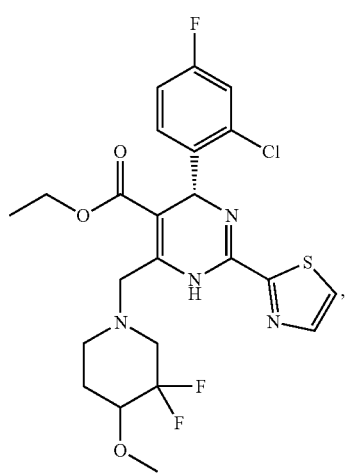
10-100
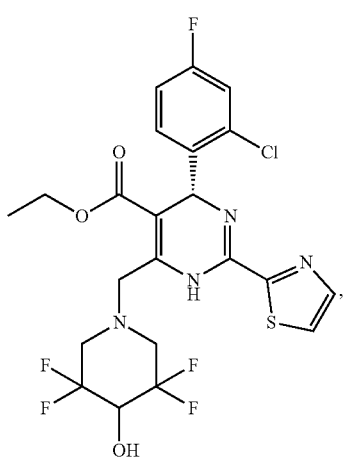
10-101
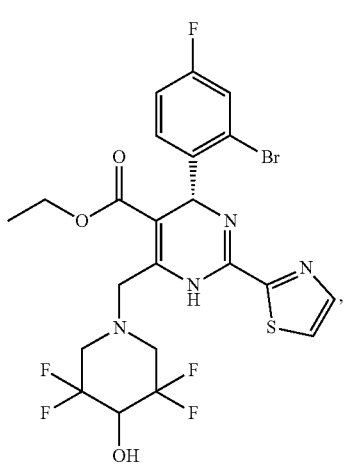
10-102
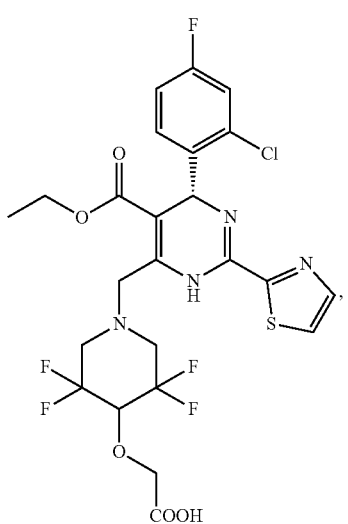

10-103
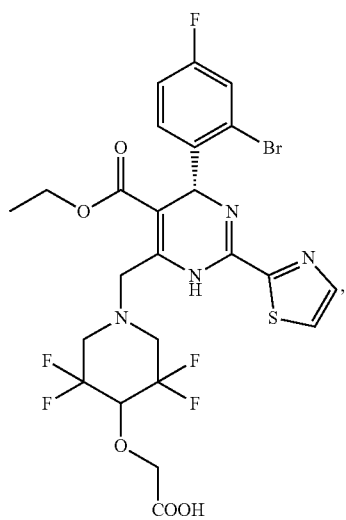
10-104
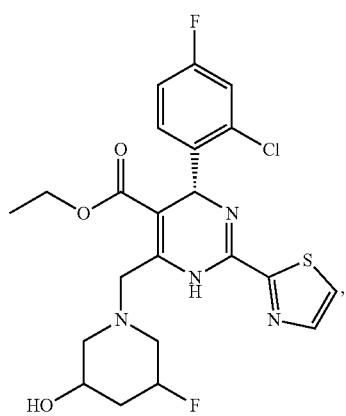
10-105
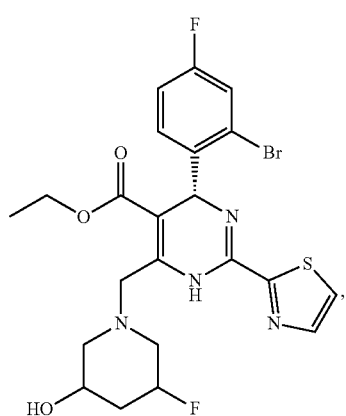
10-106
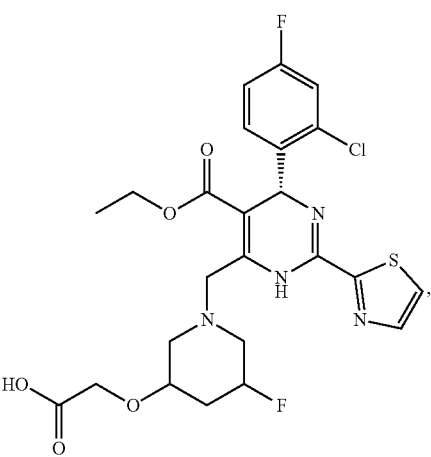
10-107
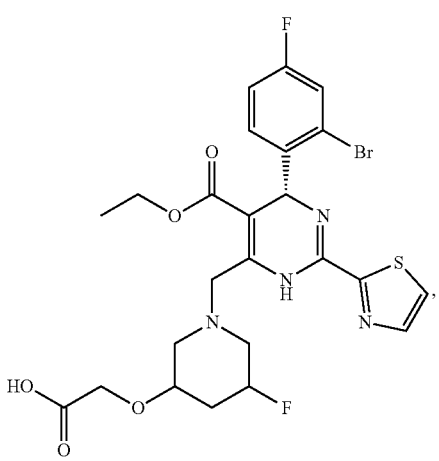
10-108
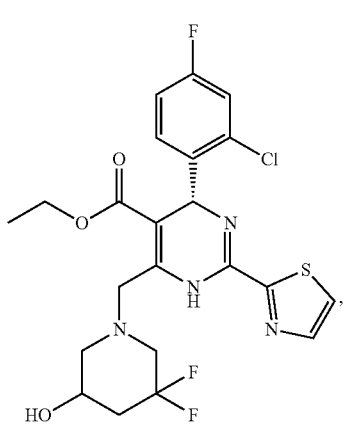

10-109
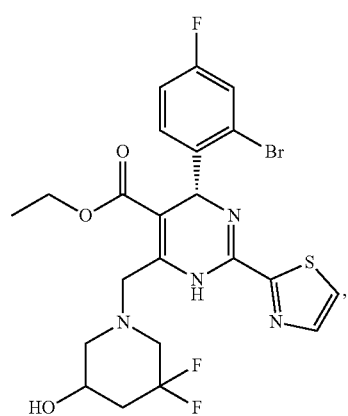
10-110
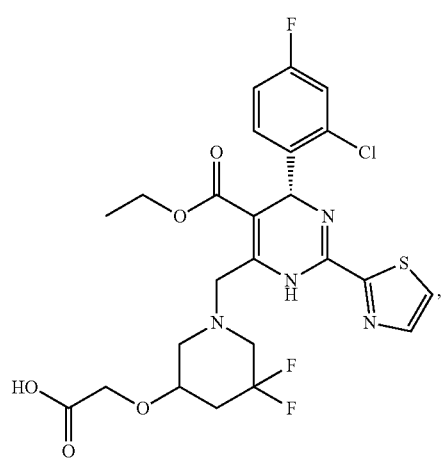
10-111
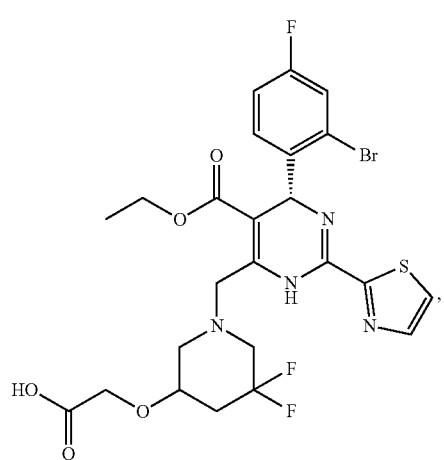
10-112
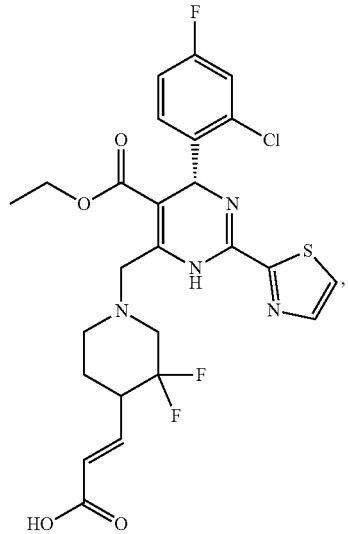
10-113
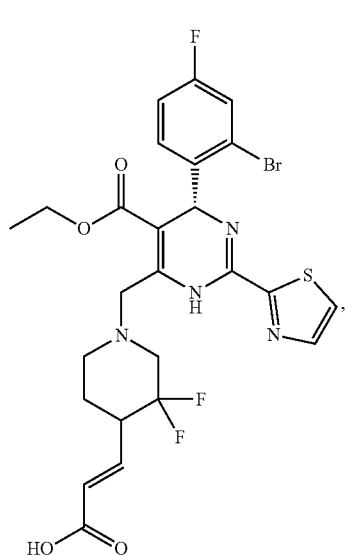
10-114
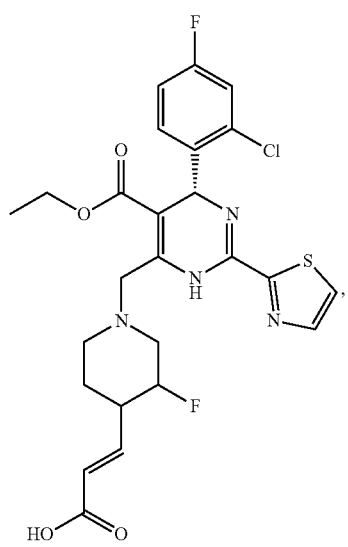

10-115
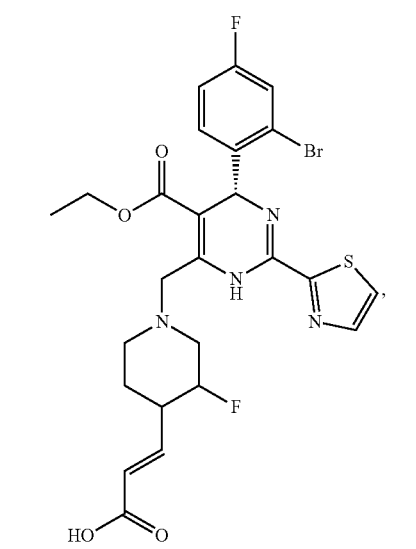
10-116
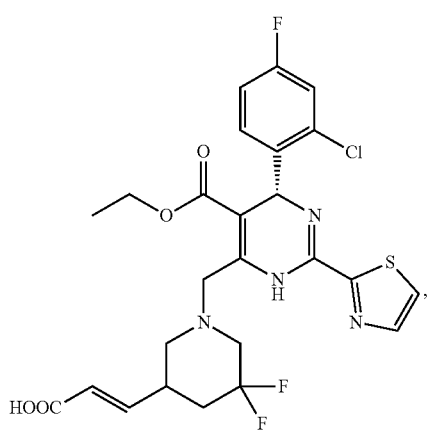
10-117
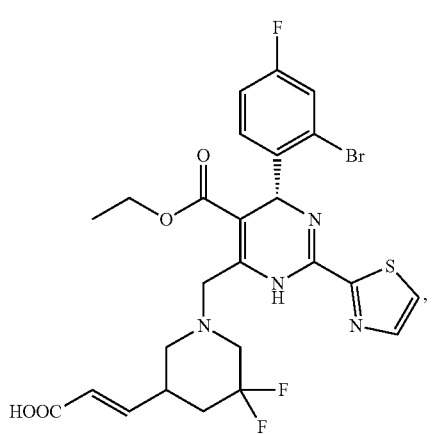
10-118
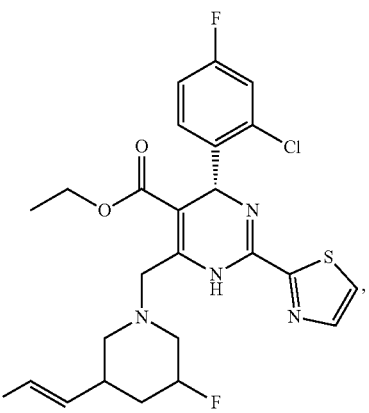
10-119
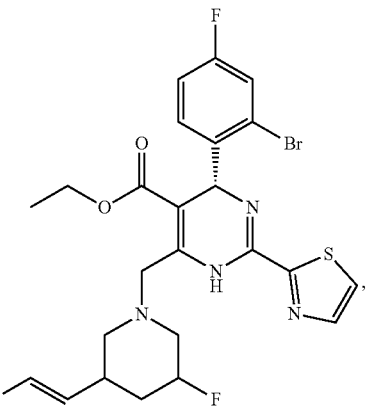
10-120
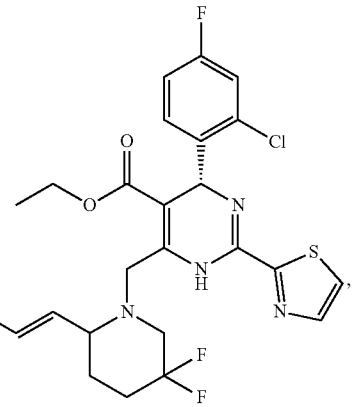
10-121
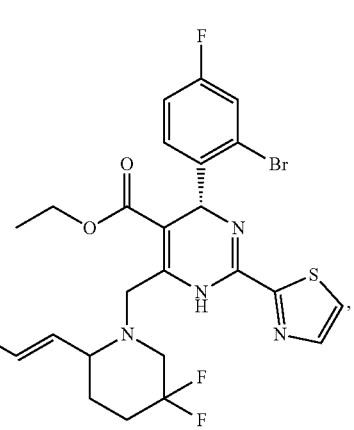

10-122
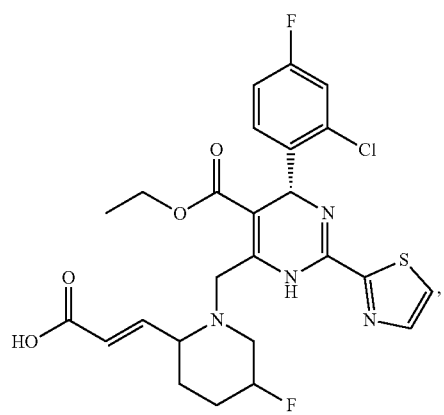
10-123
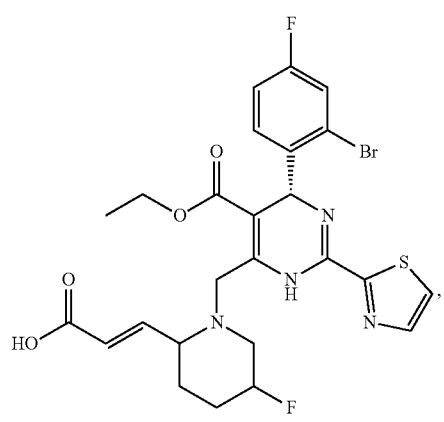
10-124
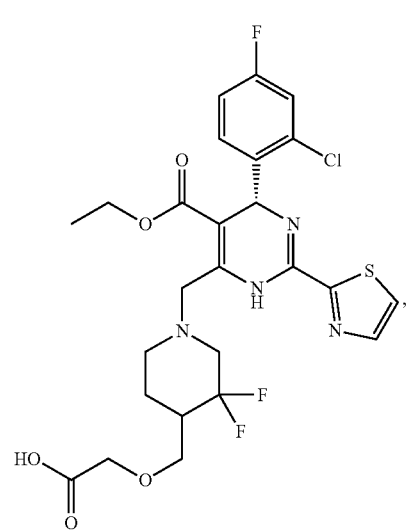
10-125
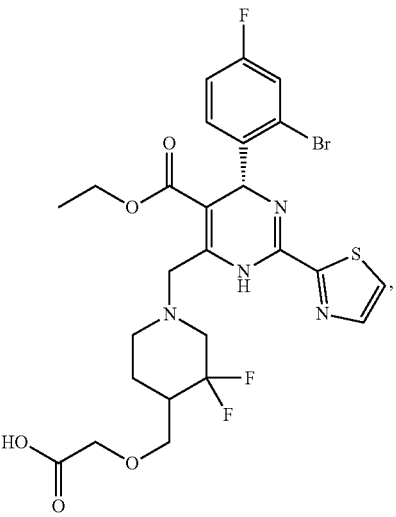
10-126
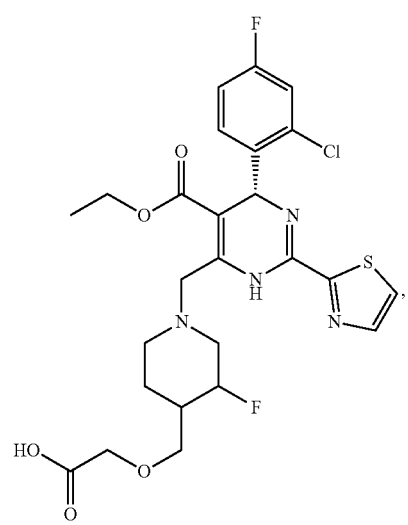
10-127

10-128
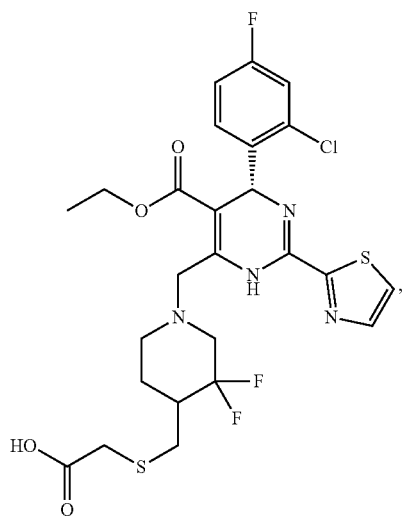
10-129
10-130
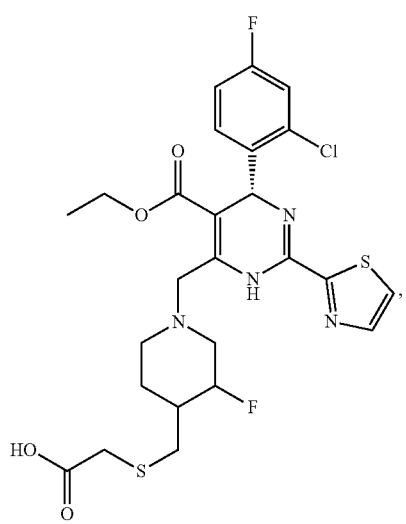
10-131
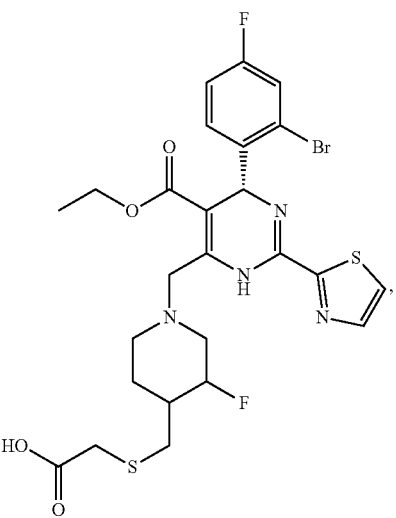
10-132
10-133
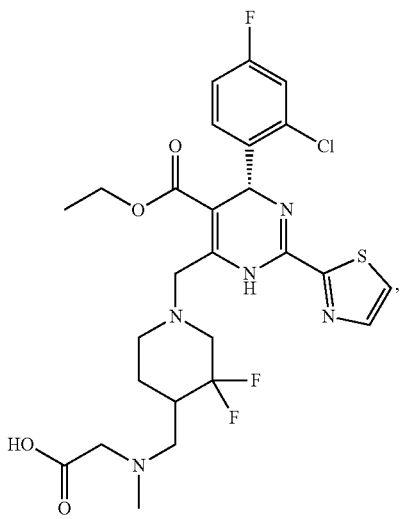

10-134
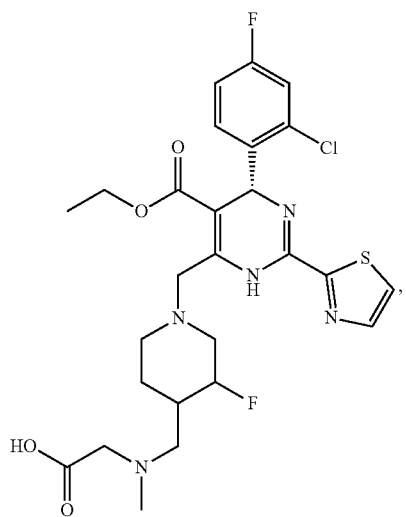
10-135
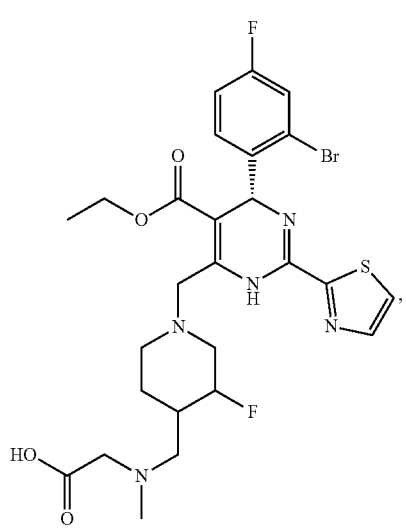
10-136
10-137
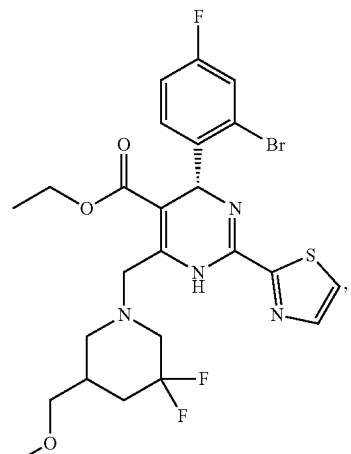
10-138
10-139
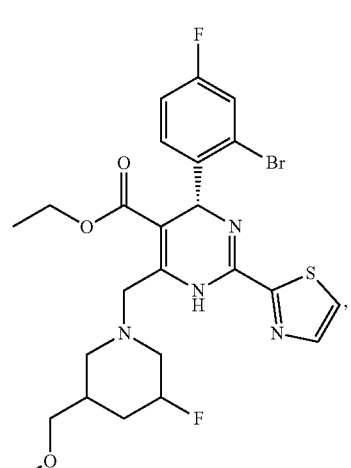

10-140
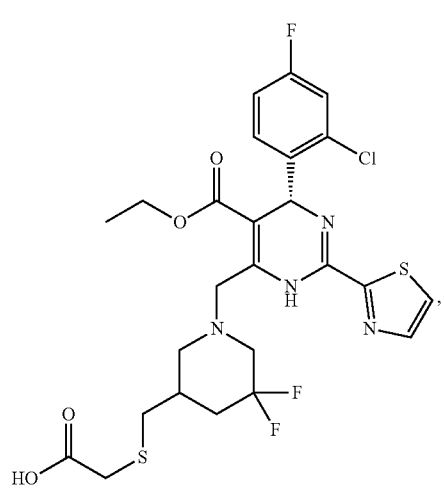
10-141
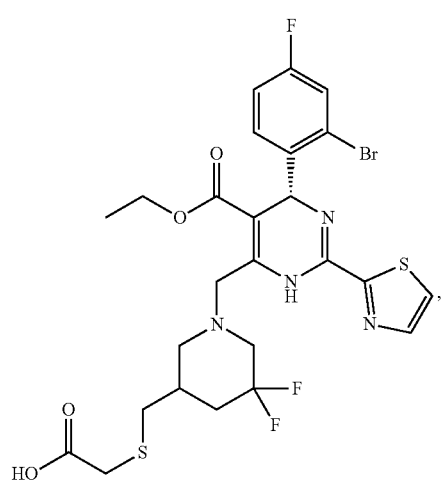
10-142
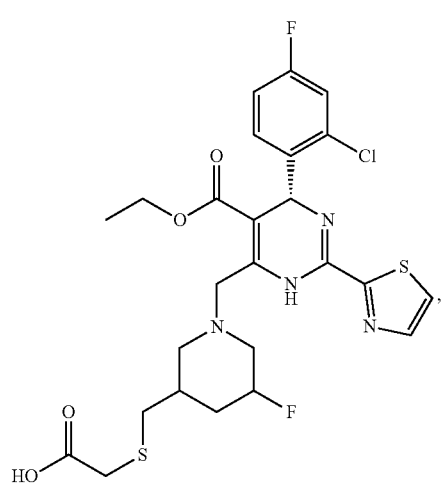
10-143
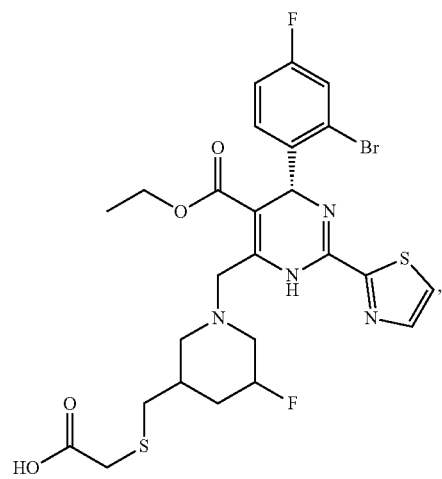
10-144
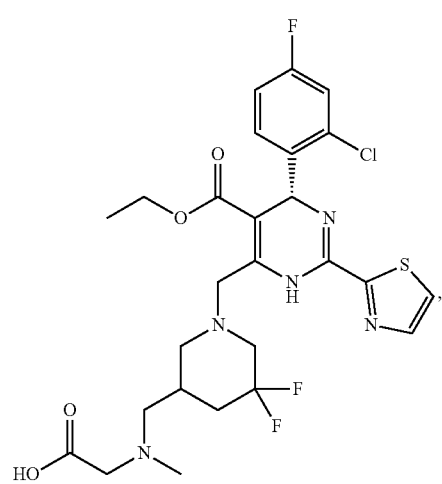
10-145
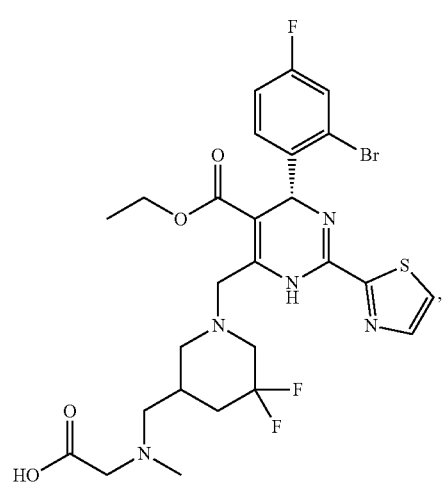

-continued
10-146
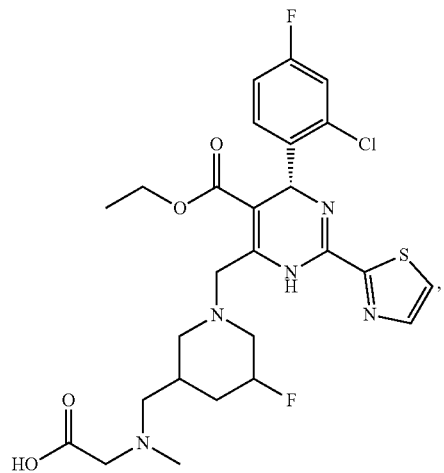
10-147
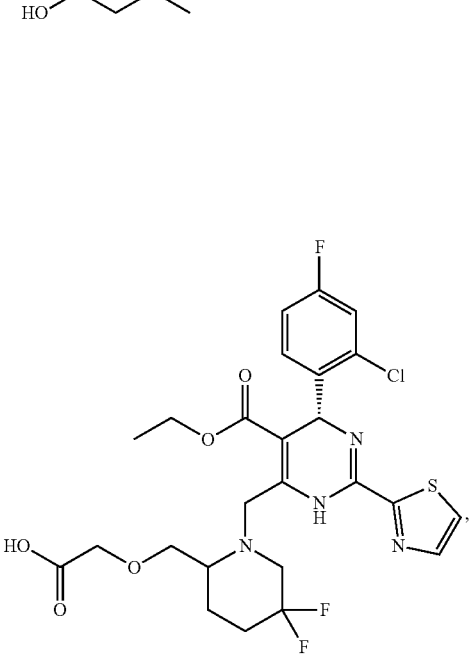
10-148
-continued
10-149
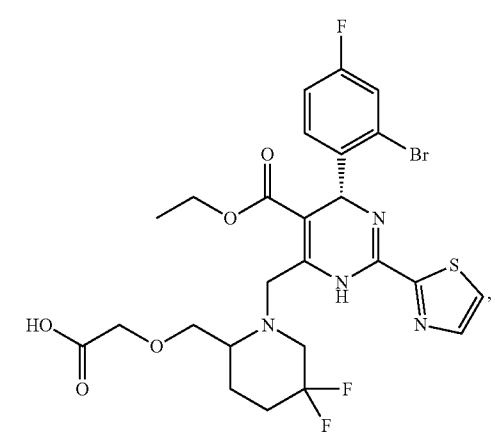
10-150
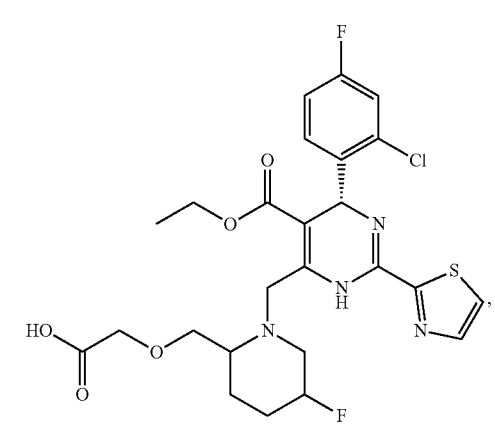
10-151
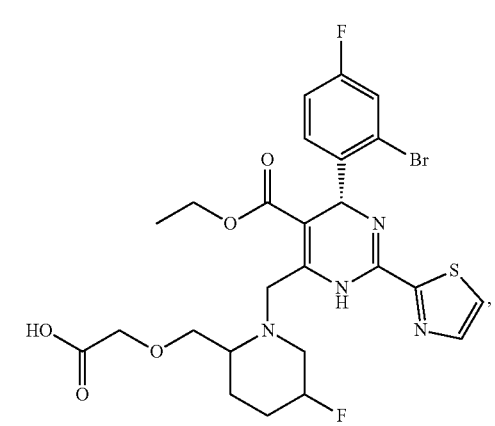

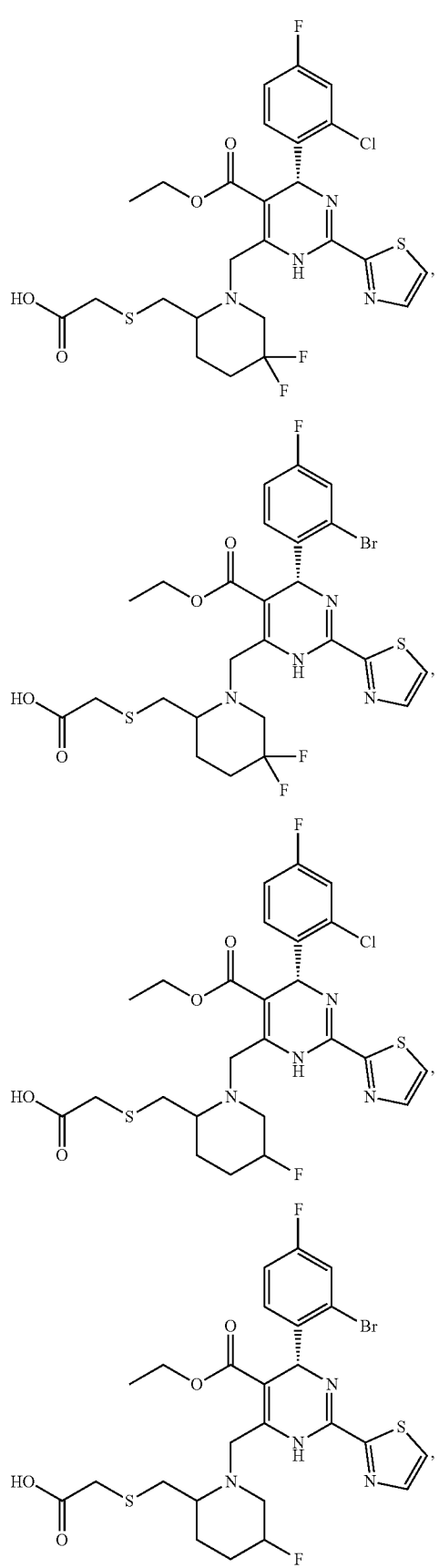
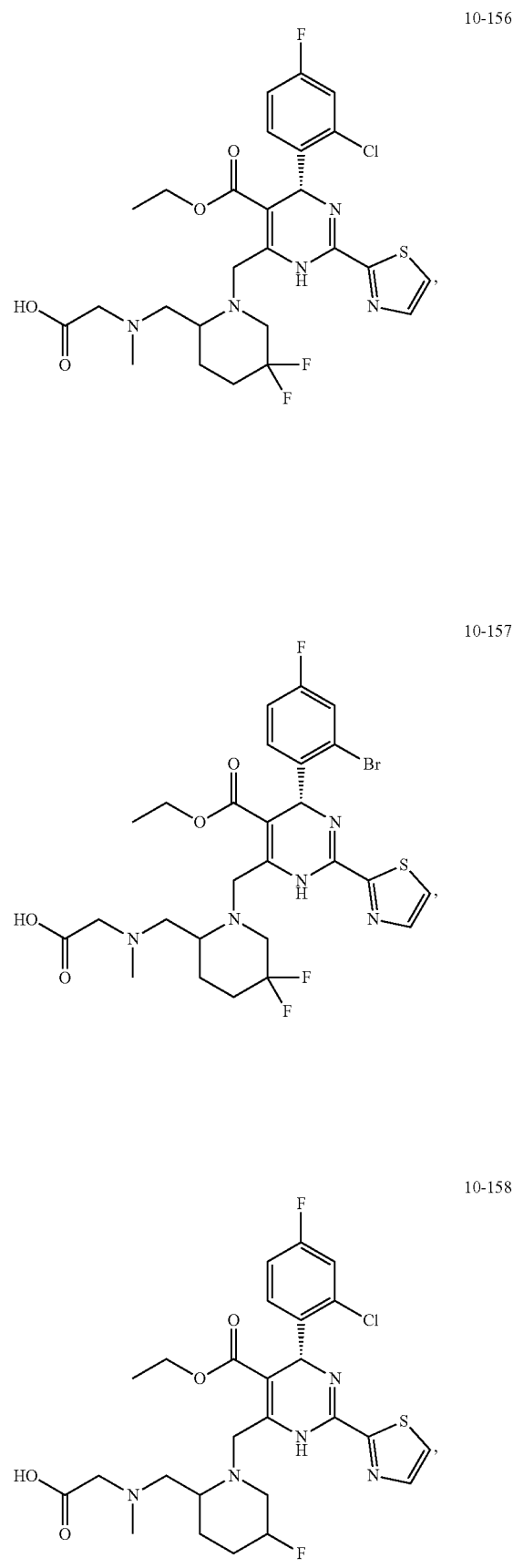

10-159
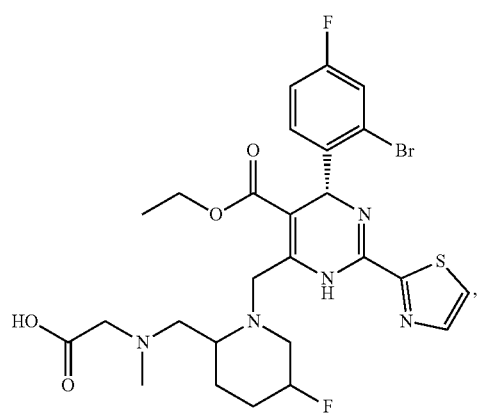
10-160
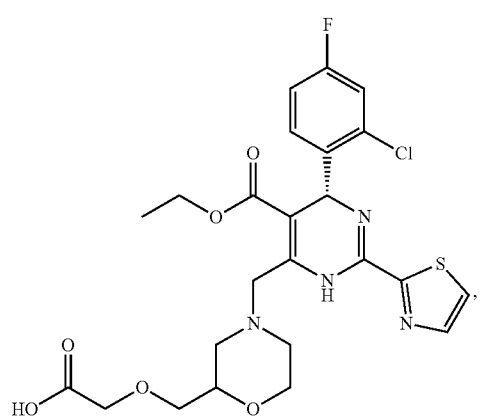
10-161
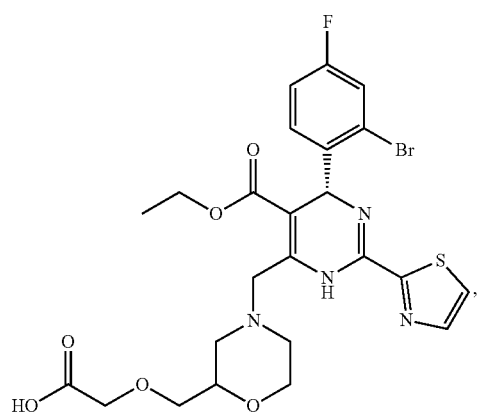
10-162
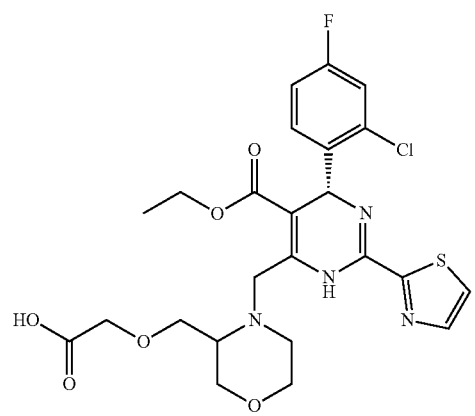
10-163
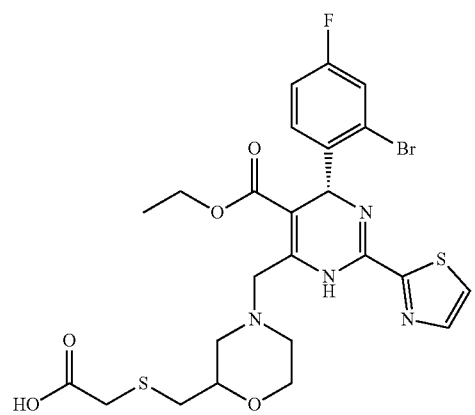
10-164
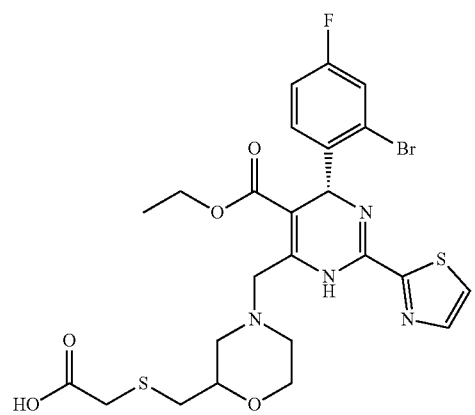
10-165
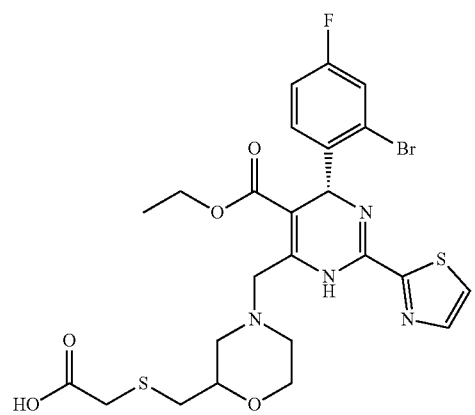

10-166
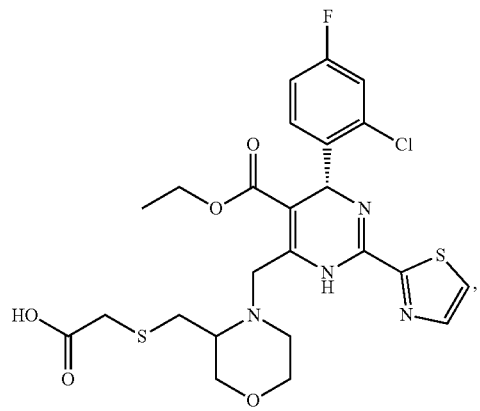
10-167
10-168
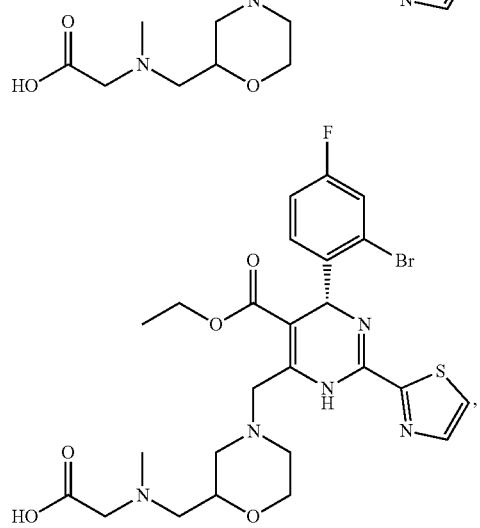
10-169
10-170
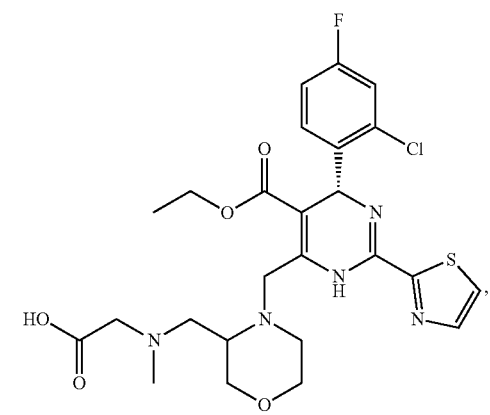
10-171
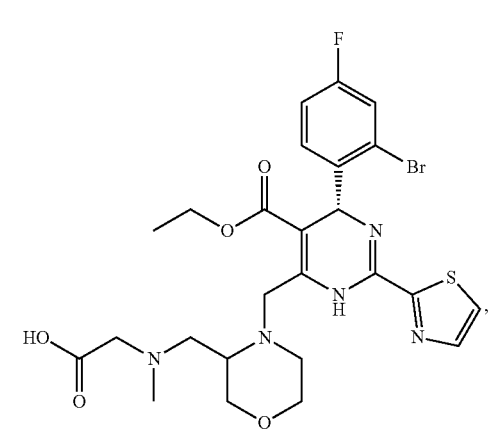
10-180
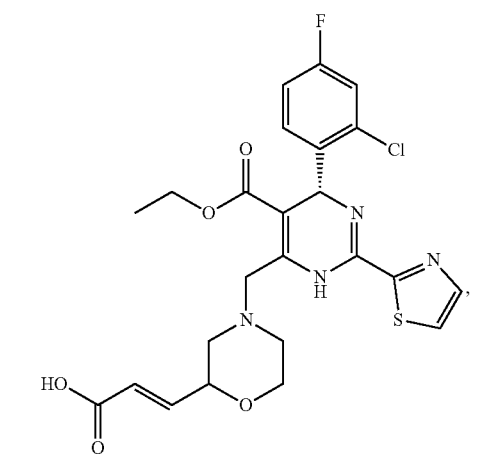

10-181
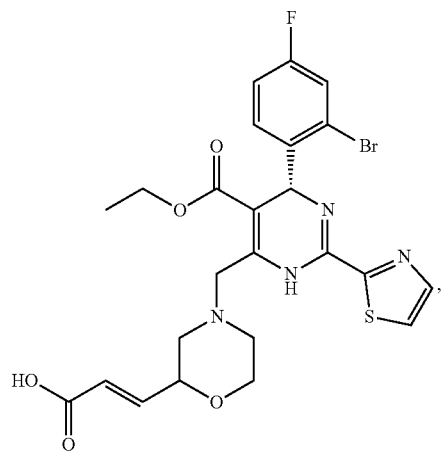
10-182
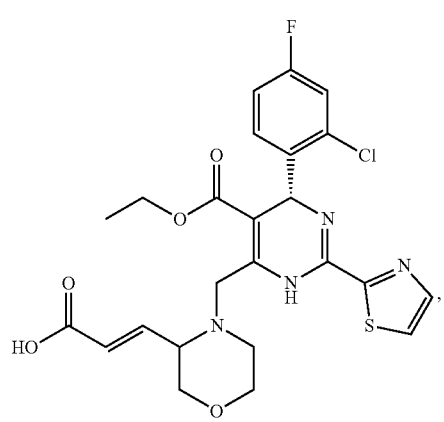
10-183
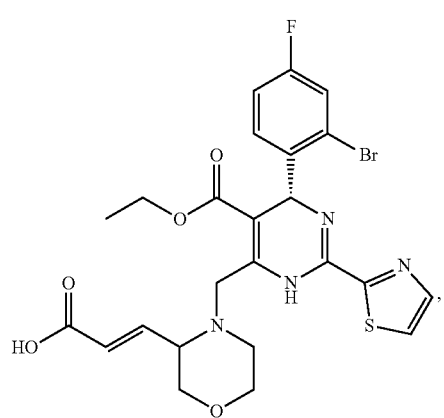
10-211
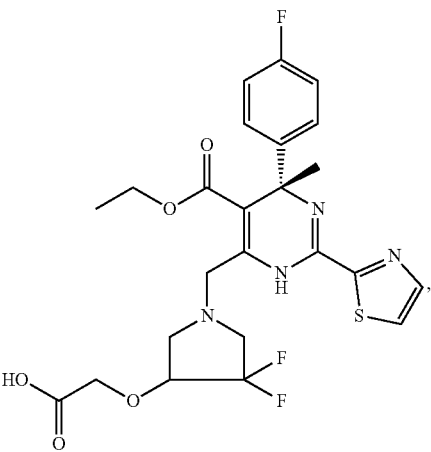
10-212
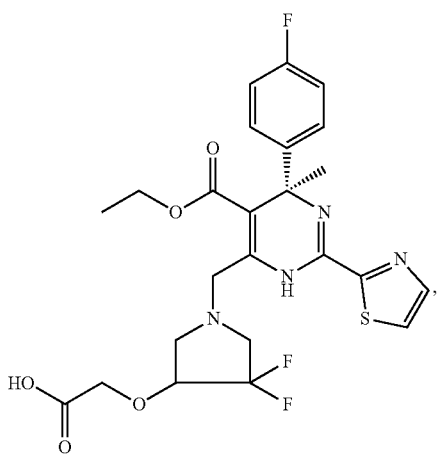
10-214
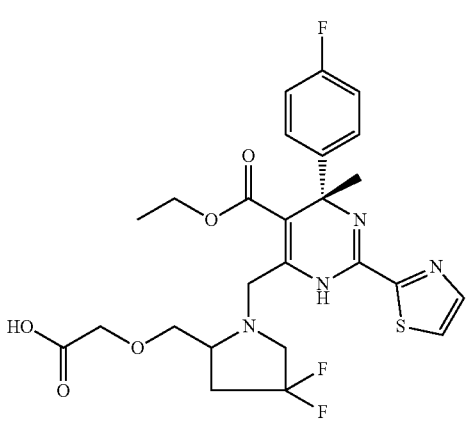

10-215
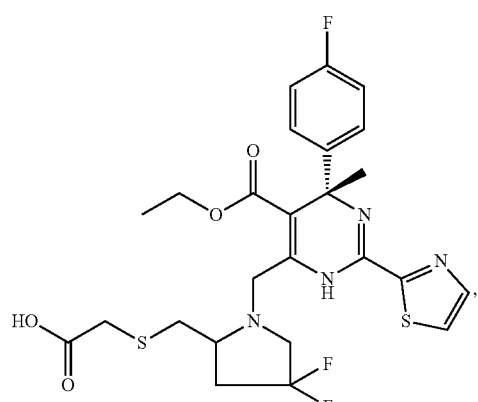
10-219
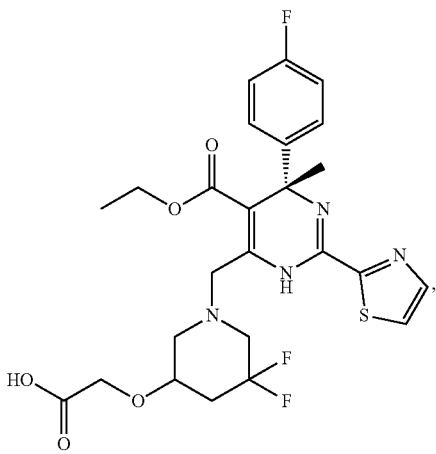
10-216
10-222
10-217
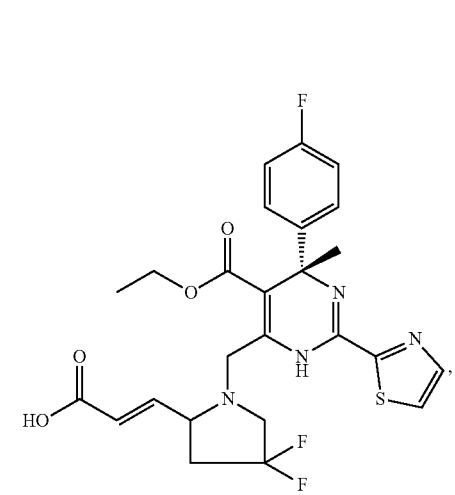
10-223
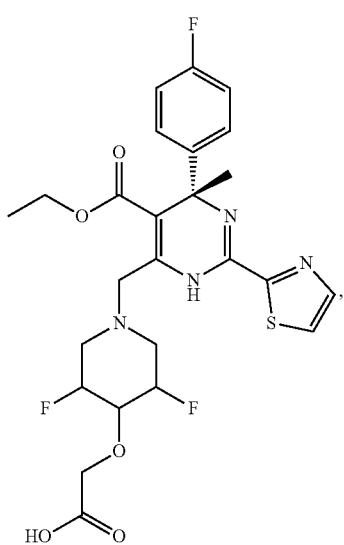

95
-continued
10-224
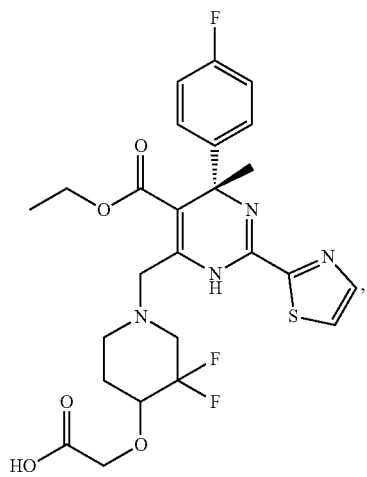
10-225
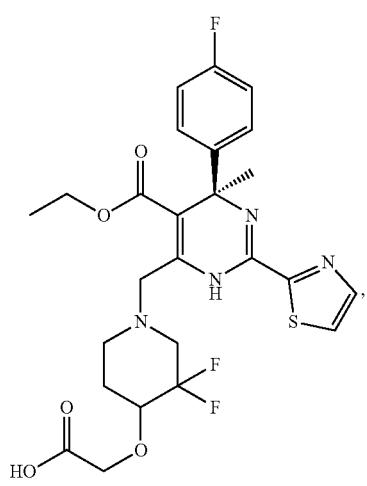
10-226
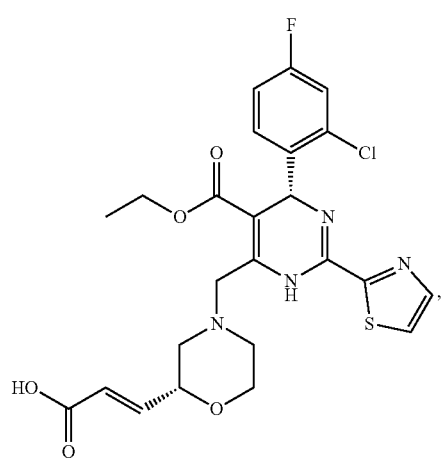
96
-continued
10-227
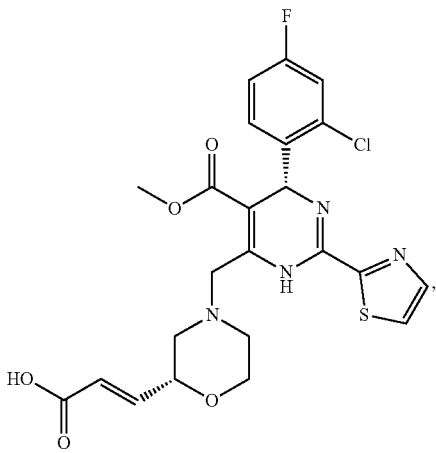
10-228
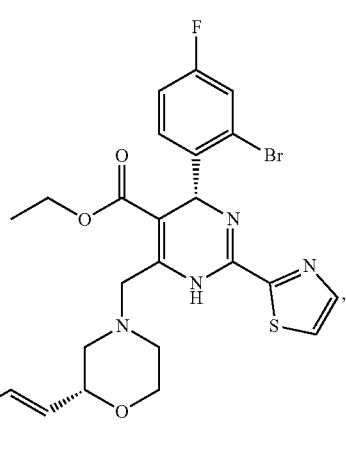
10-229
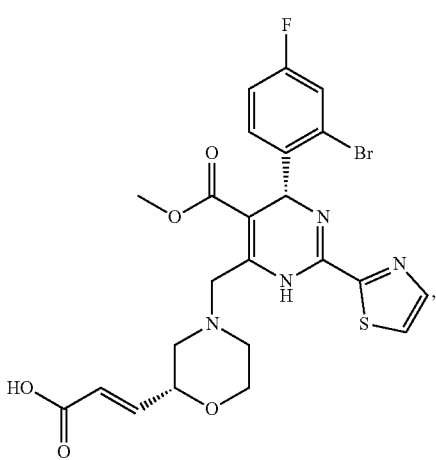

10-230
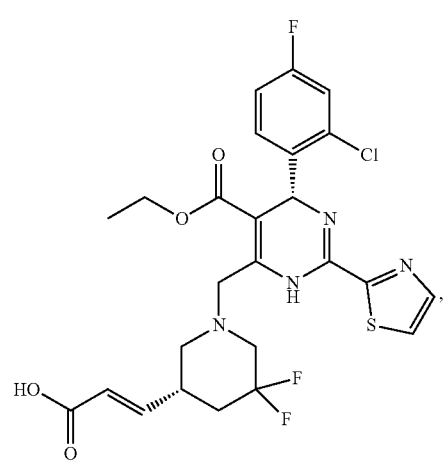
10-231
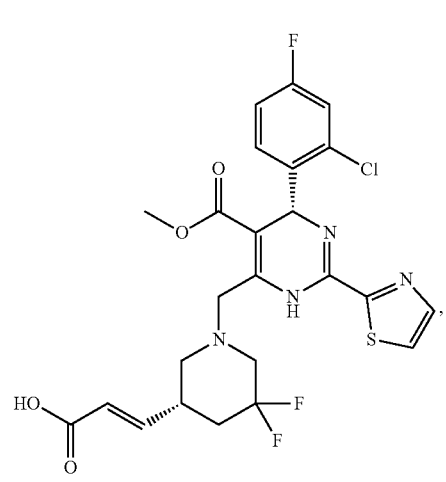
10-232
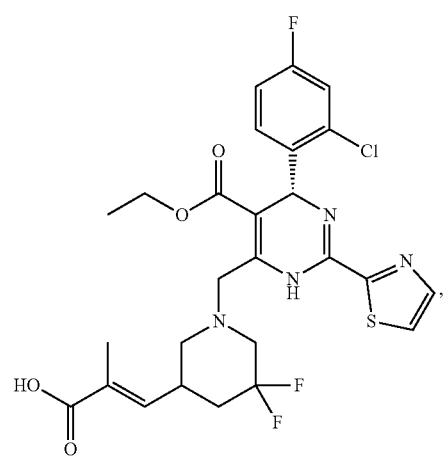
10-233
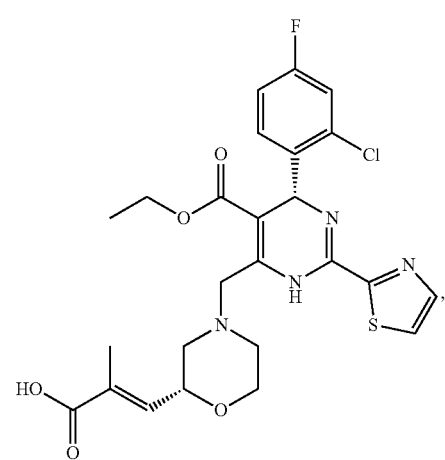
10-234
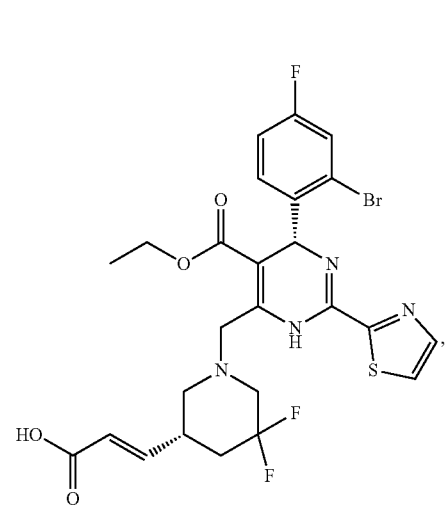
10-235
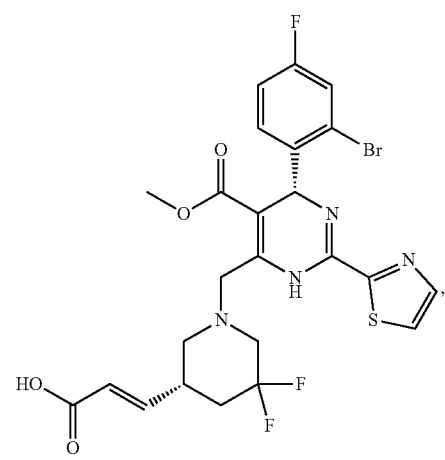

-continued
10-236
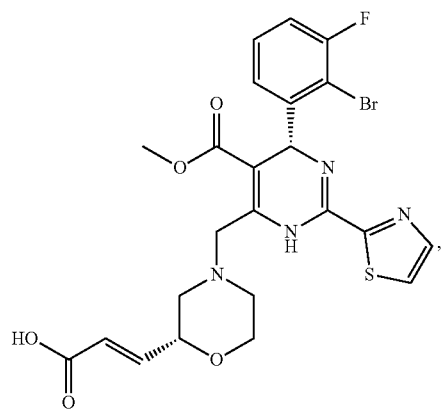
10-237
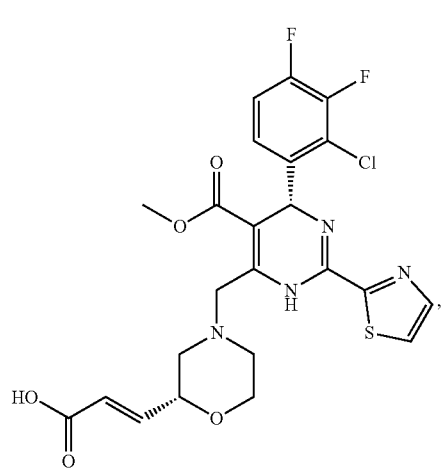
10-238
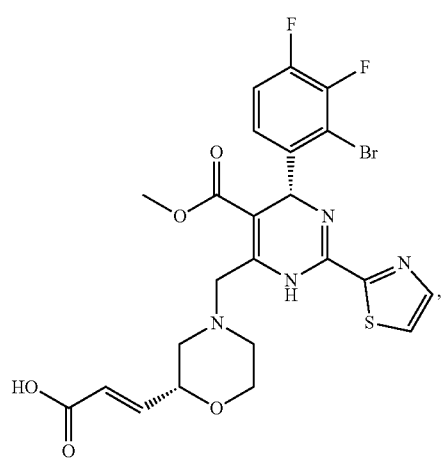
-continued
10-239
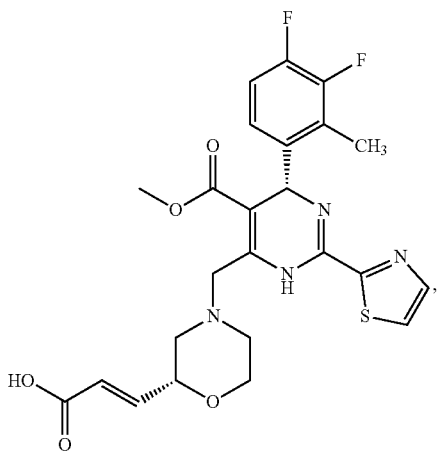
10-240
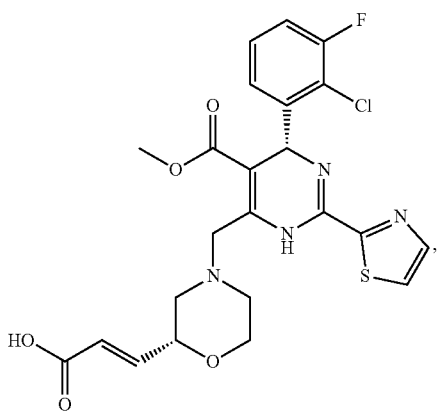
10-241
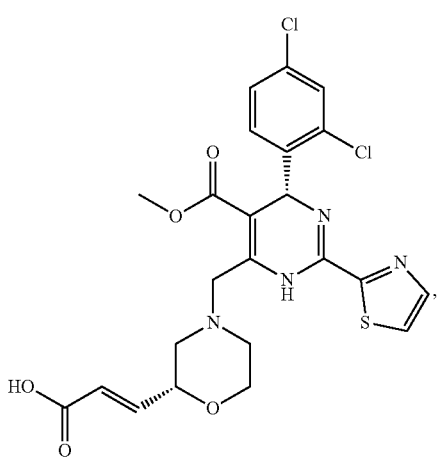

10-242
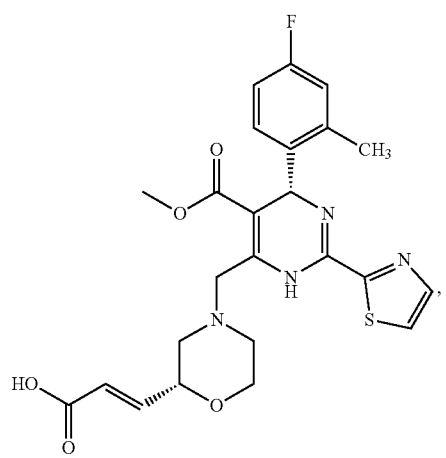
10-243
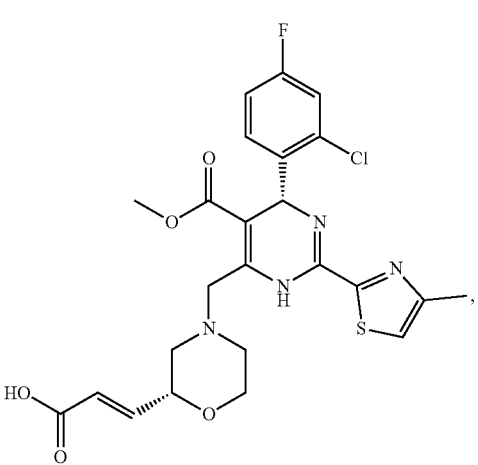
10-244
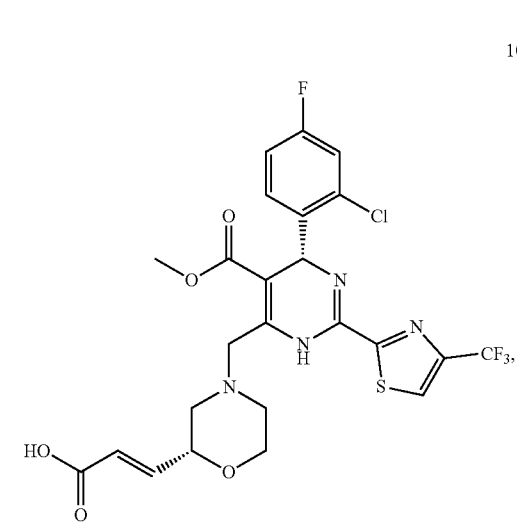
10-245
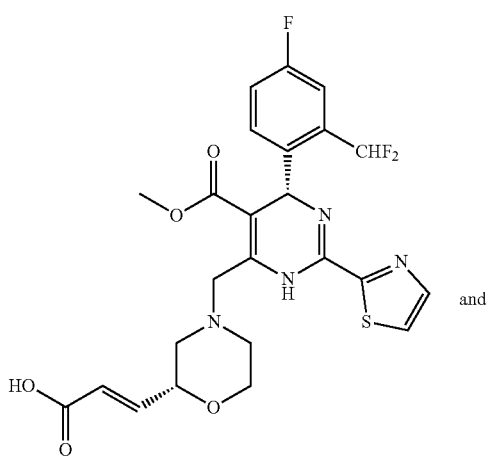
and
10-246
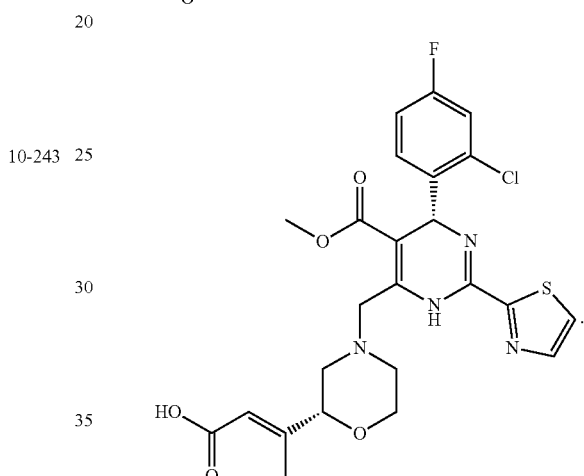
Embodiments of the present invention provide a method for the preparation of the compound of the present invention, the method comprises the following steps:
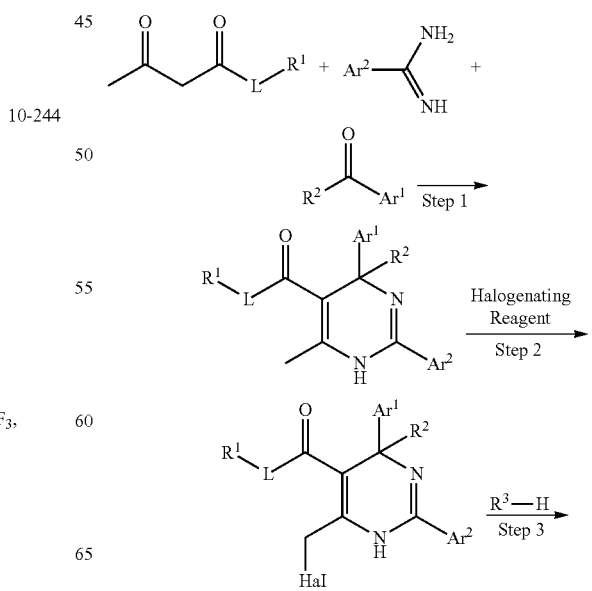

-continued

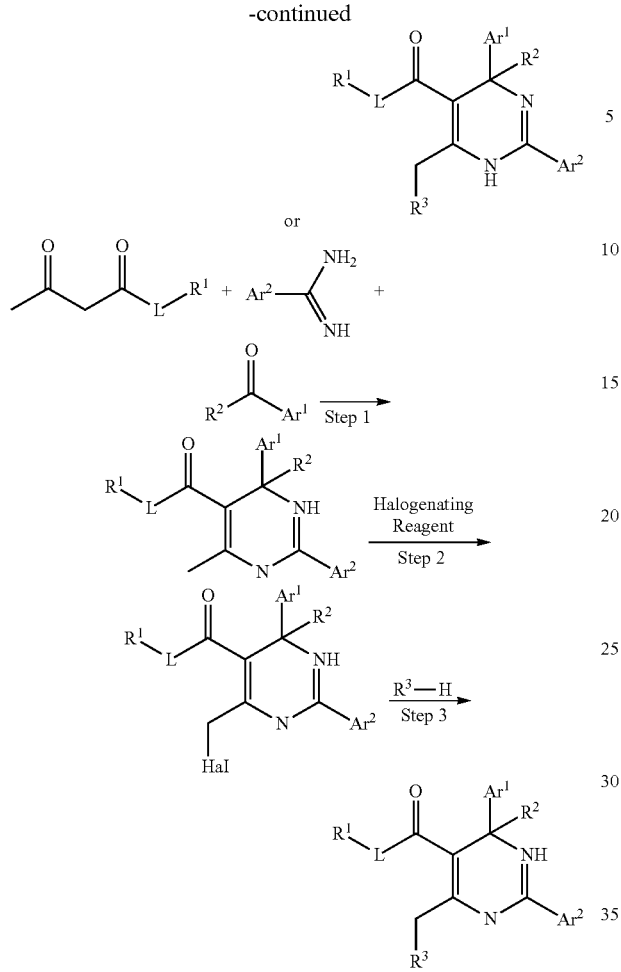

wherein:

Hal is selected from the group consisting of F, Cl, Br and I;

the halogenating reagent is selected from the group consisting of $C_2$, $Br_2$, $I_2$, N-chlorosuccinimide, N-bromosuccinimide and N-iodosuccinimide;

the remaining groups are as defined above;

step 1 is performed in a protic solvent (e.g., 2,2,2-trifluoroethanol, 2,2-difluoroethanol, 2-fluoroethanol, ethanol, fluoromethanol, hexafluoroisopropanol, etc.) in the presence of an alkali metal salt (e.g., potassium acetate, sodium acetate, potassium carbonate, sodium carbonate, cesium carbonate, sodium bicarbonate, etc.);

step 2 is performed in an aprotic solvent (e.g., carbon tetrachloride, dichloromethane, 1,2-dichloroethane, etc.); and step 3 is performed in an aprotic solvent (e.g., dichloromethane, 1,2-dichloroethane, acetonitrile, tetrahydrofuran, 2-methyl tetrahydrofuran, diethyl ether, tert-butyl methyl ether, N,N-dimethylformamide, N,N-dimethylacetamide, N-methyl pyrrolidone, etc.) in the presence of an organic base (e.g., N,N-diisopropylethylamine, triethylamine, 1,8-diazabicyclo[5.4.0]-7-undecene, 4-dimethylaminopyridine, N-methylmorpholine, N-methylpiperidine, N-methylpyrrolidine, etc.) or inorganic base (e.g., potassium acetate, sodium acetate, potassium carbonate, sodium carbonate, cesium carbonate, sodium bicarbonate, sodium hydride, potassium tert-butoxide, etc.);

when $R^2$ in the compound of formula I or formula Ia of the present invention is $C_{1-6}$ alkyl, the compound can also be synthesized by a method comprising the following steps:

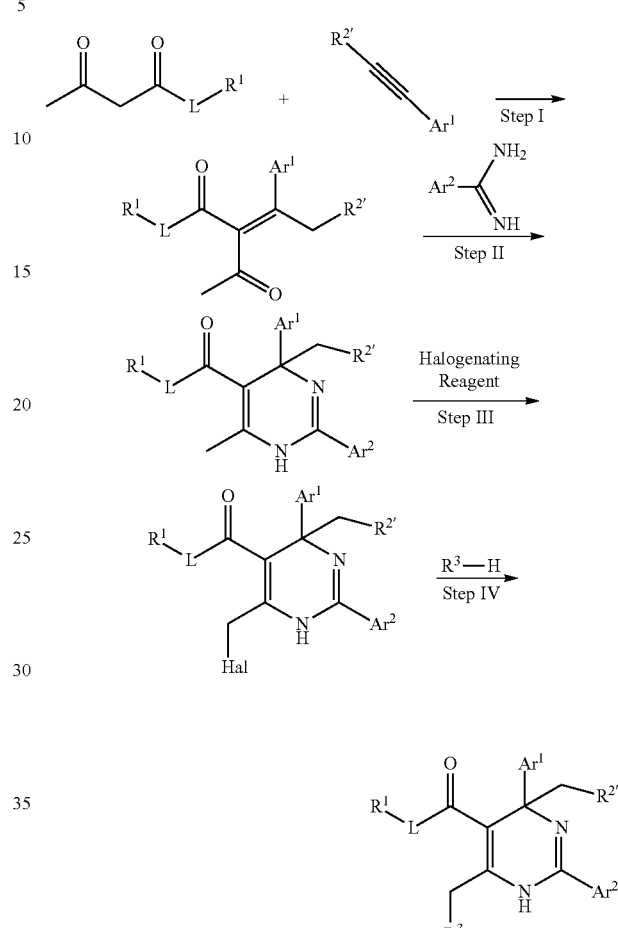

or

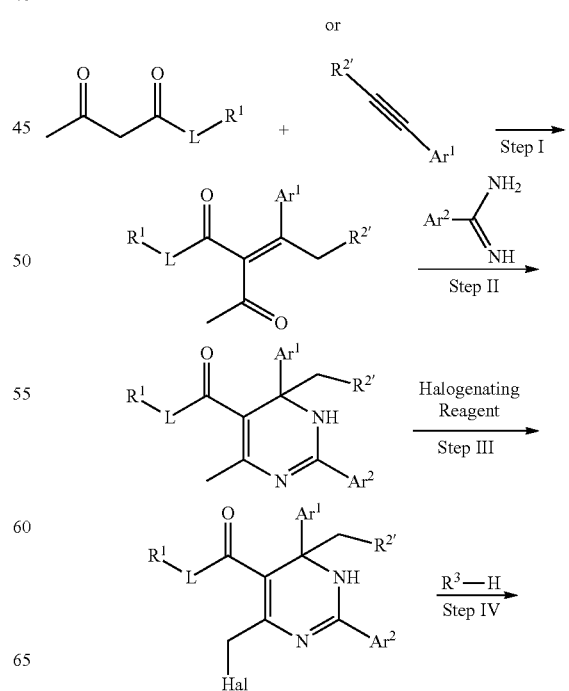

-continued

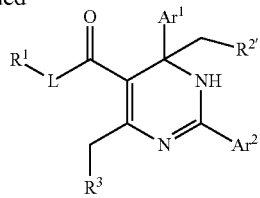

wherein:
R²' is H or C₁₋₅ alkyl;
Hal is selected from the group consisting of F, Cl, Br and I;
the halogenating reagent is selected from the group consisting of $Cl_2$, $Br_2$, $I_2$, N-chlorosuccinimide, N-bromosuccinimide and N-iodosuccinimide;
the remaining groups are as defined above;
step I is performed in a nonpolar solvent (e.g., o-xylene, toluene, anisole, etc.) in the presence of a Lewis acid (e.g., triflate salt (such as indium triflate, bismuth triflate, etc.), trifluoromethanesulfonate (such as trimethylsilyl trifluoromethanesulfonate), boron trifluoride, aluminium chloride, etc.);
step II is performed in an aprotic solvent (e.g., dichloromethane, 1,2-dichloroethane, acetonitrile, tetrahydrofuran, 2-methyl tetrahydrofuran, diethyl ether, tert-butyl methyl ether, N,N-dimethylformamide, N,N-dimethylacetamide, N-methyl pyrrolidone, etc.) in the presence of an organic base (e.g., N,N-diisopropylethylamine, triethylamine, 1,8-diazabicyclo[5.4.0]-7-undecene, 4-dimethylaminopyridine, N-methylmorpholine, N-methylpiperidine, N-methylpyrrolidine, etc.) or inorganic base (e.g., potassium acetate, sodium acetate, potassium carbonate, sodium carbonate, cesium carbonate, sodium bicarbonate, sodium hydride, potassium tert-butoxide, etc.);
step III is performed in an aprotic solvent (e.g., carbon tetrachloride, dichloromethane, 1,2-dichloroethane, etc.); and
step IV is performed in an aprotic solvent (e.g., dichloromethane, 1,2-dichloroethane, acetonitrile, tetrahydrofuran, 2-methyl tetrahydrofuran, diethyl ether, tert-butyl methyl ether, N,N-dimethylformamide, N,N-dimethylacetamide, N-methyl pyrrolidone, etc.) in the presence of an organic base (e.g., N,N-diisopropylethylamine, triethylamine, 1,8-diazabicyclo[5.4.0]-7-undecene, 4-dimethylaminopyridine, N-methylmorpholine, N-methylpiperidine, N-methylpyrrolidine, etc.) or inorganic base (e.g., potassium acetate, sodium acetate, potassium carbonate, sodium carbonate, cesium carbonate, sodium bicarbonate, sodium hydride, potassium tert-butoxide, etc.).

In preferred embodiments, when R² in the compound of formula I or formula Ia of the present invention is methyl, the compound can also be synthesized by a method comprising the following steps:

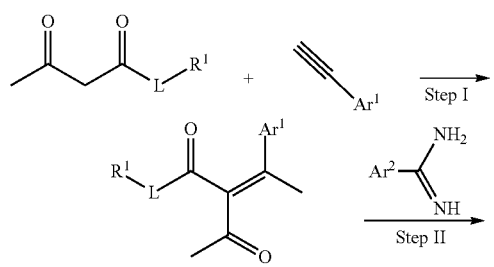

-continued

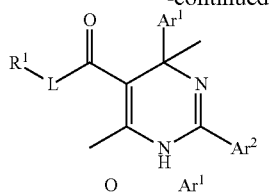

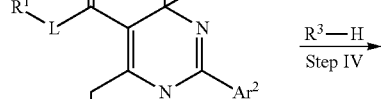

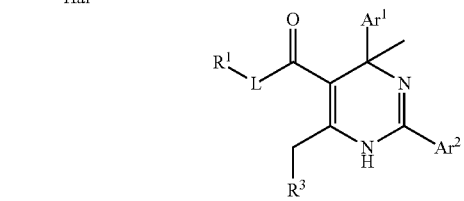

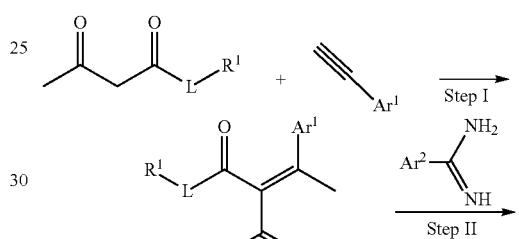

or

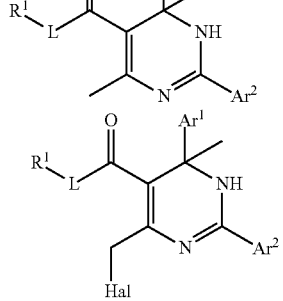

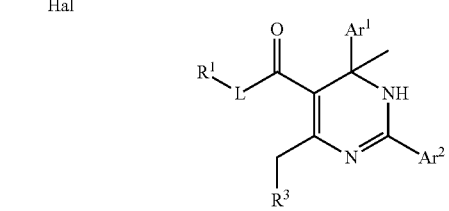

Wherein each group is as defined above, and Step I-IV are conducted as described above.

Pharmaceutical Composition and Therapeutic Method

The present invention provides a pharmaceutical composition comprising a prophylactically or therapeutically effective amount of the compound of the present invention or a pharmaceutically acceptable salt, ester, stereoisomer, tautomer, polymorph, solvate, metabolite, isotopically labeled compound, or prodrug thereof and one or more pharmaceutically acceptable carriers or excipients. In further embodiments, the pharmaceutical composition can further comprise one or more additional therapeutic agents, such as additional therapeutic agents for preventing or treating viral diseases.

The present invention further provides a method for preparing a pharmaceutical composition comprising combining the compound of the present invention or a pharmaceutically acceptable salt, ester, stereoisomer, tautomer, polymorph, solvate, metabolite, isotopically labeled compound, or prodrug thereof and one or more pharmaceutically acceptable carriers or excipients.

The present invention provides the compound of the present invention or a pharmaceutically acceptable salt, ester, stereoisomer, tautomer, polymorph, solvate, metabolite, isotopically labeled compound, or prodrug thereof or the pharmaceutical composition of the present invention in the manufacture of a medicament for preventing or treating a viral disease.

The present invention provides the compound of the present invention or a pharmaceutically acceptable salt, ester, stereoisomer, tautomer, polymorph, solvate, metabolite, isotopically labeled compound, or prodrug thereof or the pharmaceutical composition of the present invention for use in the prevention or treatment of a viral disease.

In other embodiments, the present invention provides a method for the prevention or treatment of a viral disease, comprising administering to a subject in need thereof an effective amount of the compound of the present invention or a pharmaceutically acceptable salt, ester, stereoisomer, tautomer, polymorph, solvate, metabolite, isotopically labeled compound, or prodrug thereof or the pharmaceutical composition of the present invention.

The compound of the present invention achieves its antiviral effects through inhibiting capsid protein assembly. As such, the compound of the present invention can be used for the treatment of any viral diseases involving capsid protein assembly when the virus infects a host, including, but not limited to hepatitis type A virus (HAV), hepatitis type B virus (HBV), hepatitis type C virus (HCV), influenza virus, herpes virus (HSV) and human immunodeficiency virus (HIV).

Thus, the viral diseases which can be prevented and treated by a compound of the present invention include, but are not limited to viral hepatitis type A, viral hepatitis type B, viral hepatitis type C, influenza, herpes and acquired immunodeficiency syndrome (AIDS), as well as associated symptoms or diseases resulted from the above diseases (e.g., inflammation, hepatic fibrosis, cirrhosis of liver and liver cancer, etc.).

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like.

The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation. For these routes of administration, the administration can be performed with a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single administration can be performed, several divided doses may be administered over time, or the dose may be proportionally reduced or increased in accordance with the therapeutic situation. It is to be noted that dosage values may vary with the type and severity of the condition, and may include single or multiple doses. It is to be further understood that for any particular subject, specific dosage regimens should be adjusted over time according to the individual need.

The amount of the compound of the present invention administered will be dependent on the subject being treated, the severity of the disorder or condition, the frequency of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The amount or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In other embodiments, the pharmaceutical composition of the present invention can further comprise one or more additional therapeutic agents or prophylactic agents, which are drugs for treating viral hepatitis type B, including, but not limited to, lamivudine, telbivudine, entecavir, adefovir dipivoxil, tenofovir, tenofovir disoproxil fumarate and tenofovir alafenamide fumarate.

EXAMPLES

The present invention is further described with reference to the following examples, which are not provided to limit the scope of the present invention in any fashion. Any suitable combination of the conditions is possible.

Unless otherwise noted, commercial anhydrous solvents and HPLC grade solvents were employed without further purification.

$^1$H NMR spectra were recorded at room temperature on a Bruker instrument (400 MHz) with TMS as an internal standard. Chemical shifts ($\delta$) are given in ppm and coupling constants (J) are reported in hertz (Hz). The splitting multiplicity of $^1$H NMR spectra are reported using the following abbreviations: s (singlet), d (doublet), t (triplet), q (quartet), m (multiplet), br (broad).

LC-MS was conducted on Aglient 1200 liquid chromatograph coupled to Aglient 6120 Quadrupole mass spectrometer, with detection at 214 nm and 254 inn. Preparative liquid chromatography was conducted on SHIMADZU CBM-20A and Aglient 1260 preparative liquid chromatograph, C18 OBD 19×150 mm 5 µM preparative column, detection at 214 nm, wherein mobile phase A was water, mobile phase B was acetonitrile (added with 0.5‰ formic acid), and elution was performed with a linear gradient as follows:

| Time (min) | A% | B% |
|---|---|---|
| 0 | 90 | 10 |
| 15 | 40 | 60 |
| 30 | 10 | 90 |

The abbreviations as used in the present invention have the following meanings:

| Abbreviation | Meaning | Abbreviation | Meaning |
|---|---|---|---|
| DAST | diethylaminosulfur trifluoride | HOAc | acetic acid |
| DEA | diethylamine | IPA | isopropanol |
| EA | ethyl acetate | MeOH | methanol |
| EtOH | ethanol | PE | petroleum ether |
| HEX | hexane | TLC | thin layer chromatography |

Example 1 Synthesis of ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate (10-88)

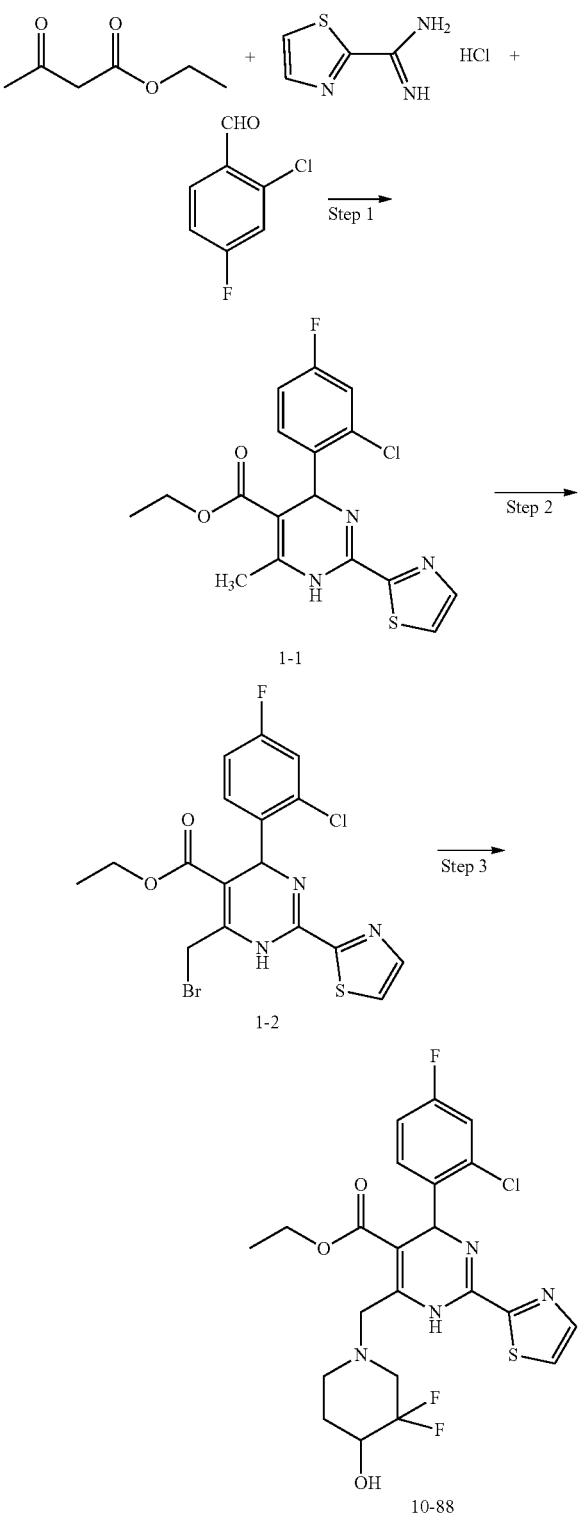

Step 1: Synthesis of ethyl 4-(2-chloro-4-fluorophenyl)-6-methyl-2-(thiazol-2-yl)-1,4-dihydropyrimidine-5-carboxylate (1-1)

At room temperature, ethyl acetoacetate (4.7 g, 36.0 mmol), thiazole-2-carboximidamide hydrochloride (5.4 g, 36.0 mmol), 2-chloro-4-fluorobenzaldehyde (5.8 g, 36.0 mmol) and potassium acetate (6.0 g, 60.0 mmol) were added to 2,2,2-trifluoroethanol (100 mL), heated to reflux, and the reaction was performed for 16 hours. The reaction solution was cooled to room temperature, the solvent was distilled off under reduced pressure, and the title compound (6.0 g) was obtained after work-up. ESI-MS (m/z): 380.1 [M+H]$^+$.

Step 2: Synthesis of ethyl 6-(bromomethyl)-4-(2-chloro-4-fluorophenyl)-2-(thiazol-2-yl)-1,4-dihydropyrimidine-5-carboxylate (1-2)

Compound (1-1) (5.7 g, 15.0 mmol) was dissolved in carbon tetrachloride (60 mL) and warmed to 50° C., N-bromosuccinimide (2.7 g, 15.0 mmol) was added in one portion, and the reaction was performed for 30 min. The reaction solution was cooled to room temperature, filtered to remove insolubles, and concentrated to give a crude product, which was purified to obtain the title compound (6.0 g). ESI-MS (m/z): 458.0 [M+H]$^+$.

Step 3: Synthesis of ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate (10-88)

At room temperature, compound (1-2) (68 mg, 0.14 mmol), 3,3-difluoropiperidin-4-ol hydrochloride (34 mg, 0.2 mmol) and N,N-diisopropylethylamine (50 mg, 0.4 mmol) were added to dichloromethane (3 mL), and the reaction was performed at room temperature overnight. The reaction solution was concentrated to give a crude product, which was purified to obtain the title compound (10-88) (27 mg).

The structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 515.2 [M+H]$^+$.

Example 2 Synthesis of ethyl 4-(2-bromo-4-fluorophenyl)-6-((3,3-difluoro-4-hydroxypiperidin-1-yl)methyl)-2-(thiazol-2-yl)-1,4-dihydropyrimidine-5-carboxylate (10-93)

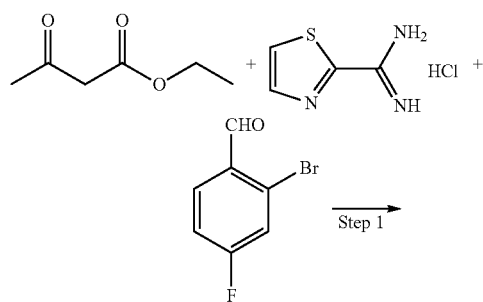

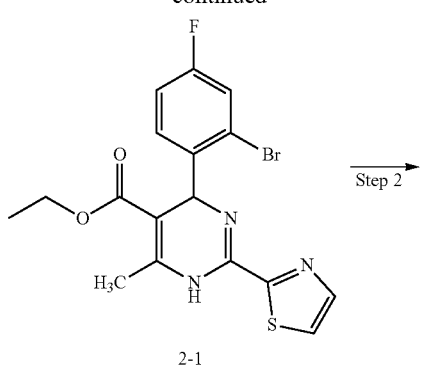

2-1

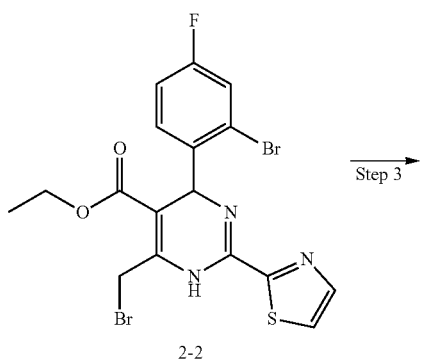

2-2

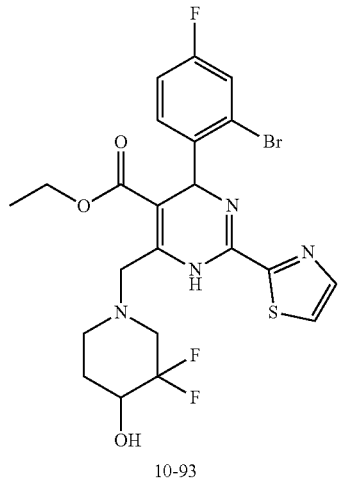

10-93

According to the above reaction scheme, employing procedures similar to those in Example 1 (except 2-chloro-4-fluorobenzaldehyde in Step 1 was replaced with 2-bromo-4-fluorobenzaldehyde), the title compound (27 mg) was prepared.

The structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 559.2 [M+H]$^+$.

Example 3 Synthesis of (S)-ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate—isomer A and (S)-ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate—isomer B

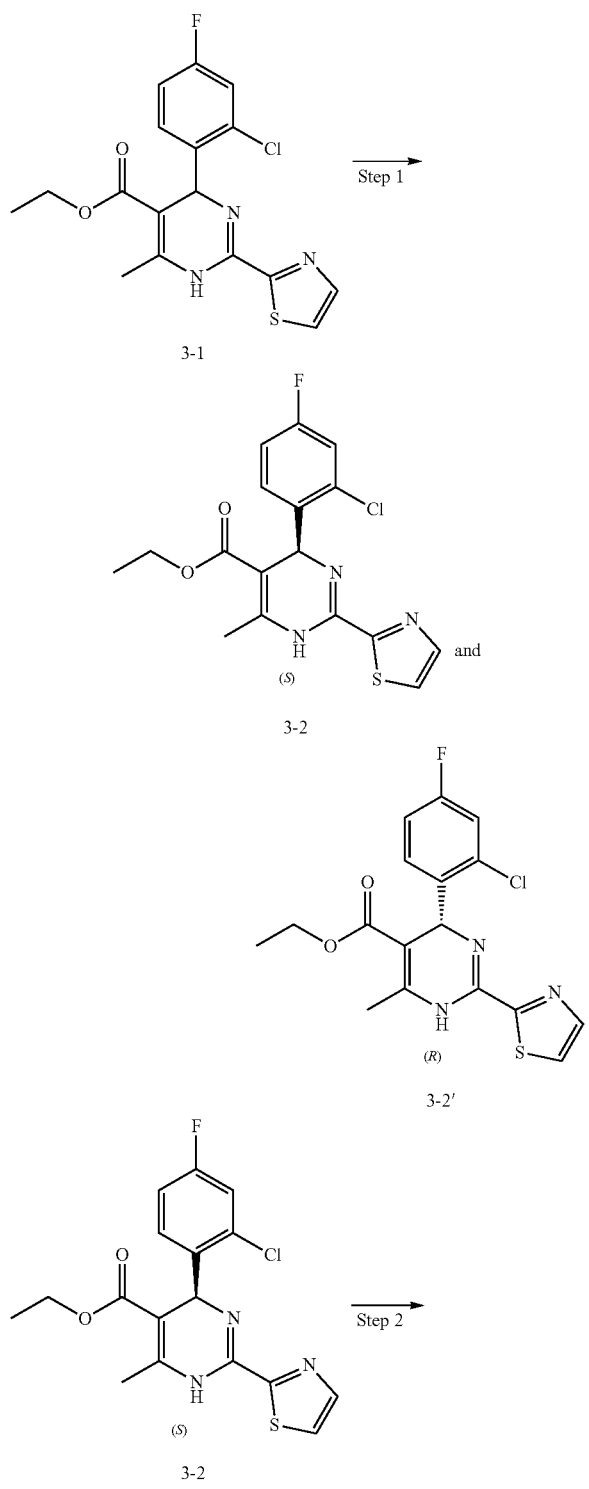

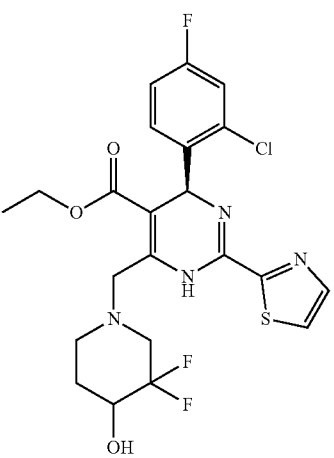

isomer A + isomer B

Step 1: Separation of ethyl 4-(2-chloro-4-fluorophenyl)-6-methyl-2-(thiazol-2-yl)-1,4-dihydropyrimidine-5-carboxylate (3-1)

Compound (3-1) (10 g) was separated by chiral chromatography, using the following separation conditions: Separation column CHIRALPAK IE 0.46 cm I.D.×15 cm L, mobile phase: MeOH/DEA=100/0.1 (V/V), flow rate: 1.0 ml/min, wavelength: UV 254 nm, temperature: 35° C.

The separation resulted in (S)-ethyl 4-(2-chloro-4-fluorophenyl)-6-methyl-2-(thiazol-2-yl)-1,4-dihydropyrimidine-5-carboxylate (3-2) 4.7 g, ee %=99.9%, $R_t$=2.642 min. ESI-MS (m/z): 380.1 [M+H]$^+$; and (R)-ethyl 4-(2-chloro-4-fluorophenyl)-6-methyl-2-(thiazol-2-yl)-1,4-dihydropyrimidine-5-carboxylate (3-2') 4.5 g, ee %=99.9%, $R_t$=4.783 min. ESI-MS (m/z): 380.1 [M+H]$^+$.

Step 2 to Step 3

(S)-ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate (3-4) was prepared using compound (3-2) as a starting material and employing procedures similar to those in Step 2 and Step 3 of Example 1. ESI-MS (m/z): 515.2 [M+H]$^+$.

Step 4: Separation of Compound (3-4)

Compound (3-4) (340 mg) was separated by chiral chromatography, using the following separation conditions: Separation column CHIRALPAK IE 0.46 cm I.D.×15 cm L, mobile phase: HEX:IPA=100/0.1 (V/V), flow rate: 1.0 ml/min, wavelength: UV 254 nm, temperature: 35° C. Among them, the product with $R_f$=5.961 min was isomer A, ee %=99.3%, 122 mg, the structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 515.2 [M+H]$^+$; and Among them, the product with R=7.130 min is isomer B, ee %=99.5%, 131 mg, the structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 515.2 [M+H]$^+$.

Example 4 Synthesis of (R)-ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate—isomer A and (R)-ethyl 4-(2-chloro-4-fluorophenyl)-6-((3,3-difluoro-4-hydroxypiperidin-1-yl)methyl)-2-(thiazol-2-yl)-1,4-dihydropyrimidine-5-carboxylate—isomer B

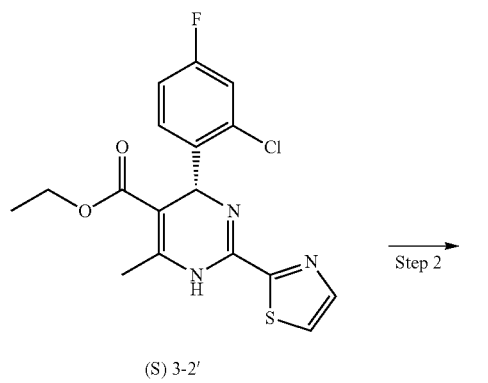

(S) 3-2'

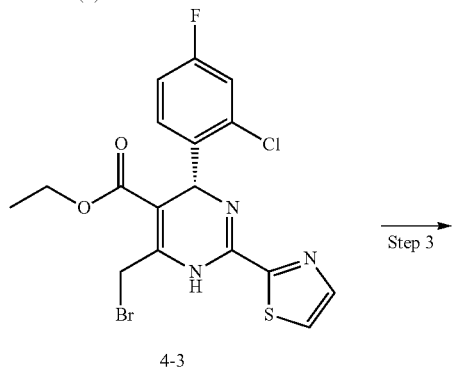

4-3

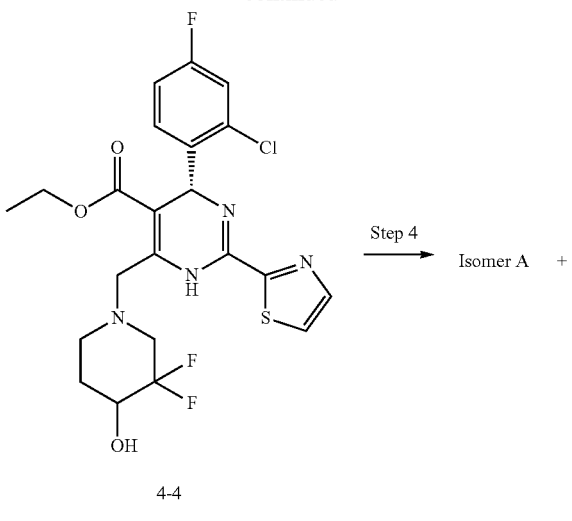

The target product was prepared using compound (3-2') as a starting material and employing procedures similar to those in Example 3. Among them, the product with $R_1$=8.171 min is isomer A, ee %=99.1%, 137 mg, the structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 515.2 [M+H]$^+$; and Among them, the product with $R_f$=7.088 min is isomer B, ee %=99.4%, 128 mg, the structure was characterized as follows:

$^1$H NMR (400 MHz, DMSO-d$_6$): δ 9.54 (s, 1H), 7.99 (d, J=3.14 Hz, 1H), 7.94 (d, J=3.14 Hz, 1H), 7.44-7.40 (m, 2H), 7.19 (td, J=8.44, 2.64 Hz, 1H), 6.05 (s, 1H), 5.62 (t, J=5.40 Hz, 1H), 4.00-3.92 (m, 4H), 3.76 (s, 1H), 3.06-2.67 (m, 4H), 1.86 (d, J=3.52 Hz, 1H), 1.74 (d, J=3.08 Hz, 1H), 1.04 (t, J=7.12 Hz, 3H). ESI-MS (m/z): 515.2 [M+H]$^+$.

Example 5 Synthesis of 2-((1-((6-(2-chloro-4-fluorophenyl)-5-(ethoxycarbonyl)-2-(thiazol-2-yl)-3,6-dihydropyrimidin-4-yl)methyl)-3,3-difluoropiperidin-4-yl)oxy)acetic acid (10-95)

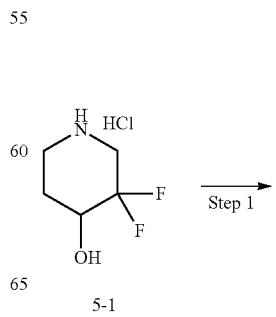

5-1

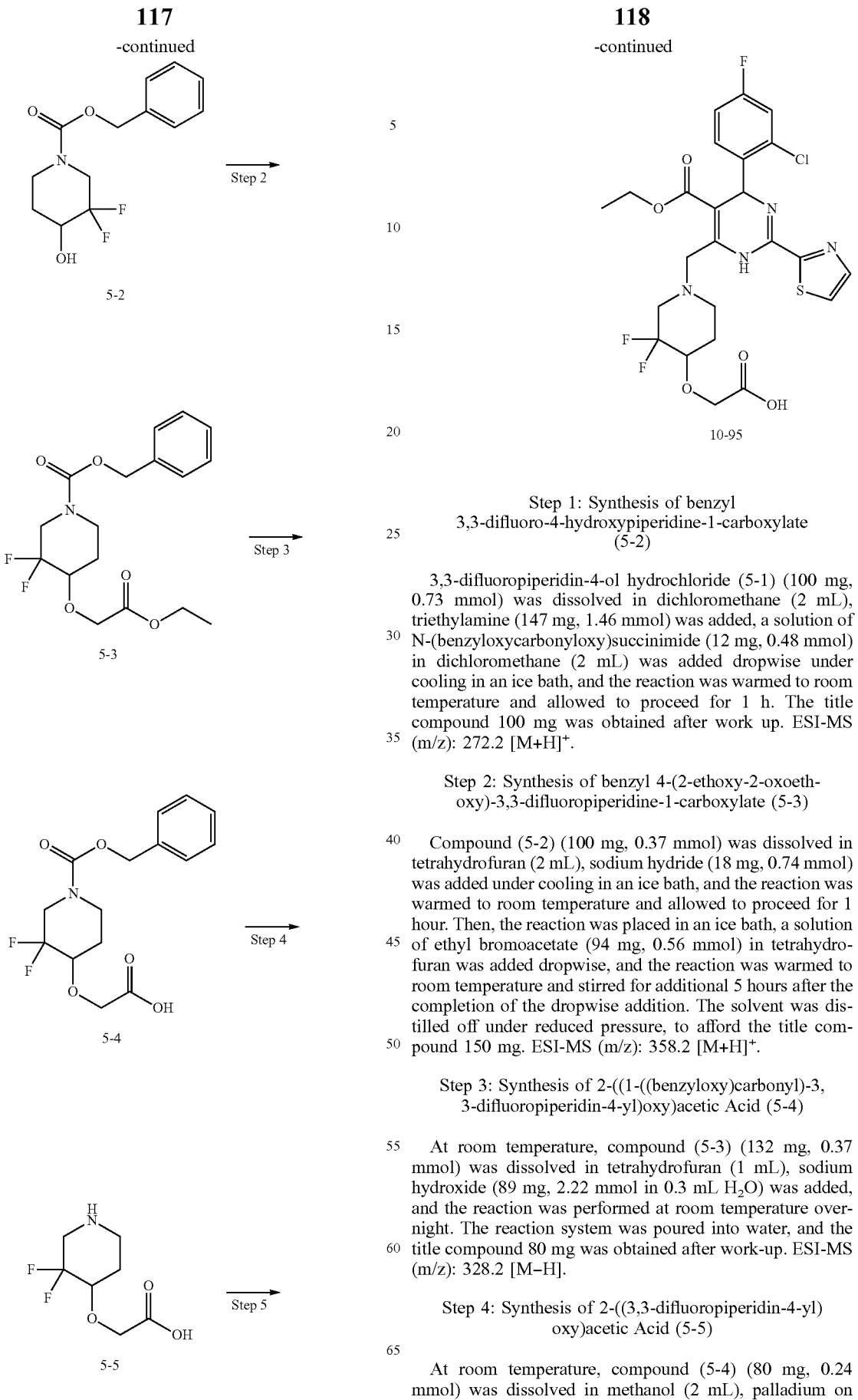

Step 1: Synthesis of benzyl 3,3-difluoro-4-hydroxypiperidine-1-carboxylate (5-2)

3,3-difluoropiperidin-4-ol hydrochloride (5-1) (100 mg, 0.73 mmol) was dissolved in dichloromethane (2 mL), triethylamine (147 mg, 1.46 mmol) was added, a solution of N-(benzyloxycarbonyloxy)succinimide (12 mg, 0.48 mmol) in dichloromethane (2 mL) was added dropwise under cooling in an ice bath, and the reaction was warmed to room temperature and allowed to proceed for 1 h. The title compound 100 mg was obtained after work up. ESI-MS (m/z): 272.2 [M+H]$^+$.

Step 2: Synthesis of benzyl 4-(2-ethoxy-2-oxoethoxy)-3,3-difluoropiperidine-1-carboxylate (5-3)

Compound (5-2) (100 mg, 0.37 mmol) was dissolved in tetrahydrofuran (2 mL), sodium hydride (18 mg, 0.74 mmol) was added under cooling in an ice bath, and the reaction was warmed to room temperature and allowed to proceed for 1 hour. Then, the reaction was placed in an ice bath, a solution of ethyl bromoacetate (94 mg, 0.56 mmol) in tetrahydrofuran was added dropwise, and the reaction was warmed to room temperature and stirred for additional 5 hours after the completion of the dropwise addition. The solvent was distilled off under reduced pressure, to afford the title compound 150 mg. ESI-MS (m/z): 358.2 [M+H]$^+$.

Step 3: Synthesis of 2-((1-((benzyloxy)carbonyl)-3,3-difluoropiperidin-4-yl)oxy)acetic Acid (5-4)

At room temperature, compound (5-3) (132 mg, 0.37 mmol) was dissolved in tetrahydrofuran (1 mL), sodium hydroxide (89 mg, 2.22 mmol in 0.3 mL H$_2$O) was added, and the reaction was performed at room temperature overnight. The reaction system was poured into water, and the title compound 80 mg was obtained after work-up. ESI-MS (m/z): 328.2 [M−H].

Step 4: Synthesis of 2-((3,3-difluoropiperidin-4-yl)oxy)acetic Acid (5-5)

At room temperature, compound (5-4) (80 mg, 0.24 mmol) was dissolved in methanol (2 mL), palladium on carbon (10%, 10 mg) was added, and the reaction was performed under a hydrogen atmosphere at room temperature for 3 hours. The insoluble material was filtered off, and the solvent was distilled off under reduced pressure, to afford the title compound 40 mg. ESI-MS (m/z): 196.2 [M+H]$^+$.

Step 5: Synthesis of 2-((1-((6-(2-chloro-4-fluorophenyl)-5-(ethoxycarbonyl)-2-(thiazol-2-yl)-3,6-dihydropyrimidin-4-yl)methyl)-3,3-difluoropiperidin-4-yl)oxy)acetic Acid (10-95)

The title compound 10 mg was prepared by a method similar to that described in Step 3 of Example 1, except 3,3-difluoropiperidin-4-ol hydrochloride was replaced by compound (5-5).

The structure was characterized as follows:
$^1$H NMR (400 MHz, DMSO-d$_6$) δ 12.66 (s, 1H), 9.54 (d, J=2.4 Hz, 1H), 8.07-7.82 (m, 2H), 7.53-7.33 (m, 2H), 7.18 (td, J=8.5, 2.7 Hz, 1H), 6.05 (s, 1H), 4.30-4.09 (m, 2H), 4.06-3.89 (m, 4H), 3.84 (s, 1H), 3.10-2.81 (m, 3H), 2.72 (s, 1H), 2.00 (s, 1H), 1.85 (s, 1H), 1.04 (t, J=7.0 Hz, 3H). ESI-MS (m/z): 573.2 [M+H]$^+$.

Example 6 Synthesis of (R)-ethyl 4-(2-chloro-4-fluorophenyl)-6-((3,3-difluoroazetidin-1-yl)methyl)-2-(thiazol-2-yl)-1,4-dihydropyrimidine-5-carboxylate (10-7)

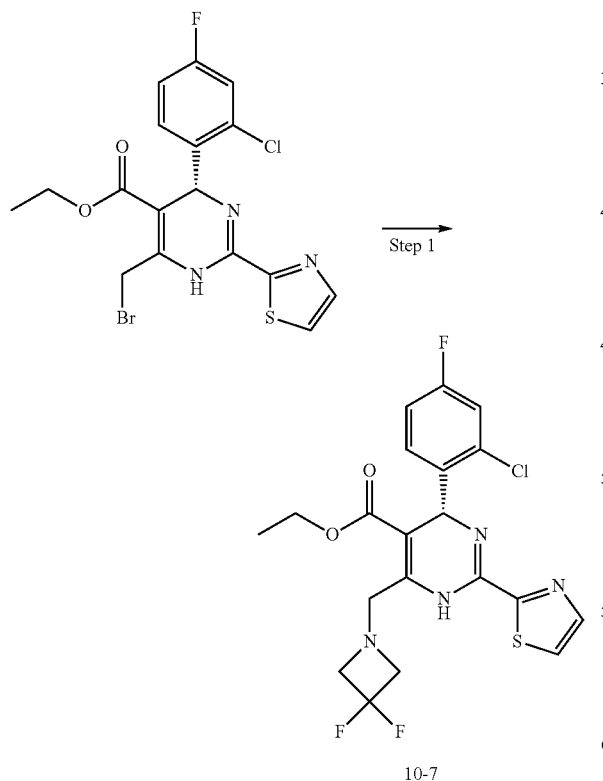

10-7

The title compound 4 mg was prepared by a method similar to that described in Step 3 of Example 1 (3,3-difluoropiperidin-4-ol hydrochloride was replaced by 3,3-difluoroazetidine hydrochloride).

The structure was characterized as follows:
$^1$H NMR (400 MHz, DMSO-d$_6$) δ 9.46 (s, 1H), 8.06-7.99 (m, 1H), 7.95 (d, J=3.1 Hz, 1H), 7.46-7.36 (m, 2H), 7.19 (td, J=8.5, 2.6 Hz, 1H), 6.03 (s, 1H), 4.15 (s, 2H), 3.97 (t, J=7.1 Hz, 2H), 3.85 (t, J=12.6 Hz, 4H), 1.05 (t, J=7.1 Hz, 3H). ESI-MS (m/z): 471.1 [M+H]$^+$.

Example 7 Synthesis of (R)-1-((6-(2-chloro-4-fluorophenyl)-5-ethoxycarbonyl-2-(thiazol-2-yl)-3,6-dihydropyrimidin-4-yl)methyl)-3-fluoroazetidine-3-carboxylic Acid (10-11)

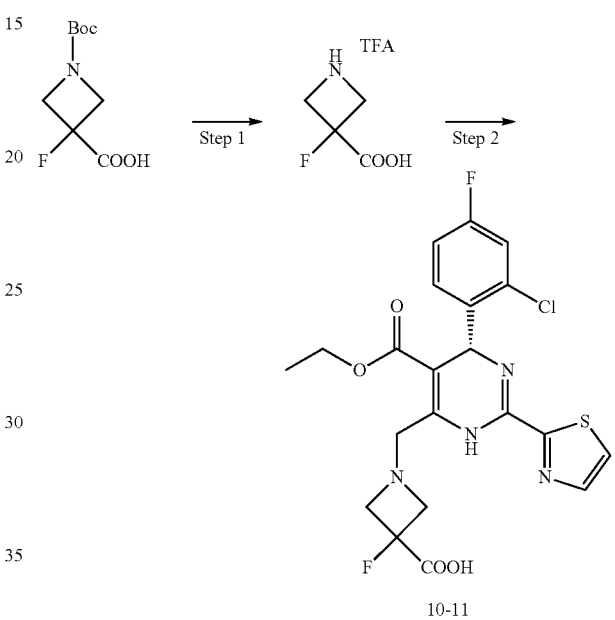

10-11

Step 1: Synthesis of 3-fluoroazetidine-3-carboxylic Acid 1-(tert-butoxycarbonyl)-3-fluoroazetidine-3-carboxylic acid (30 mg, 0.14 mmol) was dissolved in dichloromethane (2 mL), trifluoroacetic acid (0.5 mL) was added at room temperature, and the reaction was allowed to continue for 1 hour. The solvent was distilled off under reduced pressure, and a trifluoroacetate salt of the title compound 33 mg was obtained. ESI-MS (m/z): 120.1 [M+H]$^+$.

Step 2: Synthesis of (R)-1-((6-(2-chloro-4-fluorophenyl)-5-(ethoxycarbonyl)-2-(thiazol-2-yl)-3,6-dihydropyrimidin-4-yl)methyl)-3-fluoroazetidine-3-carboxylic Acid (10-11)

The title compound 6 mg was prepared by a method similar to that described in Step 3 of Example 1 (3,3-difluoropiperidin-4-ol hydrochloride was replaced by a trifluoroacetate salt of 3-fluoroazetidine-3-carboxylic acid).

The structure was characterized as follows:
1H NMR (400 MHz, DMSO-d$_6$) δ 9.47 (s, 1H), 8.01 (d, J=3.08 Hz, 1H), 7.95 (d, J=3.09 Hz, 1H), 7.40 (dd, J=15.82, 6.61 Hz, 2H), 7.21-7.15 (m, 1H), 6.02 (s, 1H), 4.12 (s, 2H), 3.96 (dd, J=14.10, 7.12 Hz, 2H), 3.91-3.81 (m, 2H), 3.71 (dd, J=20.97, 9.47 Hz, 2H), 1.05 (t, J=7.06 Hz, 3H). ESI-MS (m/z): 497.0 [M+H]$^+$.

Example 8 Synthesis of (4R)-ethyl 4-(2-chloro-4-fluorophenyl)-6-((3,3-difluoro-4-methoxypiperidin-1-yl)methyl)-2-(thiazol-2-yl)-1,4-dihydropyrimidine-5-carboxylate (10-98)

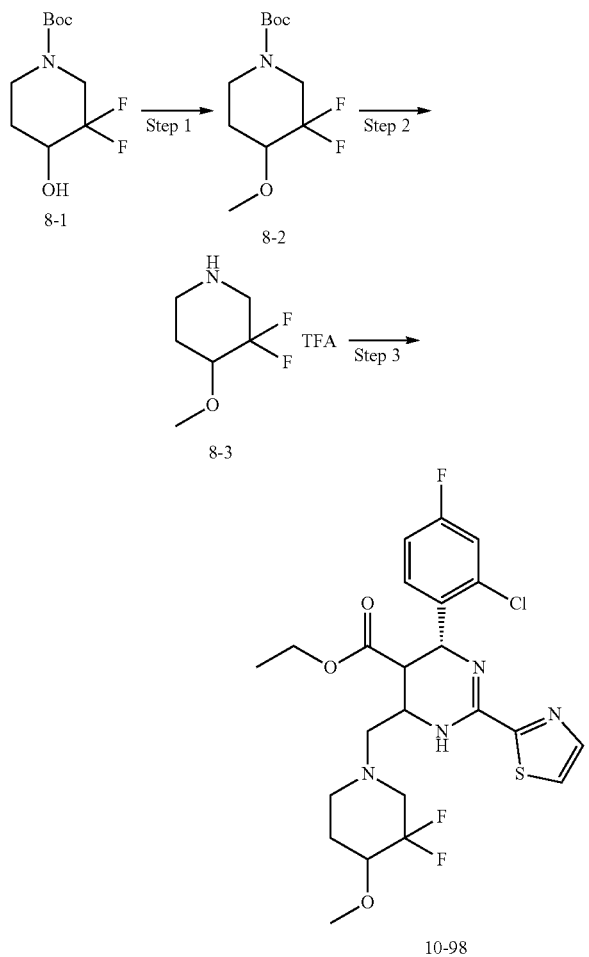

Step 1: Synthesis of tert-butyl 3,3-difluoro-4-methoxypiperidine-1-carboxylate (8-2)

Tert-butyl 3,3-difluoro-4-hydroxypiperidine-1-carboxylate (8-1) (100 mg, 0.42 mmol) and tetrahydrofuran (5 mL) were added to a 25 mL flask, and cooled to 0° C. under protection of nitrogen, sodium hydride (20 mg, 0.5 mmol) was added thereto, and the reaction was performed for 30 minutes. Iodomethane (120 mg, 0.84 mmol) was then added thereto, and the reaction was performed for 16 hours. The reaction solution was slowly poured into water, and a crude product of the title compound 100 mg was obtained after work-up, and was used directly for the next reaction without purification. ESI-MS (m/z): 252.2 [M+H]$^+$.

Step 2: Synthesis of 3,3-difluoro-4-methoxypiperidine Trifluoroacetate Salt (8-3)

Compound (8-2) (100 mg, 0.4 mmol) and dichloromethane (6 mL) were added to a 25 mL flask, the reaction was cooled to 0° C., trifluoroacetic acid (2 mL) was then added thereto, and the reaction was performed for 3 hours. The solvent was distilled off under reduced pressure, to afford a crude product 120 mg. ESI-MS (m/z): 152.2 [M+H]$^+$.

Step 3: Synthesis of (4R)-ethyl 4-(2-chloro-4-fluorophenyl)-6-((3,3-difluoro-4-methoxypiperidin-1-yl)methyl)-2-(thiazol-2-yl)-1,4-dihydropyrimidine-5-carboxylate (10-98)

The title compound 50 mg was prepared by a method similar to that described in Step 3 of Example 1 (3,3-difluoropiperidin-4-ol hydrochloride was replaced by compound (8-3)).

The structure was characterized as follows:
$^1$H NMR (400 MHz, DMSO-d) S 9.54 (s, 1H), 8.00 (dd, J=3.1, 1.7 Hz, 1H), 7.94 (d, J=3.1 Hz, 1H), 7.47-7.35 (m, 2H), 7.18 (td, J=8.5, 2.6 Hz, 1H), 6.05 (s, 1H), 4.06-3.91 (m, 4H), 3.60 (d, J=5.0 Hz, 1H), 3.41 (d, J=1.6 Hz, 3H), 3.12-2.93 (m, 1H), 2.92-2.76 (m, 1H), 2.67 (s, 1H), 1.94 (s, 1H), 1.77 (s, 1H), 1.04 (t, J=7.1 Hz, 3H). ESI-MS (m/z): 529.2 [M+H]$^+$.

Example 9 Synthesis of (R)-ethyl 4-(2-chloro-4-fluorophenyl)-6-(((3R,4R)-3-fluoro-4-hydroxypyrrolidin-1-yl)methyl)-2-(thiazol-2-yl)-1,4-dihydropyrimidine-5-carboxylate (10-34)

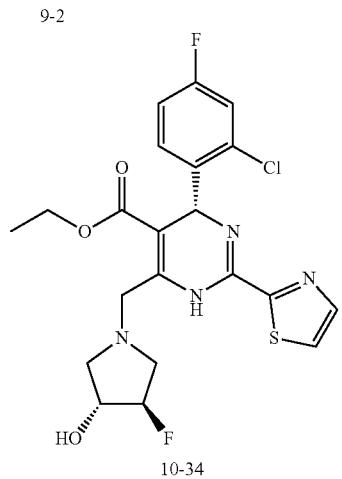

Step 1: Synthesis of (3R,4R)-4-fluoropyrrolidin-3-ol (9-2)

Under cooling in an ice bath, (3R,4R)-tert-butyl 3-hydroxy-4-fluoropyrrolidine-1-carboxylate (9-1) (60 mg, 0.3 mmol) was dissolved in dichloromethane (1 mL), trifluoroacetic acid (0.3 mL) was added, and the reaction was performed at room temperature for 1.5 h. The solvent was distilled off under reduced pressure, to afford a trifluoroacetate salt of the title compound 60 mg. ESI-MS (m/z): 106.1 [M+H]$^+$.

Step 2: Synthesis of (R)-ethyl 4-(2-chloro-4-fluorophenyl)-6-(((3R,4R)-3-fluoro-4-hydroxypyrrolidin-1-yl)methyl)-2-(thiazol-2-yl)-1,4-dihydropyrimidine-5-carboxylate (10-34)

The title compound 30 mg was prepared by a method similar to that described in Step 3 of Example 1 (3,3-difluoropiperidin-4-ol hydrochloride was replaced by compound (9-2)).

The structure was characterized as follows:

$^1$H NMR (400 MHz, CDCl$_3$) δ 7.86 (t, J=2.6 Hz, 1H), 7.59 (s, 2H), 7.49-7.33 (m, 1H), 7.16 (ddd, J=8.3, 4.3, 2.6 Hz, 1H), 7.02 (d, J=9.0 Hz, 1H), 6.18 (d, J=2.3 Hz, 1H), 5.19 (d, J=50.5 Hz, 1H), 4.93-4.26 (m, 4H), 4.06 (qd, J=7.1, 1.7 Hz, 2H), 3.53 (s, 2H), 1.10 (td, J=7.1, 4.5 Hz, 3H). ESI-MS (m/z): 483.2 [M+H]$^+$.

Example 10 Synthesis of 2-(((3R,4R)-1-(((R)-6-(2-chloro-4-fluorophenyl)-5-(ethoxycarbonyl)-2-(thiazol-2-yl)-3,6-dihydropyrimidin-4-yl)methyl)-4-fluoropyrrolidin-3-yl)oxy)acetic acid (10-36)

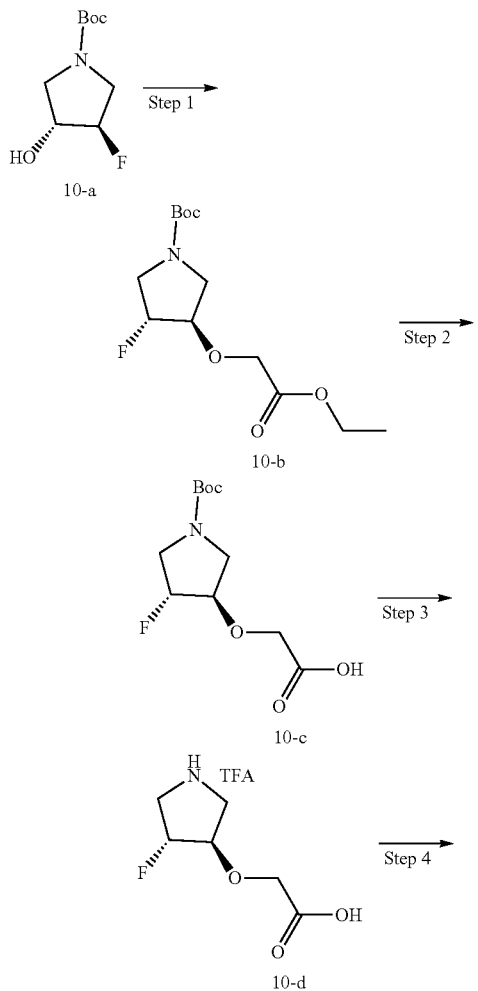

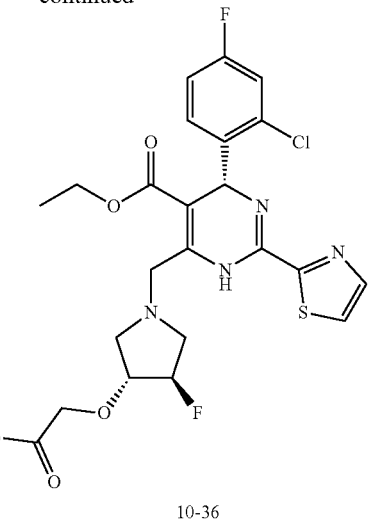

10-36

Step 1: Synthesis of (3R,4R)-tert-butyl 3-(2-ethoxy-2-oxoethoxy)-4-fluoropyrrolidine-1-carboxylate (10-b)

Tert-butyl (3R,4R)-3-hydroxy-4-fluoropyrrolidine-1-carboxylate (10-a) (100 mg, 0.49 mmol) was dissolved in tetrahydrofuran (5 mL), sodium hydride (40 mg, 60% in oil, 0.98 mmol) was added under cooling in an ice bath, and the reaction was warmed to room temperature and allowed to proceed for 2 h. Under cooling in an ice bath, ethyl bromoacetate (124 mg, 0.74 mmol) was added, and the reaction was performed at room temperature overnight. Saturated ammonium chloride (3 mL) was added, followed by dilution with dichloromethane (15 mL), the reaction was washed with saturated brine, and dried over anhydrous sodium sulfate. The drying agent was removed by filtration, the solvent was distilled off under reduced pressure, to afford the title compound 120 mg. ESI-MS (m/z): 292.2 [M+H]$^+$.

Step 2: Synthesis of 2-(((3R,4R)-1-(tert-butoxycarbonyl)-4-fluoropyrrolidin-3-yl)oxy)acetic Acid (10-c)

Compound (10-b) (120 mg, 0.41 mmol) was dissolved in a mixed solution of tetrahydrofuran and water (v:v=1:1, 3 mL), lithium hydroxide monohydrate (104 mg, 2.47 mmol) was added, and the reaction was performed at room temperature for 3.5 h. The pH was adjusted to 5 with an aqueous solution of citric acid, dichloromethane (15 mL) was added, and the reaction was washed with saturated brine, and dried over anhydrous sodium sulfate. Anhydrous sodium sulfate was removed by filtration, the solvent was distilled off under reduced pressure, to afford the title compound 100 mg. ESI-MS (m/z): 263.2 [M+H]$^+$.

Step 3: Synthesis of 2-(((3R,4R)-4-fluoropyrrolidin-3-yl)oxy)acetic Acid (10-d)

At room temperature, compound (10-c) (100 mg, 0.38 mmol) was dissolved in dichloromethane (1 mL), trifluoroacetic acid (0.3 mL) was added, and the reaction was performed at room temperature for 1.5 h. The solvent was distilled off under reduced pressure, to afford a trifluoroacetate salt of the title compound 60 mg. ESI-MS (m/z): 164.1 [M+H]⁺.

Step 4: Synthesis of 2-(((3R,4R)-1-(((R)-6-(2-chloro-4-fluorophenyl)-5-(ethoxycarbonyl)-2-(thiazol-2-yl)-3,6-dihydropyrimidin-4-yl)methyl)-4-fluoropyrrolidin-3-yl)oxy)acetic Acid (10-36)

The title compound 13 mg was prepared by a method similar to that described in Step 3 of Example 1 (3,3-difluoropiperidin-4-ol hydrochloride was replaced with compound (10-d)).

The structure was characterized as follows:
$^1$H NMR (400 MHz, DMSO-$d_6$) δ 12.66 (s, 1H), 9.47 (d, J=12.6 Hz, 1H), 7.98 (dd, J=5.1, 3.2 Hz, 1H), 7.93 (dd, J=3.2, 1.9 Hz, 11H), 7.41 (ddd, J=9.5, 6.4, 3.0 Hz, 2H), 7.19 (tt, J=8.5, 2.0 Hz, 1H), 6.04 (d, J=1.4 Hz, 1H), 5.15 (d, J=51.7 Hz, 1H), 4.40-3.77 (m, 9H), 3.12-2.87 (m, 2H), 1.04 (td, J=7.1, 2.1 Hz, 3H). ESI-MS (m/z): 541.2 [M+H]⁺.

Example 11 Synthesis of (4R)-ethyl 4-(2-chloro-4-fluorophenyl)-6-((3,3-difluoro-4-hydroxypyrrolidin-1-yl)methyl)-2-(thiazol-2-yl)-1,4-dihydropyrimidine-5-carboxylate (10-40)

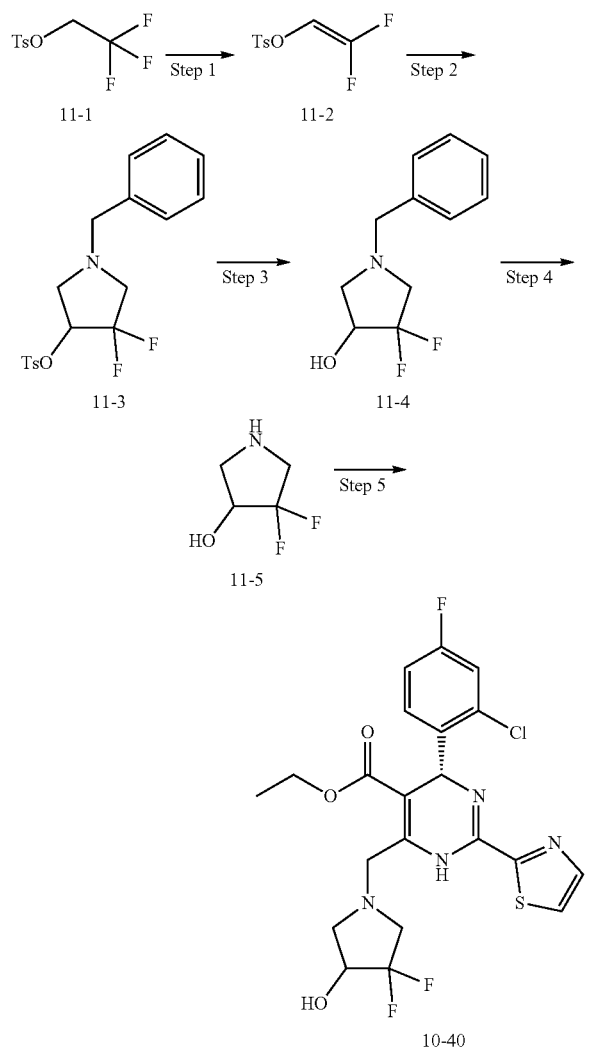

Step 1: Synthesis of 2,2-difluorovinyl p-methylbenzenesulfonate (11-2)

2,2,2-trifluoroethyl p-methylbenzenesulfonate (11-1) (2.57 g, 10.0 mmol) was dissolved in tetrahydrofuran (15 mL), the reaction solution was cooled to −78° C. under protection of nitrogen, and n-butyllithium (2.5 M in hexane, 8 mL, 20 mmol) was slowly dropwise added. The reaction solution was stirred at −78° C. for 40 minutes, and water (4.5 g, 25 mmol) and tetrahydrofuran (10 mL) were slowly dropwise added. The reaction solution was slowly warmed to room temperature. The reaction was added with water (60 mL), and extracted with ethyl acetate (30 mL×2). The organic phase was collected, washed with saturated sodium chloride solution (50 mL×2), dried over anhydrous sodium sulfate, filtered to remove anhydrous sodium sulfate, concentrated under reduced pressure, followed by purification through column chromatography, and the target compound 2.4 g was obtained. ESI-MS (m/z): 235.1 [M+H]⁺.

Step 2: Synthesis of 1-benzyl-4,4-difluoropyrrolidin-3-yl p-methylbenzenesulfonate (11-3)

Compound (11-2) (2340 mg, 10.0 mmol) and N-methoxymethyl-N-trimethylsilyl-benzylamine (9500 mg, 40.0 mmol) were stirred at 130° C. in an oil bath for 5 minutes, and trifluoroacetic acid (110 mg, 1.1 mmol) was added dropwise. The reaction was stirred for an additional 1 hour, cooled to room temperature, diluted with ethyl acetate, and purified to obtain the target compound 3.0 g. ESI-MS (m/z): 368.1 [M+H]⁺.

Step 3: Synthesis of 1-benzyl-4,4-difluoropyrrolidin-3-ol (11-4)

Compound (11-3) (500 mg, 1.35 mmol) was dissolved in methanol (5 mL), magnesium turnings (326 mg, 13.6 mmol) were added, and the reaction was stirred at room temperature for 2 hours. Ice-water (20 mL) was added, concentrated hydrochloric acid was added dropwise until all solids dissolved. The reaction was extracted with ethyl acetate, the aqueous phase was collected, adjusted to pH=7 with saturated sodium hydroxide, and extracted with ethyl acetate. The organic phase was collected, washed with saturated sodium chloride solution, dried over anhydrous sodium sulfate, filtered to remove anhydrous sodium sulfate, concentrated under reduced pressure, and the crude product was purified by preparative chromatography on silica gel (petroleum ether/ethyl acetate=3/2), to afford the target compound 240 mg. ESI-MS (m/z): 214.2 [M+H]⁺.

Step 4: Synthesis of 4,4-difluoropyrrolidin-3-ol (11-5)

Compound (11-4) (100 mg, 0.47 mmol) was dissolved in methanol (2 mL), palladium on carbon (8 mg, 10% Pd, 0.047 mmol) was added, and the reaction was stirred overnight at room temperature under a hydrogen atmosphere. Palladium on carbon was removed by filtration, and the reaction was concentrated under reduced pressure, to afford the target compound 50 mg. ESI-MS (m/z): 124.1 [M+H]⁺.

Step 5: Synthesis of (4R)-ethyl 4-(2-chloro-4-fluorophenyl)-6-((3,3-difluoro-4-hydroxypyrrolidin-1-yl)methyl)-2-(thiazol-2-yl)-1,4-dihydropyrimidine-5-carboxylate (10-40)

The title compound 33 mg was prepared by a method similar to that described in Step 3 of Example 1 (3,3-difluoropiperidin-4-ol hydrochloride was replaced with compound (11-5)).

The structure was characterized as follows:

$^1$H NMR (400 MHz, CDCl$_3$) δ 9.36 (s, 1H), 7.84 (d, J=3.1 Hz, 1H), 7.48 (s, 1H), 7.31 (s, 1H), 7.14 (dt, J=8.5, 2.5 Hz, 1H), 6.94 (s, 1H), 6.20 (d, J=6.9 Hz, 1H), 4.45-3.87 (m, 6H), 3.20 (s, 2H), 2.85 (s, 1H), 1.13 (td, J=7.1, 4.7 Hz, 3H). ESI-MS (m/z): 501.0 [M+H]$^+$.

Example 12 Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-3-yl)oxy)acetic acid (10-42)

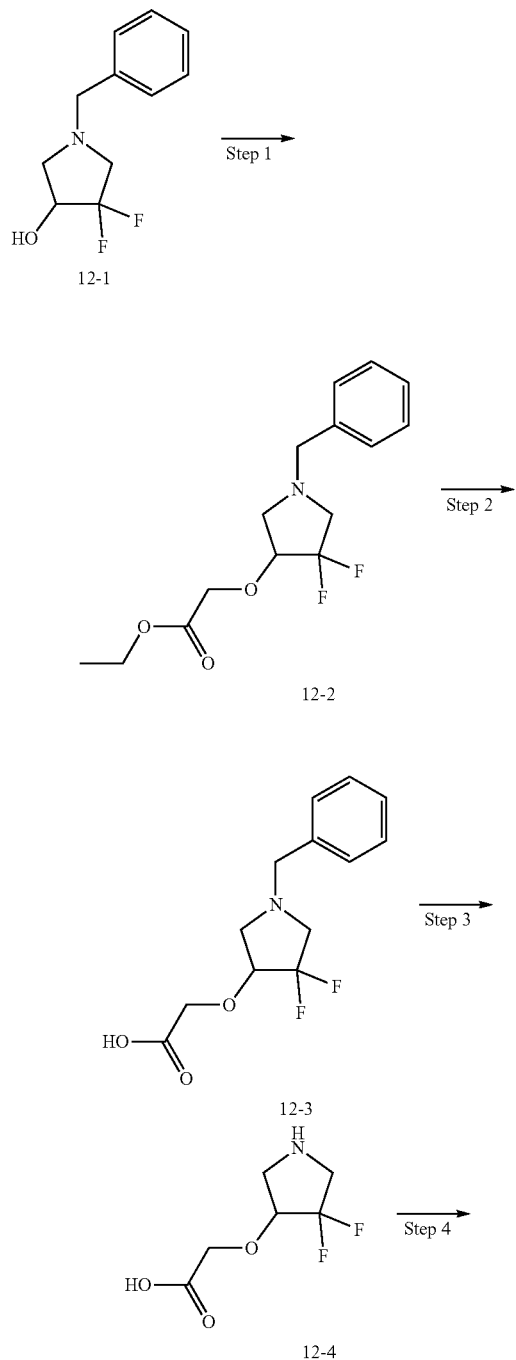

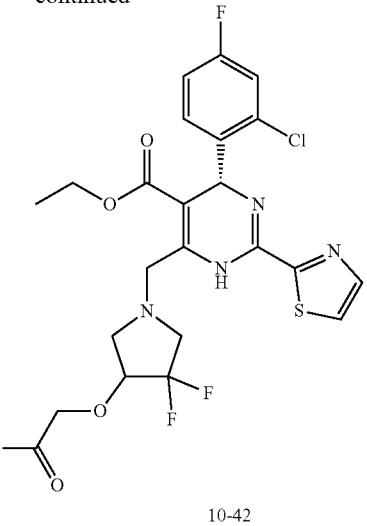

10-42

Step 1: Synthesis of ethyl 2-((1-benzyl-4,4-difluoropyrrolidin-3-yl)oxy)acetate (12-2)

1-benzyl-4,4-difluoropyrrolidin-3-ol (12-1) (100 mg, 0.47 mmol) was dissolved in tetrahydrofuran (5 mL), sodium hydride (40 mg 60% in oil, 0.94 mmol) was added under cooling in an ice bath, and the reaction was warmed to room temperature and allowed to proceed for 2 h. Ethyl bromoacetate (119 mg, 0.71 mmol) was added under cooling in an ice bath, and the reaction was perform at room temperature until completion of the reaction. The reaction was added with saturated ammonium chloride (3 mL), diluted with dichloromethane (15 mL), washed with saturated brine, and dried over anhydrous sodium sulfate. Anhydrous sodium sulfate was removed by filtration, and the solvent was distilled off under reduced pressure, to afford the title compound 123 mg, which was used directly for the next reaction without purification. ESI-MS (m/z): 300.1 [M+H]$^+$.

Step 2: Synthesis of 2-((1-benzyl-4,4-difluoropyrrolidin-3-yl)oxy)acetic acid (12-3)

Compound (12-2) (123 mg, 0.41 mmol) was dissolved in a mixed solution of tetrahydrofuran and water (v:v=1:1, 3 mL), lithium hydroxide monohydrate (104 mg, 2.47 mmol) was added, and the reaction was performed at room temperature for 3.5 h. The reaction was adjusted to pH 5 with an aqueous solution of citric acid, added with dichloromethane (15 mL), washed with saturated brine, and dried over anhydrous sodium sulfate. The drying agent was removed by filtration, the solvent was distilled off under reduced pressure, and the crude product was purified by preparative chromatography, to afford the title compound 50 mg. ESI-MS (m/z): 272.1 [M+H]$^+$.

Step 3: Synthesis of 2-((4,4-difluoropyrrolidin-3-yl)oxy)acetic acid (12-4)

Compound (12-3) (50 mg, 0.18 mmol) was dissolved in methanol (2 mL), palladium on carbon (5 mg, 10% Pd, 0.018 mmol) was added, and the reaction was stirred overnight at room temperature under a hydrogen atmosphere. The reaction was filtered to remove palladium on carbon, and concentrated under reduced pressure, to afford the target compound 30 mg. ESI-MS (m/z): 182.1 [M+H]$^+$.

Step 4: Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-3-yl)oxy)acetic acid The title compound 25 mg was prepared by a method similar to that described in Step 3 of Example 1 (3,3-difluoropiperidin-4-ol hydrochloride was replaced with compound (12-4)).

The structure was characterized as follows:

$^1$H NMR (400 MHz, CDCl$_3$) δ 7.87 (dd, J=3.1, 1.3 Hz, 1H), 7.49 (s, 1H), 7.33 (t, J=7.4 Hz, 1H), 7.14 (dd, J=8.5, 2.6 Hz, 1H), 6.96 (t, J=8.3 Hz, 1H), 6.19 (d, J=2.3 Hz, 1H), 4.44 (d, J=16.3 Hz, 1H), 4.26 (dd, J=16.3, 2.3 Hz, 4H), 4.08-4.01 (m, 2H), 3.43 (s, 4H), 1.12 (t, J=7.1 Hz, 3H). ESI-MS (m/z): 559.2 [M+H]$^+$.

Example 13 Synthesis of (E)-3-(4-(((R)-6-(2-chloro-4-fluorophenyl)-5-(ethoxycarbonyl)-2-(thiazol-2-yl)-3,6-dihydropyrimidin-4-yl)methyl)morpholin-3-yl)acrylic Acid (10-182)

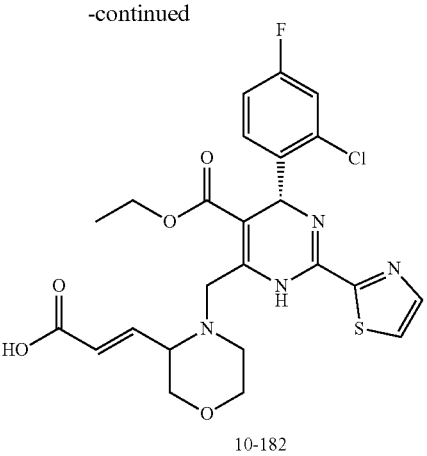

10-182

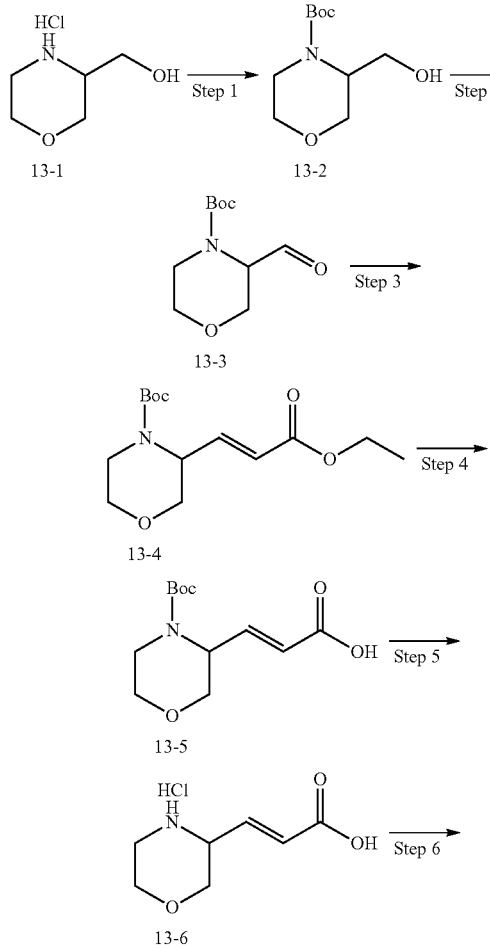

Step 1: Synthesis of tert-butyl 3-(hydroxymethyl)morpholine-4-carboxylate (13-2)

Morpholin-3-yl methanol hydrochloride (1.0 g, 6.5 mmol), triethylamine (1.64 g, 16 mmol) and dichloromethane (10 mL) were added to a 50 mL three-neck flask, stirred under protection of nitrogen, and cooled to 0° C., followed by addition of di-tert-butyl dicarbonate (2.1 g, 10 mmol). After the addition, the reaction was warmed to room temperature and allowed to proceed for 3 hours. The reaction solution was slowly poured into water, and extracted with dichloromethane. The organic phase was collected, washed with saturated brine, and dried over anhydrous sodium sulfate. Anhydrous sodium sulfate was removed by filtration, the solvent was distilled off under reduced pressure, and the target compound 1.32 g was obtained after purification. ESI-MS (m/z): 162.0 [M+H]$^+$.

Step 2: Synthesis of tert-butyl 3-formylmorpholine-4-carboxylate (13-3)

Compound (13-2) (500 mg, 2.3 mmol) and dichloromethane (10 mL) were added to a 50 mL three-neck flask, Dess-Martin reagent (1.3 g, 3.0 mmol) was added thereto at room temperature, and the reaction was stirred for 3 hours. The reaction solution was slowly poured into aqueous sodium bicarbonate, and extracted with dichloromethane. The organic phase was collected, washed with saturated brine, dried over anhydrous sodium sulfate, filtered to remove anhydrous sodium sulfate, and the solvent was distilled off under reduced pressure, to afford a crude product 520 mg. ESI-MS (m/z): 160.0 [M+H]$^+$.

Step 3: Synthesis of (E)-tert-butyl 3-(3-ethoxy-3-oxoprop-1-en-1-yl)morpholine-4-carboxylate (13-4)

Triethyl phosphonoacetate (600 mg, 3.3 mmol) and tetrahydrofuran (10 mL) were added to a 50 mL three-neck flask, stirred under protection of nitrogen, and cooled to 0° C., followed by addition of sodium hydride (320 mg, 6.6 mmol). After the addition, the reaction was performed for 10 min, and then a solution of compound (13-3) (520 mg, 3.3 mmol) in tetrahydrofuran (5 mL) was added dropwise. After the dropwise addition, the reaction was warmed to room temperature, and allowed to proceed for 16 h. The reaction solution was slowly poured into water, and extracted with ethyl acetate. The organic phase was collected, washed with saturated brine, and dried over anhydrous sodium sulfate. The drying agent was removed by filtration, and the solvent was distilled off under reduced pressure, to afford a crude product 620 mg. ESI-MS (m/z): 186.0 [M+H]$^+$.

Step 4: Synthesis of (E)-3-(4-(tert-butoxycarbonyl) morpholin-3-yl)acrylic Acid (13-5)

At room temperature, compound (13-4) (620 mg, 2.2 mmol), anhydrous ethanol (10 mL) and water (10 mL) were added to a 50 mL flask, stirred followed by addition of sodium hydroxide (260 mg, 6.6 mmol), and the reaction was performed at room temperature for 4 h. The reaction was then quenched by adding water (20 mL) thereto, subjected to rotary evaporation to remove ethanol, and extracted with methyl tert-butyl ether. The aqueous phase was adjusted to pH 2-3 with 1N aqueous hydrochloric acid, and then extracted with ethyl acetate. The organic phase was collected, washed with saturated brine, and dried over anhydrous sodium sulfate. Anhydrous sodium sulfate was removed by filtration, and the solvent was distilled off under reduced pressure, to afford a crude product 460 mg, which was used directly for the next reaction without purification. ESI-MS (m/z): 158.0 [M+H]$^+$.

Step 5: Synthesis of (E)-3-(morpholin-3-yl)acrylic Acid (13-6)

A solution of 4N hydrochloric acid in dioxane (5 mL) was added to a 25 mL flask, cooled to 0° C., followed by dropwise addition of a solution of compound (13-5) (460 mg, 1.8 mmol) in ethyl acetate (5 mL), and the reaction was performed at room temperature for 2 h. The solvent was distilled off under reduced pressure, to afford a hydrochloride salt of the title compound 300 mg. ESI-MS (m/z): 158.0 [M+H]$^+$.

Step 6: Synthesis of (E)-3-(4-(((R)-6-(2-chloro-4-fluorophenyl)-5-(ethoxycarbonyl)-2-(thiazol-2-yl)-3,6-dihydropyrimidin-4-yl)methyl)morpholin-3-yl) acrylic Acid (10-182)

The title compound 47 mg was prepared by a method similar to that described in Step 3 of Example 1 (3,3-difluoropiperidin-4-ol hydrochloride was replaced with compound (13-6)).

The structure was characterized as follows:
$^1$H NMR (400 MHz, DMSO-d$_6$) δ 12.47 (s, 1H), 9.69 (d, J=28.7 Hz, 1H), 8.11-7.91 (m, 2H), 7.53-7.27 (m, 2H), 7.23-7.10 (m, 1H), 6.66 (ddd, J=35.0, 15.8, 8.8 Hz, 1H), 6.11 (dd, J=28.6, 15.7 Hz, 1H), 6.03 (d, J=14.0 Hz, 1H), 4.02-3.85 (m, 4H), 3.84-3.70 (m, 2H), 3.70-3.57 (m, 1H), 3.46-3.35 (m, 2H), 2.84 (dd, J=38.9, 12.6 Hz, 1H), 2.48-2.41 (m, 1H), 1.03 (t, J=7.1 Hz, 3H). ESI-MS (m/z): 535.1 [M+H]$^+$.

Example 14 Synthesis of (E)-3-(4-(((R)-6-(2-chloro-4-fluorophenyl)-5-(ethoxycarbonyl)-2-(thiazol-2-yl)-3,6-dihydropyrimidin-4-yl)methyl)morpholin-2-yl)acrylic Acid (10-180)

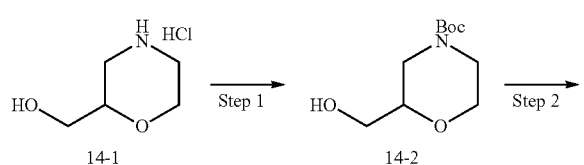

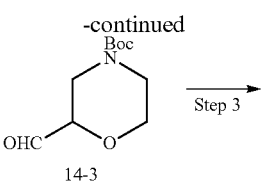

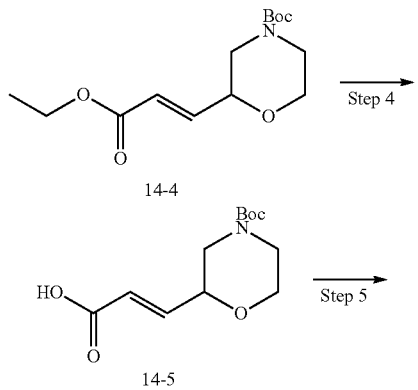

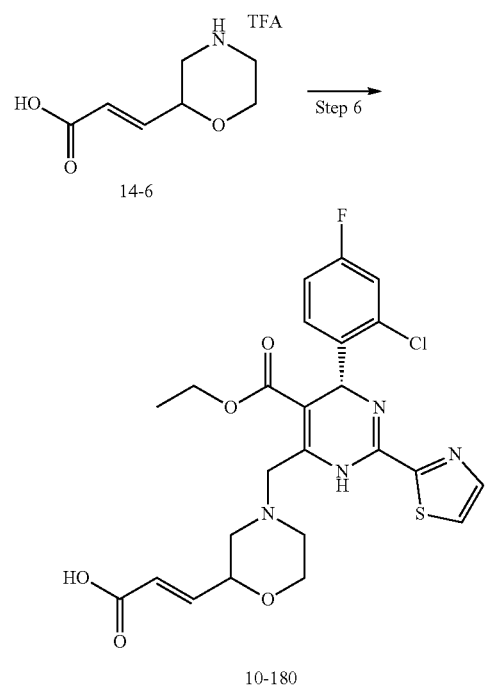

According to the above reaction scheme, employing procedures similar to those in Example 13 and using morpholin-2-yl methanol hydrochloride as a starting material, the title compound (22 mg) was prepared.

The structure was characterized as follows:
$^1$H NMR (400 MHz, DMSO-d$_6$) δ 12.40 (s, 1H), 9.64 (d, J=2.4 Hz, 1H), 8.02 (d, J=2.92 Hz, 2H), 7.95 (d, J=3.12 Hz, 2H), 7.21-7.16 (m, 1H), 6.83-6.72 (m, 1H), 6.05 (d, 1H), 6.00-5.91 (m, 1H), 4.27-4.22 (m, 1H), 4.00-3.85 (m, 5H), 3.70-3.61 (m, 1H), 3.07-2.94 (m, 1H), 2.84-2.66 (m, 1H), 2.42-2.67 (m, 1H), 2.17-2.04 (m, 1H), 1.04 (t, J=7.0 Hz, 3H). ESI-MS (m/z): 535.1 [M+H]$^+$.

Example 15 2-((4-(((R)-6-(2-chloro-4-fluorophenyl)-5-(ethoxycarbonyl)-2-(thiazol-2-yl)-3,6-dihydropyrimidin-4-yl)methyl)morpholin-3-yl)methoxy)acetic Acid (10-162)

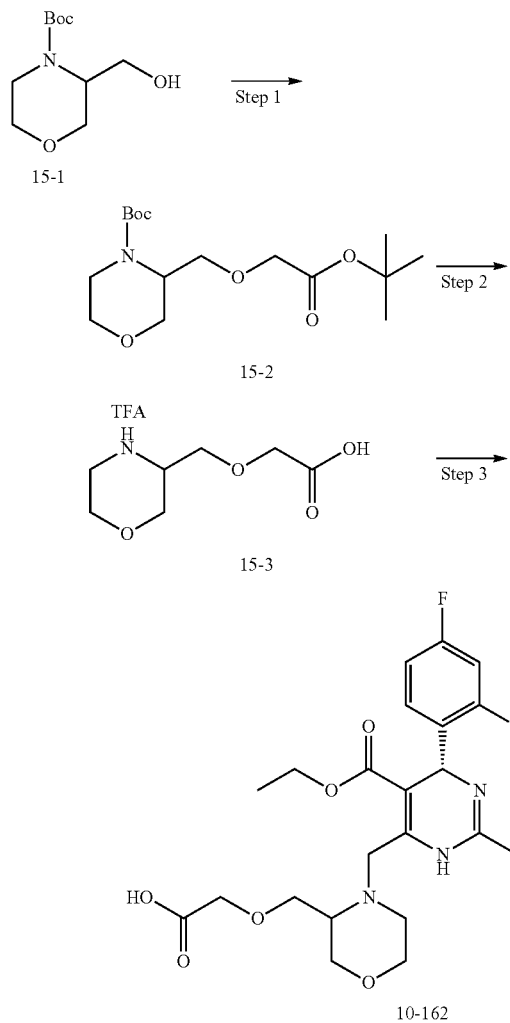

Step 1: Synthesis of tert-butyl 3-((2-(tert-butoxy)-2-oxoethoxy)methyl)morpholine-4-carboxylate (15-2)

Tert-butyl 3-(hydroxymethyl)morpholine-4-carboxylate (200 mg, 0.99 mmol) and tetrahydrofuran (6 mL) were added to a 50 mL three-neck flask, sodium hydride (47.3 mg, 1.2 mmol) was added thereto at room temperature, stirred for 30 minutes, followed by addition of tert-butyl bromoacetate (192 mg, 0.99 mmol), and the reaction was performed at room temperature for 3 hours. The reaction solution was slowly poured into 10 mL water, adjusted to pH 2-3 with 1N aqueous hydrochloric acid, and extracted with ethyl acetate. The organic phase was collected, washed with saturated brine, dried over anhydrous sodium sulfate, filtered to remove anhydrous sodium sulfate, and the solvent was distilled off under reduced pressure, to afford a crude product 300 mg. ESI-MS (m/z): 232.0 [M+H]$^+$.

Step 2: Synthesis of 2-(morpholin-3-ylmethoxy)acetic Acid Trifluoroacetate Salt (15-3)

Compound (15-2) (300 mg, 0.9 mmol) and dichloromethane (6 mL) were added to a 25 mL flask, cooled to 0° C., trifluoroacetic acid (2 mL) was then added thereto, and the reaction was performed at room temperature for 3 hours. The solvent was distilled off under reduced pressure, to afford a crude product 250 mg. ESI-MS (m/z): 176.0 [M+H]$^+$.

Step 3: Synthesis of 2-((4-(((R)-6-(2-chloro-4-fluorophenyl)-5-(ethoxycarbonyl)-2-(thiazol-2-yl)-3,6-dihydropyrimidin-4-yl)methyl)morpholin-3-yl)methoxy)acetic Acid (10-162)

The title compound 73 mg was prepared by a method similar to that described in Step 3 of Example 1 (3,3-difluoropiperidin-4-ol hydrochloride was replaced with compound (15-3)).

The structure was characterized as follows:
$^1$H NMR (400 MHz, DMSO-d$_6$) δ 12.70 (s, 1H), 9.79 (d, J=22.9 Hz, 1H), 8.01 (t, J=2.8 Hz, 1H), 7.93 (t, J=3.0 Hz, 1H), 7.50-7.37 (m, 2H), 7.18 (qd, J=8.3, 2.6 Hz, 1H), 6.04 (d, J=1.4 Hz, 1H), 4.32 (dd, J=20.0, 17.6 Hz, 1H), 4.09-3.91 (m, 4H), 3.87-3.63 (m, 3H), 3.62-3.50 (m, 3H), 3.46 (dd, J=11.2, 8.2 Hz, 1H), 2.87-2.66 (m, 2H), 2.48-2.39 (m, 1H), 1.05 (td, J=7.0, 1.5 Hz, 3H). ESI-MS (m/z): 553.1 [M+H]$^+$.

Example 16 Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-5,5-difluoropiperidin-3-yl)methoxy)acetic Acid (10-136)

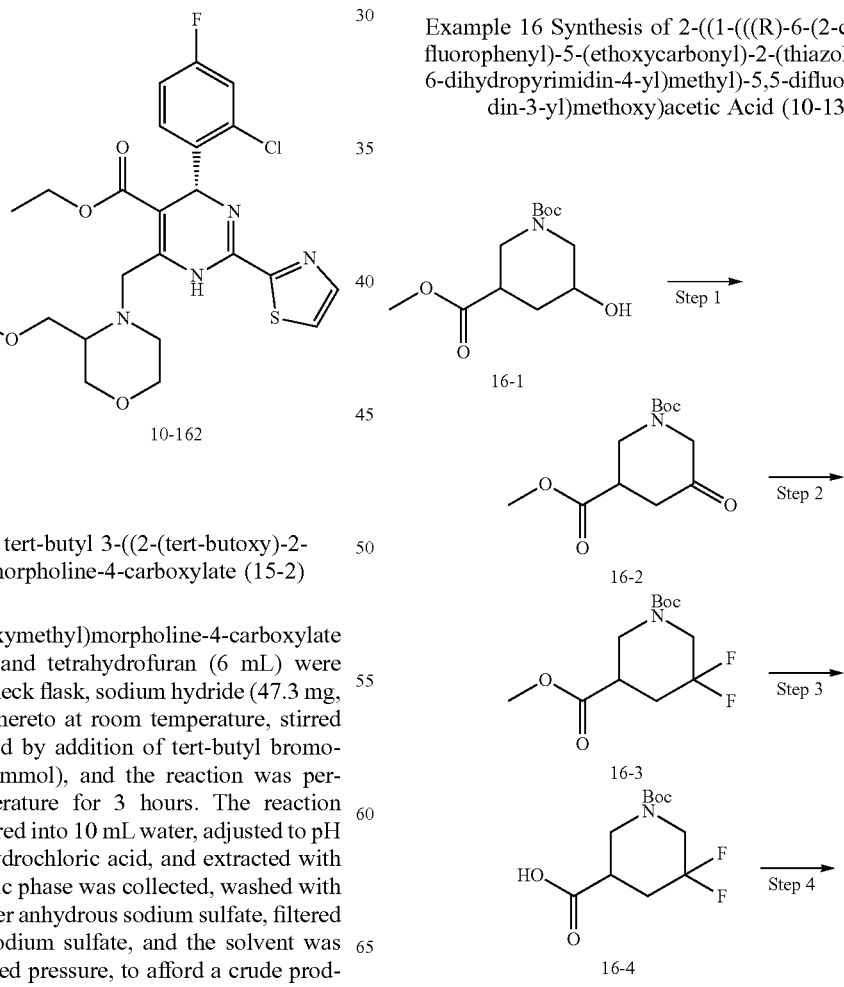

-continued

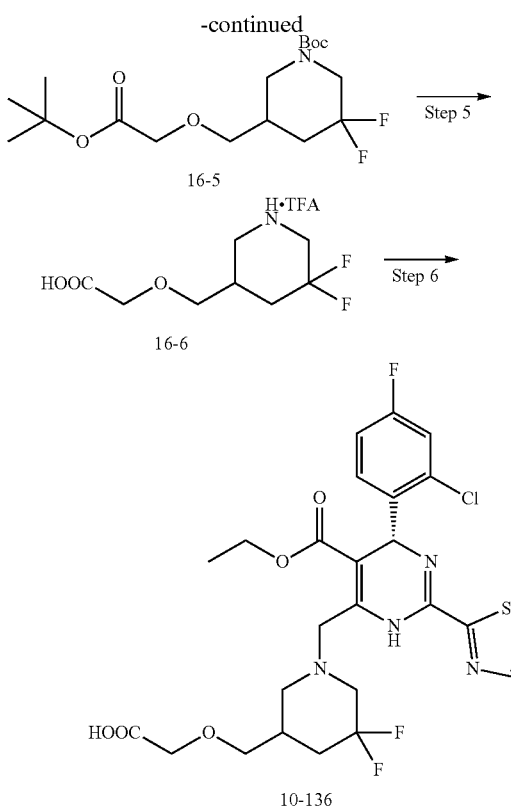

Step 1: Synthesis of 1-tert-butyl 3-methyl 5-oxopiperidine-1,3-dicarboxylate (16-2)

At room temperature, 1-tert-butyl 3-methyl 5-hydroxypiperidine-1,3-dicarboxylate (16-1) (1.0 g, 3.86 mmol) was dissolved in dichloromethane (20 mL), the reaction was cooled to 0° C. after complete dissolution, Dess-Martin reagent (3.27 g, 7.71 mmol) was added with stirring, and the reaction was stirred overnight at room temperature after the addition. A large amount of white solid precipitated in the reaction solution, which was filtered, and the filtrate was washed successively with water (50 mL) and saturated aqueous sodium carbonate (50 mL). The organic phase was dried over anhydrous sodium sulfate, and the solvent was distilled off under reduced pressure, to afford the title compound 1.0 g. ESI-MS (m/z): 202.1 [M+H−56]$^+$.

Step 2: Synthesis of 1-tert-butyl 3-methyl 5,5-difluoropiperidine-1,3-dicarboxylate (16-3)

Compound (16-2) (1.0 g, 3.89 mmol) was dissolved in dichloromethane (20 mL), the reaction was cooled to −70° C. after dissolved with stirring, DAST (1.9 g, 11.67 mmol) was slowly dropwise added, and the reaction was warmed to room temperature and allowed to proceed for 4.5 h after the dropwise addition. After complete reaction of the starting material monitored by LC-MS, the reaction solution was quenched with saturated aqueous sodium bicarbonate (20 mL), extracted with dichloromethane, dried, and purified to obtain the title compound 550 mg. ESI-MS (m/z): 224.1 [M+H−56]$^+$.

Step 3: Synthesis of tert-butyl 3,3-difluoro-5-(hydroxymethyl)piperidine-1-carboxylate (16-4)

At room temperature, compound (16-3) (500 mg, 1.79 mmol) was added to methanol (8 mL), the reaction was cooled to 0° C., and sodium borohydride (272 mg, 7.16 mmol) was slowly added in portions. After the addition, the reaction was performed at room temperature overnight, incomplete reaction of the starting material was monitored by LC-MS, sodium borohydride (136 mg, 3.58 mmol) was supplemented, and the reaction was continued overnight until complete reaction of the starting material. The reaction was quenched by adding water (20 mL), and extracted with ethyl acetate. The organic phase was combined, washed with water, dried over anhydrous sodium sulfate, and the solvent was distilled off under reduced pressure, to afford the title compound 500 mg. ESI-MS (m/z): 196.1 [M+H−56]$^+$.

Step 4: Synthesis of tert-butyl 5-((2-(tert-butoxy)-2-oxoethoxy)methyl)-3,3-difluoropiperidine-1-carboxylate (16-5)

At room temperature, compound (16-4) (150 mg, 0.60 mmol) was added to tetrahydrofuran (4 mL), the reaction was cooled to 0° C., and sodium hydride (48 mg, 1.2 mmol) was slowly added. After the addition, the reaction was stirred at 0° C. for 30 min, and then a solution of tert-butyl bromoacetate (140 mg, 0.72 mmol) in tetrahydrofuran (1.0 mL) was added. The reaction was performed at room temperature overnight, incomplete reaction of the starting material was monitored by LC-MS, tert-butyl bromoacetate (35 mg, 0.18 mmol) was supplemented, and the reaction was continued overnight until complete reaction of the starting material. The reaction solution was quenched by adding a saturated aqueous solution of ammonium chloride (5 mL), diluted with water (20 mL), and extracted with ethyl acetate. The organic phase was combined, washed with water, dried and purified, to afford the title compound 120 mg. ESI-MS (m/z): 254.1 [M+H−112]$^+$.

Step 5: Synthesis of 2-((5,5-difluoropiperidin-3-yl)methoxy)acetic acid (16-6)

At room temperature, compound (16-5) (60 mg, 0.16 mmol) was added to dichloromethane (3 mL), the reaction was cooled to 0° C., and trifluoroacetic acid (1.0 mL) was added. After the addition, the reaction was performed at room temperature for 1 h, incomplete reaction of the starting material was monitored by LC-MS, the reaction was then continued overnight until complete reaction of the starting material. The solvent was distilled off under reduced pressure, to afford a trifluoroacetate salt of the title compound 60 mg. ESI-MS (m/z): 210.1 [M+H]$^+$.

Step 6: Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-5,5-difluoropiperidin-3-yl)methoxy)acetic acid (10-136)

The title compound 19 mg was prepared by a method similar to that described in Step 3 of Example 1 (3,3-difluoropiperidin-4-ol hydrochloride was replaced with compound (16-5)).

The structure was characterized as follows:

$^1$H NMR (400 MHz, chloroform-d) δ 7.93 (dd, J=9.67, 3.06 Hz, 1H), 7.54 (s, 1H), 7.46-7.31 (m, 1H), 7.13 (ddd, J=8.55, 2.63, 1.35 Hz, 1H), 6.96 (d, J=8.50 Hz, 1H), 6.24 (d, J=3.93 Hz, 1H), 4.28 (d, J=16.74 Hz, 1H), 4.14 (d, J=16.81 Hz, 1H), 3.94 (t, J=16.64 Hz, 2H), 3.80 (t, J=8.68 Hz, 1H), 3.65 (t, J=8.64 Hz, 1H), 3.56-3.43 (m, 1H), 2.94 (d, J=53.06 Hz, 4H), 2.65 (s, 1H), 2.45 (s, 1H), 2.13 (dd, J=26.84, 13.90

Hz, 1H), 1.92 (d, J=9.36 Hz, 1H), 1.13 (td, J=7.10, 3.76 Hz, 3H). ESI-MS (m/z): 587.2 [M+H]⁺.

Example 17 Synthesis of (E)-3-(1-(((R)-6-(2-chloro-4-fluorophenyl)-5-(ethoxycarbonyl)-2-(thiazol-2-yl)-3,6-dihydropyrimidin-4-yl)methyl)-5,5-difluoropiperidin-3-yl)acrylic Acid (10-116)

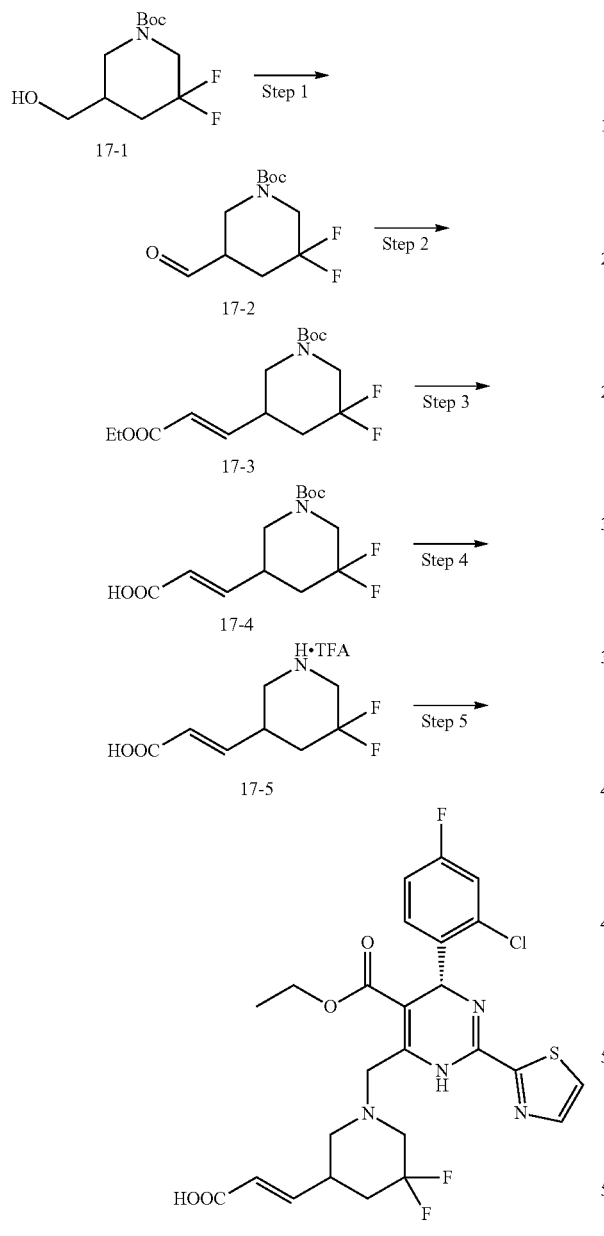

Step 1: Synthesis of tert-butyl 3,3-difluoro-5-formylpiperidine-1-carboxylate (17-2)

At room temperature, tert-butyl 3,3-difluoro-5-(hydroxymethyl)piperidine-1-carboxylate (17-1) (50 mg, 0.2 mmol) was dissolved in dichloromethane (2.0 mL), the reaction was cooled to 0° C. after complete dissolution, Dess-Martin reagent (102 mg, 0.24 mmol) was added with stirring, and the reaction was performed at room temperature for 3 h after the addition. A large amount of white solid precipitated in the reaction solution, which was filtered, and the filtrate was evaporated under reduced pressure, and the title compound 50 mg was obtained.

Step 2: Synthesis of (E)-tert-butyl 5-(3-ethoxy-3-oxoprop-1-en-1-yl)-3,3-difluoropiperidine-1-carboxylate (17-3)

At room temperature, compound (17-2) (50 mg, 0.2 mmol) was dissolved in dichloromethane (2.0 mL), (carbethoxymethylene)triphenylphosphorane (70 mg, 0.2 mmol) was added with stirring after complete dissolution, and the reaction was performed at room temperature overnight after the addition. The reaction solution was purified to afford the title compound 30 mg. ESI-MS (m/z): 264.1 [M+H−56]⁺.

Step 3: Synthesis of (E)-3-[1-(tert-butoxycarbonyl)-5,5-difluoropiperidin-3-yl)acrylic Acid (17-4)

At room temperature, compound (17-3) (30 mg, 0.1 mmol) was dissolved in tetrahydrofuran (4.0 mL) and water (2 mL), lithium hydroxide (19 mg, 0.47 mmol) was added with stirring after complete dissolution, and the reaction was performed at room temperature for 4 h after the addition. The reaction solution was diluted with water, adjusted to pH=3-4 with 1N hydrochloric acid, and extracted with ethyl acetate. The organic phase was combined, washed with water, and dried to afford the title compound 30 mg.

Step 4: Synthesis of (E)-3-(5,5-difluoropiperidin-3-yl)acrylic Acid Trifluoroacetate Salt (17-5)

At room temperature, compound (17-4) (30 mg, 0.1 mmol) was added to dichloromethane (1.5 mL), cooled to 0° C., followed by addition of trifluoroacetic acid (0.5 mL). After the addition, the reaction was performed at room temperature for 1.5 h. The solvent in the reaction solution was distilled off under reduced pressure, to afford the title compound 30 mg. ESI-MS (m/z): 192.1 [M+H]⁺.

Step 5: Synthesis of (E)-3-(1-(((R)-6-(2-chloro-4-fluorophenyl)-5-(ethoxycarbonyl)-2-(thiazol-2-yl)-3,6-dihydropyrimidin-4-yl)methyl)-5,5-difluoropiperidin-3-yl)acrylic Acid (10-116)

The title compound 10 mg was prepared by a method similar to that described in Step 3 of Example 1 (3,3-difluoropiperidin-4-ol hydrochloride was replaced with compound (17-5)).

The structure was characterized as follows:

¹H NMR (400 MHz, chloroform-d) δ 7.90 (s, 1H), 7.36 (s, 1H), 7.14 (dt, J=8.53, 2.80 Hz, 1H), 7.02-6.86 (m, 2H), 6.25 (d, J=8.50 Hz, 1H), 5.90 (dd, J=23.97, 15.72 Hz, 1H), 4.20 (d, J=15.93 Hz, 1H), 4.04 (q, J=5.70, 5.05 Hz, 3H), 3.11 (d, J=62.19 Hz, 3H), 2.71 (s, 2H), 2.36 (s, 2H), 1.14 (td, J=7.06, 5.31 Hz, 3H). ESI-MS (m/z): 569.2 [M+H]⁺.

Example 18 Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)methoxy)acetic Acid (10-56)

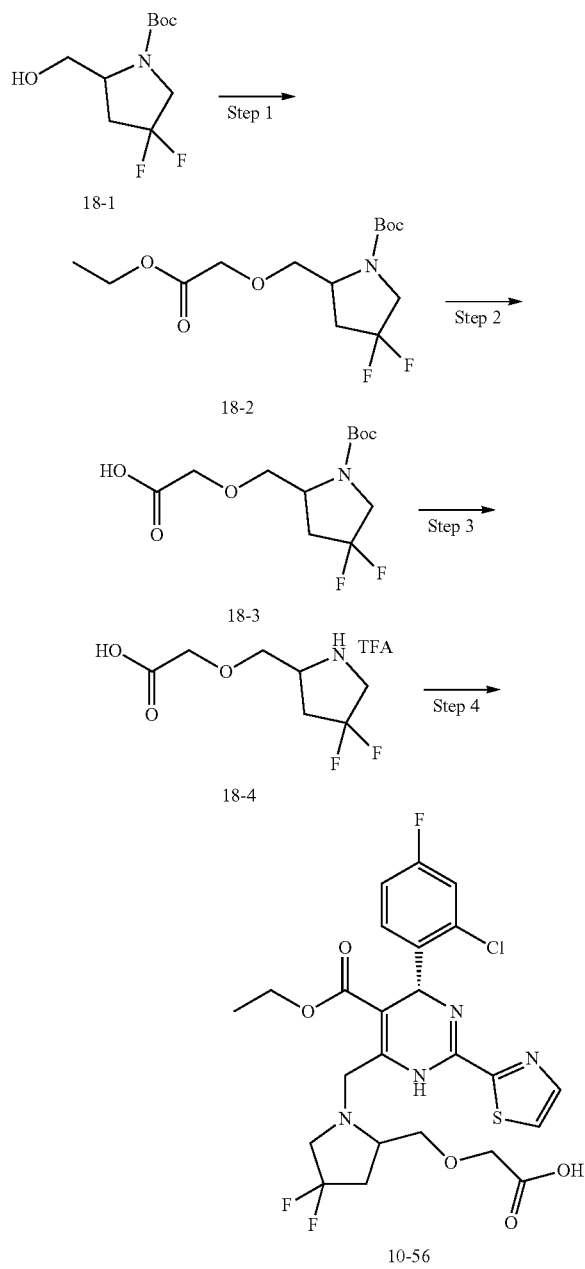

Step 1: Synthesis of tert-butyl 2-((2-ethoxy-2-oxo-ethoxy)methyl)-4,4-difluoropyrrolidine-1-carboxylate (18-2)

Tert-butyl 4,4-difluoro-2-(hydroxymethyl)pyrrolidine-1-carboxylate (18-1) (80 mg, 0.34 mmol) was dissolved in tetrahydrofuran (5 mL), sodium hydride (27 mg 60% in oil, 0.68 mmol) was added under cooling in an ice bath, and the reaction was warmed to room temperature and allowed to proceed for 2 h. Under cooling in an ice bath, ethyl bromoacetate (85 mg, 0.51 mmol) was added, and the reaction was performed at room temperature for 4 h. The reaction was added with saturated ammonium chloride (3 mL), diluted with dichloromethane (15 mL), washed with saturated brine, and dried over anhydrous sodium sulfate. The title compound 100 mg was obtained after work up, and was used directly for the next reaction without purification.

Step 2: Synthesis of 2-((1-(tert-butoxycarbonyl)-4,4-difluoropyrrolidin-2-yl)methoxy)acetic Acid (18-3)

Compound (18-2) (100 mg, 0.31 mmol) was dissolved in a mixed solution of tetrahydrofuran and water (v:v=1:1, 3 mL), lithium hydroxide monohydrate (45 mg, 1.86 mmol) was added, and the reaction was performed at room temperature for 3.5 h. The reaction was adjusted to pH 5 with an aqueous solution of citric acid, added with dichloromethane (15 mL), washed with saturated brine, and dried over anhydrous sodium sulfate, and the title compound 80 mg was obtained after work up.

Step 3: Synthesis of 2-((4,4-difluoropyrrolidin-2-yl)methoxy)acetic Acid (18-4)

At room temperature, compound (18-3) (80 mg, 0.27 mmol) was dissolved in dichloromethane (1 mL), trifluoroacetic acid (0.3 mL) was added, and the reaction was performed at room temperature for 1.5 h. The solvent was distilled off under reduced pressure, to afford a trifluoroacetate salt of the title compound 60 mg.

Step 4: Synthesis of 2-((1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)methoxy)acetic Acid (10-56)

The title compound 25 mg was prepared by a method similar to that described in Step 3 of Example 1 (3,3-difluoropiperidin-4-ol hydrochloride was replaced with compound (18-4)).

The structure was characterized as follows:
$^1$H NMR (400 MHz, DMSO-d$_6$) δ 12.52 (s, 1H), 9.54 (s, 1H), 7.96 (dd, J=27.4, 3.2 Hz, 2H), 7.51-7.27 (m, 2H), 7.19 (td, J=8.5, 2.8 Hz, 1H), 6.01 (d, J=12.5 Hz, 1H), 4.21 (d, J=2.7 Hz, 1H), 4.01-3.84 (m, 3H), 3.66-3.44 (m, 3H), 3.34-3.26 (m, 4H), 3.14-2.96 (m, 1H), 2.33-2.07 (m, 1H), 1.08-0.98 (m, 3H). ESI-MS (m/z): 573.2 [M+H]$^+$.

Example 19 Synthesis of 2-((4-(((R)-6-(2-chloro-4-fluorophenyl)-5-(ethoxycarbonyl)-2-(thiazol-2-yl)-3,6-dihydropyrimidin-4-yl)methyl)morpholin-2-yl)methoxy)acetic Acid (10-160)

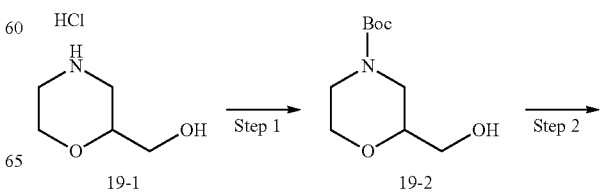

-continued

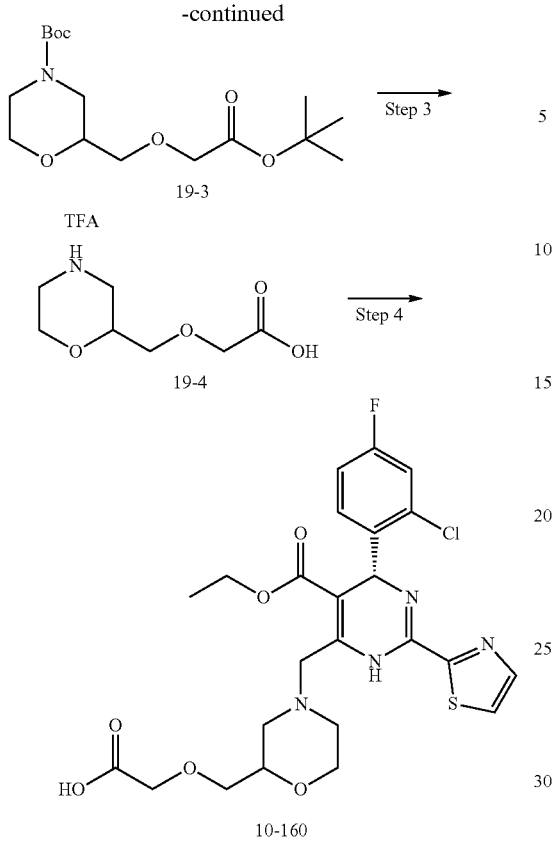

Step 1: Synthesis of tert-butyl 2-(hydroxymethyl)morpholine-4-carboxylate (19-2)

Morpholin-2-yl methanol hydrochloride (19-1) (500 mg, 3.3 mmol), triethylamine (0.82 g, 8 mmol) and dichloromethane (10 mL) were added to a 50 mL three-neck flask, stirred under protection of nitrogen, cooled to 0° C., and then di-tert-butyl dicarbonate (1.1 g, 5 mmol) was added. After the addition, the reaction was performed at room temperature for 3 hours. The reaction solution was slowly poured into water, and extracted with dichloromethane (30 mL×3). The organic phase was collected, washed with saturated brine, and dried over anhydrous sodium sulfate. Anhydrous sodium sulfate was removed by filtration, the solvent was distilled off under reduced pressure, and the title compound 0.6 g was obtained after purification. ESI-MS (m/z): 162.0 [M+H]$^+$.

Step 2 to Step 4

The title compound 70 mg was prepared from compound (19-2), employing procedures similar to those in Step 1 to Step 3 of Example 15.

The structure was characterized as follows:

$^1$H NMR (400 MHz, DMSO-d$_6$) δ 12.60 (s, 1H), 9.66 (d, J=2.7 Hz, 1H), 8.07-7.90 (m, 2H), 7.49-7.35 (m, 2H), 7.18 (td, J=8.5, 2.5 Hz, 1H), 6.05 (s, 1H), 4.04 (s, 1H), 4.01-3.80 (m, 6H), 3.68 (s, 1H), 3.63-3.43 (m, 3H), 2.78 (ddd, J=56.5, 46.6, 11.4 Hz, 2H), 2.41-2.25 (m, 1H), 2.15 (dt, J=31.9, 10.6 Hz, 1H), 1.05 (t, J=7.0 Hz, 3H). ESI-MS (m/z): 553.1 [M+H]$^+$.

Example 20 Synthesis of N-((4-(((R)-6-(2-chloro-4-fluorophenyl)-5-(ethoxycarbonyl)-2-(thiazol-2-yl)-3,6-dihydropyrimidin-4-yl)methyl)morpholin-2-yl)methyl)-N-methylglycine (10-168)

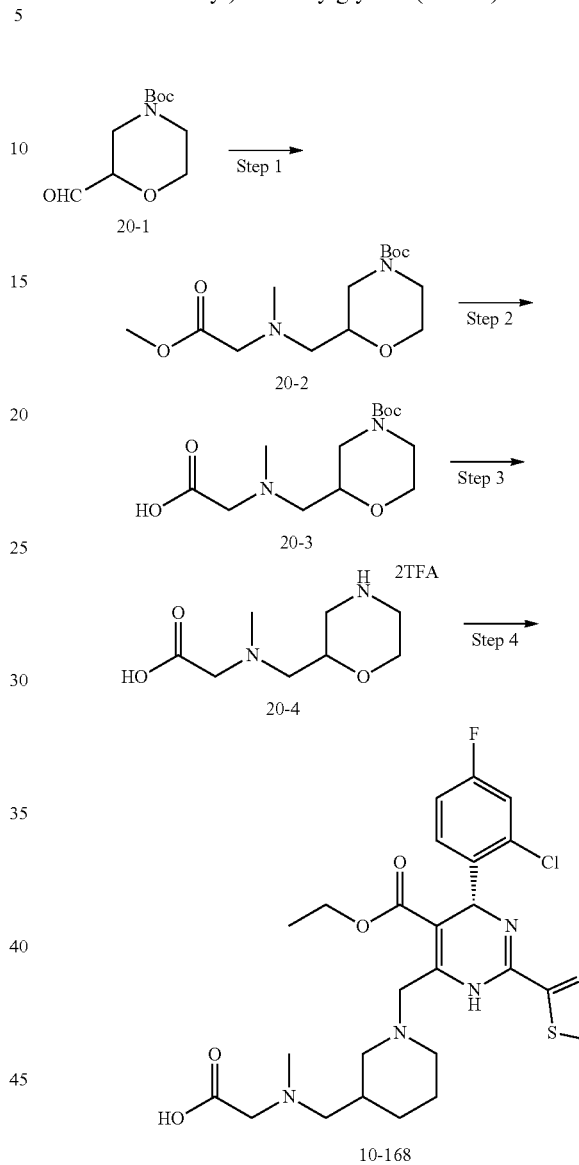

Step 1: Synthesis of tert-butyl 2-(((2-methoxy-2-oxoethyl)(methyl)amino)methyl)morpholine-4-carboxylate (20-2)

Tert-butyl 2-formylmorpholine-4-carboxylate (20-1) (117 mg, 0.5 mmol) and sarcosine methyl ester hydrochloride (84 mg, 0.6 mmol) were dissolved in methanol (3 mL), glacial acetic acid (0.2 mL) was added under cooling in an ice bath, sodium cyanoborohydride (76 mg, 1.2 mmol) was then added in portions, and the reaction was warmed to room temperature and allowed to proceed for 2 h. The reaction was added with ethyl acetate (20 mL), stirred for 10 min, filtered to remove insolubles, and the filtrate was concentrated, to afford the title compound 98 mg. ESI-MS (m/z): 303.2 [M+H]$^+$.

Step 2: Synthesis of N-((4-(tert-butoxycarbonyl) morpholin-2-yl)methyl)-N-methylglycine (20-3)

Compound (20-2) (98 mg, 0.3 mmol) was dissolved in a mixed solvent of methanol and water (v:v=1:1, 4 mL), lithium hydroxide monohydrate (84 mg, 2 mmol) was added, and the reaction was stirred overnight. The pH was adjusted to 2 with a 1N hydrochloric acid solution, and the solvent was distilled off under reduced pressure, to afford the title compound 80 mg, which was used directly for the next reaction without purification. ESI-MS (m/z): 289.2 [M+H]$^+$.

Step 3: Synthesis of N-methyl-N-((morpholin-2-ylmethyl)glycine (20-4)

At room temperature, compound (20-3) (80 mg, 0.28 mmol) was dissolved in dichloromethane (3 mL), trifluoroacetic acid (t mL) was added, and the reaction was performed at room temperature for 3 h. The solvent was distilled off under reduced pressure, to afford a trifluoroacetate salt of the title compound 94 mg. ESI-MS (m/z): 189.2 [M+H]$^+$.

Step 4: Synthesis of N-((4-(((R)-6-(2-chloro-4-fluorophenyl)-5-ethoxycarbonyl-2-(thiazol-2-yl)-3,6-dihydropyrimidin-4-yl)methyl)morpholin-2-yl)methyl)-N-methylglycine (10-168)

The title compound 9 mg was prepared by a method similar to that described in Step 3 of Example 1 (3,3-difluoropiperidin-4-ol hydrochloride was replaced with compound (20-4)).

The structure was characterized as follows:
$^1$H NMR (400 MHz, DMSO-d$_6$) δ 9.66 (d, 1H), 8.03-8.01 (m, 1H), 7.95-7.94 (m, 1H), 7.44-7.39 (m, 2H), 7.22-7.17 (m, 1H), 6.05 (d, 1H), 3.99-3.82 (m, 5H), 3.70-3.68 (m, 1H), 3.63-3.54 (m, 1H), 3.25 (d, 1H), 3.16 (d, 1H), 2.92-2.56 (m, 4H), 2.34 (d, 3H), 2.35-2.24 (m, 1H), 2.14-1.98 (m, 1H), 1.04 (t, J=7.1 Hz, 3H). ESI-MS (m/z): 566.1 [M+H]$^+$.

Example 21 Synthesis of 2-((1-(((S)-5-(ethoxycarbonyl)-6-(4-fluorophenyl)-6-methyl-2-(thiazol-2-yl)-3,6-dihydropyrimidin-4-yl)methyl)-3,3-difluoropiperidin-4-yl)oxy)acetic Acid (10-224)

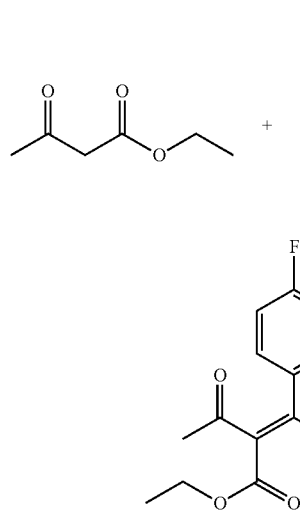

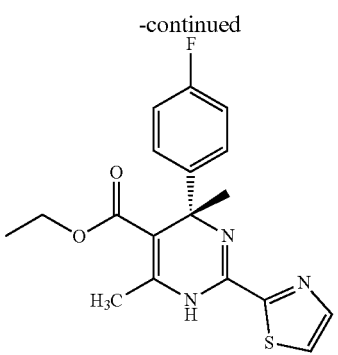

21-2

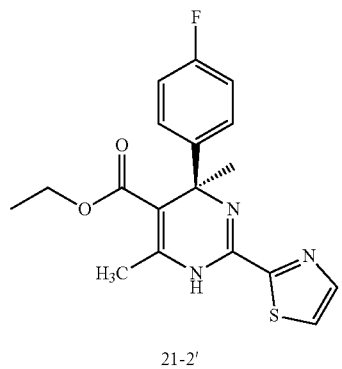

21-2'

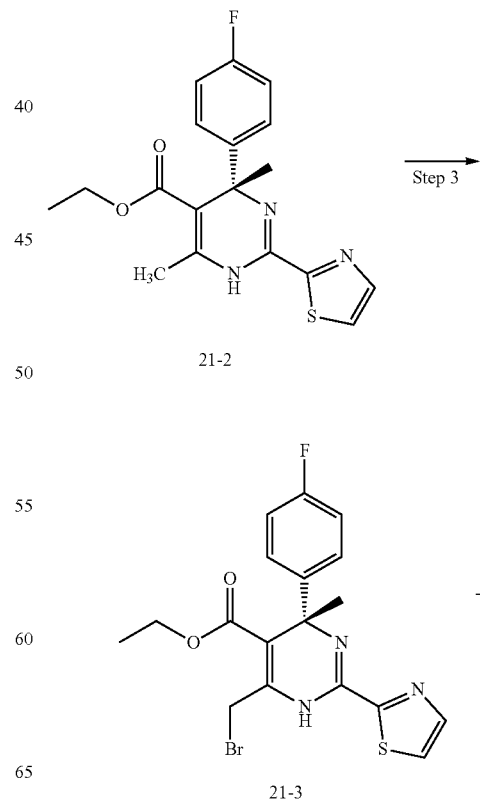

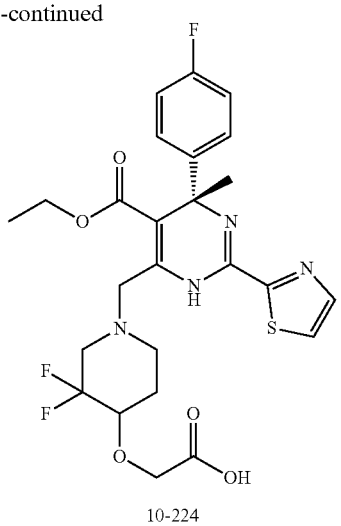

10-224

Step 1: Synthesis of (E)-ethyl 2-acetyl-3-(4-fluorophenyl)but-2-enoate

At room temperature, ethyl acetoacetate (3.12 g, 24.0 mmol), 4-fluorophenylethyne (2.88 g, 24.0 mmol) and indium triflate (216 mg, 0.384 mmol) were added to o-xylene (15 mL), the reaction was heated to 120° C., and held at this temperature for 2 hours, LC-MS detected the completion of the reaction. The reaction was cooled to room temperature, and the solvent was distilled off under reduced pressure to afford a crude product 6.0 g. ESI-MS (m/z): 251.1 [M+H]$^+$.

Step 2: Synthesis of ethyl 4-(4-fluorophenyl)-4,6-dimethyl-2-(thiazol-2-yl)-1,4-dihydropyrimidine-5-carboxylate Thiazole-2-carboximidamide hydrochloride (3.03 g, 18.5 mmol), sodium bicarbonate (3.15 g, 37.5 mmol) were added to N-methyl pyrrolidone (40 mL), the reaction was warmed to 120° C., dropwise added with compound (21-1) (3.12 g, 12.5 mmol), and incubated for 1 hour, LC-MS detected the completion of the reaction. The reaction was cooled to room temperature, added with ethyl acetate (60 mL), washed with water and saturated brine, and dried over anhydrous sodium sulfate. Anhydrous sodium sulfate was removed by filtration, and the solvent was distilled off under reduced pressure to give a crude product. The crude product was purified by flash column chromatography on silica gel (petroleum ether: ethyl acetate=10:1) to afford the title compound as a yellow solid (2.11 g). The above product 350 mg was separated by chiral chromatography, using the following separation conditions: separation column: CHIRALPAK IC 0.46 cm I.D.× 15 cm L, mobile phase: hexane/IPA/DEA=90/10/0.1 (V/V), flow rate: 1.0 ml/min, wavelength: UV 254 nm, temperature: 35° C.

The following products were obtained by separation: (S)-ethyl 4-(4-fluorophenyl)-4,6-dimethyl-2-(thiazol-2-yl)-1,4-dihydropyrimidine-5-carboxylate (21-2) 172 mg, ee %=99.3%, $R_t$=3.555 min. ESI-MS (m/z): 360.1 [M+H]$^+$; and (R)-ethyl 4-(4-fluorophenyl)-4,6-dimethyl-2-(thiazol-2-yl)-1,4-dihydropyrimidine-5-carboxylate (21-2') 171 mg, ee %=98.1%, $R_t$=4.873 min. ESI-MS (m/z): 360.1 [M+H]$^+$.

Step 3 to Step 4: 2-((1-(((S)-5-(ethoxycarbonyl)-6-(4-fluorophenyl)-6-methyl-2-(thiazol-2-yl)-3,6-dihydropyrimidin-4-yl)methyl)-3,3-difluoropiperidin-4-yl)oxy)acetic Acid (10-224)

Employing procedures similar to those described in Step 2 and Step 3 of Example 1, the title compound 15 mg was obtained by reacting compound (21-2), after subjected to a bromination reaction, with 2-((3,3-difluoropiperidin-4-yl)oxy)acetic acid (compound 5-5 in Example 5).

The structure was characterized as follows:
$^1$H NMR (400 MHz, DMSO-d$_6$) δ 9.35 (s, 1H), 8.01 (d, J=3.2 Hz, 1H), 7.92 (d, J=3.2 Hz, 1H), 7.41 (dd, J=8.8, 5.5 Hz, 2H), 7.11 (t, J=8.8 Hz, 2H), 4.18-4.06 (m, 2H), 3.89-3.53 (m, 6H), 3.04-2.60 (m, 4H), 2.44 (s, 1H), 1.97 (s, 1H), 1.80 (s, 3H), 0.92 (td, J=7.1, 1.4 Hz, 3H). ESI-MS (m/z): 553.2 [M+H]$^+$.

Example 22 Synthesis of 2-((1-(((R)-5-(ethoxycarbonyl)-6-(4-fluorophenyl)-6-methyl-2-(thiazol-2-yl)-3,6-dihydropyrimidin-4-yl)methyl)-3,3-difluoropiperidin-4-yl)oxy)acetic Acid (10-225)

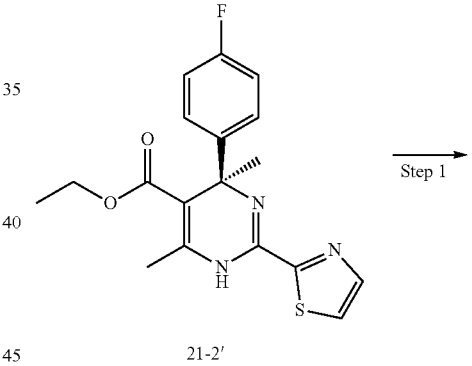

21-2'

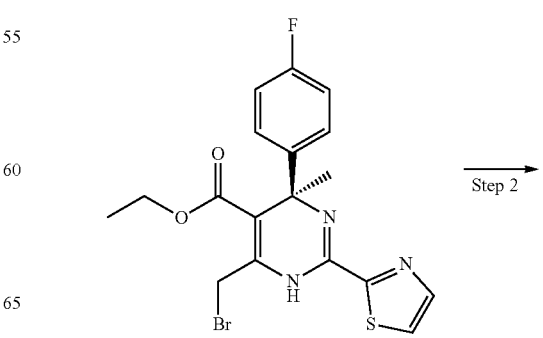

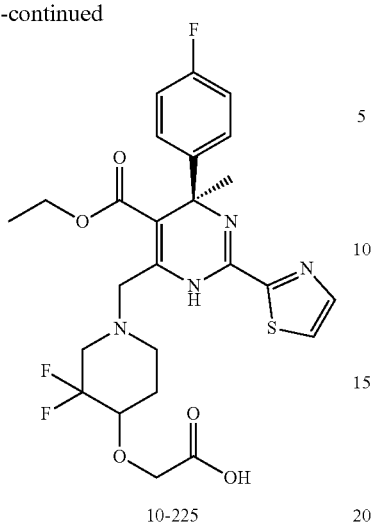

10-225

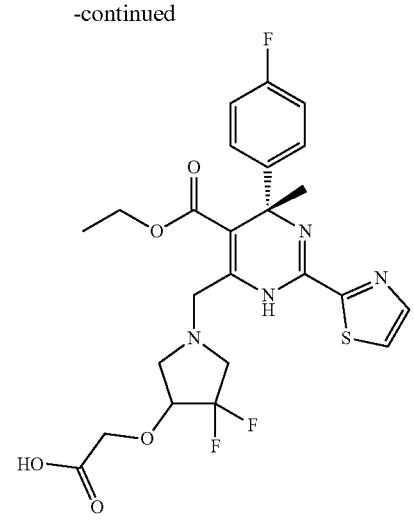

10-211

The title compound 15 mg was prepared from compound (21-2') in Example 21, employing procedures similar to those described in Step 3 to Step 4 of Example 21.

The structure was characterized as follows:

$^1$H NMR (400 MHz, DMSO-$d_6$) δ 9.35 (s, 1H), 8.01 (d, J=3.2 Hz, 1H), 7.92 (d, J=3.2 Hz, 1H), 7.41 (dd, J=8.8, 5.5 Hz, 2H), 7.11 (t, J=8.8 Hz, 2H), 4.21-4.11 (m, 2H), 3.94-3.54 (m, 6H), 3.14-2.70 (m, 4H), 2.45 (s, 1H), 1.97 (s, 1H), 1.80 (s, 4H), 0.92 (td, J=7.1, 1.4 Hz, 3H). ESI-MS (m/z): 553.2 [M+H]$^+$.

Example 23 Synthesis of 2-((1-(((S)-5-(ethoxycarbonyl)-6-(4-fluorophenyl)-6-methyl-2-(thiazol-2-yl)-3,6-dihydropyrimidin-4-yl)methyl)-4,4-difluoropyrrolidin-3-yl)oxy)acetic Acid (10-211)

Employing procedures similar to those described in Step 2 and Step 3 of Example 1, the title compound 2 mg was obtained by reacting compound (21-2) in Example 21, after subjected to a bromination reaction, with 2-((4,4-difluoropyrrolidin-3-yl)oxy)acetic acid (compound (12-4) in Example 12).

The structure was characterized as follows:

$^1$H NMR (400 MHz, CDCl$_3$) δ 7.85 (s, 1H), 7.50-7.35 (m, 3H), 6.99 (t, J=8.6 Hz, 2H), 4.22-4.12 (m, 1H), 3.94-3.84 (m, 3H), 3.30-3.17 (m, 3H), 3.08-2.93 (m, 2H), 2.27-1.99 (m, 1H), 1.91 (s, 3H), 1.68-1.48 (m, 1H), 0.97 (t, J=7.0 Hz, 3H). ESI-MS (m/z): 539.2 [M+H]$^+$.

Example 24 Synthesis of 2-((1-(((R)-5-(ethoxycarbonyl)-6-(4-fluorophenyl)-6-methyl-2-(thiazol-2-yl)-3,6-dihydropyrimidin-4-yl)methyl)-4,4-difluoropyrrolidin-3-yl)oxy)acetic Acid (10-212)

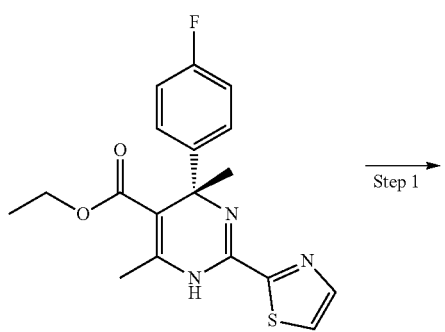

21-2

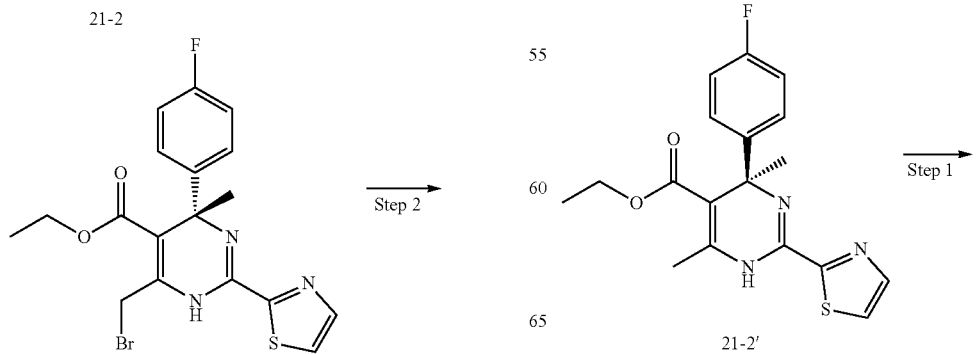

21-2'

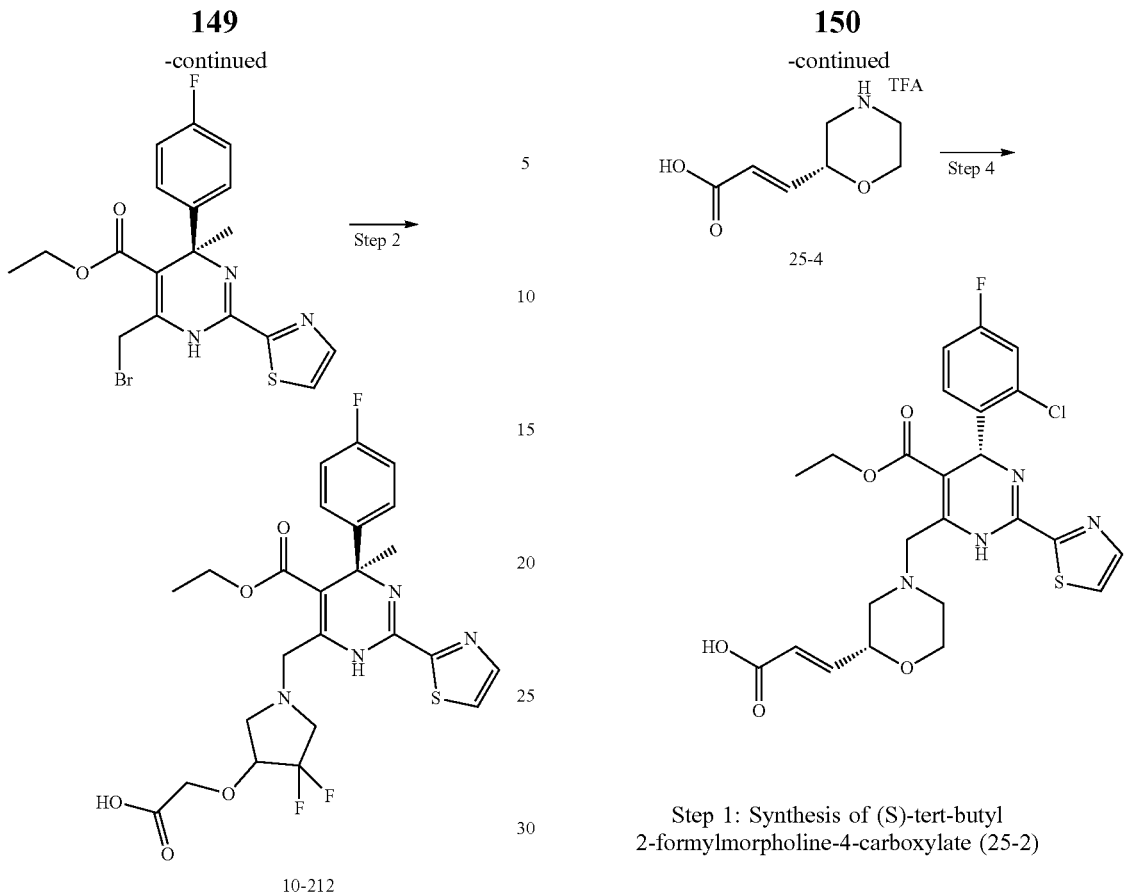

Employing procedures similar to those described in Step 2 and Step 3 of Example 1, the title compound 4 mg was obtained by reacting compound (21-2') in Example 21, after subjected to a bromination reaction, with 2-((4,4-difluoropyrrolidin-3-yl)oxy)acetic acid (compound (12-4) in Example 12).

The structure was characterized as follows:
$^1$H NMR (400 MHz, CDCl$_3$) δ 7.85 (s, 1H), 7.51-7.35 (m, 3H), 6.99 (t, J=8.6 Hz, 2H), 4.23-4.09 (m, 1H), 3.94-3.82 (m, 3H), 3.33-3.17 (m, 3H), 3.13-2.90 (m, 2H), 2.27-1.98 (m, 1H), 1.91 (s, 3H), 1.68-1.45 (m, 1H), 0.97 (t, J=7.0 Hz, 3H). ESI-MS (m/z): 539.2 [M+H]$^+$.

Example 25 Synthesis of (E)-3-((R)-4-(((R)-6-(2-chloro-4-fluorophenyl)-5-(ethoxycarbonyl)-2-(thiazol-2-yl)-3,6-dihydropyrimidin-4-yl)methyl)morpholin-2-yl)acrylic Acid (10-226)

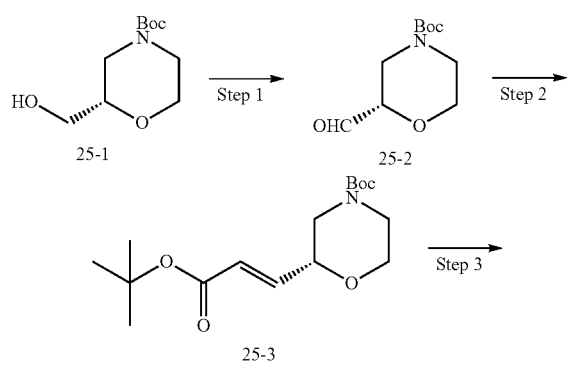

Step 1: Synthesis of (S)-tert-butyl 2-formylmorpholine-4-carboxylate (25-2)

Under cooling in an ice bath, (S)-tert-butyl 2-(hydroxymethyl)morpholine-4-carboxylate (25-1) (1.0 g, 4.6 mmol) was dissolved in dichloromethane (10 mL), Dess-Martin reagent (2.9 g, 6.9 mmol) was added in portions, and the reaction was stirred at 15° C. for 4 h. A large amount of solid precipitated in the reaction solution, which was filtered, the filter cake was discarded, the filtrate was added with a saturated solution of sodium thiosulfate, stirred for 30 min, and the layers were settled and separated. The organic layer was washed with a saturated solution of sodium bicarbonate and brine, dried over anhydrous sodium sulfate, and concentrated under reduced pressure, to afford a crude product 980 mg. The crude product was used for the next reaction without purification.

Step 2: Synthesis of (R,E)-tert-butyl 2-(3-(tert-butoxy)-3-oxoprop-1-en-1-yl)morpholine-4-carboxylate (25-3)

At room temperature, NaH (60%, 182 mg, 4.55 mmol) was dispersed in dry tetrahydrofuran (7 mL), stirred for 5 min, then a solution of tert-butyl diethylphosphonoacetate (1.21 g, 4.78 mmol) in dry tetrahydrofuran (3 mL) was slowly added dropwise, and the reaction was stirred at room temperature for 2 h. Then, the reaction solution was added to a solution of compound (25-2) (980 mg, 4.55 mmol) in dry tetrahydrofuran (5 mL), and the reaction was stirred overnight at room temperature after the dropwise addition. The solvent was distilled off under reduced pressure, and the residue was purified by column chromatography to afford a colorless oil (520 mg), which was settled at room temperature to allow solid precipitation, HPLC detection indicated Z/E<1/35, ee (enantiomeric excess) value is 94%. ESI-MS (m/z): 214.1 [M+1−100]$^+$.

Step 3: Synthesis of (R,E)-3-(morpholin-2-yl) acrylic Acid Trifluoroacetate Salt (25-4)

At room temperature, compound (25-3) (520 mg, 1.66 mmol) was dissolved in dichloromethane (10 mL), trifluoroacetic acid (5 mL) was added, and the reaction was performed at room temperature for 3 h. The insolubles were filtered off, and the filtrate was concentrated to afford a crude product of the title compound 423 mg, which was used directly for the next reaction without purification. ESI-MS (m/z): 158.1 [M+H]$^+$.

Step 4: Synthesis of (E)-3-((R)-4-(((R)-6-(2-chloro-4-fluorophenyl)-5-(ethoxycarbonyl)-2-(thiazol-2-yl)-3,6-dihydropyrimidin-4-yl)methyl)morpholin-2-yl) acrylic Acid (10-226)

At room temperature, (R)-ethyl 6-(bromomethyl)-4-(2-chloro-4-fluorophenyl)-2-(thiazol-2-yl)-1,4-dihydropyrimidine-5-carboxylate (400 mg, 0.87 mmol), compound (25-4) (423 mg, 1.66 mmol) and N,N-diisopropylethylamine (451 mg, 3.49 mmol) were added to dichloromethane (10 mL), and the reaction was performed at room temperature overnight. The reaction solution was concentrated to afford a crude product, which was purified by preparative liquid chromatography to afford the title compound 200 mg. Z/E<1/35, ee value is 95.5%.

The structure was characterized as follows:

$^1$H NMR (400 MHz, DMSO-d$_6$) δ 12.50 (s, 1H), 9.63 (s, 1H), 8.02 (d, J=3.12 Hz, 1H), 7.95 (d, J=3.16 Hz, 1H), 7.44-7.40 (m, 2H), 7.18 (td, J=8.48, 2.64 Hz, 1H), 6.73 (dd, J=15.80, 4.08 Hz, 1H), 6.05 (s, 1H), 5.93 (dd, J=15.80, 1.76 Hz, 1H), 4.24-4.21 (m, 1H), 3.98-3.92 (m, 5H), 3.68 (td, J=10.92, 1.72 Hz, 1H), 2.95 (d, J=11.12 Hz, 1H), 2.83 (d, J=10.92 Hz, 1H), 2.40 (td, J=11.16, 2.68 Hz, 1H), 2.07 (t, J=10.64 Hz, 1H), 1.04 (t, J=7.08 Hz, 3H). ESI-MS (m/z): 535.2 [M+H]$^+$.

Example 26 Synthesis of (E)-3-((R)-1-(((R)-6-(2-chloro-4-fluorophenyl)-5-(ethoxycarbonyl)-2-(thiazol-2-yl)-3,6-dihydropyrimidin-4-yl)methyl)-5,5-difluoropiperidin-3-yl)acrylic Acid (10-230)

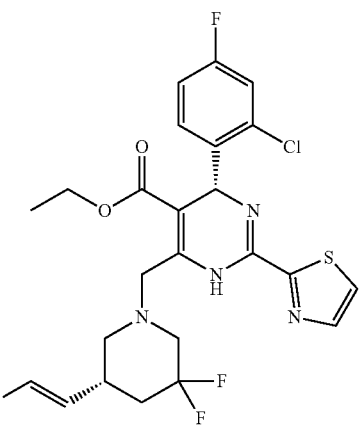

The compound of Example 17 (608 mg) was separated by chiral chromatography, using the following separation conditions: separation column: CHIRALPAK IG 0.46 cm I.D.× 15 cm L, mobile phase: hexane/EtOH/HOAc=75/25/0.1 (V/V/V), flow rate: 1.0 ml/min, wavelength: UV 254 nm, temperature: 35° C. The title compound 277 mg was obtained by separation, ee %=99.5%, R$_t$=15.656 min, and the structural characterization data were as follows:

$^1$H NMR (400 MHz, DMSO-d$_6$) δ 12.32 (brs, 1H), 9.55 (s, 1H), 8.00 (d, J=3.12 Hz, 1H), 7.94 (d, J=3.12 Hz, 1H), 7.45-7.41 (m, 2H), 7.19 (td, J=8.48 Hz, 2.68 Hz, 1H), 6.76 (dd, J=15.85 Hz, 6.64 Hz, 1H), 6.06 (s, 1H), 5.82 (dd, J=15.85 Hz, 1.16 Hz, 1H), 4.08 (d, J=16.53 Hz, 1H), 4.01 (d, J=16.53 Hz, 1H), 3.98-3.92 (m, 2H), 3.26-3.13 (m, 1H), 2.90 (brd, J=11.08 Hz, 1H), 2.79-2.69 (m, 2H), 2.29 (t, J=10.80 Hz, 2H), 1.94-1.77 (m, 1H), 1.04 (t, J=7.12 Hz, 3H). ESI-MS (m/z): 569.2 [M+H]$^+$.

Example 27 Synthesis of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)acrylic Acid (10-227)

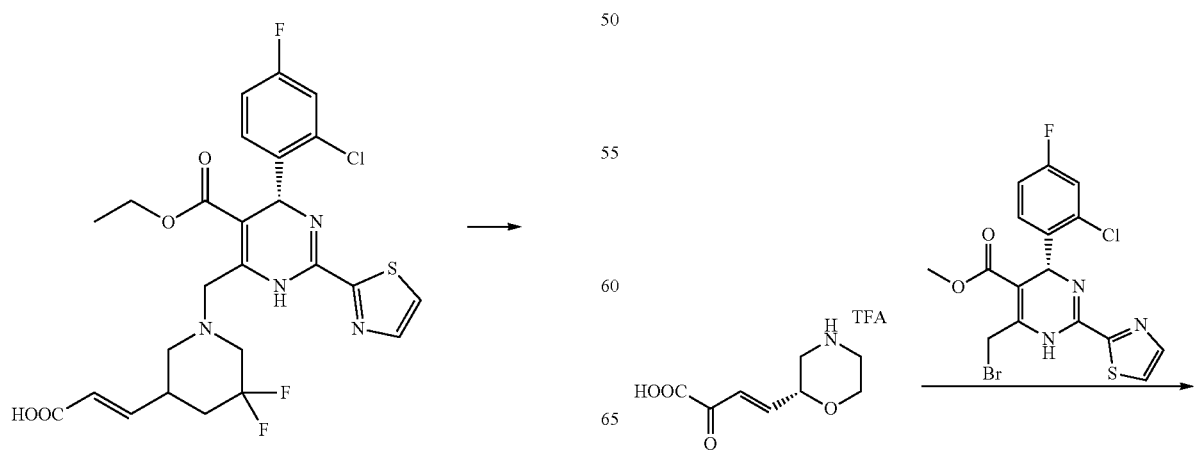

153

-continued

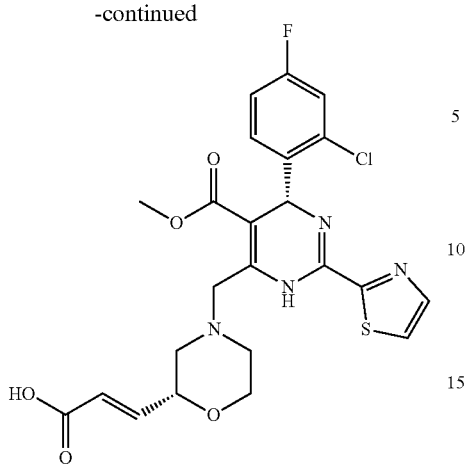

At room temperature, (R)-methyl 6-(bromomethyl)-4-(2-chloro-4-fluorophenyl)-2-(thiazol-2-yl)-1,4-dihydropyrimidine-5-carboxylate (400 mg, 0.90 mmol) and compound (25-4) (488 mg, 1.80 mmol) in Example 25 were dissolved in dichloromethane (10 mL), N,N-diisopropylethylamine (696 mg, 5.40 mmol) was added, and the reaction was performed at room temperature overnight. The reaction solution was concentrated to give a crude product, which was purified by preparative liquid chromatography, to afford the title compound 205 mg.

The structure was characterized as follows:

$^1$H NMR (400 MHz, DMSO-d$_6$) δ 12.44 (s, 1H), 9.68 (s, 1H), 7.98 (dd, J=27.6, 3.1 Hz, 2H), 7.48-7.36 (m, 2H), 7.18 (td, J=8.5, 2.6 Hz, 1H), 6.73 (dd, J=15.8, 4.1 Hz, 1H), 6.04 (s, 1H), 5.93 (dd, J=15.8, 1.6 Hz, 1H), 4.23 (d, J=9.3 Hz, 1H), 4.01-3.90 (m, 3H), 3.68 (t, J=10.2 Hz, 1H), 3.52 (s, 3H), 2.94 (d, J=11.0 Hz, 1H), 2.82 (d, J=11.1 Hz, 1H), 2.41 (dd, J=11.0, 8.6 Hz, 1H), 2.08 (t, J=10.7 Hz, 1H). ESI-MS (m/z): 521.1 [M+H]$^+$.

Example 28 Synthesis of (E)-3-((R)-4-(((R)-6-(2-bromo-4-fluorophenyl)-5-(methoxycarbonyl)-2-(thiazol-2-yl)-3,6-dihydropyrimidin-4-yl)methyl)morpholin-2-yl)acrylic Acid (10-229)

154

-continued

At room temperature, (R)-methyl 6-(bromomethyl)-4-(2-bromo-4-fluorophenyl)-2-(thiazol-2-yl)-1,4-dihydropyrimidine-5-carboxylate (400 mg, 0.82 mmol) and compound (25-4) (443 mg, 1.63 mmol) in Example 25 were dissolved in dichloromethane (10 mL), N,N-diisopropylethylamine (635 mg, 4.92 mmol) was then added, and the reaction was performed at room temperature overnight. The reaction solution was concentrated to give a crude product, which was purified by preparative liquid chromatography, to afford the title compound 200 mg.

The structure was characterized as follows:

$^1$H NMR (400 MHz, DMSO-d$_6$) δ 12.49 (s, 1H), 9.68 (s, 1H), 8.01 (d, J=3.1 Hz, 1H), 7.95 (d, J=3.1 Hz, 1H), 7.57 (dd, J=8.6, 2.6 Hz, 1H), 7.38 (dd, J=8.7, 6.2 Hz, 1H), 7.22 (td, J=8.5, 2.6 Hz, 1H), 6.73 (dd, J=15.8, 4.1 Hz, 1H), 6.02 (s, 1H), 5.93 (dd, J=15.8, 1.7 Hz, 1H), 4.27-4.19 (m, 1H), 4.01-3.89 (m, 3H), 3.68 (t, J=10.2 Hz, 1H), 3.52 (s, 3H), 2.94 (d, J=11.0 Hz, 1H), 2.83 (d, J=11.3 Hz, 1H), 2.41 (dd, J=11.1, 8.4 Hz, 1H), 2.08 (t, J=10.6 Hz, 1H). ESI-MS (m/z): 567.1 [M+H]$^+$.

Example 29 Synthesis of (E)-3-((R)-4-(((R)-6-(2-bromo-3-fluorophenyl)-5-(methoxycarbonyl)-2-(thiazol-2-yl)-3,6-dihydropyrimidin-4-yl)methyl)morpholin-2-yl)acrylic Acid (10-236)

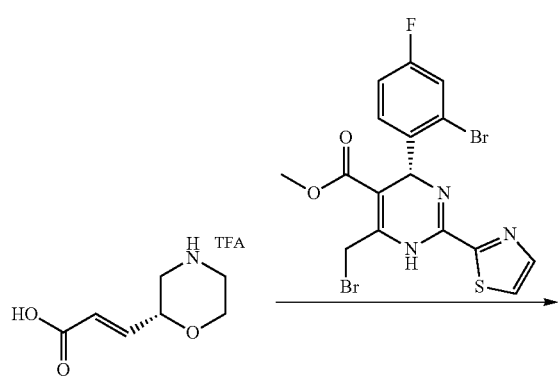

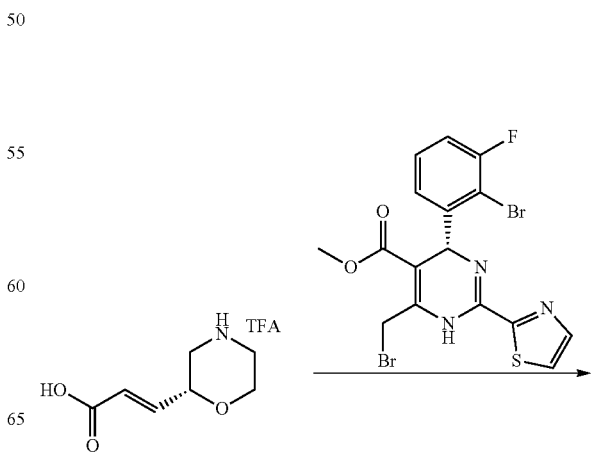

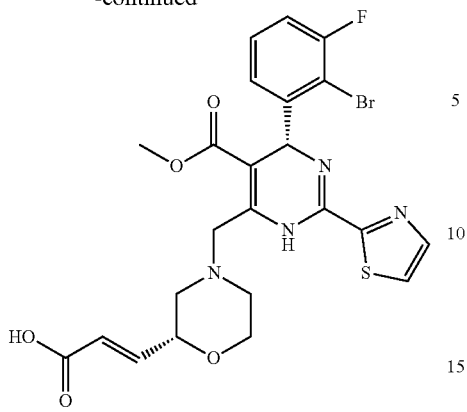

The title compound 25 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 4-(2-bromo-3-fluorophenyl)-6-(bromomethyl)-2-(thiazol-2-yl)-1,4-dihydropyrimidine-5-carboxylate.

The structure was characterized as follows:

$^1$H NMR (400 MHz, DMSO-d$_6$) δ 9.70 (s, 1H), 8.02 (d, J=3.2 Hz, 1H), 7.95 (d, J=3.2 Hz, 1H), 7.39 (m, J=7.9, 5.5 Hz, 1H), 7.31-7.17 (m, 2H), 6.74 (dd, J=15.8, 4.1 Hz, 1H), 6.09 (s, 1H), 5.93 (d, J=15.9 Hz, 1H), 4.27-4.19 (m, 1H), 4.02 (m, J=16.8, 9.4 Hz, 1H), 3.95 (d, J=7.7 Hz, 2H), 3.68 (td, J=11.4, 2.5 Hz, 1H), 3.51 (s, 3H), 2.99-2.92 (m, 11H), 2.83 (d, J=11.4 Hz, 1H), 2.42 (td, J=11.4, 3.3 Hz, 1H), 2.09 (t, J=10.6 Hz, 1H), 1.41 (s, 1H). ESI-MS (m/z): 567.0 [M+H]$^+$.

Example 30 Synthesis of (E)-3-((R)-4-(((R)-6-(2-chloro-3,4-difluorophenyl)-5-(methoxycarbonyl)-2-(thiazol-2-yl)-3,6-dihydropyrimidin-4-yl)methyl)morpholin-2-yl)acrylic Acid

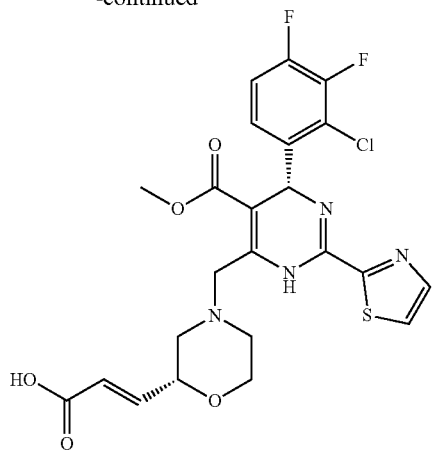

The title compound 25 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-chloro-3,4-difluorophenyl)-2-(thiazol-2-yl)-1,4-dihydropyrimidine-5-carboxylate.

The structure was characterized as follows:

$^1$H NMR (400 MHz, CDCl$_3$) δ 7.79 (d, J=3.1 Hz, 1H), 7.45 (d, J=3.1 Hz, 1H), 7.12-6.94 (m, 2H), 6.78 (dd, J=15.7, 4.0 Hz, 1H), 6.11 (s, 1H), 6.06 (d, J=15.6 Hz, 1H), 4.53 (s, 1H), 4.31 (d, J=15.8 Hz, 1H), 4.13 (d, J=15.3 Hz, 1H), 4.01 (s, 2H), 3.54 (s, 3H), 3.27 (d, J=70.2 Hz, 2H), 2.76 (s, 1H). ESI-MS (m/z): 539.2 [M+H]$^+$.

Example 31 Synthesis of (E)-3-((R)-4-(((R)-6-(2-bromo-3,4-difluorophenyl)-5-(methoxycarbonyl)-2-(thiazol-2-yl)-3,6-dihydropyrimidin-4-yl)methyl)morpholin-2-yl)acrylic Acid (10-238)

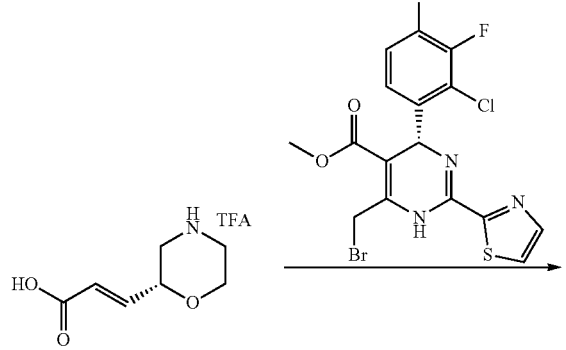

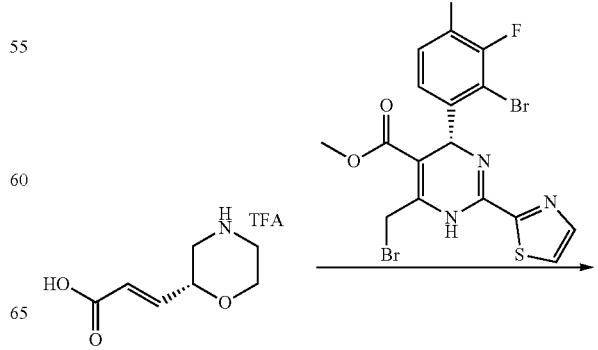

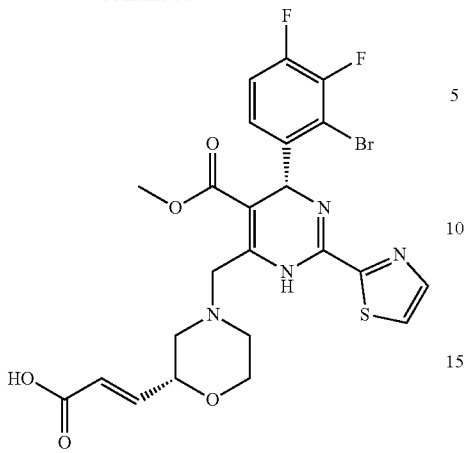

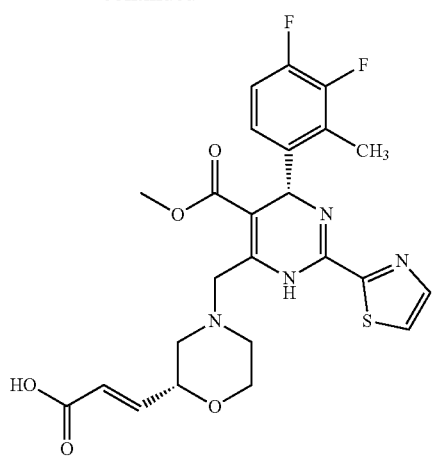

The title compound 70 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 4-(2-bromo-3,4-difluorophenyl)-6-(bromomethyl)-2-(thiazol-2-yl)-1,4-dihydropyrimidine-5-carboxylate.

The structure was characterized as follows:

$^1$H NMR (400 MHz, CDCl$_3$) δ 9.66 (s, 1H), 7.85 (d, J=3.1 Hz, 1H), 7.47 (d, J=3.1 Hz, 1H), 7.12-7.01 (m, 2H), 6.92-6.87 (m, 1H), 6.19 (s, 1H), 6.13-6.09 (m, 1H), 4.50-4.35 (m, 1H), 4.20-4.05 (m, 3H), 4.00-3.80 (m, 2H), 3.62 (s, 3H), 3.05-2.75 (m, 2H), 2.71-2.55 (m, 1H), 2.30-2.15 (m, 1H). ESI-MS (m/z): 584.0 [M+H]$^+$.

Example 32 Synthesis of (E)-3-((R)-4-(((S)-6-(3,4-difluoro-2-methylphenyl)-5-(methoxycarbonyl)-2-(thiazol-2-yl)-3,6-dihydropyrimidin-4-yl)methyl)morpholin-2-yl)acrylic Acid (10-239)

The title compound 22 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (S)-methyl 6-(bromomethyl)-4-(3,4-difluoro-2-methylphenyl)-2-(thiazol-2-yl)-1,4-dihydropyrimidine-5-carboxylate.

The structure was characterized as follows:

$^1$H NMR (400 MHz, CDCl$_3$) δ 7.93 (dd, J=3.2, 1.5 Hz, 1H), 7.72 (t, J=2.7 Hz, 1H), 7.02 (m, J=7.2, 3.3 Hz, 2H), 6.82 (m, J=15.8, 4.2 Hz, 1H), 6.16-5.96 (m, 1H), 5.91 (s, 1H), 4.37 (d, J=9.8 Hz, 1H), 4.20-3.75 (m, 4H), 3.60 (s, 3H), 3.14-2.64 (m, 2H), 2.55 (d, J=2.4 Hz, 3H), 2.60-2.41 (m, J=11.7, 5.8 Hz, 1H), 2.29-2.20 (m, J=10.6 Hz, 1H). ESI-MS (m/z): 519.2 [M+H]$^+$.

Example 33 Synthesis of (E)-3-((R)-4-(((R)-6-(2-chloro-3-fluorophenyl)-5-(methoxycarbonyl)-2-(thiazol-2-yl)-3,6-dihydropyrimidin-4-yl)methyl)morpholin-2-yl)acrylic Acid (10-240)

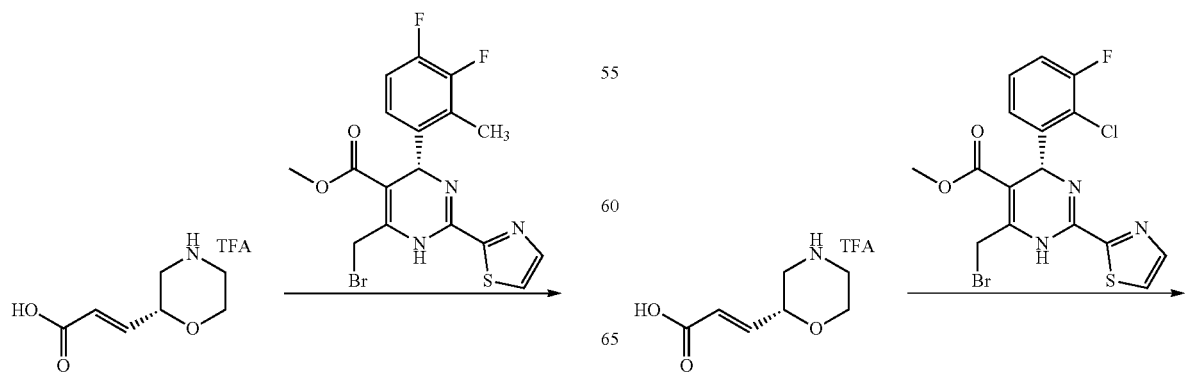

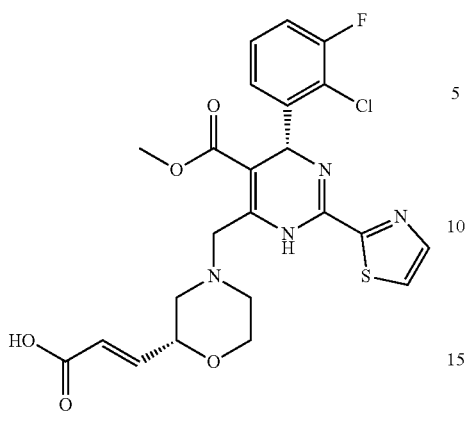

The title compound 36 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-chloro-3-fluorophenyl)-2-(thiazol-2-yl)-1,4-dihydropyrimidine-5-carboxylate.

The structure was characterized as follows:

$^1$H NMR (400 MHz, CDCl$_3$) δ 7.84 (d, J=3.1 Hz, 1H), 7.48 (s, 1H), 7.22-7.16 (m, J=16.5 Hz, 2H), 7.06 (s, 1H), 6.89 (d, J=15.7 Hz, 1H), 6.25 (s, 1H), 6.11 (d, J=15.7 Hz, 1H), 4.50 (s, 1H), 4.22 (d, J=15.6 Hz, 1H), 4.03 (dd, J=31.8, 9.3 Hz, 3H), 3.60 (s, 3H), 3.04 (s, 2H), 2.70 (s, 1H), 2.35 (s, 1H). ESI-MS (m/z): 521.2 [M+H]$^+$.

Example 34 Synthesis of (E)-3-((R)-4-(((R)-6-(2,4-dichlorophenyl)-5-(methoxycarbonyl)-2-(thiazol-2-yl)-3,6-dihydropyrimidin-4-yl)methyl)morpholin-2-yl)acrylic Acid (10-241)

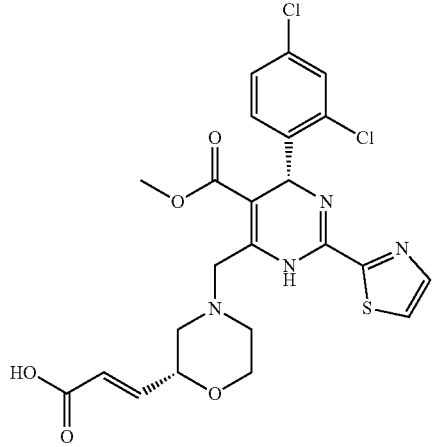

The title compound 400 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2,4-dichlorophenyl)-2-(thiazol-2-yl)-1,4-dihydropyrimidine-5-carboxylate.

The structure was characterized as follows:

$^1$H NMR (400 MHz, CDCl$_3$) δ 9.64 (s, 1H), 7.86 (d, J=3.1 Hz, 1H), 7.47 (d, J=3.1 Hz, 1H), 7.42 (d, J=2.1 Hz, 1H), 7.28 (d, J=6.5 Hz, 1H), 7.19 (dd, J=8.4, 2.1 Hz, 1H), 6.93 (dd, J=15.7, 4.1 Hz, 1H), 6.22 (s, 1H), 6.12 (dd, J=15.7, 1.8 Hz, 1H), 4.40 (d, J=9.9 Hz, 1H), 4.12-4.01 (m, 2H), 3.96-3.85 (m, 2H), 3.62 (s, 3H), 2.89-2.75 (m, 2H), 2.60 (td, J=10.9, 2.8 Hz, 1H), 2.23 (t, J=10.7 Hz, 1H). ESI-MS (m/z): 537.2 [M+H]$^+$.

Example 35 Synthesis of (E)-3-((R)-4-(((S)-6-(4-fluoro-2-methylphenyl)-5-(methoxycarbonyl)-2-(thiazol-2-yl)-3,6-dihydropyrimidin-4-yl)methyl)morpholin-2-yl)acrylic Acid (10-242)

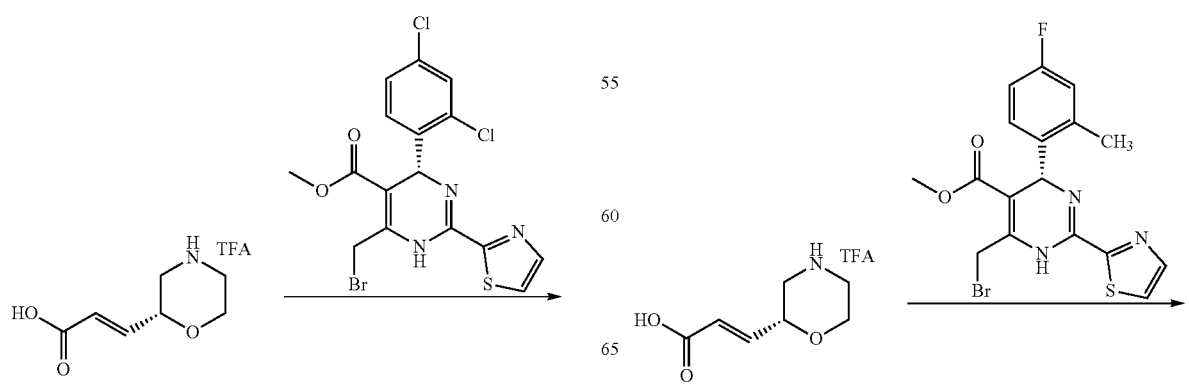

-continued

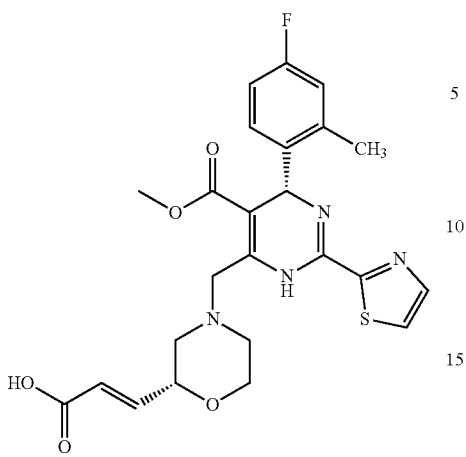

The title compound 80 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (S)-methyl 6-(bromomethyl)-4-(4-fluoro-2-methylphenyl)-2-(thiazol-2-yl)-1,4-dihydropyrimidine-5-carboxylate.

The structure was characterized as follows:

$^1$H NMR (400 MHz, CDCl$_3$) δ 9.59 (s, 1H), 7.82 (d, J=3.1 Hz, 1H), 7.44 (s, 1H), 7.13 (t, J=7.1 Hz, 1H), 6.90 (t, J=4.1 Hz, 2H), 6.80 (t, J=3.6 Hz, 1H), 6.12 (dd, J=15.7, 1.2 Hz, 1H), 5.96 (s, 1H), 4.40 (s, 1H), 4.05 (d, J=11.3 Hz, 2H), 3.93 (d, J=16.0 Hz, 2H), 3.61 (s, 3H), 2.81 (s, 2H), 2.63 (s, 3H), 2.57 (s, 1H), 2.20 (s, 1H). ESI-MS (m/z): 501.2 [M+H]$^+$.

Example 36 Synthesis of (E)-3-((R)-4-(((R)-6-(2-chloro-4-fluorophenyl)-5-(methoxycarbonyl)-2-(4-methylthiazol-2-yl)-3,6-dihydropyrimidin-4-yl)methyl)morpholin-2-yl)acrylic Acid (10-243)

-continued

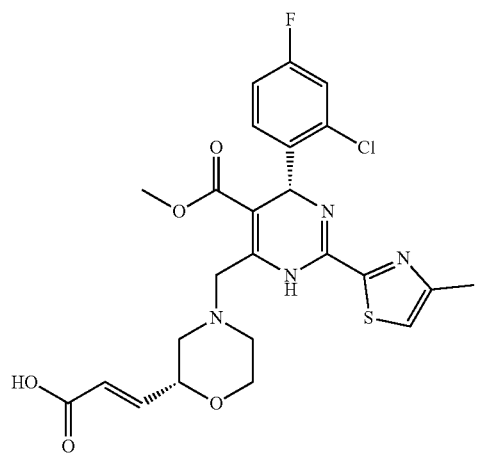

The title compound 400 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-methyl-4-fluorophenyl)-2-(4-methylthiazol-2-yl)-1,4-dihydropyrimidine-5-carboxylate.

The structure was characterized as follows:

$^1$H NMR (400 MHz, CDCl$_3$) δ 9.65 (s, 1H), 7.29-7.25 (m, 1H), 7.13 (dd, J=8.6, 2.6 Hz, 1H), 7.01 (s, 1H), 6.93-6.88 (m, 2H), 6.19 (s, 1H), 6.10 (d, J=15.7 Hz, 1H), 4.38 (s, 1H), 4.06 (d, J=12.5 Hz, 2H), 3.90-3.86 (m, 2H), 3.60 (s, 3H), 2.81 (s, 2H), 2.60 (s, 1H), 2.45 (s, 3H), 2.20 (s, 1H). ESI-MS (m/z): 535.1 [M+H]$^+$.

Example 37 Synthesis of (E)-3-((R)-4-(((R)-6-(2-chloro-4-fluorophenyl)-5-(methoxycarbonyl)-2-(4-(trifluoromethyl)thiazol-2-yl)-3,6-dihydropyrimidin-4-yl)methyl)morpholin-2-yl)acrylic Acid (10-244)

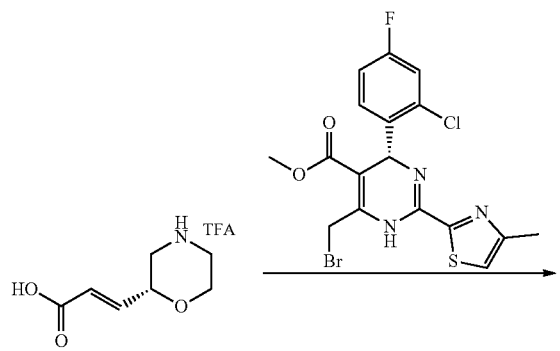

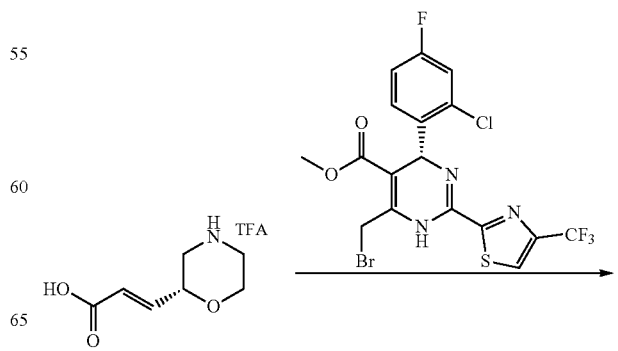

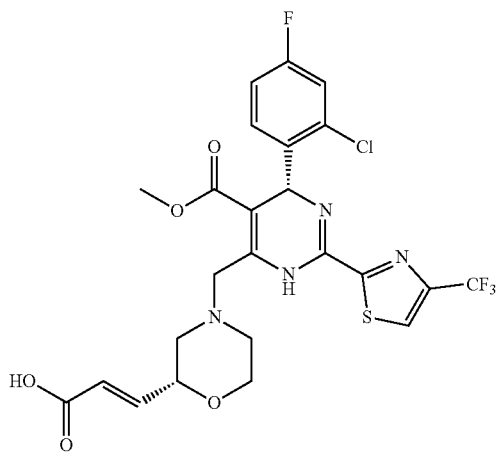

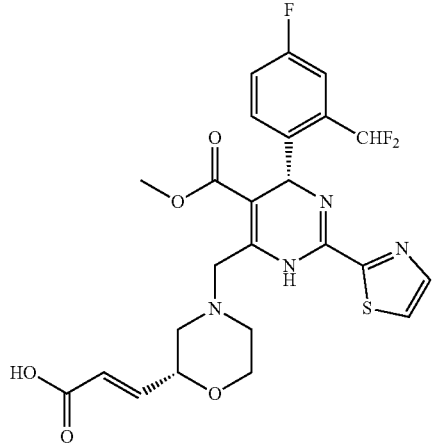

The title compound 80 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-chloro-4-fluorophenyl)-2-(4-(trifluoromethyl)thiazol-2-yl)-1,4-dihydropyrimidine-5-carboxylate.

The structure was characterized as follows:

$^1$H NMR (400 MHz, CDCl$_3$) δ 9.70 (s, 1H), 7.86 (s, 1H), 7.27 (s, 1H), 7.17 (dd, J=8.6, 2.6 Hz, 1H), 6.96 (ddd, J=11.3, 10.6, 3.4 Hz, 2H), 6.24 (s, 1H), 6.18 (d, J=15.4 Hz, 1H), 4.38 (d, J=10.4 Hz, 1H), 4.19-4.10 (m, 1H), 4.02 (d, J=11.1 Hz, 1H), 3.83 (dd, J=13.3, 9.8 Hz, 2H), 3.63 (s, 3H), 2.95 (d, J=10.8 Hz, 1H), 2.66 (d, J=11.6 Hz, 1H), 2.51-2.33 (m, 2H). ESI-MS (m/z): 589.1 [M+H]$^+$.

Example 38 Synthesis of (E)-3-((R)-4-(((S)-6-(2-(difluoromethyl)-4-fluorophenyl)-5-(methoxycarbonyl)-2-(thiazol-2-yl)-3,6-dihydropyrimidin-4-yl)methyl)morpholin-2-yl)acrylic Acid (10-245)

The title compound 70 mg was obtained employing procedures similar to those described in Example 27, and replacing (R)-methyl 6-(bromomethyl)-4-(2-chloro-4-fluorophenyl)-2-(thiazol-2-yl)-1,4-dihydropyrimidine-5-carboxylate with (S)-methyl 6-(bromomethyl)-4-(2-(difluoromethyl)-4-fluorophenyl)-2-(thiazol-2-yl)-1,4-dihydropyrimidine-5-carboxylate.

The structure was characterized as follows:

$^1$H NMR (400 MHz, CDCl$_3$) δ 9.68 (s, 1H), 7.83 (d, J=3.1 Hz, 1H), 7.69-7.55 (m, 1H), 7.46 (d, J=2.9 Hz, 1H), 7.40 (d, J=7.5 Hz, 1H), 7.20 (s, 1H), 7.08 (t, J=7.5 Hz, 1H), 6.96 (dd, J=15.7, 3.9 Hz, 1H), 6.15 (dd, J=15.7, 1.5 Hz, 1H), 6.08 (s, 1H), 4.40 (d, J=5.0 Hz, 1H), 4.16 (d, J=17.6 Hz, 1H), 4.00 (d, J=11.4 Hz, 1H), 3.93-3.80 (m, 2H), 3.62 (s, 3H), 2.93 (d, J=9.2 Hz, 1H), 2.65 (d, J=9.7 Hz, 1H), 2.46 (t, J=11.1 Hz, 1H), 2.36 (d, J=9.6 Hz, 1H). ESI-MS (m/z): 537.2 [M+H]$^+$.

Example 39 Synthesis of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)but-2-enoic Acid (10-246)

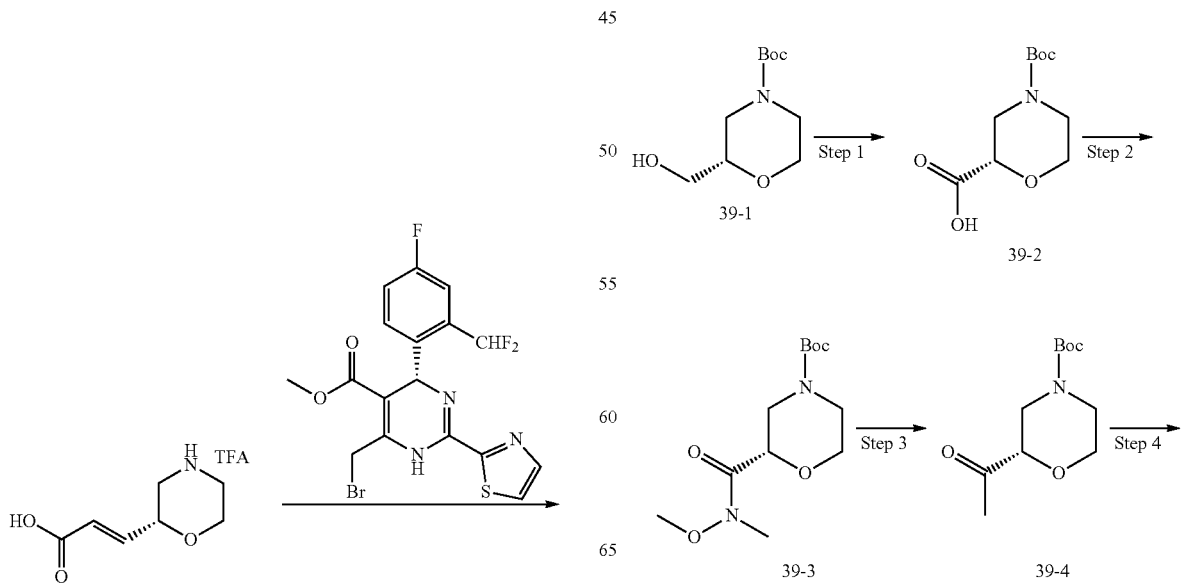

-continued

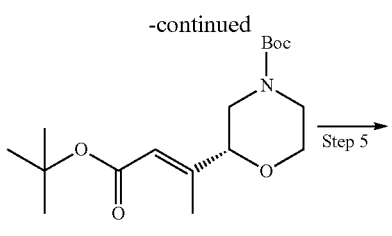

39-5

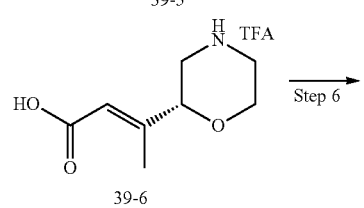

39-6

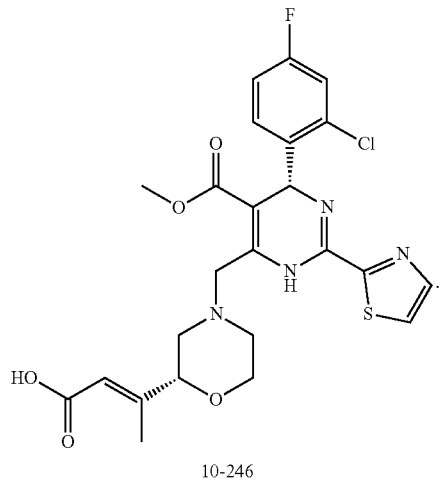

10-246

Step 1: Synthesis of (S)-4-(tert-butoxycarbonyl) morpholine-2-carboxylic Acid (39-2)

At room temperature, (S)-tert-butyl 2-(hydroxymethyl) morpholine-4-carboxylate (39-1) (5 g, 23.01 mmol) was dissolved in acetone (250 mL), and a saturated solution of sodium bicarbonate (75 mL) was added. The reaction was cooled to 0° C. in an ice bath, sodium bromide (474 mg, 4.6 mmol) and tetramethylpiperidinyloxy (65 mg, 0.46 mmol) were added, followed by slow addition of trichloroisocyanuric acid (10.7 g, 46.03 mmol), and the reaction was performed at room temperature overnight. The reaction was added with isopropanol (15 mL), stirred for 30 min, filtered with suction, and the filter cake was discarded. The filtrate was concentrated, added with a saturated solution of sodium carbonate (75 mL), extracted with ethyl acetate (50 mL×2), and the organic phase was discarded. The aqueous phase was neutralized with 6N hydrochloric acid, and extracted with ethyl acetate (50 mL×3). The organic phase was combined, dried over anhydrous sodium sulfate, the drying agent was filtered off, and the filtrate was concentrated to afford the title compound 3 g, which was used directly for the next reaction without purification. ESI-MS (m/z): 176.1 [M+1-56]$^+$.

Step 2: Synthesis of (S)-tert-butyl 2-(methoxy(methyl)carbamoyl)morpholine-4-carboxylate (39-3)

At room temperature, compound (39-2) (2 g, 8.65 mmol) was dissolved in dichloromethane (20 mL), 2-(7-azabenzo-triazol-1-yl)-N,N,N',N'-tetramethyluronium hexafluorophosphate (3.95 g, 10.38 mmol) was added, and the reaction was performed at room temperature for 30 min. N,N-diisopropylethylamine (2.57 g, 19.89 mmol) and N,O-dimethylhydroxylamine hydrochloride (1.01 g, 10.38 mmol) were added, and the reaction was performed overnight. The reaction was added with water (20 mL), and extracted with dichloromethane (20 mL×3). The organic phase was combined, which was successively washed with 0.05N hydrochloric acid (20 mL), a saturated solution of sodium bicarbonate, water and a saturated solution of sodium chloride, and dried over anhydrous sodium sulfate, the drying agent was filtered off, and the filtrate was concentrated to afford the title compound (2 g), which was used directly for the next reaction without purification. ESI-MS (m/z): 219.1 [M+1-56]$^+$.

Step 3: Synthesis of (S)-tert-butyl 2-acetylmorpholine-4-carboxylate (39-4)

At room temperature, compound (39-3) (2 g, 7.29 mmol) was dissolved in anhydrous tetrahydrofuran (40 mL), cooled to −20° C. under protection of nitrogen, methyl magnesium bromide (3M, 7.29 mL, 21.87 mmol) was added dropwise, and the reaction was performed at −20° C. of 4 h. The reaction was added with saturated ammonium chloride (20 mL), and extracted with ethyl acetate (20 mL×3). The organic phase was combined, successively washed with 0.05N hydrochloric acid (20 mL), a saturated solution of sodium bicarbonate, water and a saturated solution of sodium chloride, and dried over anhydrous sodium sulfate, the drying agent was filtered off, and the filtrate was concentrated to afford the title compound (1.5 g), which was used directly for the next reaction without purification. ESI-MS (m/z): 174.1 [M+1−56]$^+$.

Step 4: Synthesis of (R,E)-tert-butyl 2-(4-(tert-butoxy)-4-oxobut-2-en-2-yl)morpholine-4-carboxylate (39-5)

The title compound (1.1 g) was obtained by employing procedures similar to those described in Step 2 of Example 25, and replacing (S)-tert-butyl 2-formylmorpholine-4-carboxylate with compound (39-4). ESI-MS (m/z): 172.1 [M+1−100−56]$^+$.

Step 5: Synthesis of (R,E)-3-(morpholin-2-yl)but-2-enoic Acid Trifluoroacetate Salt (39-6)

The title compound (491 mg) was obtained by employing procedures similar to those described in Step 3 of Example 25, and replacing (R,E)-tert-butyl 2-(3-(tert-butoxy)-3-oxoprop-1-en-1-yl)morpholine-4-carboxylate with compound (39-5). ESI-MS (m/z): 172.1 [M+H]$^+$.

Step 6: Synthesis of (E)-3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)but-2-enoic Acid (10-246)

The title compound (180 mg) was obtained by employing procedures similar to those described in Example 27, and replacing (R,E)-3-(morpholin-2-yl)acrylic acid trifluoroacetate salt with compound (39-6).

The structure was characterized as follows:
$^1$H NMR (400 MHz, CDCl$_3$) δ 7.85 (d, J=3.1 Hz, 1H), 7.51 (d, J=3.0 Hz, 1H), 7.33 (dd, J=8.6, 2.0 Hz, 1H), 7.14

(dd, J=8.5, 2.6 Hz, 1H), 6.95 (td, J=8.3, 2.6 Hz, 1H), 6.18 (s, 1H), 6.04 (s, 1H), 4.37-4.22 (m, 2H), 4.10-4.07 (m, 2H), 3.62 (s, 3H), 3.27 (s, 1H), 2.83 (s, 1H), 2.43 (s, 1H), 2.08 (s, 3H). ESI-MS (m/z): 535.1 [M+H]$^+$.

The additional compounds can be synthesized by methods similar to those in the above Examples.

In the following pharmacological tests, comparison between the compound of the present invention and compound GLS4 (Control compound 1), the compound of Example 9 in WO2015144093 (Control compound 2) and the compound of Example 5 in WO2014037480 (Control compound 3) mentioned in the "Background of the invention" section of the present application was conducted, so as to adequately illustrate the advantages of the examples of the present invention.

The structure of Control compound 1 is

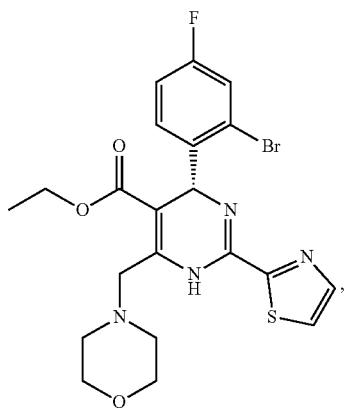

that of Control compound 2 is

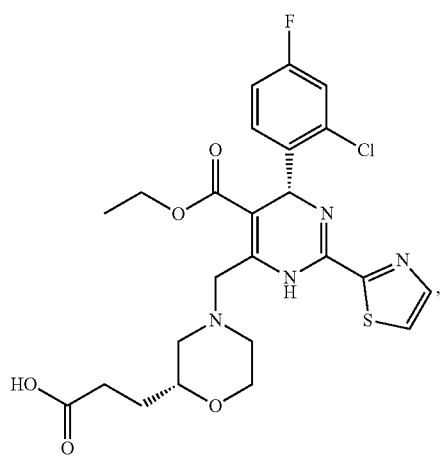

and that of Control compound 3 is

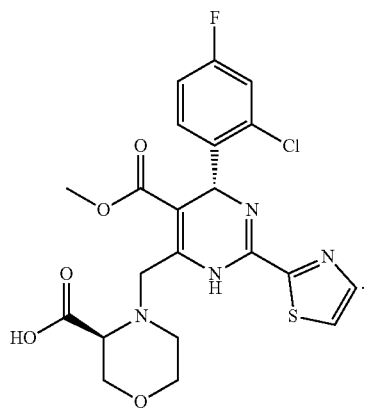

Experimental Example 1: Biological Activity Assay

The inhibitory effect of the compounds of the present invention on hepatitis type B virus (HBV) was tested. Cytotoxicity and effects on nucleic acid (DNA) replication level of the virus (HBV) of the compounds of the present invention were tested at a virus-cell level.

Test Method

HepG2.2.15 cells in the logarithmic growth phase were plated in a 96-well plate at a cell concentration of 40 cells per μL. The cells were incubated in a 5% $CO_2$ incubator at 37° C. for 3 days; and the culture medium was replaced with a new one (200 L/well) before adding compounds. The concentration of the stock solution of each Example compound is 200 μM. With 200 μM as the highest concentration, the solution was diluted as various concentrations with DMSO, and 1 μL of a test compound was added into a corresponding culture medium well, and the final test concentrations of the compound were 0.06, 0.24, 0.98, 3.9, 15.6, 62.5, 250, 1000 nM (used for calculating the half effective concentration ($EC_{50}$)). The test results are shown in Table 1-1 and Table 1-2.

TABLE 1-1

| Compound No. | $EC_{50}$ (nM) |
|---|---|
| 10-7 of Example 6 | 102.3 |
| 10-34 of Example 9 | 13.2 |
| 10-36 of Example 10 | 98.1 |
| 10-40 of Example 11 | 6.2 |
| 10-42 of Example 12 | 164.5 |
| 10-88 of Example 1 | 24.7 |
| Isomer B of Example 4 | 34.7 |
| Isomer A of Example 4 | 35.1 |
| 10-95 of Example 5 | 314.4 |
| 10-136 of Example 16 | 110.4 |
| 10-162 of Example 15 | 213.1 |
| 10-180 of Example 14 | 23.5 |
| 10-182 of Example 13 | 61.8 |

As shown in Table 1-1, the test compounds have potent inhibitory activity on hepatitis type B virus (HBV).

TABLE 1-2

| Compound No. | $EC_{50}$ (nM) |
|---|---|
| Control compound 2 | 89 |
| 10-226 of Example 25 | 9.2 |
| 10-227 of Example 27 | 10.0 |

TABLE 1-2-continued

| Compound No. | EC$_{50}$ (nM) |
|---|---|
| 10-229 of Example 28 | 8.3 |
| 10-230 of Example 26 | 11.2 |
| 10-237 of Example 30 | 10.9 |
| 10-238 of Example 31 | 10.2 |
| 10-239 of Example 32 | 28.9 |
| 10-240 of Example 33 | 21.1 |

As shown in Table 1-2, the anti-HBV activity of the compounds having a single configuration of the present invention is about 10 times of that of Control compound 2, indicating the compounds of the present invention have stronger inhibitory activity on hepatitis type B virus (HBV). The remaining compounds of the present invention have inhibitory activity similar to the above.

Experimental Example 2: Cytotoxicity Detection

The test compounds were diluted to 30 mM with DMSO, with 30 mM as the highest concentration, the compounds were subjected to three-fold serial dilution to various concentrations. 0.2 µL of the compounds at various concentrations were added to a 384-well plate, HepG2.2.15 cells having a concentration of 2000 cells per 50 µL were added to each well, and the highest concentration of the test compounds was 150 µM. 1 µL of DMSO was added to corresponding wells for control. The plate was incubated in a 5% CO$_2$ incubator at 37° C. for 4 days; and 50 µL of CellTiter-Glo was added to each well after 4 days. The plate was read for detection, and a half cytotoxic concentration (CC$_{50}$) was calculated. The test results are as shown in Table 2.

TABLE 2

| Compound No. | CC$_{50}$ (µM) |
|---|---|
| 10-7 of Example 6 | 129.5 |
| 10-34 of Example 9 | 79.6 |
| 10-36 of Example 10 | >150.0 |
| 10-40 of Example 11 | 73.5 |
| 10-42 of Example 12 | >150.0 |
| 10-88 of Example 1 | 61.1 |
| Isomer B of Example 4 | 51.3 |
| Isomer A of Example 4 | 43.9 |
| 10-95 of Example 5 | 131.3 |
| 10-136 of Example 16 | 122.3 |
| 10-162 of Example 15 | >150.0 |
| 10-180 of Example 14 | >150.0 |
| 10-182 of Example 13 | >150.0 |
| 10-226 of Example 25 | >150.0 |
| 10-230 of Example 26 | 137.0 |
| 10-227 of Example 27 | >150.0 |
| 10-229 of Example 28 | >150.0 |
| 10-237 of Example 30 | >150.0 |
| 10-238 of Example 31 | >150.0 |
| 10-239 of Example 32 | >150.0 |
| 10-240 of Example 33 | >150.0 |

The tested compounds of the present invention have relatively low cytotoxicity and relatively high safety. The remaining compounds of the present invention have similar safety characteristics.

Experimental Example 3: hERG Inhibitory Effect Assay

In cardiac muscle cells, hERG (human Ether-a-go-go Related Gene) coded potassium channel mediates delayed rectifier potassium currents (IKr). IKr inhibition is the most important mechanism of QT interval prolongation caused by a drug. In a hERG test, the evaluation criterion is as follows: if IC$_{50}$ of a compound is greater than 10 µM, then the compound is determined as not having any inhibitory effect on the hERG.

Employing the Predictor™ hERG Fluorescence Polarization Assay, the effect of the compounds on a hERG potassium ion channel was detected. The test results are as shown in Table 3 as follows:

TABLE 3

| Compound No. | IC$_{50}$ value (µM) |
|---|---|
| Control compound 1 | 2.85 |
| Control compound 2 | 1~10 |
| 10-36 of Example 10 | >10 |
| 10-40 of Example 11 | >10 |
| 10-42 of Example 12 | >10 |
| 10-88 of Example 1 | >10 |
| Isomer B of Example 4 | >10 |
| Isomer A of Example 4 | >10 |
| 10-93 of Example 2 | >10 |
| 10-95 of Example 5 | >10 |
| 10-226 of Example 25 | >10 |
| 10-227 of Example 27 | >10 |
| 10-230 of Example 26 | >10 |

According to the above data, control compound 1 and control compound 2 have cardiotoxicity at different degrees (having a significant inhibitory effect on the hERG potassium ion channel in the cardiac muscle cells), and thus have a potential risk of inducing arrhythmia; while the tested compounds of the present invention do not have an inhibitory effect on the hERG potassium ion channel, and thus do not have significant cardiotoxicity, thereby achieving higher safety. The remaining compounds of the present invention have similar safety.

Experimental Example 4: In Vivo Study on Pharmacokinetics (PK) in Rats

The test compounds were administered to male SD rats by intravenous (iv) and by gavage (po), respectively, the doses of the iv and po administration were respectively 1 mg/kg and 2 mg/kg, the solvent system for iv administration was 5% DMSO:5% solutol:90% physiological saline, and the solvent system for po administration was 0.5% MC. Blood was collected at multiple time points after iv administration and po administration for the PK study. Plasma samples and liver tissue samples were subjected to protein precipitation, followed by LC-MS/MS analysis. The mass spectrometer was API 5500, and the liquid chromatograph is a Waters ACQUITY I CLASS system; the chromatographic column was an Agela ASB C$_{18}$ column (2.1 mm×50 mm, 1.9 µm); mobile phase A was water+0.1% formic acid, and phase B was acetonitrile; the flow rate was 0.4 mL/min, and the column temperature was 40° C. The ion source was an ESI source in a positive ion mode, and the scanning manner is multiple reaction monitoring (MRM). The test results are shown in the following table:

TABLE 4

| Compound No. | Administration route | Dosage mg/kg | $AUC_{INF}$ h * ng/ml | $C_{max}$ ng/ml |
|---|---|---|---|---|
| Control compound 2 | iv | 1.00 | 2150 | 2470 |
| 10-226 of Example 25 | iv | 1.00 | 2400 | 2890 |

According to the data in Table 4, compared with Control compound 2, the compound of the present invention (e.g., 10-226 of Example 25) intravenously administered at 1.00 mg/kg has better drug exposure ($AUC_{INF}$) and higher blood-drug concentration ($C_{max}$) in blood in vivo, and thus possesses better pharmacokinetic parameters.

TABLE 5

Pharmacokinetic parameters in plasma

| Compound No. | Administration route | Dosage mg/kg | $AUC_{INF}$ h * ng/ml | $C_{max}$ ng/ml |
|---|---|---|---|---|
| Control compound 2 | po | 2.00 | 897 | 1250 |
| 10-226 of Example 25 | po | 2.00 | 2290 | 2180 |

According to the data in Table 5, compared with Control compound 2, the compound of the present invention (e.g., 10-226 of Example 25) administered by gavage at 2.00 mg/kg has better drug exposure ($AUC_{INF}$) and higher blood-drug concentration ($C_{max}$) in blood in vivo, and thus possesses better absorption properties.

TABLE 6

Pharmacokinetic parameters in liver

| Compound No. | Administration route | Dosage mg/kg | $AUC_{INF}$ h * ng/ml | $C_{max}$ ng/ml |
|---|---|---|---|---|
| Control compound 2 | po | 2.00 | 1490 | 547 |
| 10-226 of Example 25 | po | 2.00 | 3030 | 1690 |

According to the data in Table 6, compared with Control compound 2, the compound of the present invention (e.g., 10-226 of Example 25) administered by gavage at 2.00 mg/kg has better drug exposure ($AUC_{INF}$) and higher blood-drug concentration ($C_{max}$) in liver in vivo, which further indicates that the compound of the present invention (e.g., 10-226 of Example 25) has better absorption properties. In addition, the bioavailability (F) of the compound of the present invention (e.g., 10-226 of Example 25) administered by gavage at 2.00 mg/kg is 47.6%, which is significantly higher than that (20.9%) of Control compound 2.

TABLE 7

| Compound No. | Administration route | Sample | Dosage mg/kg | $AUC_{INF}$ h * ng/ml | $C_{max}$ ng/ml |
|---|---|---|---|---|---|
| Control compound 2 | po | plasma | 2.00 | 897 | 1250 |
|  |  | liver | 2.00 | 1490 | 547 |
| 10-230 of Example 26 | po | plasma | 2.00 | 236 | 179 |
|  |  | liver | 2.00 | 2340 | 1520 |

As shown in Table 7, the amount of exposure of the compound of the present invention (e.g., 10-230 of Example 26) in liver in vivo is about 10 times of that in plasma, and the blood-drug concentration in liver in vivo is about 10 times of that in plasma; while the amount of exposure of control compound 2 in liver in vivo is about 1.5 times of that in plasma, and the blood-drug concentration in liver in vivo is about 0.5 time of that in plasma. The above indicates that the compound of the present invention has excellent drug exposure ($AUC_{INF}$) and blood-drug concentration ($C_{max}$) in liver in vivo, and thus has liver targeting properties.

Experimental Example 5: In Vivo Study on Pharmacokinetics (PK) in Beagle Dogs

The test compounds were administered to male Beagle dogs by intravenous (iv) and by gavage (po), respectively, the doses of the iv and po administration were respectively 0.5 mg/kg and 2.5 mg/kg, the solvent system for iv administration was 5% DMSO:5% solutol:90% physiological saline, and the solvent system for po administration was 0.5% MC. Blood was collected at multiple time points after iv administration and po administration for the PK study. Plasma samples were subjected to protein precipitation, followed by LC-MS/MS analysis. The mass spectrometer was API 5500, and the liquid chromatograph was a Waters ACQUITY I CLASS system; the chromatographic column was an Agela ASB $C_{18}$ column (2.1 mm×50 mm, 1.9 μm); mobile phase A was water+0.1% formic acid, and phase B was acetonitrile; the flow rate was 0.4 mL/min, and the column temperature was 40° C. The ion source was an ESI source in a positive ion mode, and the scanning manner is multiple reaction monitoring (MRM). The test results are shown in the following table:

TABLE 8

| Compound No. | Administration route | Dosage mg/kg | $AUC_{INF}$ h * ng/ml | $AUC_{last}$ h * ng/ml | $C_{max}$ ng/ml |
|---|---|---|---|---|---|
| Control compound 3 | iv | 0.50 | 1130 | 1120 | 2130 |
| 10-227 of Example 27 | iv | 0.50 | 8750 | 8690 | 2310 |

According to the data in Table 8, compared with Control compound 3, the compound of the present invention (e.g., 10-227 of Example 27) intravenously administered at 0.50 mg/kg has better drug exposure ($AUC_{INF}$) and higher blood-drug concentration ($C_{max}$) in blood in vivo, and thus possesses better pharmacokinetic parameters.

TABLE 9

| Compound No. | Administration route | Dosage mg/kg | $AUC_{INF}$ h * ng/ml | $AUC_{last}$ h * ng/ml | $C_{max}$ ng/ml |
|---|---|---|---|---|---|
| Control compound 3 | po | 2.50 | 2360 | 2330 | 1210 |
| 10-227 of Example 27 | po | 2.50 | 33200 | 32900 | 7200 |

As shown in Table 9, the amount of exposure in plasma of the compound of the present invention (e.g., 10-227 of Example 27) administered by gavage at 2.50 mg/kg is about 14 times of that of control compound 3, and the blood-drug concentration is about 6 times of that of control compound 3, which further indicates that the compounds of the present invention (e.g., 10-227 of Example 27) have better absorption properties. In addition, the bioavailability (F) of the compound of the present invention (e.g., 10-227 of Example 27) administered by gavage at 2.50 mg/kg is 75.9%, which is significantly better than that (41.7%) of Control compound 3.

Experimental Example 6: In Vivo Study on Pharmacokinetics (PK) in Cynomolgus Macaques The test compounds were administrated to male cynomolgus macaques by intravenous (iv) and by gavage (po), respectively, the doses of the iv and po administration were respectively 0.5 mg/kg and 2.5 mg/kg, the solvent system for iv administration was 5% DMSO:5% solutol:90% physiological saline, and the solvent system for po administration was 0.5% MC. Blood was collected at multiple time points after iv administration and po administration for the PK study. Plasma samples were subjected to protein precipitation, followed by LC-MS/MS analysis. The mass spectrometer was API 5500, the liquid chromatograph was a Waters ACQUITY I CLASS system; the chromatographic column was an Agela ASB $C_{18}$ column (2.1 mm×50 mm, 1.9 μm); mobile phase A was water+0.1% formic acid, and phase B was acetonitrile; the flow rate was 0.4 mL/min, and the column temperature was 40° C. The ion source was an ESI source in a positive ion mode, and the scanning manner is multiple reaction monitoring (MRM). The test results are shown in the following table:

TABLE 10

| Compound No. | Administration route | Dosage mg/kg | $AUC_{INF}$ h * ng/ml | $AUC_{last}$ h * ng/ml | $C_{max}$ ng/ml |
|---|---|---|---|---|---|
| Control compound 3 | iv | 0.50 | 623 | 623 | 1607 |
| 10-227 of Example 27 | iv | 0.50 | 2463 | 2441 | 1673 |

According to the data in Table 10, in the study on PK in cynomolgus macaques, compared with Control compound 3, the compound of the present invention (e.g., 10-227 of Example 27) intravenously administered at 0.50 mg/kg has better drug exposure ($AUC_{INF}$) and higher blood-drug concentration ($C_{max}$) in blood in vivo, and thus possesses better pharmacokinetic parameters.

TABLE 11

| Compound No. | Administration route | Dosage mg/kg | $AUC_{INF}$ h * ng/ml | $AUC_{last}$ h * ng/ml | $C_{max}$ ng/ml |
|---|---|---|---|---|---|
| Control compound 3 | po | 2.50 | 211 | 208 | 32 |
| 10-227 of Example 27 | po | 2.50 | 4566 | 4417 | 1069 |

As shown in Table 11, in the study on PK in cynomolgus macaques, the amount of exposure in plasma of the compound of the present invention (e.g., 10-227 of Example 27) administered by gavage at 2.50 mg/kg is about 21 times of that of control compound 3, and the blood-drug concentration is about 33 times of that of control compound 3, which further indicates that the compound of the present invention (e.g., 10-227 of Example 27) has better absorption properties. In addition, the bioavailability (F) of the compound of the present invention (e.g., 10-227 of Example 27) administered by gavage at 2.50 mg/kg is 37.2%, which is significantly better than that (6.77%) of Control compound 3.

Experimental Example 7: Study on CYP450 Enzyme Induction

Cell Recovery

A test tube of HepG2 C3A/pCYP3A4-Luc, C8 cells was taken out of a liquid nitrogen tank, the cells were recovered in a sterile water bath at 37° C.; and the test tube was gently shaken until ice completely melted. The recovered cells were transferred to a 15 mL sterile centrifuge tube, and 5-10 mL pre-heated basal cell culture medium at 37° C. was added; the cells were naturally settled for 2 minutes and centrifuged (1000 rpm) for 8 minutes. The supernatant was discarded, and the cells were re-suspended with 10 mL pre-heated cell culture medium. The cell suspension was transferred to a 10 cm cell-culture dish and incubated in a 5% $CO_2$ incubator at 37° C. The original cell culture medium was replaced with a selective cell culture medium after 24 hours.

Cell Proliferation

The cells were digested after growing in 80%-90% of the culture dish, and then transferred to a 15 mL sterile centrifuge tube. Centrifugation was performed at 1000 rpm for 8 minutes, and the cells were collected. The supernatant was discarded, and the cells were re-suspended with 3 mL pre-heated complete medium. The cell suspension was sub-cultured by a ratio of 1:3 or 1:5.

CYP3A4 Induction Test

A cell plate was prepared on the first day. 5 μL 1× Matrigel was added into a 384-well white cell plate, and centrifugation was performed at 600 rpm for 1 minute. The culture dish was taken out, the culture medium was discarded, the cells were washed with 1 mL PBS which was then sucked out, 2 mL of 0.25% pancreatin was added, and the cells were incubated in an incubator for 2-3 minutes. 5 mL of cell culture medium was added for termination after complete trypsination of the cells, and then transferred to a centrifuge tube. Centrifugation was performed at 1000 rpm for 8 minutes. The supernatant was discarded, the cells were re-suspended and counted, and the suspension was diluted to $4\times10^5$ cells per mL. The cell suspension was plated to the 384-well white cell plate at 25 μL per well. The cell plate was centrifuged at 300 rpm for 1 minute and incubated in a 5% $CO_2$ incubator at 37° C. for 24 hours. On the second day, 300 nL 100× compounds were transferred to the cell plate from the compound plate. The cell plate was centrifuged at 300 rpm for 1 minute and incubated in the 5% $CO_2$ incubator at 37° C. for 72 hours. On the fifth day, the cell plate and a Bright-Glo luciferase reagent were taken out and equilibrated to room temperature. The Bright-Glo luciferase reagent was added to the cell plate (at 30 μL per well). The cell plate was centrifuged at 1000 rpm for 1 minute and incubated at the room temperature for 2 minutes. The fluorescence signal was measured on a plate reader.

Data Processing

A concentration curve of the tested compounds was plotted by using software Prism 5, and the $EC_{50}$ values were calculated.

TABLE 12

| Compound No. | 10-227 of Example 27 | Control compound 3 | Rifampicin |
|---|---|---|---|
| $EC_{50}$ (μM) | 122.8 | 5.641 | 1.828 |

As shown in Table 12, compared with control compound 3 and rifampicin, the compound of the present invention (e.g., 10-227 of Example 27) has a weaker inductive effect on CYP450 isoform 3A4, and thus has better safety.

As shown in FIG. 1, at a concentration of 10 μM, compared with control compound 3 and rifampicin, the compound of the present invention (e.g., 10-227 of Example 27) has a weaker inductive effect on CYP450 isoform 3A4, which is about 29% of that of rifampicin; while the inductive effect of control compound 3 on CYP450 isoform 3A4 at the same concentration is comparable to that of rifampicin. The above data indicate that the compound of the present invention (e.g., 10-227 of Example 27) has better safety.

Experimental Example 8: In Vivo Study on the Pharmaceutical Effect

The in vivo inhibitory effect on hepatitis B virus of the compound of the present invention was evaluated by employing a mouse HBV model via tail vein hydrodynamic injection (HDI).

A suspension of compound 10-227 of the present invention was prepared with a 0.5% MC solution as the solvent. Female BALB/c mice were injected with pAAV2-HBV 1.3mer (type D) plasmid DNA via tail vein hydrodynamic injection, and then divided into the control group, test group 1 and test group 2 (5 mice in each group). Oral gavage administration was initiated one day later. The control group was given the 0.5% MC solution each time. The test groups 1 and 2 each time were given compound 10-227 (in the form of the suspension prepared above) at a dosage of 1 mg/kg and 3 mg/kg, respectively. The administration was continued for 7 days, twice a day, at an administration interval of 10 hours or 14 hours. Mouse plasma was collected at different time points (e.g., 1 day, 3 days, 5 days or 7 days after the HDI), and the HBV DNA levels in the plasma samples were detected by the RT-qPCR method. The test results are shown in the following table.

TABLE 13

| | HBV DNA Level in Mous Plasma | | | | |
|---|---|---|---|---|---|
| Days after HDI | | 1 day | 3 days | 5 days | 7 days |
| HBV DNA level in plasma (log (HBV DNA copies/μl)) | Control group | 1.99 ± 0.11 | 4.34 ± 0.17 | 4.56 ± 0.13 | 3.69 ± 0.12 |
| | Test group 1 | 1.95 ± 0.09 | 2.28 ± 0.17 | 2.77 ± 0.11 | 2.77 ± 0.14 |
| | Test group 2 | 1.99 ± 0.09 | 1.95 ± 0.15 | 1.57 ± 0.08 | 1.42 ± 0.31 |

According to the data in the above table, the compounds of the present invention (e.g., compound 10-227) can significantly inhibit the HBV DNA replication.

In addition, throughout the entire in vivo test, the weight and body condition of the mice were measured and observed everyday according to an IACUC (Institutional Animal Care and Use Committee) protocol. No mice showed significant variation in body weight (<10%) during the administration, indicating the mice were in good body condition.

In summary, the compounds of the present invention (e.g., compound 10-227) showed a significant therapeutic effect on hepatitis B with a good safety profile.

In addition to those described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A method for treating a viral disease, comprising administering to a subject in need thereof a compound, or a pharmaceutically acceptable salt, ester, stereoisomer, tautomer, polymorph, solvate, metabolite, isotopically labeled compound, or prodrug thereof, wherein the compound has the following structure:

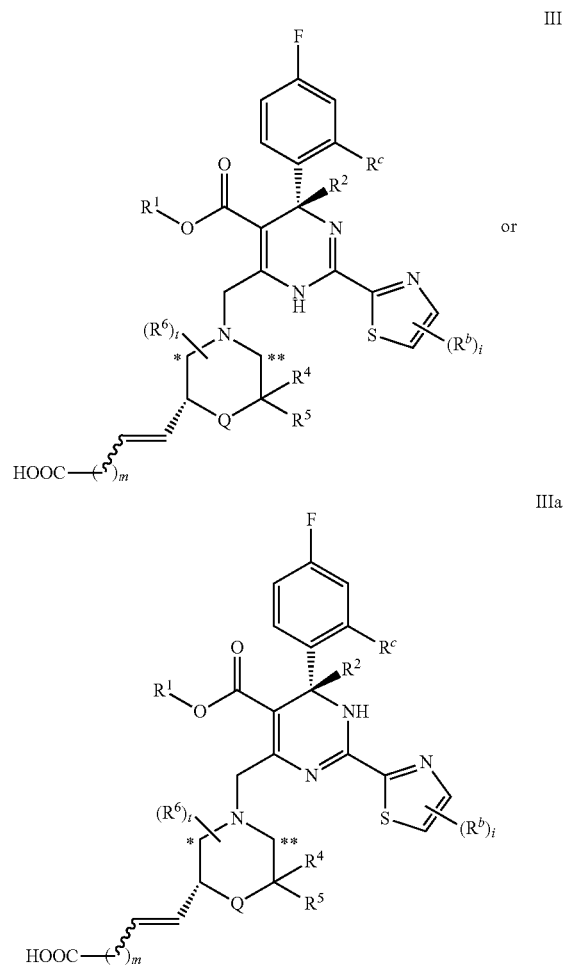

wherein:
$R^1$ and $R^2$ are each independently selected from the group consisting of H (including $^1$H, $^2$H, $^3$H), $C_{1-6}$ alkyl (e.g., $C_{1-6}$ deuteroalkyl) and $C_{3-6}$ cycloalkyl;
Q is —$(CR^aR^{a'})_g$— or —O—;
$R^a$, $R^{a'}$, $R^4$, $R^5$ and $R^6$, at each occurrence, are each independently selected from the group consisting of H, halogen, —OH, —COOH, —CN, —NO$_2$, —N(R)$_2$, $C_{1-6}$ alkyl, $C_{1-6}$ haloalkyl, —W—$C_{1-6}$ alkyl, —$C_{1-6}$ alkylene-W—R, —W—$C_{1-6}$ alkylene-W'—R, —W—$C_{2-6}$ alkenyl, —$C_{2-6}$ alkenylene-W—R, —W—$C_{2-6}$ alkenylene-W'—R and $C_{3-6}$ cycloalkyl, wherein the alkylene and alkenylene are optionally further interrupted by one or more W;
$R^b$, at each occurrence, is each independently selected from the group consisting of H, halogen, $C_{1-6}$ haloalkyl, $C_{1-6}$ alkyl and $C_{3-6}$ cycloalkyl;

R$^c$, at each occurrence, is each independently selected from the group consisting of F, Cl, Br, I, C$_{1-6}$ haloalkyl, C$_{1-6}$ alkyl and C$_{3-6}$ cycloalkyl;

R$^6$ is attached to the ring carbon atom(s) marked with * and/or ** in the general formula;

W and W', at each occurrence, are each independently selected from the group consisting of O, C(=O), C(=O)O, NR, NC(=O), N(S=O), NS(=O)$_2$, S, S=O and S(=O)$_2$;

R, at each occurrence, is each independently selected from the group consisting of H, C$_{1-6}$ alkyl and C$_{3-6}$ cycloalkyl;

g is 1 or 2;

i is 0, 1 or 2;

m is 0, 1, 2, 3 or 4; and t is 0, 1 or 2, provided that when t is greater than 1, each R$^6$ can be the same or different.

2. The method according to claim 1,
wherein R$^b$, at each occurrence, is each independently selected from the group consisting of H, halogen, C$_{1-6}$ alkyl and C$_{3-6}$ cycloalkyl;

R$^c$, at each occurrence, is each independently selected from the group consisting of F, Cl, Br, I, C$_{1-6}$ alkyl and C$_{3-6}$ cycloalkyl.

3. The method according to claim 1, wherein the compound has the following structure:

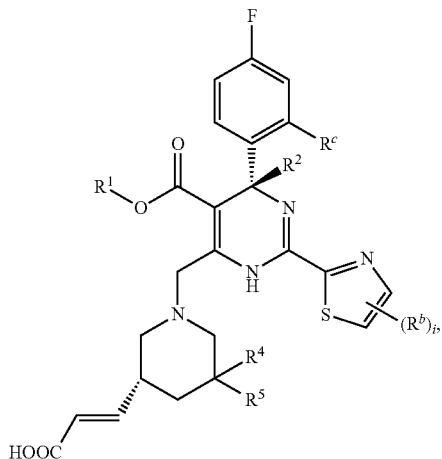

IV

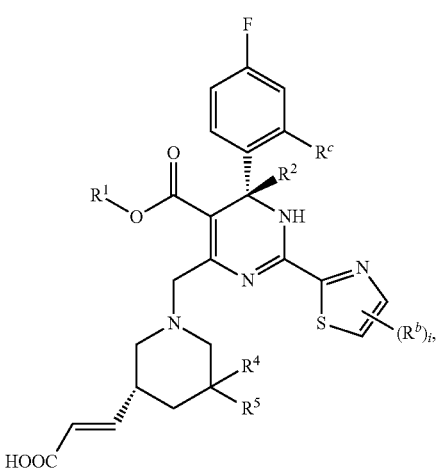

IVa

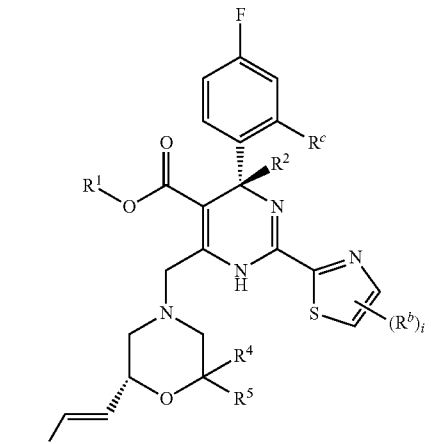

V or

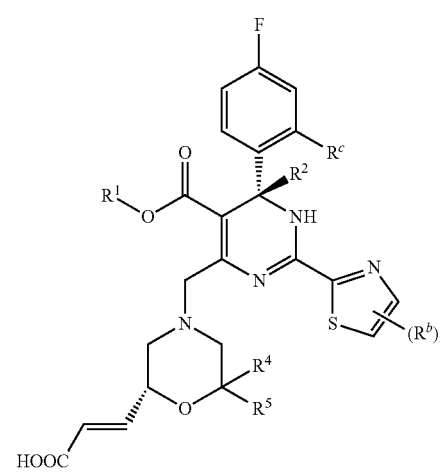

Va

4. The method according to claim 1, wherein the compound is administered orally, intravenously, intraarterially, subcutaneously, intraperitoneally, intramuscularly, or transdermally.

5. The method according to claim 1, wherein the viral disease is selected from the group consisting of viral hepatitis type A, viral hepatitis type B, viral hepatitis type C, influenza, herpes and acquired immunodeficiency syndrome (AIDS).

6. The method according to claim 1, wherein the compound is selected from the group consisting of:

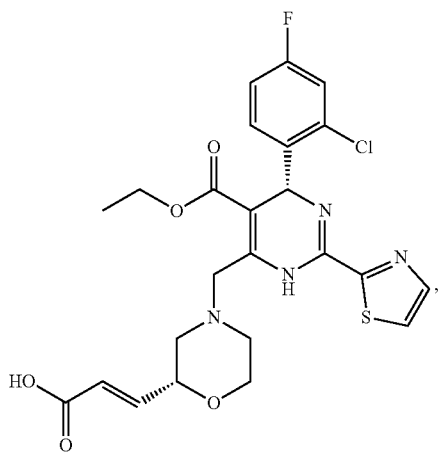

10-226

10-227
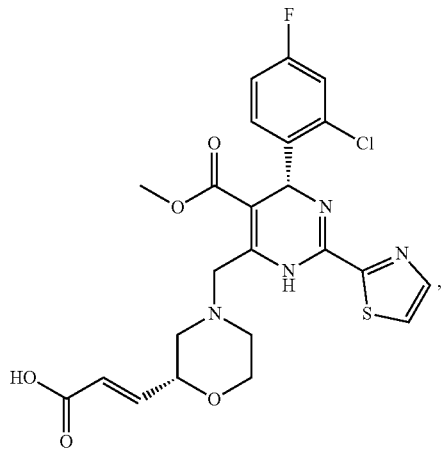
10-230
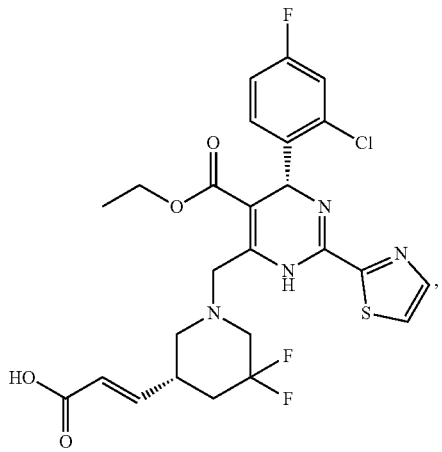
10-228
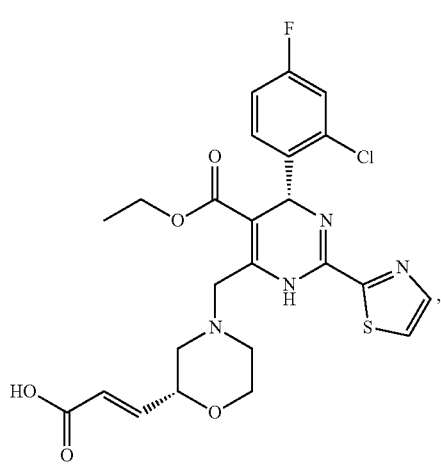
10-231
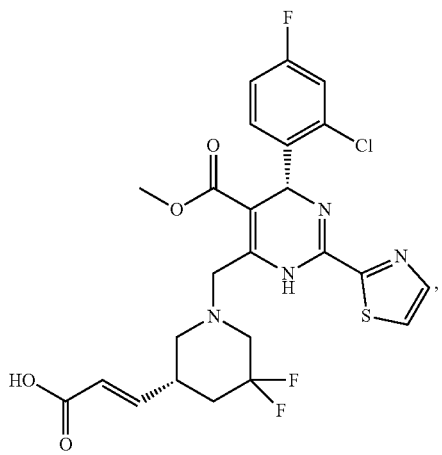
10-229
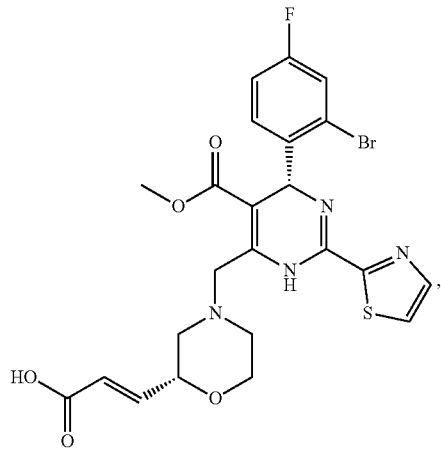
10-234
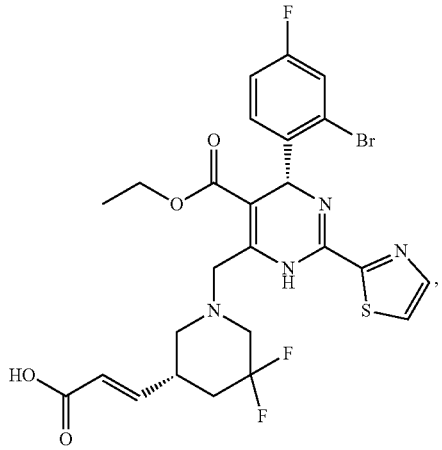

10-235

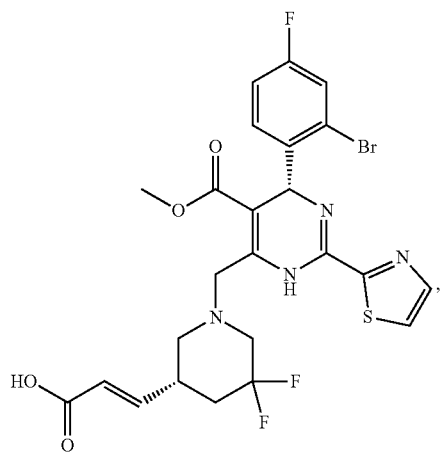

10-242

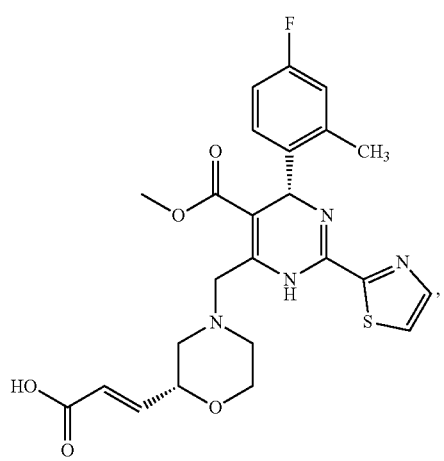

10-243

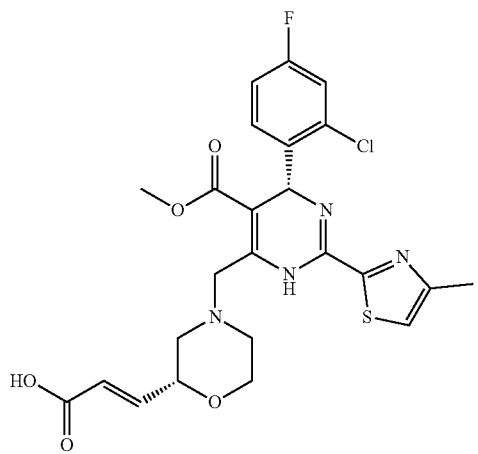

10-244

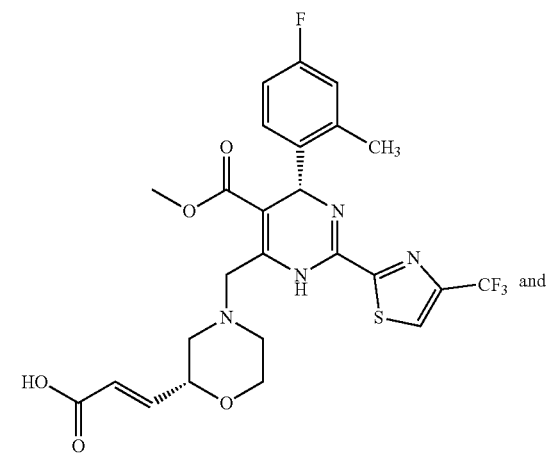

and 10-245

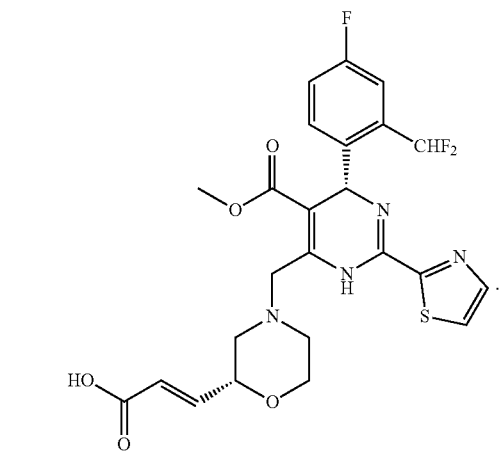

7. The method according to claim 1,
wherein $R^1$ and $R^2$ are each independently selected from the group consisting of H (including $^1$H, $^2$H, $^3$H), methyl, ethyl, n-propyl and isopropyl.

8. The method according to claim 1,
wherein $R^a$, $R^{a'}$, $R^4$, $R^5$ and $R^6$, at each occurrence, are each independently selected from the group consisting of H, F, —OH, —CH$_2$OH, —OCH$_3$, —COOH, —CH$_2$COOH, —(CH$_2$)$_2$COOH, —(CH$_2$)$_3$COOH, —CH=CHCOOH, —OCH$_2$COOH, —SCH$_2$COOH, —N(CH$_3$)CH$_2$COOH, —CH$_2$OCH$_2$COOH, —CH$_2$SCH$_2$COOH, —CH$_2$N(CH$_3$)CH$_2$COOH, —C(CH$_3$)=CHCOOH and —CH=C(CH$_3$)COOH.

9. The method according to claim 1,
wherein $R^a$, $R^{a'}$, $R^4$, $R^5$ and $R^6$, at each occurrence, are each independently selected from the group consisting of H, F, —OH, —CH$_2$OH, —OCH$_3$, —COOH, —CH$_2$COOH, —(CH$_2$)$_2$COOH, —(CH$_2$)$_3$COOH, —CH=CHCOOH, —OCH$_2$COOH, —SCH$_2$COOH, —N(CH$_3$)CH$_2$COOH, —CH$_2$OCH$_2$COOH, —CH$_2$SCH$_2$COOH and —CH$_2$N(CH$_3$)CH$_2$COOH.

\* \* \* \* \*